United States Patent [19]

Taguchi et al.

[11] Patent Number: 5,807,256

[45] Date of Patent: Sep. 15, 1998

[54] MEDICAL INFORMATION PROCESSING SYSTEM FOR SUPPORTING DIAGNOSIS

[75] Inventors: Katsuyuki Taguchi; Shinich Yamada, both of Tochigiken, Japan; Takehiro Ema, Westmont, Ill.

[73] Assignee: Kabushiki Kaisha Toshiba, Kawasakishi, Japan

[21] Appl. No.: 775,893

[22] Filed: Jan. 2, 1997

Related U.S. Application Data

[63] Continuation of Ser. No. 202,744, Feb. 28, 1994, abandoned.

[30] Foreign Application Priority Data

| Mar. 1, 1993 | [JP] | Japan | 5-039996 |
| Mar. 9, 1993 | [JP] | Japan | 5-048366 |
| Apr. 12, 1993 | [JP] | Japan | 5-084296 |
| Jul. 19, 1993 | [JP] | Japan | 5-177859 |
| Jul. 20, 1993 | [JP] | Japan | 5-178934 |
| Jul. 23, 1993 | [JP] | Japan | 5-182319 |

[51] Int. Cl.$^6$ ..................................................... A61B 5/00
[52] U.S. Cl. ........................................... 600/425; 600/300
[58] Field of Search ................................ 128/630, 653.1, 128/653.2; 600/300, 407, 425, 410

[56] References Cited

U.S. PATENT DOCUMENTS

| 4,839,807 | 6/1989 | Doi et al. . |
| 4,851,984 | 7/1989 | Doi et al. . |
| 4,945,476 | 7/1990 | Bodick et al. . |
| 5,233,519 | 8/1993 | Ito . |
| 5,289,374 | 2/1994 | Doi et al. ............................ 364/413.13 |

FOREIGN PATENT DOCUMENTS 0 487 110   5/1992   European Pat. Off. .

OTHER PUBLICATIONS

Patent Abstracts of Japan, vol. 14, No. 581 (P–1147), Dec. 26, 1990, JP–A–02 250180, Oct. 5, 1990.

Proceedings of the Fourth Annual IEEE Symposium on Computer–Based Medical Systems, pp. 28–35, May 1991, Chong–Yen Lee, et al., "Recommending Tests In A Multi-membership Bayesian Diagnostic Expert System".

Medical Physics, vol. 15, No. 2, pp. 158–166, Mar. 1988, Giger, et al., "Image Feature Analysis And Computer–Aided Diagnosis In Digital Radiography. 3. Automated Detection Of Modules In Peripheral Lung Fields".

Diagnostic Imaging International, vol. 8, No. 5, pp. 29–31 and 35–37, Jul. 1992, Swett, "Computers: Power Tool For Imaging Diagnosis".

Shortcliffe et al, Readings in Medical Artificial Intelligence, "Knowledge Engineering For Medical Decision Making: A Review Of Computer–Based Clinical Decision Aids", pp. 35–71, 1984.

*Primary Examiner*—Ruth S. Smith
*Attorney, Agent, or Firm*—Oblon, Spivak, McClelland, Maier & Neustadt, P.C.

[57] ABSTRACT

A medical information processing system for supporting diagnosis, capable of displaying an original image and a minified image over the original image without being interfered to each other, capable of optimal man-power & time saving configurations and methods, capable of realizing an optimal classifying technique for doctor's interpretation and CAD-processed result, and capable of optimizing efficiency in forming accurate interpretation report by using PACS in a mass survey. The system includes: a detecting unit for detecting location of abnormality from a first medical image in accordance with a predetermined algorithm; an image forming unit for forming a second medical image in which a marker indicating the location of the abnormality is overlapped; and a display unit for displaying the first medical image and the second medical image in an optimally efficient way.

4 Claims, 110 Drawing Sheets

32 PIXELS

WHITE COLOR

32 PIXELS

CENTER POSITION

| EXAMINATION ID NUMBER | DISEASE HISTORY | PULMONARY TUBECULOSIS (YES / NO) |
|---|---|---|
| PATIENT ID NUMBER | | |
| NAME OF PATIENT | | HAS LUNG BEEN REMOVED BY OPERATION (YES / NO) |
| BIRTHDAY | | OTHERS |
| SEX DISTINCTION | CONDITION (SYMPTOMS) OF PATIENT | |
| ADDRESS | | COUGH (YES / NO) |
| FAMILY MEMBERS | | SPUTUM |
| ANY FAMILY MEMBERS DIED OF CANCER (YES / NO) | | FEVER (YES / NO) |
| | | OTHERS |

FIG.18

| |
|---|
| HEADER |
| PATIENT IDENTIFYING NUMBER |
| EXAMINATION ID NUMBER |
| NUMBER OF EXAMINATION IN THE PAST |
| EXAM. ID NUMBER 1 IN THE PAST |
| EXAM. ID NUMBER 2 IN THE PAST |
| EXAM. ID NUMBER 3 IN THE PAST |
| EXAM. ID NUMBER n IN THE PAST |
| MODALITY |
| OBJECT |
| EXAM. DIRECTION |
| IMAGING CONDITION |
| EXAMINATION DATE |
| PIXEL SIZE 1 OF IMAGE (LATERAL LENGTH) |
| PIXEL SIZE 2 OF IMAGE (LONGITUDINAL LENGTH) |
| MATRIX SIZE 1 OF IMAGE (NO. OF PIXELS IN LATERAL DIRECTION) |
| MATRIX SIZE 2 OF IMAGE (NO. OF PIXELS IN LONGITUDINAL DIRECTION) |
| BIT LENGTH OF IMAGE PIXEL |
| DATA AMOUNT OF IMAGE |

FIG.22

| DISPLAY COLOR | BIT VALUE OF RED-COLOR OVERLAY MEMORY | BIT VALUE OF GREEN-COLOR OVERLAY MEMORY | BIT VALUE OF BLUE-COLOR OVERLAY MEMORY |
|---|---|---|---|
| BLACK COLOR | 0 | 0 | 0 |
| RED COLOR | 1 | 0 | 0 |
| GREEN COLOR | 0 | 1 | 0 |
| BLUE COLOR | 0 | 0 | 1 |
| YELLOW COLOR | 1 | 1 | 0 |
| PURPLE COLOR | 1 | 0 | 1 |
| LIGHT-BLUE COLOR | 0 | 1 | 1 |
| WHITE COLOR | 1 | 1 | 1 |

FIG.23

| |
|---|
| EXAMINATION ID NUMBER |
| PATIENT ID NUMBER |
| NAME OF PATIENT |
| BIRTHDAY |
| SEX DISTINCTION |
| MODALITY |
| OBJECT |
| EXAM. METHOD |
| EXAM. DATE |
| NUMBER OF IMAGES |
| ⋮ |
| MEMORY ADDRESS (SLOW MEDIUM) OF IMAGE ASSOCIATED DATA OF FIRST IMAGE |
| DATA AMOUNT OF IMAGE ASSOCIATED DATA OF FIRST IMAGE |
| MEMORY ADDRESS (SLOW MEDIUM) OF IMAGE DATA OF FIRST IMAGE |
| DATA AMOUNT OF IMAGE DATA OF FIRST IMAGE |
| ⋮ |
| MEMORY ADDRESS (SLOW MEDIUM) OF IMAGE ASSOCIATED DATA OF N-TH IMAGE |
| DATA AMOUNT OF IMAGE ASSOCIATED DATA OF N-TH IMAGE |
| MEMORY ADDRESS (SLOW MEDIUM) OF IMAGE DATA OF N-TH IMAGE |
| DATA AMOUNT OF IMAGE DATA OF N-TH IMAGE |

| ABNORMALITY NUMBER | TYPE OF ABNORMALITY | LOCATION OF ABNORMALITY | ABNORMALITY JUDGMENT ON ENTIRE IMAGE |
|---|---|---|---|
| N1 | PULMONARY NODULE | (700,1200) | "DOUBTFULLY ABNORMAL" |
| N2 | PULMONARY NODULE | (1500,1000) | |

FIG.26

| ABNORMALITY NUMBER | TYPE OF ABNORMALITY | LOCATION OF ABNORMALITY | ABNORMALITY JUDGMENT ON ENTIRE IMAGE |
|---|---|---|---|
|  |  |  | "NORMAL" |

FIG.27

| ABNORMALITY NUMBER | TYPE OF ABNORMALITY | LOCATION OF ABNORMALITY | ABNORMALITY JUDGMENT ON ENTIRE IMAGE |
|---|---|---|---|
| N1 | PULMONARY NODULE | (562,723) | "NORMAL" |

FIG.28

| ABNORMALITY NUMBER | TYPE OF ABNORMALITY | LOCATION OF ABNORMALITY | ABNORMALITY JUDGMENT ON ENTIRE IMAGE |
|---|---|---|---|
| | | | "NORMAL" |

FIG.29

| ABNORMALITY NUMBER | TYPE OF ABNORMALITY | LOCATION OF ABNORMALITY | ABNORMALITY JUDGMENT ON ENTIRE IMAGE |
|---|---|---|---|
| N1 | PULMONARY NODULE | (548,1086) | "DOUBTFULLY ABNORMAL" |
| N2 | PULMONARY NODULE | (1655,1272) | |

FIG.30

| REMARKS NUMBER | ABNORMALITY DISPLAY NUMBER | TYPE OF ABNORMALITY | LOCATION OF ABNORMALITY | ABNORMALITY JUDGMENT ON ENTIRE IMAGE |
|---|---|---|---|---|
| 1 | A1 | PULMONARY NODULE | (1520,1040) | "ABNORMAL" |
| 2 | A2 | PULMONARY NODULE | (1430, 659) | |

FIG.31

| DISPLAY NUMBER | LOCATION OF DISPLAY | FORM OF DIAGRAM | DISPLAYING COLOR | CONTROL DATA ON DISPLAY AND NO-DISPLAY | |
|---|---|---|---|---|---|
| A1 | (1520,1040) | ARROW MARK | WHITE | DISPLAY | |
| A2 | (1430, 659) | ARROW MARK | WHITE | DISPLAY | |

FIG.32

| DISPLAY NUMBER | LOCATION OF DISPLAY | FORM OF DIAGRAM | DISPLAYING COLOR | CONTROL DATA ON DISPLAY AND NO-DISPLAY | |
|---|---|---|---|---|---|
| N1 | (700,1200) | ARROW MARK | RED | DISPLAY | |
| N2 | (1500,1000) | ARROW MARK | RED | DISPLAY | |

FIG.33

| EXAMINATION ID NUMBER | INTERPRETATION (READING) RESULT BY DOCTOR | CAD-PROCESSED RESULT | CLASSIFI-CATION |
|---|---|---|---|
| 920001 | "ABNORMAL" | "DOUBTFULLY ABNORMAL" | b |
| 920002 | "NORMAL" | "NORMAL" | c |
| 920003 | "NORMAL" | "DOUBTFULLY ABNORMAL" | d |
| 920004 | "ABNORMAL" | "NORMAL" | a |
| 920005 | "NORMAL" | "DOUBTFULLY ABNORMAL" | d |
| ⋮ | | | |

FIG.38

| PATIENT ID NUMBER |
| --- |
| NAME OF PATIENT |
| BIRTHDAY |
| SEX DISTINCTION |
| MODALITY |
| OBJECT |
| EXAMINATION METHOD |
| NAME OF EXAM. REQUEST DEPT. |
| NAME OF EXAM. REQUEST DOCTOR |
| DATE OF EXAM. REQUESTED |
| DESIRED DATE OF EXAM. |
| DESIRED TIME OF EXAM. |
| OBJECT OF EXAM. |
| CLINICAL DATA OF PATIENT |
| NAME OF PATIENT ALREADY GIVEN |
| ⋮ |

FIG.40

| OBJECT | MODALITY | EXAMINATION METHOD | IMAGING DIRECTION | TYPE OF DETECTABLE DISEASE |
|---|---|---|---|---|
| CHEST | X RAY | PLAIN IMAGING | P → A | INTERSTITIAL LUNG DISEASE |
| CHEST | X RAY | PLAIN IMAGING | P → A | PULMONARY NODULE |
| MAMMA | X RAY | PLAIN IMAGING | [NOT SPECIFIED] | FINE CALCIFICATION |

FIG.41

| IMAGING DIRECTION OF IMAGE | RELATIVE DISPLAY POSITION OF IMAGE |
|:---:|:---:|
| P → A | C |
| L → R | L |
| R → L | R |

FIG.42

| ID NUMBER OF RADIOLOGIST | NAME OF RADIOLOGIST |
|:---:|:---:|
| 1856 | |
| 2965 | |
| 3476 | |
| ⋮ | ⋮ |

| DISPLACED AMOUNT OF ORIGIN DUE TO COORDINATE TRANSFORMATION | ANGULAR ROTATION AMOUNT DUE TO COORDINATE TRANSFORMATION | NAME OF DISSECTION STRUCTURE ON IMEGE | FOURTH RIB ||||
|---|---|---|---|---|---|---|
| | | | | UPPER END | LOWER END | RIGHT END | LEFT END |
| (1005,1850) | 0.02 (cad) | POSITION AT TRANSFORMED COORDINATE | y=190 | y=230 | x=−390 | x=395 |

| ELEVENTH RIB | | | |
|---|---|---|---|
| UPPER END | LOWER END | RIGHT END | LEFT END |
| y=20 | y=−20 | x=−890 | x=870 |

FIG.43

| EXAM. ID NUMBER | READING REFERENCE PRIORITY ORDER |
|---|---|
| 103541 | 0 |
| 100902 | 1 |
| 102287 | 2 |
| 60563 | 3 |

INSIDE DOTTED LINE : RANGE POSSIBLE TO ANALYZE

☐ : ROI, REGION TO BE ANALYZED

☐ : ROI JUDGED AS "NORMAL" BY CAD

■ : ROI JUDGED AS "ABNORMAL" BY CAD

FIG.49

| ARRANGEMENT NUMBER | ABNORMALITY DISPLAY NUMBER | EXAM. ID NUMBER | TYPE OF ABNORMALITY | CENTRAL POSITION OF ABNORMALITY ON IMAGE (ABSOLUTE COORDINATE) (LATERAL, LONGITUDINAL) | POSITION OF ABNORMALITY ON IMEGE (RELATIVE POSITION) |
|---|---|---|---|---|---|
| 1 | Z1 | 103541 | PULMONARY NODULE | (1450,1350) | |
| 2 | Z2 | 103541 | PULMONARY NODULE | ( 500,1300) | |
| 3 | Y1 | 103541 | INTERSTITIAL LUNG DISEASE | ( 610, 710) | |
| 4 | Y2 | 103541 | INTERSTITIAL LUNG DISEASE | (1700,1300) | |
| | | | | | |

FIG.50

| ARRANGEMENT NUMBER | ABNORMALITY DISPLAY NUMBER | EXAM. ID NUMBER | TYPE OF ABNORMALITY | CENTRAL POSITION OF ABNORMALITY ON IMAGE (ABSOLUTE COORDINATE) (LATERAL, LONGITUDINAL) | POSITION OF ABNORMALITY ON IMEGE (RELATIVE POSITION) |
|---|---|---|---|---|---|
| 1 | Z1 | 103541 | PULMONARY NODULE | (1450, 1350) | (PULMONARY FIELD, LEFT, 8, 9, 0.56) |
| 2 | Z2 | 103541 | PULMONARY NODULE | (500, 1300) | (PULMONARY FIELD, RIGHT, 8, 9, 0.63) |
| 3 | Y1 | 103541 | INTERSTITIAL LUNG DISEASE | (610, 710) | (PULMONARY FIELD, RIGHT, 5, 6, 0.62) |
| 4 | Y2 | 103541 | INTERSTITIAL LUNG DISEASE | (1700, 1300) | (PULMONARY FIELD, LEFT, 8, 9, 0.86) |
| | | | | | |

FIG.51

| DATA NUMBER | ABNORMALITY DISPALY NUMBER | DISPLAY POSITION | FORM OF FIGURE | DISPLAY COLOR | CONTROL DATA ON DISPLAY OR NO-DISPLAY |
|---|---|---|---|---|---|
| 1 | Z1 | (1450,1350) | ARROW MARK | RED | DISPLAY |
| 2 | Z2 | (500,1300) | ARROW MARK | RED | DISPLAY |
| 3 | Y1 | (500,710), (750,550), (770,550), (770,570), (760,760), (500,760) | REGION CONNECTED TO LEFT POINT | RED | DISPLAY |
| 4 | Y2 | (1690,1290), (1710,1290), (1710,1310), (1690,1310) | REGION CONNECTED TO LEFT POINT | RED | DISPLAY |

FIG.52

| | DATA ITEM | DATA VALUE |
|---|---|---|
| FIRST IMAGE | EXAM. ID NUMBER | 103541 |
| | IMAGE NUMBER (OF EXAM. IN QESTION) | 1 |
| | IMAGE PIXEL SIZE 1 (LATERAL LENGTH OF PIXEL) | 0.016cm |
| | IMAGE PIXEL SIZE 2 (VERTICAL LENGTH OF PIXEL) | 0.016cm |
| | IMAGE MATRIX SIZE 1 (NO. OF PIXELS IN LATERAL DIRECTION) | 2048 |
| | IMAGE MATRIX SIZE 2 (NO. OF PIXELS IN LONGITUDINAL DIRECTION) | 2048 |
| | BIT LENGTH OF IMAGE PIXEL | 10 |
| | DATA AMOUNT OF IMAGE | 5MB |
| | PHOTOGRAPHING DIRECTION IMAGE | P → A |
| | ... | ... |

| REMARK NO. | TYPE OF ABNORMALITY | NUMBER INDICATING ABNORMALITY ON OVERLAY | POSITION & REGION WHERE ABNORMALITY EXISTS |
|---|---|---|---|
| 1 | | | |
| 2 | | | |
| 3 | | | |
| | | | |

CONCLUSION :

(PLACE PROVIDED FOR DISPLAYING TERMINOLOGY OR ELSE)

| REMARK NO. | TYPE OF ABNORMALITY | NUMBER INDICATING ABNORMALITY ON OVERLAY |
|---|---|---|
| 1 | PULMONARY NODULE | A1 |
| 2 | INTERSTITIAL LUNG DISEASE | B1 |
| 3 | INTERSTITIAL LUNG DISEASE | B2 |
| 4 | INTERSTITIAL LUNG DISEASE | B3 |
|  |  |  |

FIG.65A

| PATIENT ID NUMBER | EXAM. ID NUMBER |
|---|---|
|  |  |
| 89001 | XR89423102 |
|  | CT89425003 |
|  | MR91912004 |
|  | CT91A02203 |
| 89002 | XR89424242 |
|  | BD89629311 |
| 89003 | XR89425112 |
|  | BD89425332 |
| 89004 |  |

FIG.65B

| EXAM. ID NUMBER | EXAM. DATA ID NUMBER |
|---|---|
|  |  |
| XR89423101 | XPA00231 |
| XR89423102 | XPA00232 |
|  | XRL00210 |
| XR89423103 | XPA00233 |
|  | XRL00211 |
| XR89423104 | XRL00212 |
|  | XLGL0001 |
|  |  |

FIG.66A

| EXAM. DATA ID NUMBER | EXAM. ID NUMBER |
|---|---|
|  |  |
| XPA00231 | XR89423101 |
| XPA00232 | XR89423102 |
| XPA00233 | XR89423103 |
| XPA00234 | XR89423105 |
| ⋮ | ⋮ |
| XRL00210 | XR89423102 |
| XRL00211 | XR89423103 |
| XRL00212 | XR89423104 |
|  |  |

FIG.66B

| EXAM. ID NUMBER | PATIENT ID NUMBER |
|---|---|
|  |  |
| XR89423101 | 88845 |
| XR89423102 | 89001 |
| XR89423103 | 88323 |
| XR89423104 | 88992 |
| ⋮ | ⋮ |
| CT89425001 | 88765 |
| CT89425002 | 88045 |
| CT89425003 | 89001 |
|  |  |

FIG. 70

| DETECTING MEANS | DETECTION RESULT |
|---|---|
| Nodule 1 | "ABNORMAL" |
| Nodule 2 | "ABNORMAL" |
| ILD 1 | "ABNORMAL" |
| ILD 2 | "NORMAL" |

FIG. 71

| DETECTING MEANS | DETECTION RESULT |
|---|---|
| Nodule 1 | "ABNORMAL" |
| Nodule 2 | "NORMAL" |
| ILD 1 | "NORMAL" |
| ILD 2 | "NORMAL" |

FIG. 72

| DETECTING MEANS | DETECTION RESULT |
|---|---|
| Nodule 1 | "NORMAL" |
| Nodule 2 | "NORMAL" |
| ILD 1 | "NORMAL" |
| ILD 2 | "NORMAL" |

FIG. 73

| DETECTING MEANS | DETECTION RESULT |
|---|---|
| Nodule 1 | "NORMAL" |
| Nodule 2 | "NORMAL" |
| ILD 1 | "ABNORMAL" |
| ILD 2 | "NORMAL" |

FIG. 74

| DETECTING MEANS | DETECTION RESULT |
|---|---|
| Nodule 1 | "NORMAL" |
| Nodule 2 | "NORMAL" |
| ILD 1 | "ABNORMAL" |
| ILD 2 | "ABNORMAL" |

FIG. 75

| DETECTING MEANS | DETECTION RESULT |
|---|---|
| Nodule 1 | "ABNORMAL" |
| Nodule 2 | "NORMAL" |
| ILD 1 | "ABNORMAL" |
| ILD 2 | "ABNORMAL" |

FIG. 76

| DETECTING MEANS | DETECTION RESULT |
|---|---|
| Nodule 1 | "ABNORMAL" |
| Nodule 2 | "NORMAL" |
| ILD 1 | "ABNORMAL" |
| ILD 2 | "NORMAL" |

FIG. 77

| DETECTING MEANS | DETECTION RESULT |
|---|---|
| Nodule 1 | "ABNORMAL" |
| Nodule 2 | "ABNORMAL" |
| ILD 1 | "ABNORMAL" |
| ILD 2 | "ABNORMAL" |

FIG. 78

| DETECTING MEANS | DETECTION RESULT |
|---|---|
| Nodule 1 | "ABNORMAL" |
| Nodule 2 | "ABNORMAL" |
| ILD 1 | "NORMAL" |
| ILD 2 | "NORMAL" |

FIG. 79

| DETECTING MEANS | DETECTION RESULT |
|---|---|
| Nodule 1 | "ABNORMAL" |
| Nodule 2 | "NORMAL" |
| ILD 1 | "ABNORMAL" |
| ILD 2 | "NORMAL" |

FIG. 80

| EXAM. ID NUMBER | RESULT OF FIRST CLASSIFICATION (Nodule) | RESULT OF FIRST CLASSIFICATION (ILD) | RESULT OF SECOND CLASSIFICATION |
|---|---|---|---|
| 920001 | case 3 | case 2 | case B |
| 920002 | case 2 | case 1 | case C |
| 920003 | case 1 | case 1 | case A |
| 920004 | case 1 | case 2 | case C |
| 920005 | case 1 | case 3 | case B |
| 920006 | case 2 | case 3 | case B |
| 920007 | case 2 | case 2 | case C |
| 920008 | case 3 | case 3 | case B |
| 920009 | case 3 | case 1 | case B |
| 920010 | case 2 | case 2 | case C |
| ... | ... | ... | ... |

FIG. 81

| EXAM. ID NUMBER |
|---|
| 920003 ... |

FIG. 82

| EXAM. ID NUMBER |
|---|
| 920001 920005 920006 920008 920009 ... |

FIG. 83

| EXAM. ID NUMBER |
|---|
| 920002 920004 920007 920010 ... |

FIG. 84

| DETECTING MEANS | DETECTION RESULT |
|---|---|
| Nodule 1 | "ABNORMAL" |
| Nodule 2 | "ABNORMAL" |
| ILD 1 | "NORMAL" |
| ILD 2 | "ABNORMAL" |

FIG. 85

| EXAM. ID NUMBER | RESULT OF FIRST DETECTING MEANS | RESULT OF SECOND DETECTING MEANS | RESULT OF FIRST CLASSIFICATION (Nodule) | RESULT OF FIRST DETECTING MEANS | RESULT OF SECOND DETECTING MEANS | RESULT OF FIRST CLASSIFICATION (ILD) | RESULT OF SECOND CLASSIFICATION |
|---|---|---|---|---|---|---|---|
| 930001 | "ABNORMAL" | "ABNORMAL" | case 3 | "NORMAL" | "ABNORMAL" | case 2 | case B |
| 930002 | "NORMAL" | "ABNORMAL" | case 2 | "NORMAL" | "NORMAL" | case 1 | case C |
| 930003 | "ABNORMAL" | "NORMAL" | case 2 | "ABNORMAL" | "ABNORMAL" | case 3 | case B |
| 930004 | "ABNORMAL" | "ABNORMAL" | case 3 | "ABNORMAL" | "NORMAL" | case 2 | case B |
| 930005 | "ABNORMAL" | "NORMAL" | case 2 | "NORMAL" | "ABNORMAL" | case 2 | case C |
| 930006 | "NORMAL" | "NORMAL" | case 1 | "NORMAL" | "NORMAL" | case 1 | case A |
| 930007 | "ABNORMAL" | "NORMAL" | case 2 | "ABNORMAL" | "NORMAL" | case 2 | case C |
| 930008 | "NORMAL" | "NORMAL" | case 1 | "ABNORMAL" | "ABNORMAL" | case 3 | case B |
| 930009 | "NORMAL" | "ABNORMAL" | case 2 | "ABNORMAL" | "ABNORMAL" | case 2 | case C |
| 930010 | "NORMAL" | "NORMAL" | case 1 | "NORMAL" | "ABNORMAL" | case 2 | case C |
| ... | ... | ... | ... | ... | ... | ... | ... |

LIST A

| EXAM. ID NUMBER |
|---|
| 930006 ... |

FIG. 86

LIST B

| EXAM. ID NUMBER |
|---|
| 930001 930003 930004 930008 ... |

FIG. 87

LIST C

| EXAM. ID NUMBER |
|---|
| 930002 930005 930007 930009 930010 ... |

|  | TEST 1 | TEST 2 | TEST 3 | ABNORMALITY VALUE |
|---|---|---|---|---|
| NUMBER OF CANDID ABNORMAL SHADE IN THIS IMAGE THAT PASSED THE TEST | 20 | 7 | 1 | |
| NUMBER OF CANDID ABNORMAL SHADE IN TEST-PASSED ENTIRE IMAGES IN DB | 18.23 | 5.37 | 0.05 | |
| DEVIATION VALUE OF NUMBER OF CANDID ABNORMAL SHADE IN THIS IMAGE | 51.77 | 55.43 | 73.75 | 73.75 |

FIG. 90

| ROI NUMBER | SINGLE INDEX | ORER WITHIN IMAGE | AVERAGE VALUE OF UPPER 5 ROI IN DB | DEVIATION VALUE OF UPPER 5 ROI | IAMGE CHARACTERISTIC VALUE |
|---|---|---|---|---|---|
| 1 | 0.29 | 15 | 0.88 | | 70.84 |
| 2 | 1.21 | 6 | | | |
| 3 | 0.83 | 11 | | | |
| 4 | 2.27 | 5 | | 63.9 | |
| 5 | 0.52 | 13 | | | |
| 6 | −0.33 | 19 | | | |
| 7 | 3.31 | 2 | | 74.3 | |
| 8 | 2.93 | 3 | | 70.5 | |
| 9 | −1.10 | 20 | | | |
| 10 | 0.51 | 14 | | | |
| 11 | 0.94 | 10 | | | |
| 12 | 0.30 | 15 | | | |
| 13 | 1.18 | 7 | | | |
| 14 | −0.29 | 17 | | | |
| 15 | −0.53 | 18 | | | |
| 16 | 1.18 | 7 | | | |
| 17 | 3.93 | 1 | | 60.5 | |
| 18 | 2.38 | 4 | | 55.0 | |
| 19 | 1.10 | 9 | | | |
| 20 | 0.82 | 12 | | | |

FIG. 91

| ABNORMALITY VALUE OF NODULE | ABNORMAL VALUE OF INTERSTITIAL LUNG DESEASE | IAMGE CHARACTERISTIC VALUE |
|---|---|---|
| 73.75 | 70.84 | 73.75 |

FIG. 92

| EXAM. ID NUMBER | ABNORMAL VALUE OF NODULE | ABNORMAL VALUE INTERSTITIAL LUNG DESEASE | IAMGE CHARAC- TERISTIC VALUE | CLASSIFI- CATION RESULT |
|---|---|---|---|---|
| 940001 | 73.75 | 70.84 | 73.75 | case B |
| 940002 | 48.32 | 55.43 | 55.43 | case C |
| 940003 | 36.12 | 63.29 | 63.29 | case C |
| 940004 | 48.32 | 53.22 | 53.22 | case C |
| 940005 | 30.89 | 30.76 | 30.89 | case A |
| 940006 | 55.62 | 45.43 | 55.62 | case C |
| 940007 | 49.92 | 30.94 | 49.92 | case C |
| 940008 | 69.92 | 41.99 | 69.92 | case B |
| 940009 | 55.29 | 72.91 | 72.91 | case B |
| 940010 | 31.20 | 29.30 | 31.20 | case A |
| ... | ... | ... | ... | ... |

FIG. 93

LIST A

| EXAM. ID NUMBER |
|---|
| 940005 |
| 940010 |
| ... |

FIG. 94

LIST B

| EXAM. ID NUMBER |
|---|
| 940001 |
| 940008 |
| 940009 |
| ... |

FIG. 95

LIST C

| EXAM. ID NUMBER |
|---|
| 940002 |
| 940003 |
| 940004 |
| 940006 |
| 940007 |
| ... |

FIG. 96

| DETECTING MEANS | RESULT OF DETECTION |
|---|---|
| Nodule 1 | "ABNORMAL" |
| Nodule 2 | "ABNORMAL" |
| ILD 1 | "ABNORMAL" |
| ILD 2 | "NORMAL" |

FIG. 97

| EXAM. ID NUMBER | RESULT OF FIRST DETECTING MEANS | RESULT OF SECOND DETECTING MEANS | RESULT OF FIRST CLASSIFI-CATION (Nodule) | RESULT OF FIRST DETECTING MEANS | RESULT OF SECOND DETECTING MEANS | FIRST CLASSIFI-CATION RESULT (ILD) | SECOND CLASSIFI-CATION RESULT |
|---|---|---|---|---|---|---|---|
| 920001 | "ABNORMAL" | "ABNORMAL" | case 3 | "ABNORMAL" | "NORMAL" | case 2 | case B |
| 920002 | "ABNORMAL" | "NORMAL" | case 2 | "NORMAL" | "NORMAL" | case 1 | case C |
| 920003 | "ABNORMAL" | "NORMAL" | case 2 | "ABNORMAL" | "NORMAL" | case 2 | case C |
| 920004 | "ABNORMAL" | "NORMAL" | case 2 | "ABNORMAL" | "NORMAL" | case 2 | case C |
| 920005 | "ABNORMAL" | "NORMAL" | case 1 | "ABNORMAL" | "NORMAL" | case 2 | case C |
| 920006 | "NORMAL" | "NORMAL" | case 2 | "NORMAL" | "NORMAL" | case 1 | case A |
| 920007 | "ABNORMAL" | "NORMAL" | case 1 | "ABNORMAL" | "NORMAL" | case 2 | case C |
| 920008 | "NORMAL" | "NORMAL" | case 2 | "ABNORMAL" | "NORMAL" | case 2 | case C |
| 920009 | "ABNORMAL" | "NORMAL" | case 1 | "ABNORMAL" | "NORMAL" | case 2 | case C |
| 920010 | "NORMAL" | "NORMAL" | case 3 | "ABNORMAL" | "NORMAL" | case 2 | case B |
| 920011 | "ABNORMAL" | "ABNORMAL" | case 2 | "ABNORMAL" | "NORMAL" | case 2 | case C |
| 920012 | "ABNORMAL" | "NORMAL" | case 2 | "ABNORMAL" | "NORMAL" | case 1 | case B |
| 920013 | "ABNORMAL" | "NORMAL" | case 1 | "ABNORMAL" | "NORMAL" | case 3 | case B |
| 920014 | "ABNORMAL" | "NORMAL" | case 2 | "ABNORMAL" | "NORMAL" | case 2 | case C |
| 920015 | "ABNORMAL" | "NORMAL" | case 2 | "ABNORMAL" | "ABNORMAL" | case 2 | case C |
| 920016 | "NORMAL" | "NORMAL" | case 1 | "NORMAL" | "NORMAL" | case 1 | case A |
| 920017 | "ABNORMAL" | "NORMAL" | case 2 | "ABNORMAL" | "NORMAL" | case 2 | case C |
| 920018 | "NORMAL" | "NORMAL" | case 1 | "NORMAL" | "ABNORMAL" | case 3 | case B |
| 920019 | "ABNORMAL" | "NORMAL" | case 1 | "ABNORMAL" | "NORMAL" | case 1 | case C |
| 920020 | "NORMAL" | "ABNORMAL" | case 3 | "ABNORMAL" | "NORMAL" | case 2 | case C |
| 920021 | "ABNORMAL" | "NORMAL" | case 1 | "ABNORMAL" | "NORMAL" | case 2 | case B |
| 920022 | "NORMAL" | "NORMAL" | case 3 | "NORMAL" | "NORMAL" | case 1 | case A |
| 920023 | "ABNORMAL" | "NORMAL" | case 3 | "ABNORMAL" | "NORMAL" | case 2 | case C |
| 920024 | "ABNORMAL" | "ABNORMAL" | case 2 | "ABNORMAL" | "NORMAL" | case 2 | case B |
| 920025 | "ABNORMAL" | "NORMAL" | case 2 | "NORMAL" | "NORMAL" | case 1 | case C |
| 920026 | "NORMAL" | "NORMAL" | case 1 | "ABNORMAL" | "NORMAL" | case 2 | case A |
| 920027 | "ABNORMAL" | "NORMAL" | case 2 | "NORMAL" | "NORMAL" | case 1 | case C |
| 920028 | "NORMAL" | "NORMAL" | case 1 | "NORMAL" | "NORMAL" | case 2 | case A |
| 920029 | "ABNORMAL" | "NORMAL" | case 2 | "ABNORMAL" | "NORMAL" | case 2 | case C |
| 920030 | "ABNORMAL" | "NORMAL" | case 2 | "ABNORMAL" | "NORMAL" | case 2 | case C |
| ... | | | | | | | |

FIG.98

LIST A

| EXAM. ID NUMBER |
| --- |
| 920006 |
| 920016 |
| 920022 |
| 920026 |
| 920028 |
| ... |

FIG.99

LIST B

| EXAM. ID NUMBER |
| --- |
| 920001 |
| 920011 |
| 920013 |
| 920018 |
| 920021 |
| 920024 |
| ... |

FIG.100

LIST C

| EXAM. ID NUMBER |
| --- |
| 920002 |
| 920003 |
| 920004 |
| 920005 |
| 920007 |
| 920008 |
| 920009 |
| 920010 |
| 920012 |
| 920014 |
| 920015 |
| 920017 |
| 920019 |
| 920020 |
| 920023 |
| 920025 |
| 920027 |
| 920029 |
| 920030 |
| ... |

FIG.101

| ABNORMALITY NUMBER | TYPE OF ABNORMALITY | POSITION OF ABNORMALITY | ABNORMALITY JUDGMENT FOR ENTIRE IMAGE |
|---|---|---|---|
| N1 | PULMONARY NODULE | (700,1200) | "ABNORMAL" |
| N2 | PULMONARY NODULE | (1500,1000) | |

FIG.102

| REMARK NUMBER | TYPE OF ABNORMALITY | POSITION OF ABNORMALITY | ABNORMALITY JUDGMENT FOR ENTIRE IMAGE |
|---|---|---|---|
| N1 | PULMONARY NODULE | (1520,1040) | "ABNORMAL" |
| N2 | PULMONARY NODULE | (1430, 659) | |

FIG.103

DOCTOR'S READING

| DISPLAY NUMBER | DISPLAY LOCATION | FORM OF FIGURE | DISPLAYING COLOR | CONTROL DATA ON DISPLAY OR NO-DISPLAY | |
|---|---|---|---|---|---|
| A1 | (1520,1040) | ARROW MARK | WHITE | DISPLAY | |
| A2 | (1430, 659) | ARROW MARK | WHITE | DISPLAY | |

FIG.104

CAD-PROCESS RESULT

| DISPLAY NUMBER | DISPLAY LOCATION | FORM OF FIGURE | DISPLAYING COLOR | CONTROL DATA ON DISPLAY OR NO-DISPLAY | |
|---|---|---|---|---|---|
| N1 | ( 700,1200) | ARROW MARK | RED | DISPLAY | |
| N2 | (1500,1000) | ARROW MARK | RED | DISPLAY | |

FIG.105

| EXAM. ID NUMBER |
|---|
| 920005 |
| 920008 |
| 920019 |
| 920027 |

FIG.106

| EXAM. ID NUMBER | READING RESULT OF DOCTOR | CAD-PROCESS RESULT (THIRD THRESHOLD) | CLASSIFICATION |
|---|---|---|---|
| 920002 | "ABNORMAL" | "ABNORMAL" | case b |
| 920003 | "NORMAL" | "NORMAL" | case c |
| 920004 | "ABNORMAL" | "ABNORMAL" | case b |
| 920005 | "NORMAL" | "ABNORMAL" | case d |
| 920007 | "NORMAL" | "NORMAL" | case c |
| 920008 | "NORMAL" | "ABNORMAL" | case d |
| 920009 | "ABNORMAL" | "ABNORMAL" | case b |
| 920010 | "NORMAL" | "NORMAL" | case c |
| 920012 | "ABNORMAL" | "NORMAL" | case a |
| 920014 | "ABNORMAL" | "ABNORMAL" | case b |
| 920015 | "NORMAL" | "NORMAL" | case c |
| 920017 | "ABNORMAL" | "NORMAL" | case a |
| 920019 | "NORMAL" | "ABNORMAL" | case d |
| 920020 | "NORMAL" | "NORMAL" | case c |
| 920023 | "ABNORMAL" | "NORMAL" | case a |
| 920025 | "ABNORMAL" | "ABNORMAL" | case b |
| 920027 | "NORMAL" | "ABNORMAL" | case d |
| 920029 | "NORMAL" | "NORMAL" | case c |
| 920030 | "ABNORMAL" | "ABNORMAL" | case b |
| ... | ... | ... | ... |

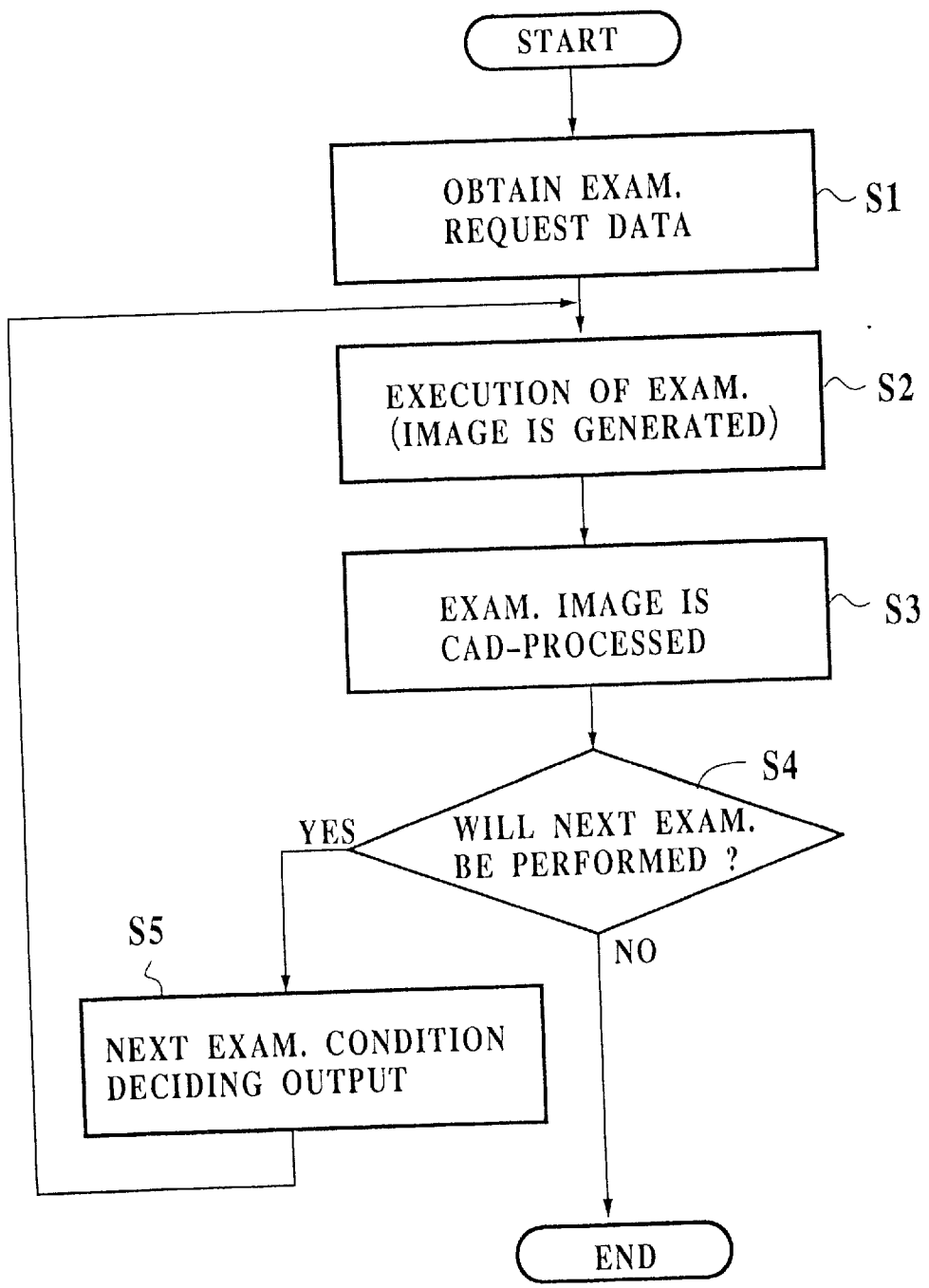

FIG.120

| INFORMATION OF PATIENT | PATIENT ID NUMBER |
| | NAME OF PATIENT |
| | DATE OF BIRTH OF PATIENT |
| | SEX OF PATIENT |
| INFORMATION OF EXAM. | MODALITY |
| | OBJECT |
| | EXAM. PROCEDURE |
| | NAME OF EXAM. REQUESTING DEPT. |
| | NAME OF EXAM. REQUEST DOCTOR |
| | DATE OF EXAM. REQUEST |
| | DESIRED DATE OF EXAM. |
| | DESIRED TIME OF EXAM. |
| | PURPOSE OF EXAM. |
| | EXAM. ID |
| | PATIENT CLINICAL INFO |
| | DISCLOSED DISEASE NAME |
| | ⋮ |

FIG.121

| EXAM. ID | |
|---|---|
| DATE OF EXAM. | |
| NUMBER OF SHEET OF IMAGE | |
| INFO OF FIRST SHEET OF IMAGE | IMAGE NUMBER |
| | LATERAL LENGTH OF PIXEL |
| | LONGITUDINAL LENGTH OF PIXEL |
| | LATERAL SIZE OF MATRIX |
| | LONGITUDINAL SIZE OF MATRIX |
| | PIXEL BIT LENGTH OF IMAGE |
| | DATA AMOUNT |
| | IMAGE DIRECTION |
| INFO OF SECOND SHEET OF IMAGE | |

FIG.122

| INFO (DATA) ON PATIENT | PATIENT ID NUMBER |
| --- | --- |
| | NAME OF PATIENT |
| | DATE OF BIRTH OF PATIENT |
| | SEX OF PATIENT |
| INFO ON EXAM. | EXAM. ID NUMBER |
| | MODALITY |
| | OBJECT |
| | PROCEDURE OF EXAM. |
| | NAME OF EXAM. REQUESTING DEPT. |
| | NAME OF EXAM. REQUESTING DOCTOR |
| | DATE OF EXAMINATION |
| | NAME OF INTERPRETING DOCTOR |
| FINDING (REMARK) | FINDING 1 |
| | FINDING 2 |
| | |
| | FINDING N |
| | CONCLUSION |

FIG.123

(a) A first priority is an examination that is applied to
the identical examination portion and by the identical modality (X-ray)
to an uninterpreted examination ; and that
has the identical type of an abnormality and the identical
position of an abnormality to CAD processing results an unin-
terpreted examination ; and that
is before an examination for starting a medical treatment or
an examination having a change in the condition of a disease of
a patient.

(b) A second priority is, in the sequential order of a date, all
examinations that
are applied to the identical examination portion and by the
identical modality (X-ray) to an uninterpreted examination ; and that
have the identical type of an abnormality and the identical
position of an abnormality to CAD processing results of an unin-
terpreted examination ; and that
have a later date of an examination than that of (a).

FIG.124

(a) A first priority is an examination that
is applied to the identical examination portion and by the
identical modality (X-ray) to an uninterpreted examination ; and
that
has the identical type of an abnormality and the identical
position of an abnormality to CAD processing results of an unin-
terpreted examination ; and that
has an older date of an examination.

(b) A second priority is, in the sequential order of a date, all
examinations that
are applied to the identical examination portion and by the
identical modality (X-ray) to an uninterpreted examination ; and
that
have the identical type of an abnormality and the identical
position of an abnormality to CAD processing results of an unin-
terpreted examination ; and that
have a later date of an examination than that of (C).

FIG.125

(a) A first priority is an examination that
   has CAD processing results of an uninterpreted examination ;
   and that
     is applied to the identical examination portion to and by
   the different modality (tomography) from an uninterpreted examination ; and that
     has a later date of an examination.

(b) A second priority is an examination that
   has CAD processing results of an uninterpreted examination ;
   and that
     is applied to the identical examination portion to and by
   the different modality (CT) from an uninterpreted examination ;
   and that
     has a later date of an examination.

(c) A third priority is an examination that
   has CAD processing results an uninterpreted examination ;
   and that
     is applied to the identical examination portion to and by
   the different modality (MR) from an uninterpreted examination ;
   and that
     has a later date of an examination

FIG.126

(a) A first priority is an examination that
  CAD processing results of an uninterpreted examination are an interstitial lung disease ; and that
    is applied to the identical examination portion to and by the different modality (Ga scintillation) from an uninterpreted examination ; and that
    has a later date of an examination.

(b) A first priority is an examination that
  CAD processing results of an uninterpreted examination are a pulmonary emphysema ; and that
    is applied to the identical examination portion to and by the different modality (pulmonary hematocele, pulmonary inhalation scintillation) from an uninterpreted examination ; and that
    has a later date of an examination.

(c) A first priority is an examination that
  CAD processing results of an uninterpreted examination are a cancer ; and that
    is applied to the identical examination portion to and by the different modality (RI) from an uninterpreted examination ; and that
    has a later date of an examination.

(d) A second priority is an examination that
  CAD processing results of an uninterpreted examination are a cancer ; and that
    is applied to the identical examination portion to and by the different modality (Ga scintillation) from an uninterpreted examination ; and that
    has a later date of an examination.

(e) A third priority is an examination that
  CAD processing results of an uninterpreted examination are a cancer ; and that
    is applied by the different modality (bone scintillation) from an uninterpreted examination ; and that
    has a later data of an examination.

(f) A fourth priority is an examination that
  CAD processing results of an uninterpreted examination are a cancer ; and that
    is applied by the different modality (head CT) from an uninterpreted examination ; and that
    has a later date of an examination.

FIG.127

(a) A first priority is an examination that
is applied to the identical examination portion to and by
the identical modality to an uninterpreted examination ; and that
has a later date of an examination.

(b) A second priority is an examination that
is applied to the identical examination portion to and by
the identical modality to an uninterpreted examination ; and that
has an older date of an examination.

(c) A third priority is an examination that
is applied to the identical examination portion to and by
the different modality from an uninterpreted examination ; and that
has a later date of an examination.

(d) A fourth priority is an examination that
is applied to the identical examination portion to and by
the different modality from an uninterpreted examination ; and that
has an older date of an examination.

(e) A fifth priority is an examination that
is applied to the different examination portion from and by
the identical modality to an uninterpreted examination ; and that
has a later date of an examination.

(f) A sixth priority is an examination that
is applied to the different examination portion from and by
the identical modality to an uninterpreted examination ; and that
has an older date of an examination.

(g) A seventh priority is an examination that
is applied to the different examination portion from and by
the different modality from an uninterpreted examination ; and that
has a later date of an examination.

(h) An eighth priority is an examination that
is applied to the different examination portion from and by
the different modality from an uninterpreted examination ; and that
has an older date of an examination.

FIG.128

In a typical disease example image.
(a) A first priority is an examination that
CAD processing results of an uninterpreted examination are a cancer ; and that
its size is 1cm or more ; and that
is applied to the identical examination portion to and by
the identical modality to an uninterpreted examination ; and that
is a plurality of typical disease examples that are made a benign judgement.
(b) A second priority is an examination that
is applied to the identical type of an abnormality to and
the identical position of an abnormality to CAD processing results of an uninterpreted examination.

(c) A third priority is an examination that
is applied to the identical type of an abnormality to and
the different position of an abnormality from CAD processing results of an uninterpreted examination.

FIG.129

| REFERENCE NUMBER |
| --- |
| EXAM. ID NUMBER |
| IMAGE NUMBER |
| TYPE OF ABNORMALITY |
| CENTER POSITION OF ABNORMALITY (ABSCISSA, ORDINATE) |
| DEGREE OR SIZE OF ABNORMALITY |
| AREA CONTAINING ABNORMALITY |

FIG.130

| PATIENT INFO | PATIENT ID NUMBER |
| --- | --- |
| | PATIENT NAME |
| | DATE OF BIRTH OF PATIENT |
| | SEX OF PATIENT |
| FIRST EXAM. INFO | EXAM. ID NUMBER |
| | MODALITY |
| | OBJECT |
| | PROCEDURE OF EXAM. |
| | NAME OF EXAM. REQUESTING DEPT. |
| | NAME OF EXAM. REQUESTING DOCTOR |
| | DATE OF EXAMINATION |
| | NUMBER OF SHEET OF IMAGE |
| | CLINICAL INFO |
| SECOND EXAM. INFO | |

FIG.131

|  | DISEASE NUMBER | 05 |
|---|---|---|
| INFO ON EXAM. | SEX OF PATIENT | MALE |
|  | AGE OF PATIENT | 78 |
|  | MODALITY | X-RAY |
|  | OBJECT | CHEST |
|  | PROCEDURE OF EXAM | PLAIN IMAGING |
| INFO ON FINDING (REMARK) | REMARK 1 |  |
|  | TYPE OF ABNORMALITY | INTERSTITIAL LUNG DISEASE |
|  | LOCATION OF ABNORMALITY | MIDDLE RIGHT LUNG FIELD |
|  | DEGREE OF ABNORMALITY | FAIRLY LARGE |
|  | REMARK 2 |  |
| INFO OF FIRST SHEET OF IMAGE | IMAGE NUMBER |  |
|  | LATERAL LENGTH OF PIXEL |  |
|  | LONGITUDINAL LENGTH OF PIXEL |  |
|  | LATERAL SIZE OF MATRIX |  |
|  | LONGITUDINAL SIZE OF MATRIX |  |
|  | PIXEL BIT LENGTH OF IMAGE |  |
|  | DATA AMOUNT |  |
|  | IMAGE DIRECTION |  |
| INFO OF SECOND SHEET OF IMAGE |  |  |

FIG.132

| PATIENT INFO | PATIENT ID NUMBER | 870802 |
|---|---|---|
| | NAME OF PATIENT | T.K. |
| | DATE OF BIRTH OF PATIENT | AUGUST 6, 1952 |
| | SEX OF PATIENT | MALE |
| INFO OF EXAM. | MODALITY | X-RAY |
| | OBJECT | CHEST |
| | EXAM. PROCEDURE | PLAIN IMAGE |
| | NAME OF EXAM. REQUESTING DEPT. | INTERNAL DEPT. |
| | NAME OF EXAM. REQUESTING DOCTOR | Y.S. |
| | DATE OF EXAM. REQUEST | MAY 10, 1992 |
| | DESIRED DATE OF EXAM. | MAY 10, 1992 |
| | DESIRED TIME OF EXAM. | 14 : 00 |
| | PURPOSE OF EXAM. | — |
| | PATIENT CLINICAL INFO | — |
| | DISCLOSED DISEASE NAME | |
| | ⋮ | |
| | EXAM. ID | 108801 |

FIG.133

| | EXAM. ID | 108801 |
|---|---|---|
| | DATE OF EXAM. | MAY 10, 1952 |
| | NUMBER OF SHEET OF IMAGE | 2 |
| INFO OF FIRST SHEET OF IMAGE | IMAGE NUMBER | 1 |
| | LATERAL LENGTH OF PIXEL | 0.016 cm |
| | LONGITUDINAL LENGTH OF PIXEL | 0.016 cm |
| | LATERAL SIZE OF MATRIX | 2048 |
| | LONGITUDINAL SIZE OF MATRIX | 2048 |
| | PIXEL BIT LENGTH OF IMAGE | 10 |
| | DATA AMOUNT | 5MB |
| | IMAGE DIRECTION | P→A |
| INFO OF SECOND SHEET OF IMAGE | | |

| FIG.134A |
|----------|
| FIG.134B |

|  | DATA ITEMS | DATA VALUES |
|---|---|---|
| INFORMATION OF PATIENT | PATIENT ID NUMBER | 870802 |
|  | PATIENT NAME | T.K. |
|  | DATE OF BIRTH OF PATIENT | AUGUST 6, 1952 |
|  | SEX OF PATIENT | MALE |
| INFO OF FIRST EXAM. | EXAM. ID NUMBER | 60563 |
|  | MODALITY | X-RAY |
|  | OBJECT | HEAD |
|  | PROCEDURE OF EXAM. | IMAGE FORMING |
|  | NAME OF EXAM. REQUESTING DEPT. | NEURO-SURGERY DEPT. |
|  | NAME OF EXAM. REQUESTING DOCTOR | Y.S. |
|  | DATE OF EXAMINATION | APRIL 15, 1989 |
|  | NUMBER OF SHEET OF IMAGE | 2 |
|  | CLINICAL INFO | — |
| INFO OF SECOND EXAM. | EXAM. ID NUMBER | 100902 |
|  | MODALITY | X-RAY |
|  | OBJECT | CHEST |
|  | PROCEDURE OF EXAM. | PLAIN IMAGING |
|  | NAME OF EXAM. REQUESTING DEPT. | INTERNAL DEPT. |
|  | NAME OF EXAM. REQUESTING DOCTOR | E.T. |
|  | DATE OF EXAMINATION | JANUARY 12, 1990 |
|  | NUMBER OF SHEET OF IMAGE | 2 |
|  | CLINICAL INFO | — |

| | | |
|---|---|---|
| INFO OF THIRD EXAM. | EXAM. ID NUMBER | 102287 |
| | MODALITY | X-RAY |
| | OBJECT | RIGHT LEG |
| | PROCEDURE OF EXAM. | PLAIN IMAGING |
| | NAME OF EXAM. REQUESTING DEPT. | ORTHOPEDICS DEPT. |
| | NAME OF EXAM. REQUESTING DOCTOR | R.T. |
| | DATE OF EXAMINATION | JANUARY 17, 1990 |
| | NUMBER OF SHEET OF IMAGE | 2 |
| | CLINICAL INFO | — |
| INFO OF FOURTH EXAM. | EXAM. ID NUMBER | 103541 |
| | MODALITY | X-RAY |
| | OBJECT | CHEST |
| | PROCEDURE OF EXAM. | PLAIN IMAGING |
| | NAME OF EXAM. REQUESTING DEPT. | INTERNAL DEPT. |
| | NAME OF EXAM. REQUESTING DOCTOR | E.T. |
| | DATE OF EXAMINATION | JANUARY 22, 1990 |
| | NUMBER OF SHEET OF IMAGE | 2 |
| | CLINICAL INFO | — |
| EXAM. INFO OF UNINTERPRETED IMAGE ADDED NEWLY | EXAM. ID NUMBER | 108801 |
| | MODALITY | X-RAY |
| | OBJECT | CHEST |
| | PROCEDURE OF EXAM. | PLAIN IMAGING |
| | NAME OF EXAM. REQUESTING DEPT. | INTERNAL DEPT. |
| | NAME OF EXAM. REQUESTING DOCTOR | S.K. |
| | DATE OF EXAMINATION | MAY 10, 1992 |
| | NUMBER OF SHEET OF IMAGE | 2 |
| | CLINICAL INFO | — |

| REFERENCE NUMBER | EXAM. ID NUMBER | IMAGE NUMBER | TYPE OF ABNORMALITY | CENTER POSITION ON SCREEN (ABSCISSA, ORDINATE) | DEGREE OR SIZE OF ABNORMALITY | AREA CONTAINING ABNORMALITY |
|---|---|---|---|---|---|---|
| 1 | 108807 | 1 | INTERSTITIAL LUNG DISEASE | (350, 1350) | 9 | LOWER RIGHT LUNG FIELD |
| 2 | 108801 | 1 | INTERSTITIAL LUNG DISEASE | (400, 1500) | 8 | MIDDLE RIGHT LUNG FIELD |
| 3 | 103541 | 1 | INTERSTITIAL LUNG DISEASE | (300, 1500) | 8 | MIDDLE RIGHT LUNG FIELD |
| 4 | 103541 | 1 | INTERSTITIAL LUNG DISEASE | (1600, 1300) | 8 | MIDDLE LEFT LUNG FIELD |
| 5 | 100902 | 1 | INTERSTITIAL LUNG DISEASE | (350, 1350) | 7 | MIDDLE RIGHT LUNG FIELD |
| 6 | 100902 | 1 | INTERSTITIAL LUNG DISEASE | (400, 1500) | 7 | MIDDLE RIGHT LUNG FIELD |
| 7 | 100902 | 1 | PULMONARY NODULE | (1500, 300) | 1 cm | UPPER LEFT LUNG FIELD |

FIG.136

| DEGREE OF REFERENCE PRIORITY | EXAM. ID |
|---|---|
| 1 | 100902 |
| 2 | 103541 |
| | |

FIG.137A

| DISEASE NUMBER | 05 |
|---|---|
| SEX | MALE |
| AGE | 78 |
| MODALITY | X-RAY |
| OBJECT | CHEST |
| PROCEDURE OF EXAM | PLAIN IMAGING |
| TYPE OF ABNORMALITY | INTERSTITIAL LUNG DISEASE |
| LOCATION OF ABNORMALITY | MIDDLE RIGHT LUNG FIELD |
| ⋮ | |

FIG.137B

| DISEASE NUMBER | 10 |
|---|---|
| SEX | MALE |
| AGE | 60 |
| MODALITY | X-RAY |
| OBJECT | CHEST |
| PROCEDURE OF EXAM | PLAIN IMAGING |
| TYPE OF ABNORMALITY | INTERSTITIAL LUNG DISEASE |
| LOCATION OF ABNORMALITY | UPPER LEFT LUNG FIELD |
| ⋮ | |

FIG.138

| DEGREE OF PRIORITY | EXAM. ID | TYPICAL DISEASE EXAMPLE IMAGE TAG |
|---|---|---|
| 1 | 100902 | |
| 2 | 103541 | |
| 3 | 05 | DISEASE EXAMPLE |
| 4 | 10 | DISEASE EXAMPLE |

FIG.139

| NAME OF DISEASE DETECTED | DEGREE OF ABNORMALITY | DISEASE LOCATION | EXAM. DIRECTION AT LAST TIME | EXAM. CONDITION AT LAST TIME (TUBE VOLTAGE) | NEXT EXAM. DIRECTION | CONDITION FOR NEXT EXAM. |
|---|---|---|---|---|---|---|
| INTERSTITIAL LUNG DISEASE | 1~4 | RIGHT LUNG FIELD | P→A, A→P | 120 KV | N/A | N/A |
| | | LEFT LUNG FIELD | | 90KV | N/A | N/A |
| | 5~7 | RIGHT LUNG FIELD | P→A, A→P | 120 KV | N/A | N/A |
| | | LEFT LUNG FIELD | | 90KV | N/A | N/A |
| | | RIGHT LUNG FIELD | P→A, A→P | 120 KV | L→R | 115KV, 200mA, 0.15 Sec |
| | | LEFT LUNG FIELD | | 90KV | L→R | 90KV, 200mA, 0.2 Sec |
| | 8~10 | RIGHT LUNG FIELD | P→A, A→P | 120 KV | R→L | 115KV, 200mA, 0.15 Sec |
| | | LEFT LUNG FIELD | | 90KV | R→L | 90KV, 200mA, 0.2 Sec |
| | | RIGHT LUNG FIELD | P→A, A→P | 120 KV | N/A | N/A |
| | | LEFT LUNG FIELD | | 90KV | N/A | N/A |
| | | RIGHT LUNG FIELD | P→A, A→P | 120 KV | N/A | N/A |
| | | LEFT LUNG FIELD | | 90KV | N/A | N/A |

FIG.140

| NAME OF DISEASE DETECTED | SIZE OF SHADOW | DISEASE LOCATION POSITION OF ABNOR-MALITY | EXAM. DIRECTION AT LAST TIME | EXAM. CONDITION AT LAST TIME (TUBE VOLTAGE) | NEXT EXAM. DIRECTION | CONDITION FOR NEXT EXAM. |
|---|---|---|---|---|---|---|
| PULMONARY NODULE | ~ 5 cm | MEDIAS-TINUM REGION | P → A, A → P | 120 KV | P → A | ENLARGEMENT IMAGING 120KV, 100mA, 0.06 Sec, ENLARGEMENT OF ABNORMALITY POSITION |
| | | | | 90KV | P → A | 120KV, 100mA, 0.06 Sec |
| | | RIGHT LUNG FIELD | P → A, A → P | 120 KV | L → R | 115KV, 200mA, 0.15 Sec |
| | | | | 90KV | L → R | 90KV, 200mA, 0.2 Sec |
| | | LEFT LUNG FIELD | P → A, A → P | 120 KV | R → L | 115KV, 200mA, 0.15 Sec |
| | | | | 90KV | R → L | 90KV, 200mA, 0.2 Sec |
| | ~ 5 cm | VERTICAL | P → A, A → P | 120 KV | N/A | N/A |
| | | | | 90KV | N/A | N/A |
| | | RIGHT | P → A, A → P | 120 KV | N/A | N/A |
| | | | | 90KV | N/A | N/A |
| | | LEFT | P → A, A → P | 120 KV | N/A | N/A |
| | | | | 90KV | N/A | N/A |

FIG.142

| NUMBER | ABNORMALITY FINDINGS | | | | FIXED-FORM SENTENCE |
|---|---|---|---|---|---|
| | TYPE | POSITION | DEGREE | CONDITION | |
| 1 | ○ | — | — | — | "TYPE is observed". |
| 2 | — | ○ | — | — | "Abnormality shadow is observed in POSITION". |
| 3 | ○ | ○ | — | — | "TYPE is observed". |
| 4 | ○ | — | ○ | — | "TYPE is observed with DEGREE". |
| 5 | — | ○ | ○ | — | "Abnormality shadow is acknowledged in POSITION with DEGREE". |
| 6 | ○ | ○ | ○ | — | "TYPE is observed in POSITION with DEGREE". |
| 7 | ○ | — | — | ○ | "TYPE is observed by CONDITION". |
| 8 | — | ○ | — | ○ | "Abnormality shadow is observed in POSITION by CONDITION". |
| 9 | ○ | ○ | — | ○ | "TYPE is observed in POSITION by CONDITION". |
| 10 | ○ | — | ○ | ○ | "TYPE is observed with DEGREE by CONDITION". |
| 11 | — | ○ | ○ | ○ | "Abnormality shadow is observed in POSITION with DEGREE by CONDITION". |
| 12 | ○ | ○ | ○ | ○ | "TYPE is observed in POSITION with DEGREE by CONDITION". |

FIG.143

| |
|---|
| EXAM. ID |
| IMAGE NUMBER |
| REFERENCE NUMBER |
| TYPE OF GRAPHIC |
| SIZE OF GRAPHIC |
| COORDINATES |
| DISPLAY COLOR |
| TYPE OF ABNORMALITY |
| DEGREE OF ABNORMALITY |
| POSITION OF ABNORMALITY |

FIG.144

| | |
|---|---|
| EXAMINATION ID | 108801 |
| IMAGE NUMBER | 1 |
| REFERENCE NUMBER | 1 |
| TYPE OF GRAPHIC | ARROWHEADED SOLID LINE |
| SIZE OF GRAPHIC | 32DOTS |
| COORDINATES | (350, 1350) |
| DISPLAY COLOR | WHITE |
| TYPE OF ABNORMALITY | INTERSTITIAL LUNG DISEASE |
| DEGREE OF ABNORMALITY | 9 |
| POSITION | LOWER RIGHT LUNG FIELD |
| REFERENCE NUMBER | 2 |
| TYPE OF GRAPHIC | ARROWHEADED SOLID LINE |
| SIZE OF GRAPHIC | 32DOTS |
| COORDINATES | (400, 1500) |
| TYPE OF ABNORMALITY | INTERSTITIAL LUNG DISEASE |
| DEGREE OF ABNORMALITY | 8 |
| POSITION | MIDDLE RIGHT LUNG FIELD |

FIG. 145

| PATIENT ID NUMBER | 870802 |
|---|---|
| NAME OF PATIENT | T.K. |
| BIRTHDAY OF PATIENT | AUGUST 6, 1952 |
| SEX OF PATIENT | MALE |
| EXAM. ID NUMBER | 108801 |
| MODALITY | X-RAY |
| OBJECT | CHEST |
| PROCEDURE OF EXAM. | PLAIN IMAGING |
| NAME OF EXAM. REQUESTING DEPT. | INTERNAL DEPT. |
| NAME OF EXAM. REQUESTING DOCTOR | T.C. |
| DATE OF EXAMINATION | MAY 10, 1992 |
| NAME OF INTERPRETING DOCTOR | R.A. |
| FINDING 1 | INTERSTITIAL LUNG DISEASE IS FOUND IN LOWER RIGHT LUNG FIELD WITH ABNORMALITY DEGREE OF 9 |
| FINDING 2 | INTERSTITIAL LUNG DISEASE IS FOUND IN MIDDLE RIGHT LUNG FIELD WITH ABNORMALITY OF 8 |

FIG.146

| | |
|---|---|
| PATIENT ID NUMBER | 870802 |
| NAME OF PATIENT | T.K. |
| BIRTHDAY OF PATIENT | AUGUST 6, 1952 |
| SEX OF PATIENT | MALE |
| EXAM. ID NUMBER | 108801 |
| MODALITY | X-RAY |
| OBJECT | CHEST |
| PROCEDURE OF EXAM. | PLAIN IMAGING |
| NAME OF EXAM. REQUESTING DEPT. | INTERNAL DEPT. |
| NAME OF EXAM. REQUESTING DOCTOR | T.C. |
| DATE OF EXAMINATION | MAY 10, 1992 |
| NAME OF INTERPRETING DOCTOR | R.A. |
| FINDING 1 | INTERSTITIAL LUNG DISEASE IS FOUND IN LOWER RIGHT LUNG FIELD WITH ABNORMALITY DEGREE OF 9 |
| FINDING 2 | INTERSTITIAL LUNG DISEASE IS FOUND IN LOWER RIGHT LUNG FIELD WITH ABNORMALITY DEGREE OF 6 |

FIG.147

| PATIENT ID NUMBER | 870802 |
|---|---|
| NAME OF PATIENT | T.K. |
| BIRTHDAY OF PATIENT | AUGUST 6, 1952 |
| SEX OF PATIENT | MALE |
| EXAM. ID NUMBER | 108801 |
| MODALITY | X-RAY |
| OBJECT | CHEST |
| PROCEDURE OF EXAM. | PLAIN IMAGING |
| NAME OF EXAM. REQUESTING DEPT. | INTERNAL DEPT. |
| NAME OF EXAM. REQUESTING DOCTOR | T.C. |
| DATE OF EXAMINATION | MAY 10, 1992 |
| NAME OF INTERPRETING DOCTOR | R.A. |
| FINDING 1 | INTERSTITIAL LUNG DISEASE IS FOUND SPREADING IN LOWER RIGHT LUNG FIELD WITH ABNORMALITY DEGREE OF 9 |
| FINDING 2 | SHADOW OF PULMONARY NODULE IS FOUND IN LOWER RIGHT LUNG FIELD WITH ABNORMALITY DEGREE OF 6 |

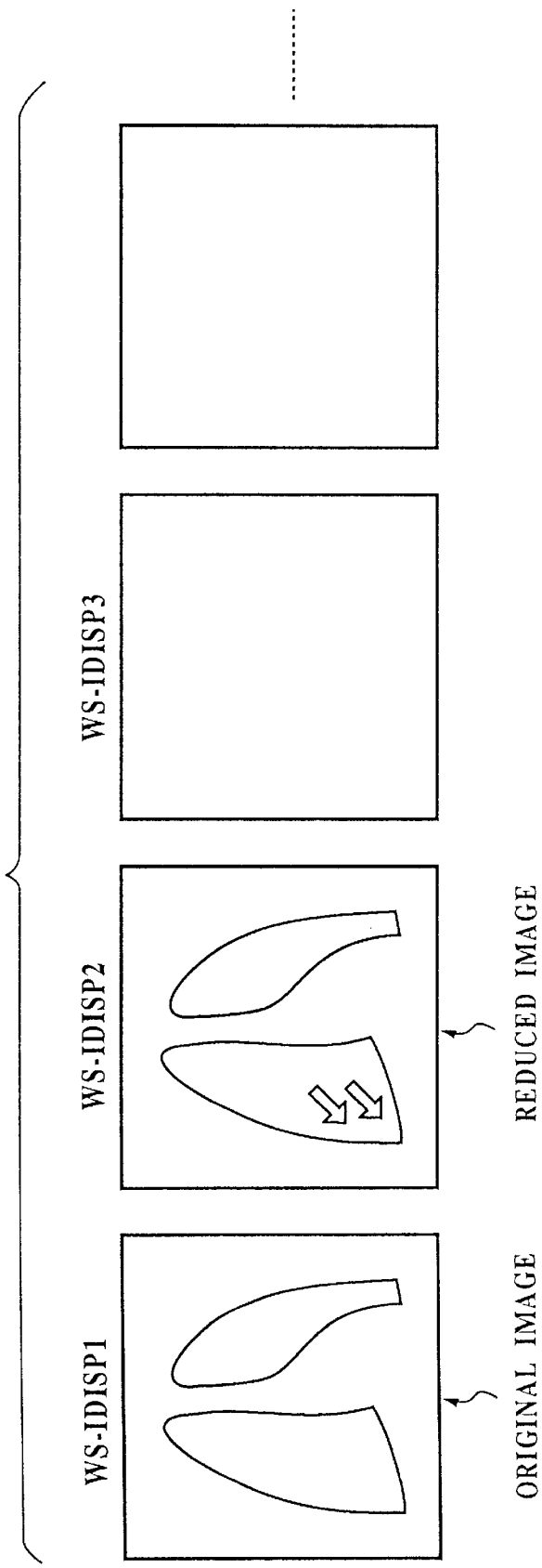

MEDICAL INFORMATION PROCESSING SYSTEM FOR SUPPORTING DIAGNOSIS

This application is a Continuation of application Ser. No. 08/202,744, filed on Feb. 28, 1994, now abandoned.

BACKGROUND OF THE INVENTION

1. Technical Field

The present invention relates to a medical information processing system for comparing a plurality of diagnostic information including doctors' findings and results of computerized analysis of images and other examination data and thus supporting doctors in evaluating examination more efficiently.

2. Background Art

Generally, an image diagnosis in medical institutes will be carried out according to the following procedures:

(1) An examination requesting department (for example, the Department of Internal Medicine) requests the Department of Radiology to carry out an image examination for a patient (for example, X-rays, CT, MRI or the like). This request is performed by issuing an examination request sheet in which the following items are written:

The items of the examination request sheet contain: a patient ID number, a patient name, a date of birth, a sex, a name of examination requesting department, a name of examination requesting doctor, an examination modality (an X-ray machine, an X-ray computed tomography machine, a magnetic resonance imaging machine etc.), a region to be examined, a procedure of examination, a purpose of examination, clinical information and the like;

(2) An examination engineer of the Department of Radiology makes an examination (an image acquisition) of a patient according to contents of the examination request sheet to develop it on a film;

(3) An interpreting doctor interprets the developed films. At this time, it is often material to refer to the past examination results (the past image) of the patient to obtain higher interpreting quality. When the interpreting doctor has completed the image, he/she will prepare an interpretation report. The following items will be described in this interpretation report:

These items include a finding from interpretation, a conclusion, a name of the interpreting doctor, a date of the interpretation, and the like; and (4) This interpretation report is returned to the examination requesting doctor to finish image diagnostic operations.

By the way, as a digital image has a characteristic that it simplifies a computerized image processing, this feature facilitates attempts of analyzing digital images using a computer to detect patient abnormalities. This has born fruits. The technology is called a Computer-Aided Diagnosis (CAD), which is expected to further improve accuracy in the image diagnosis and reduce a load to the interpreting doctor and the doctor in charge of the patient.

A great number of literatures are described concerning an algorithm for detecting patient abnormalities in this computer-aided diagnosis. For instance, the following literatures are to be referred to:

(1) Katsuragawa, S. et al: Image Feature Analysis and Computer-Aided Disgnosis in Digital Radiography: Classification of Normal and Abnormal Lungs with Interstitial Disease in Chest Images. Medical Physics 16.38–44(1989).

(2) Giger, M. L. et al: Image Feature Analysis and Computer-Aided Disgnosis in Digital Radiography: 3. Automated Detection of Nodules in Peripheral Lung Fields. Medical Physics 15.158–166 (1988).

(3) Chan, H. P. et al: Image Feature Analysis and Computer-Aided Diagnosis in Digital Radiography: 1. Automated Detection of Microcalcifications in Mammography. Medical Physics 14.538–548 (1987).

(4) Doi, K. et al: Possibility of Computer-aided Diagnosis in Digital Radiography. Nippon Acta Radiologica 1989; 45(5): 653–663.

(5) Obatake, H., Kubo, J., Okada, M.: Pneumoconiosis Shadow Abstraction in X-ray Radiography by Equidensity Ray Processing and Applications to Automatic Diagnosis. Electronic Intelligence and Communication Academic Paper; D-Vol.J76-D-No.2 pp.261–267, February, 1993.

(6) Shimizu, A., Hasegawa, J., Toriwaki, J.: Minimum Orientation Differential Filter for Detecting Massive Shadow in Chest X-ray Image and its Nature. Electronic Intelligence and Communication. Academic Paper; D-Vol.J76-D-No.2 pp.241–249, February, 1993.

(7) Matsumoto, K., Kin, K., Obata, H.: Growth Shadow Detection in DR Image—Iris Filter; Electronic Intelligence and Communication Academic Paper; D-Vol.J75-D-No.3 pp.663–670, March, 1992.

(8) Suzuku, H., Inaoka, N., Takahana, H., Morimasa, M., Sasaoka, S., Natori, H., Suzuku, A.: Lung Growth Automatic Detecting System in Chest X-ray Direct Radiographing Image—Diagnosis Support for Lung Cancer.

The description concerning a device implementing technologies for detecting abnormalities has been disclosed in the following official gazettes: Japanese Patent Laid-Open No. 2-185240, Japanese Patent Laid-Open No. 2-152443, and Japanese Patent Laid-Open No. 1-125675.

Each of the devices for detecting abnormalities which are disclosed in these literatures is common in that a certain type of abnormality is automatically detected from images for digital medical purposes by using computing means and that this detected abnormality is superposed on such images to display it. FIG. 1 shows a display embodiment in which this detected abnormality changes itself in its shape according to its type and is superposed on such images to display it.

Furthermore, with the progress of digitized imaging, a Picture Archiving Communication System (hereinafter, PACS) has been used to realize a smoothness in this image diagnosis business and space-saving for keeping data. The PACS stores, communicates, and displays medical images (X-ray images, CT images, MR images, or the like) produced in the medical institutes, thus contributing to assist doctors in the business of observing the medical images. Therefore, the PACS stores image data sent from various modalities in a database and transfers requested image data from a database in reply to a demand made from an image workstation located in each consultation room etc., and the image workstation displays such image on its Cathode Ray Tube (hereinafter, CRT) etc. An interpretation report can be prepared on the image workstation in the PACS and stored therein.

This PACS arranges and stores films in a storing rack. It becomes unnecessary to search objective films from the storing rack, carry films, hook or unhook films on a film viewer, or the like, thereby participating in the benefits of the system unusing films. This PACS has been disclosed in many literatures: Japanese Patent Laid-Open No. 62-121576, Japanese Patent Laid-Open No. 63-10269, Japanese Patent Laid-Open No. 64-13837, Japanese Patent Laid-Open No. 64-17154, Japanese Patent Laid-Open No. 2-103668, Japanese Patent Laid-Open No. 2-119840 etc.

For example, Japanese Patent Laid-Open No. 2-185240 has disclosed the PACS having IA (a function of inputting images), WS-ANA (a function of abstracting the feature amount by analyzing images), and WS-OUT (a function of displaying images and overlays), as shown in a function block of FIG. 11.

A series of operations from an input of image to an output of analyzed results is carried out in the following procedures:

(1) A doctor inputs digital images (hereinafter referred to as an "original image") of a specific chest X-ray radiography by the IA.

(2) A Computer-Aided Diagnosis processing (CAD processing) is performed for the original image by the WS-ANA. The original image is fractionated so that, for example, about 1 to 2 minute region(s) having 6.4 mm square exists among respective ribs. The original image is computer-analyzed to output the feature amount each region corresponding to a shadow scope of each region. Presence or absence of abnormalities of a pulmonary interstitial disease or its progressing degree is examined and a type of abnormalities is classified based on the feature amount in each region. For example, presence or absence of abnormalities is decided corresponding to a magnitude of the feature amount. Furthermore, the classification is carried out corresponding to comparative results of the feature amount with a plurality of threshold values set previously. The progressing degree is computed corresponding to the degree of difference between the feature amount and the feature value of the threshold value.

(3) According to a doctor's request, the PACS displays in a condition that CAD processing results are superposed on the original image. As shown in FIG. 12, a shape of marker is changed corresponding to a type of abnormalities and a magnitude of marker is changed corresponding to the progressing degree to display CAD processing results which are superposed on images. Herein, markers are distinguished as follows: a marker "square" is a reticular type; a marker "hexagon" is a honeycomb type; and a marker "circle" is a nodular type.

As described above, as a marker of the CAD processing results is superposed on the original image to display them, the image of a marker portion is interfered with the marker and is not seen behind it. Then, since it was necessary that a doctor switched a display mode alternatively or frequently into a mode displaying only the original image and a mode displaying by superposing a marker of the CAD processing results on the original image to advance interpreting operations, not only was it extremely troublesome, but also the interpreting time was prolonged and efficiency in the interpreting operations was reduced. These were drawbacks.

At present, various medical group examinations are made in Japan, including therein examinations accompanying a medical image diagnosis (one of medical examination data) such as a chest X-ray examination, a stomach X-ray radiography examination, or the like. When a lung cancer examination is picked up as an example, a flow of business from an examination to a report of results is carried out in the following procedures:

Step 1) Decide a date of a medical examination and notify a person to be examined of the date.

Step 2) Make an oral examination. Information such as a previous illness of the examined person, late conditions of the illness, a smoker or a non-smoker, a degree of smoking, or the like is available in the oral examination.

Step 3) Perform a chest X-ray radiography. In many cases, the radiography is performed in a car for a medical examination.

Step 4) Interpret a chest X-ray image. The interpretation of an image is carried out by two or more doctors. If they recognize a doubtful abnormal finding, they judge that a close examination for the person is required.

Step 5) Notify the examined person of the results.

In this connection, the examination of sputum is also made in the lung cancer examination, however its description is omitted here. There are a plurality of types of examination in said Step 4, and for example, when two doctors carries out the interpretation of an image, the following types of examination are typical:

(a) Two doctors independently interpret an image in separate places (refer to FIG. 36A).

(b) Two doctors simultaneously interpret the same image (refer to FIG. 36B).

In the both types (a) and (b), if one of two doctors indicates a doubtful abnormality, he/she judges that the examined person of the image is required to make a close examination.

There are two methods of executing such medical group examination, namely a case where a local self-government body or a public health center carries out Steps 1 to 5 and a case where a company to which a person to be examined belongs carries out Steps 1, 5 and a specific medical institute or a technical company for a medical examination carries out Steps 2 to 4. The place in which the procedures of Steps 2 to 4 are carried out is called a center. The center has a film storage for keeping examination films of each year and a data storage for keeping data such as doctors' interpretation results, oral information obtained by examining the person, and the like. As for the chest X-ray radiography, the center prepares a chest X-ray radiography car and a radiologist on a reqested date for the radiography, and the center requests a doctor of the other medical institute to interpret an image to be examined. Further, the center delivers a doctor images and printed forms for interpretation findings and comes to receive the images and the printed forms into which the interpretation findings are filled after completing interpretation of the images. According to the interpretation results, the images are classified into ones requiring a close examination and ones being normal, and then the center sends the ordered company information such as classification results, doctor's interpretation results concerning a person requiring a close examination, examination images, oral examinations, or the like (carry out said Step 5).

A doctor who is requested to interpret an image on a lung cancer examination works overtime after the normal business hours, and a time for interpreting an image is limited. Furthermore, it takes a few minutes per sheet of image to interpret an image in the normal business, while as the number of sheets of image which is requested to interpret expands to several hundred sheets at one time, it takes about 10 seconds per sheet of image to interpret an image and it is considerably short. Furthermore, a chest X-ray radiograph to be interpreted in the normal business is imaged in a direct radiography and its image has a size of 14 inches×14 inches (about 35 cm) or more and excellent image quality, while an image for a lung cancer examination is imaged in a mirror indirect radiography, and has a small size of 10 cm×10 cm with a roll film and inferior image quality. Accordingly, although the medical group examination is a job having an object of discovering a lung cancer in an earlier stage, it is pointed out that a lung cancer in an earlier stage is often overlooked.

At present, it takes a week until the center delivers an interpretation material to a first doctor after the medical examination and it also takes a week until the center receives interpretation results after the delivery to the doctor, and namely it takes two weeks by two doctors. As it takes a week until the center reports the results to the examined person after the receipt of the results obtained by two doctors, and namely it takes a month until the examined person receives the results after the medical examination. Furthermore, the person is then made a close examination to be diagnosed as a tumor and judged as a malignancy or a benignancy so that, an operation or an appropriate medical treatment shall be performed. Accordingly, it is ordinary that a considerable time further passes after the medical examination. On the other hand, since a cancer (malign tumor) grows fairly faster and the more a cancer is discovered in the early stage, the more the person is convalescing satisfactorily, it is desired to shorten a period from a medical examination to an operation or a commencement of a medical treatment. Also, it is the present conditions that a digital image system for a medical group examination has not been constructed.

By the way, since a digital image has a feature that it is easy to perform an image processing by a computer unlike an analog image such as radiographic films etc., this digital image is analyzed by a computer to detect abnormalities and fruits are obtained in this operations. This technique is, as have been described, called a Computer-Aided Diagnosis (hereinafter referred to as "CAD") and it is expected to enhance accuracy in an image diagnosis and to diminish a load to doctors.

As described above, it is pointed out that a doctor often overlooks abnormalities in interpreting an examination image of a medical group examination. It is considered to interpret it by making use of the CAD. However, when an interpreting doctor makes use of the CAD in the conventional practice, whenever the interpreting doctor interprets just a sheet of image, diagnostic results of the doctor and the results of the CAD processing are displayed parallel and the interpreting doctor himself/herself successively compares the two results, and when the results are inconsistent by the doctor's overlooks of abnormalities or over-interpretations, it is necessary for the doctor to interpret the image again to carry out operations such as a correction of the diagnostic results or the like and consequently the work amount of the interpreting doctor increases and a time needed for the interpretation also increases. Furthermore, in a method of interpreting examination images in a medical group examination by an interpreting doctor, he/she interprets continuously all examination images at one time. A CAD using system realizing this interpreting method has not yet been known. Some people demands that it is convenient to realize such CAD using system. Furthermore, even in such CAD using system, when an interpreting doctor interprets images once more after he/she compares CAD processing results with interpreting results, the images to re-interpreted are different in the doctor's personal way of thinking. For example, an interpreting doctor A desires to interpret once more all images concerning overlooks, and an interpreting doctor B desires to interpret once more all images having a contradiction between its own diagnostic results and the CAD processing results, and an interpreting doctor C also desires to confirm a type indicated as an abnormality and a discrepancy of its position, and the like. When realizing the CAD using system, it is necessary to flexibly cope with the each interpreting doctor's way of thinking in conformity with it.

Furthermore, from a viewpoint of personal likings of interpreting doctors, their requirements are different in referring to the CAD processing results under a certain situation and timing at interpreting examination images. For example, the doctor basically desires to interpret the images collectively and comes to desire to sometimes refer to the CAD processing results even during the interpretation of the images, and the like. At this time, some people demands that the CAD using system should have means capable of referring to the CAD processing results whenever the doctor desires to refer to them.

Furthermore, the center requests a plurality of doctors to interpret the examination images. Then, persons to be required a close examination are listed up by comparing the interpretation results obtained by the plurality of doctors, and the images of the specified persons are sent from the film storage and the data such as the doctor's interpretation results, information at oral examinations, or the like are retrieved and sent from the data storage. Furthermore, the examination results of persons who are not required a close examination must be sent to them. As the enormous work amount is entirely carried out by manpower, the work is troublesome. That is, since, in the stage from the entire examination of the medical group examination to the resultant outputs, there are several works with a great deal of work amount such as the two doctors' interpretation, its interpretation results, or the like, a period from the medical examination to the output of examination results is prolonged. Accordingly, some people demands that this part is worth using the CAD using system.

SUMMARY OF THE INVENTION

In view of the foregoing drawbacks, it is therefore an object of the present invention to provide a medical information processing system for supporting diagnosis, capable of displaying an original image and a CAD-processed result without being interfered therebetween.

Another object of the present invention is to provide a medical information processing system capable of achieving a continuous and rapid interpretation for entire examination images in a mass survey so that work amount and time spent for interpretation by medical doctors are significantly reduced.

Still another object of the present invention is to provide a medical information processing system in which patients having high probability of abnormality or normality are extracted by a CAD processing in the mass survey.

Still another object of the present invention is to provide a medical information processing system capable of preparing previous images and typical disease images to be referred to for interpretation, without involving an operator.

Still another object of the present invention is to provide to further optimize efficiency in forming interpretation report by using PACS.

According to one aspect of the present invention, there is provided a medical information processing system comprising: detecting means for detecting location of abnormality from a first medical image in accordance with a predetermined algorithm; image forming means for forming a second medical image in which a marker indicating the location of the abnormality is overlapped; and display means for displaying the first medical image and the second medical image, wherein the display means include minification means by which a size of the second medical image is minified, and both the minified second image and the first medical image are displayed simultaneously in a single image frame.

According to another aspect of the present invention there is provided a system comprising: diagnosis result obtaining means for obtaining a first diagnosis result from a medical image, by detecting at least one of location and type of abnormality according to a predetermined algorithm; externally inputting means for externally inputting a second diagnosis result containing data on at least one of the location and type of the abnormality; and comparison means for comparing at least one of the location and type of the abnormality confirmed from the first diagnosis result and at least one of the location and type of the abnormality confirmed from the second diagnosis result.

According to still another aspect of the present invention there is provided a system comprising: first diagnosis acquiring means for obtaining first diagnosis results by detecting abnormality in a plurality of medical images, in accordance with a predetermined algorithm; externally inputting means for externally inputting second diagnosis results for the plurality of medical images; comparison means by which the first diagnosis results and the second diagnosis results are compared, and the plurality of the medical images are classified into plural categories based on resultant comparison between the first and the second diagnosis results; and output means for outputting a medical image corresponding to at least one of a predetermined category and identifying data thereof among the plurality of medical images.

According to still another aspect of the present invention, there is provided a system comprising: storage means for storing a plurality of medical images; input means for inputting an examination medical image to be examined; abnormality detection means for detecting a type of abnormality in the examination medical image; selection means for selecting the medical image whose type of abnormality is same with the examination medical image; and display means for displaying simultaneously the medical image selected by the selection means, and the examination medical image.

According to still another aspect of the present invention, there is provided a system comprising: input means for inputting an image; detection means for detecting a type and location of abnormality existent in the image; memory means for storing the type and location of abnormality in a fixed sentence form so as to be expressed into a predetermined sentence structure; and generating means for generating a sentence including at least one of the type and the location of abnormality detected by the detection means, in accordance with the fixed sentence form.

BRIEF DESCRIPTION OF THE DRAWINGS

These and other objects, features and advantages of the present invention will become more apparent from the following description of the preferred embodiment taken in conjunction with the accompanying drawings, in which:

FIG. 18 is a table listing information including patient identifying number, accompanied data thereto and data structure.

FIG. 22 shows relationship between a display color and a bit value of each pixel.

FIG. 23 is a table showing types of directory data.

FIGS. 26 through 29 are tables showing abnormality data.

FIG. 30 is a table showing remarks (findings) data.

FIG. 31 is a table showing overlay display information created by image display manager (WS-IDM), indicating a doctor's remark (finding).

FIG. 32 is a table showing overlay display information, indicating a CAD-processed result.

FIG. 33 is a table showing a part of results, by doctor and CAD, compared and classified by control unit (WS-CTRL).

FIG. 38 is a table showing types of data included in the examination request information.

FIG. 40 is a table showing the abnormality detecting means selecting data.

FIG. 41 is a table showing relation between the imaging direction of image obtained from the chest plain X-ray image and the relative display position.

FIG. 42 is a table showing a reading (interpreting) doctor's data.

FIG. 43 is a table showing position data of the normal dissection structure.

FIG. 49 shows data representing a position (location) of abnormality.

FIG. 50 is a table showing the abnormality data.

FIG. 51 is a table showing overlay display information whereby the position (location) of abnormality is shown.

FIG. 52 is a table showing the data attached to the image.

FIGS. 62A–107 show the fifth and sixth embodiments.

FIGS. 62A and 62B are flowcharts and configurations for explaining the gist of the fifth embodiment in the broadest sense.

FIG. 64 is tree-type chart showing relationship between the patient ID number, examination ID number and the examination data ID number.

FIGS. 65A and 65B illustrates a case where the examination data ID number is searched from the examined patient ID number.

FIGS. 66A and 66B illustrates a case where the examined patient ID number is searched from the examination data ID.

FIGS. 67 through 69 show abnormality data tables with various judgment values set according to the first variation of the fifth embodiment.

FIGS. 70 through 79 show abnormality data tables in the images of the examination ID numbers 920002 to 920010.

FIG. 80 shows the classified results of the images of the examination ID numbers 920001 to 020010.

FIGS. 81, 82, 83 show the created lists A, B, C, respectively.

FIG. 84 shows a abnormality data table.

FIG. 85 shows the classified result of the images of the examination ID numbers 930001 to 930010.

FIGS. 86, 87, 88 are created lists A, B, C, respectively.

FIG. 89 is a table showing a process for calculating abnormality values in the lung nodule of an image whose examination ID number is 940001.

FIG. 90 is a table showing a process for calculating abnormality values in the interstitial lung disease of an image whose examination ID number is 940001.

FIG. 91 is a table showing abnormality data of the image whose examination ID number is 940001.

FIG. 92 is a table showing the classified result of the images of the examination ID numbers 940001 through 940010.

FIGS. 93, 94, 95 are created lists A, B, C, respectively, where the classified results falling under case A, case B and case C are respectively registered in list A, list B and list C.

FIG. 96 is an abnormality data table for the image whose examination ID number is 920001.

FIG. 97 is a table showing the classified results of the images of examination ID numbers 920001 through 920030, according to embodiment no. 6-1.

FIGS. 98, 99, 100 are the created lists A, B, C, respectively, where the second classified results falling under case A, case B and case C are respectively registered in list A, list B and list C.

FIG. 101 is the abnormality detailed data table concerning the image of the examination ID number 920002.

FIG. 102 is a finding data table for the image of the examination ID number 920002.

FIG. 103 shows overlay display data for the doctor's reading.

FIG. 104 shows overlay display data for the CAD-processed result, concerning the examination ID number 920002.

FIG. 105 is a list showing the abnormality detection result.

FIG. 106 is a table showing the results where the doctor's interpretation results and the CAD-processed results are compared and classified.

FIG. 107 illustrates the classification obtained from the comparison result, expressed in a set (in a type of Venn diagram).

FIG. 119 is a display image plane indicating a case where the next examination is to be conducted.

FIG. 120 is a table showing an example of the examination request information, according to embodiment no. 7-1.

FIG. 121 is a table showing an example of the annexed information.

FIG. 122 is a table showing an example of the interpretation report.

FIGS. 123–128 show various reference order rules.

FIG. 129 is a table showing an example of the abnormality data.

FIG. 130 is a table showing an example of he examination histories.

FIG. 131 is a table showing an embodiment of the annexed information.

FIG. 132 is a table showing an embodiment of the examination request information.

FIG. 133 is a table showing an embodiment of the annexed information.

FIG. 134 is a table showing an embodiment of the renewed examination histories.

FIG. 135 is a table showing an embodiment of the renewed abnormality data.

FIG. 136 is a table where the first and second priority orders of the reference priority order information are written in this order.

FIGS. 137A and 137B are tables showing an embodiment of the annexed information of the typical disease example image having the identical type of abnormality (interstitial lung disease) to the uninterpreted image.

FIG. 138 is a table showing an embodiment of created reference priority order information.

FIG. 139 is a table showing an example in the case where a type of abnormality is interstitial lung disease.

FIG. 140 is a table showing an example in the case where the type of abnormality is lung nodule.

FIG. 142 is a table showing an example of the typical sentences, according to the eighth embodiment.

FIG. 143 is a table showing an example of the overlay display information.

FIG. 144 is a table showing an embodiment of the overlay display information.

FIG. 145 is a table showing an interpretation report made based on the overlay display information of FIG. 144.

FIG. 146 is a table showing a new interpretation report.

FIG. 147 is a table showing another new interpretation report to which paragraph "expanding to a wide scope" is added.

FIG. 148 illustrates construction of workstation according to the eighth embodiment.

FIG. 149 illustrates a moving pitch of a cursor displayed on the image plane.

FIG. 150 shows a figure made in the overlay data forming portion.

FIG. 151 illustrates an example of the display screen where a type of arrow in a solid line is used.

Figure 152:
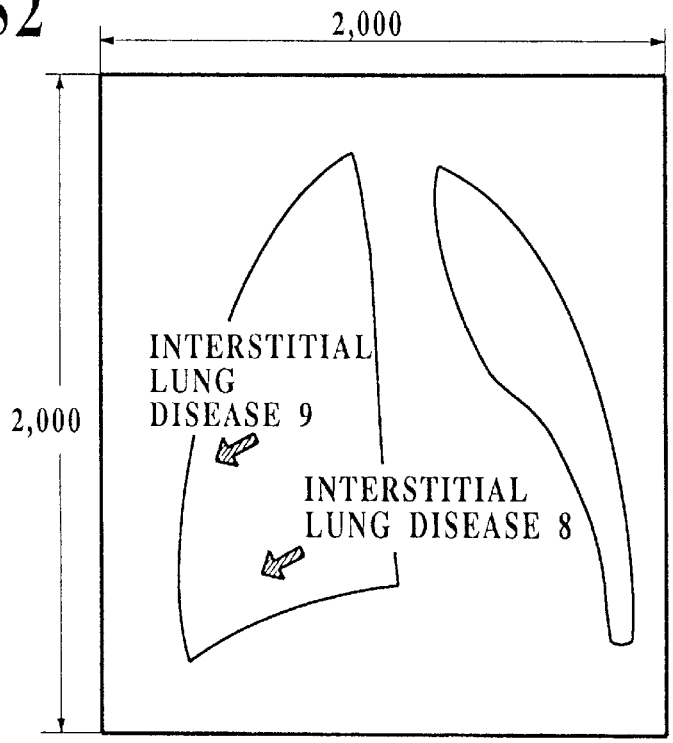

FIG. 152 another example of the display screen where other type such as an arrow in a dotted line can be selectively added thereto.

FIG. 153 shows an example where the minified image is displayed in an image display unit different from another image display unit displaying the original image thereon, according to the first embodiment.

DETAILED DESCRIPTION OF PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

Embodiment No. 1

Figure 1:
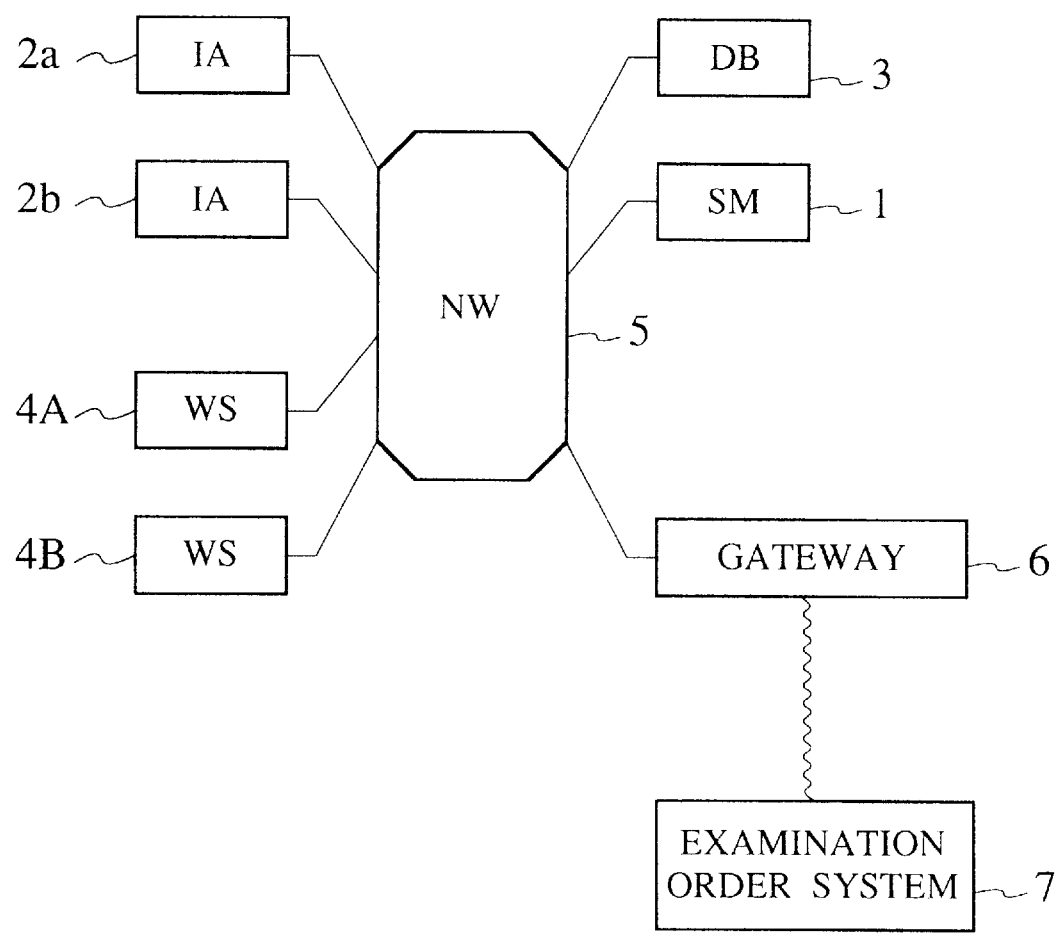
FIG. 1 is a block diagram showing the entire configuration of PACS.

Hereinafter, a first embodiment according to the present invention will be described with reference to the accompanying drawings. FIG. 1 is a block diagram showing the entire configuration of a Picture Archiving Communication System (hereinafter referred to as "PACS") containing a medical information processing system according to this embodiment.

A network 5 serves as transmission paths for commands and data communicated among components. Optical fibers are used as transmission media. The network 5 is herein formed as a ring local area network. Of course, a star or other networks will also do.

The network 5 is connected with a system manager (SM) 1, image acquisition apparatuses (IA) 2a, 2b, a database (DB) 3 for storing medical images acquired by the image acqusition apparatuses 2a, 2b, and workstations (WS) 4A, 4B, and this system can respectively be communicated each other with a communication protocol.

Furthermore, this network 5 is connected with an examination order system 7 through a gateway 6. This examination order system 7 is located in a room of an examination request; department and indicates the request of image examination by preparing examination request information. This examination request information contains respective items such as a patient ID number, a patient name, a date of birth, a sex, an examination requesting department, a name of examination requesting doctor, an examination modality (an X-ray machine, an X-ray computered tomography machine, a magnetic resonance imaging machine, or the like), a region to be examined, a procedure of examination, a purpose of examination, a clinical information, and the like. The information of each item is manually inputted into the examination order system 7 by the examination requesting doctor.

TABLE 1

| | |
|---|---|
| Patient info | Patient ID number |
| | Patient name |
| | Date of birth of patient |
| | Sex of patient |
| Exam. info | Modality |
| | Region to be examined |
| | Procedure of examination |
| | Name of examination requesting department |
| | Name of examination requesting doctor |
| | Date of examination request |
| | Desired date of examination |
| | Desired time of examination |
| | Purpose of examination |
| | Examination ID |
| | Clinical information of patient |
| | Disclosed name of disease |
| | . |
| | . |
| | . |

This examination request information is transferred 35 to the system manager 1 after required items have been finished inputting and appropriate image acquisition apparatuses 2a, 2b are selected therein in accordance with this requesting contents to transfer the information again from the system manager 1 to such selected image acquisition apparatuses 2a, 2b.

The image acquisition apparatuses 2a, 2b are apparatuses for aquiring a medical image (hereinafter referred simplly to as "image") such as an X-ray machine, an X-ray computed tomography machine, a magnetic resonance imaging machine, a film digitizer, or the like. Additional information as shown in Table 2 is attached to this image, which is transferred to the database 3 to be stored therein.

TABLE 2

|  |  |
| --- | --- |
|  | Examination ID |
|  | Date of Examination |
|  | Number of Sheet of Images |
| First Sheet | Image number |
| of Image | Lateral length of pixel |
| Information | Longitudinal length of pixel |
|  | Lateral size of matrix |
|  | Longitudinal size of matrix |
|  | Pixel bit length of image |
|  | Data amount |
|  | Imaging Diredtion |
| Second Sheet |  |
| of Image |  |
| Information |  |

As shown in Table 2, the additional information or data is prepared per examination unit, including an examination ID, a date of examination, and the information of each image acquired by such examination. Furthermore, the information of image includes an image number, an image size, a data amount, and an imaging direction.

After the image acqusition has been completed, the system manager 1 creates an examination history from the examination request information (data) and the additional information (data). Furthermore, an interpreting doctor prepares an interpretation report of the image and manually inputs it by using the image acqusition apparatuses 2a, 2b. (Terms interpreting doctor, reading doctor and radiologist are interchangeably used throughout this application.) One example of the examination histories will be hereinafter described.

TABLE 3

|  |  |
| --- | --- |
| Patient | Patient ID number |
| Info | Patient name |
|  | Patient name |
|  | Date of birth of patient |
|  | Sex of patient |
| First Exam. | Examination ID number |
| Information | Modality |
|  | Region to be examined |
|  | Procedure of examination |
|  | Name of exam. requesting department |
|  | Name of examination requesting doctor |
|  | Date of examination |
|  | Number of sheet of image |
| Second Exam. |  |
| Information |  |

One example of the interpretation report will be hereinafter described.

(To be continued)

TABLE 4

|  |  |
| --- | --- |
| Information | Patient ID number |
| on Patient | Name of patient |
|  | Date of birth of patient |
|  | Sex of patient |
| Information | Examination ID number |
| on Exam. | Modality |

TABLE 4-continued

|  |  |
| --- | --- |
|  | Region to be examined |
|  | Procedure of examination |
|  | Name of exam. requesting department |
|  | Name of examination requesting doctor |
|  | Date of examination |
|  | Name of interpreting doctor |
| Findings | Finding 1 |
|  | Finding 2 |
|  | . |
|  | . |
|  | . |
|  | Finding N |
|  | Conclusion |

Terms finding and remark are interchangeably used in this patent application.

These examination histories and interpretation report are transferred to an image storage 4f described below to be stored therein.

The medical computer-aided diagnosis system according to the present invention is incorporated into the workstations 4A, 4B in this PACS. The workstations 4A, 4B will be hereinafter explained.

The workstations 4A, 4B are provided with the following functions:

(1) A function of displaying examination request information (data), examination histories, an image, an interpretation (reading) report, and the like;

(2) A function of deciding presence or absence of abnormalities of image data by a Computer-Aided Diagnosis (CAD), searching its progressing degree, and classifying its type of abnormalities;

(3) A function of storing CAD processing results;

(4) A function of displaying CAD processing results;

(5) A function of inputting findings on the image; and (6) Other standard function of the workstation.

Figure 2:
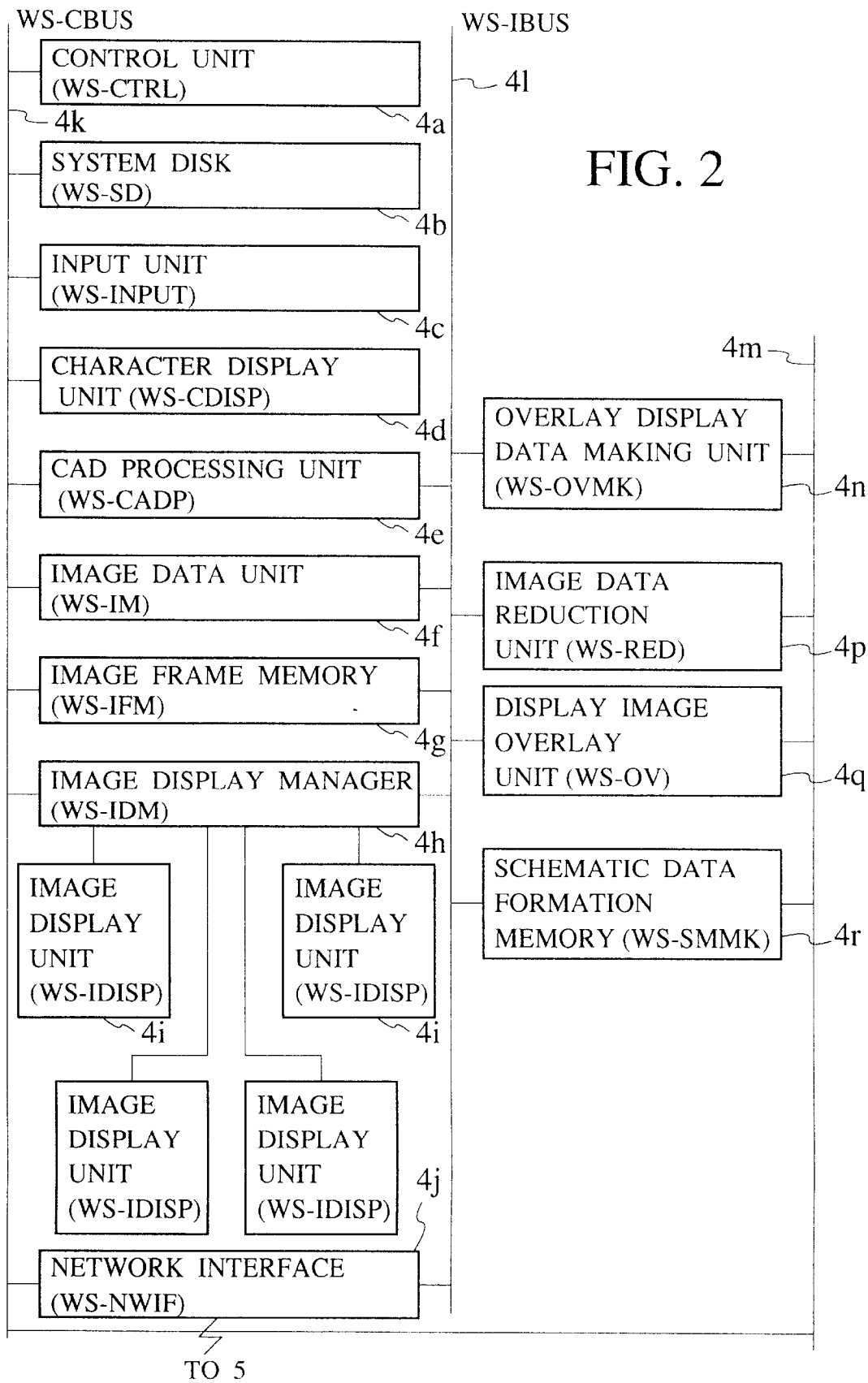
FIG. 2 is a block diagram showing construction of the workstation shown in FIG. 1.

In order to accomplish the above-mentioned respective functions, the workstations 4A, 4B are constituted as shown in FIG. 2.

Each device described below is connected with control buses (WS-CBUS) 4k, 4m and an image bus (WS-IBUS) 4l. These control buses 4k, 4m or the image bus 4l are(is) connected with the network 5 through a network interface 4j.

<Control (WS--CTRL)>

A control 4a contains a central processing unit (CPU) or a system memory (for example, a semiconductor memory device), and controls the operations of the entire workstation and also executes various oparating processes.

<System Disk (WS-SD)>

A system disk 4b is, for example, a magnetic disk, and stores programs or data described below and also reads out these programs or data when an electric power is switched on to supply them to a system memory within the control 4a.

Stored in the system disk are the program (OS) and abnormality detection means selecting data for operating in relation to each part constituting the workstation.

Herein, the abnormality detecting means denotes an algorithm capable of detecting a specified abnormality, and is stored in a CAD processor 4e. As for a typical device of the abnormality detecting means, there are three species of abnormality detecting means capable of detecting a pulmonary interstitial disease, abnormality detecting means capable of detecting pulmonary nodules, and abnormality detecting means capable of detecting a fine calcification of a breast. The abnormality detection means selecting data is a table of a type of image (an examined region, a modality, a procedure of examination, an imaging direction) corresponding to a type of abnormalities. The type of abnormalities capable of detecting corresponding to the type of images is determined. The above correspondence is based on it.

One example of the abnormality detection means select information is shown below.

TABLE 5

| Examined Region | Modality | Examination Procedure | Imaging Direction | Types of Detectable Abnomality |
|---|---|---|---|---|
| Chest | X-ray | Plain Radiography | P → A | Interstitial Lung Disease |
| Chest | X-ray | Plain Radiography | P → A | Lung Nodules |
| Breast (Mamma) | X-ray | Plain Radiography | (not specified) | Micro-Calcification |

This abnormality detection means selecting information is used when selecting the abnormality detecting means capable of analizing such image at diagnosing images by the CAD processor 4e. Of course, this abnormality detection means selecting data can be rewritten (renewed) and added thereto.

<Input Unit (WS-INPUT)>

An input unit 4c is means for inputting various commands such as an image retrieval or the like by a doctor and also manually inputting finding data after he/she observes the image, and for example, a keyboard or a mouse is used. Herein, the finding data consists of a type of abnormality, its position (XY-coordinates of an image matrix), a degree of abnormality, or the like. Incidentally, these finding data are summarized in a finding data table for each type of abnormality. This finding data table is identical to the abnormality data table which is outputted as a result of diagnosis in the below-mentioned CAD processor 4e in items of its contents.

Herein, one example of a procedure for inputting the finding data will simply be described. First, a cursor is doubly displayed on the original image corresponding to movements of a mouse. The cursor is put upon the image showing abnormalities by moving the mouse. When a left button of the mouse is clicked, the position is recognized. Incidentally, when the input position is erroneous, the system acknowledges that such input position has not been inputted by clicking an inside button of the mouse. It is fairly favorable in operating the system that a move pitch of the cursor is set as about 32 pixels when an image matrix is 2,048×2,048 pixels. The system synchronizes with the click of the left button of the mouse to display a message, for example, "input the type of abnormality" on the screen. By inputting from keys on a keyboard in reply to this message, input the type of abnormality such as "pulmonary interstitial disease" or the like. The system synchronizes with this input completion to display a message, for example, "input the degree of abnormality" on the screen. By inputting from keys on a keyboard in reply to this message, input the degree of abnormality, for example, as a level of 1 to 10 (10 is such a condition that abnormality makes the worst). The position, type, and degree of abnormality are summarized in the finding data table together with a reference number, an examination ID number, and an image number, and such information is transferred to the image storage 4f described below and stored therein.

<Character Display (WS-CDISP)>

A character display 4d is a device for displaying mainly characters such as interpretation (reading) reports etc., and for example, a CRT (Cathode Ray Tube) display, a liquid crystal panel display, or the like is used.

<CAD Processor (WS-CADP)>

A CAD processor 4e is provided with a function of a Computer-Aided Diagnosis, receives an instruction of activation from the control 4a, performs the CAD processing (diagnosis processing) on inputted images by this function, and creates the abnormality data table finally. Hereinafter, one example of the abnormality data table will be shown.

TABLE 6

| Reference number |
| Examination ID number |
| Image number |
| Type of abnormality |
| Central position of abnormality on image |
| (lateral coordinate, longitudinal coordinate) |
| Degree: of abnormality |

As shown in Table 6, the abnormality data table consists of respective items of a reference number, an examination ID number, a type of abnormality, a central position of abnormality on an image, and a degree of abnormality.

The CAD processor 4e contains the plural species of abnormality detecting means as described above. That is, as a typical embodiment, there are provided: (a) means for detecting a shadow of a pulmonary interstitial disease in a front side image of a chest plain X-ray image; (b) means for detecting a shadow of a pulmonary nodules in a front side image of a chest plain X-ray image; and (c) means for detecting a shadow of a fine calcification of a breast in a breast X-ray image.

Incidentally, algorithms of detecting abnormalities in each abnormality detecting means are detailed in respective literatures of Japanese Patent Application Laid-Open No. 2-185240, Japanese Patent Application Laid-Open No. 2-250180, Japanese Patent Application Laid-Open No. 2-152443, Japanese Patent Application Laid-Open No. 2-125675, and the like. The detailed description therefor is omitted.

A digital image (hereinafter referred to as an "original image") is transferred from the database 3 to the CAD processor 4e. Furthermore, under an instruction of the control 4a, information of the type of abnormality corresponding to such original image of the abnormality detection means selecting data of the system disk 4b is transferred. Any abnormality detecting means is selected corresponding to the type of this abnormality. The original image is analyzed by the selected abnormality detecting means. If there is an abnormality, the central position on an image of this abnormality (XY-coordinates of an image matrix) and the degree of the abnormality are acquired. The above-mentioned abnormality data table containing these position and degree of abnormality is created by the CAD processor 4e. The abnormality data table is transferred to the below-mentioned image storage 4f and stored therein.

<Image Storage (WS-IM)>

An image storage 4f is, for example, a magnetic disk, and a device for temporarily storing examination request information derived from the examination order system 7, examination histories, an interpretation (reading) report, additional information to image, original image data, overlay display information (image data showing abnormalities), an abnormality data table, and a finding data table.

<Image Frame Memory (WS-IFM)>

An image frame memory 4g is, for example, a semiconductor memory and a device for temporarily storing at least a sheet of original image to be interpreted which is transferred from the database 3.

<Image Display (WS-IDISP)>

An image display 4i is, for example, a color CRT display and a plurality of image displays, herein four image displays, are prepared. This image display 4i is a device for displaying mainly an image.

It shall be appreciated that respective image display units may present different resolutions and so on.

<Image Data Reduction Unit (WS-RED)>

Figure 4A:
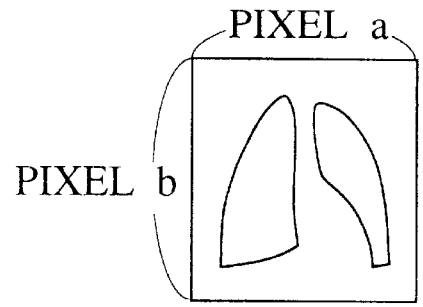
FIG. 4A and FIG. 4B are an original image and a minified image by image data reduction (minification) unit, respectively.
Figure 4B:
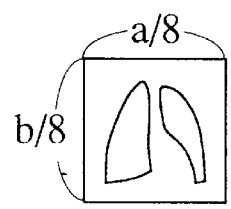

An image data reduction unit 4p receives the original image of the image frame memory 4g through the image bus 4l, and for example, this is minified to a reduced image of 1/8. That is, as shown in FIGS. 4A, 4B, if an image matrix size of the original image is a×b pixels, the reduced image is an image matrix size of a/8×b/8. For example, if the image matrix size of the original image is 2,048×2,048 pixels, the reduced image consists of 256×256 image matrixes. This reduction processing is, for example, a leveling reduction filter processing. The leveling reduction filter processing is that the original image is partitioned into a plurality of minute areas of 8×8 pixels and a simplified average or a weighted average of a pixel value in each area is defined as a pixel value of one pixel of the reduced image. Of course, the other reduction processing may be adopted. The reduced image created by the image data reduction unit 4p is sent to a display image data overlay unit 4q as described later.

It shall be appreciated that though we have described minification of 1/8 for the minified image over the original image, a minifying factor may be 1/1.

<Display Image Data Overlay Unit (WS-OV)>

A display image data overlay unit 4q synthesizes the original image to be interpreted which is stored in the image storage 4f with the reduced image of this original image which is created by the image data reduction unit 4p to generate a sheet of composite image to be displayed. Here, a composite processing will be explained with reference to FIG. 5.

Figure 5:
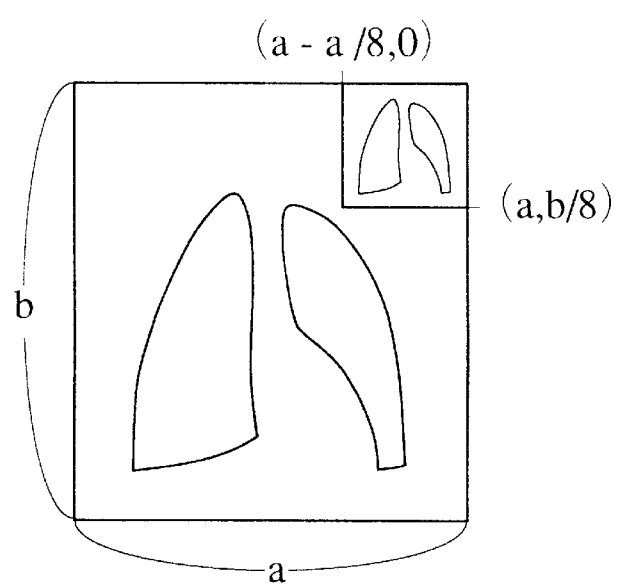
FIG. 5 illustrates a display image obtained by display image overlay unit shown in FIG. 2.

Referring to FIG. 5, if a pixel matrix size of the original image is a×b pixels, the pixel matrix size of the reduced image is a/8×b/8 pixels as described above. A part of the original image is completely substituted for pixels of the reduced image. Herein, when a left upper corner of the original image is the origin to locate the reduced image to a right upper part of the original image, a substituted area is specified by four points (a-a/8, 0), (a, 0), (a, b/8), (a-a/8, b/8) in the original image. Thus, the original image is synthesized with the reduced image to create a synthetic image. This synthetic image is transferred to the image storage 4f and stored therein.

<Schema Data Making Storage (WS-SMMK)>

Figure 6:
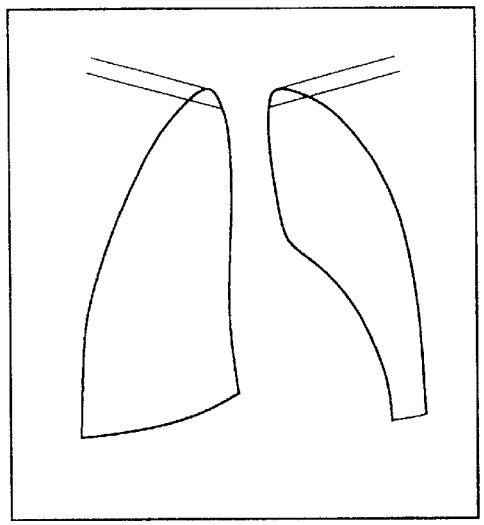
FIG. 6 is a schematic image obtained from schematic data making storage unit shown FIG. 2.

A schema data (or schematic diagram data) making storage 4r inputs an image, digitizes it to abstract an outline of lungs or ribs, makes a schema (or schematic) image (contour image) as shown in FIG. 6, and stores it.

For example, if a threshold value of digitization is 512, and when a pixel value f (x,y) of a certain pixel (x,y) is the threshold value or greater, such pixel value is substituted for 1023. Furthermore, the pixel value f (x,y) of the certain pixel (x,y) is less than the threshold value, such pixel value is substituted for 0. After this scheme image is minified in the image data reduction unit 4p, it is sent to the display image data overlay unit 4q to synthesize it with the original image instead of the above-mentioned reduced image, thereby creating a synthetic image. In order to select as to whether the synthetic image is an image in which the original image is synthesized with the reduced image of this original image, or the synthetic image is an image in which the original image is synthesized with the reduced image of this schema image, an operator will set its selection from the input unit 4c.

<Overlay Display Information Maker (WS-OVMK)>

An overlay display information maker 4n inputs either the abnormality data table or the finding data table concerning such original image stored in the image storage 4f, the overlay display information maker 4n makes overlay display information as shown in the following Table 7:

TABLE 7

Figure 7:
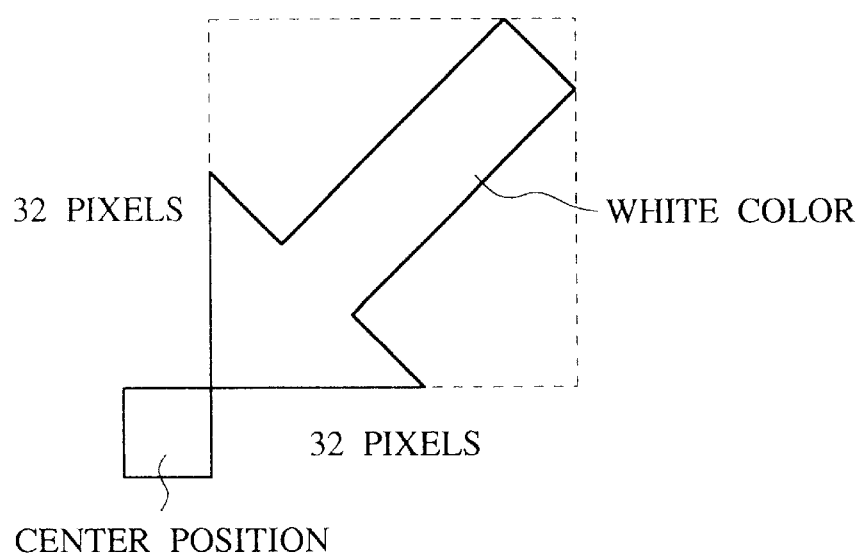
FIG. 7 illustrates a diagram showing a position (location) of abnormality formed by overlay data forming portion.

Examination ID
Image Number
Reference Number
Type of Graphic
Size of Graphic
Coordinates (Central Position of Abnormality)
Display Color
Type of Abnormality
Degree of Abnormality In this overlay display information, information of each of items of a type of a graphic, a size of a graphic, and a display color is added to the items of the abnormality data table and the finding data table. These additional information is required to superimpose information of abnormalities on the synthetic images, and as shown in FIG. 7, the contents have beforehand been set. The type of a graphic indicates a graphic for showing the position of abnormality on the image, and for example, this is information indicating to display as a shape of an arrow.

The size of a graphic is information indicating that such arrow should be shown in a size to be received within a scope of, for example, 32×32 pixels. The display color is one of such arrow, and information indicating that such arrow should be shown in white. Here, the coordinates of overlay display information are that the coordinates indicating a central position of the abnormality which is written into the abnormality data table are converted into coordinates on the reduced image of the sysnthetic image. The overlay display information is transferred to the image storage 4d to be once stored therein.

<Image Display Manager (WS-IDM)>

Figure 3:
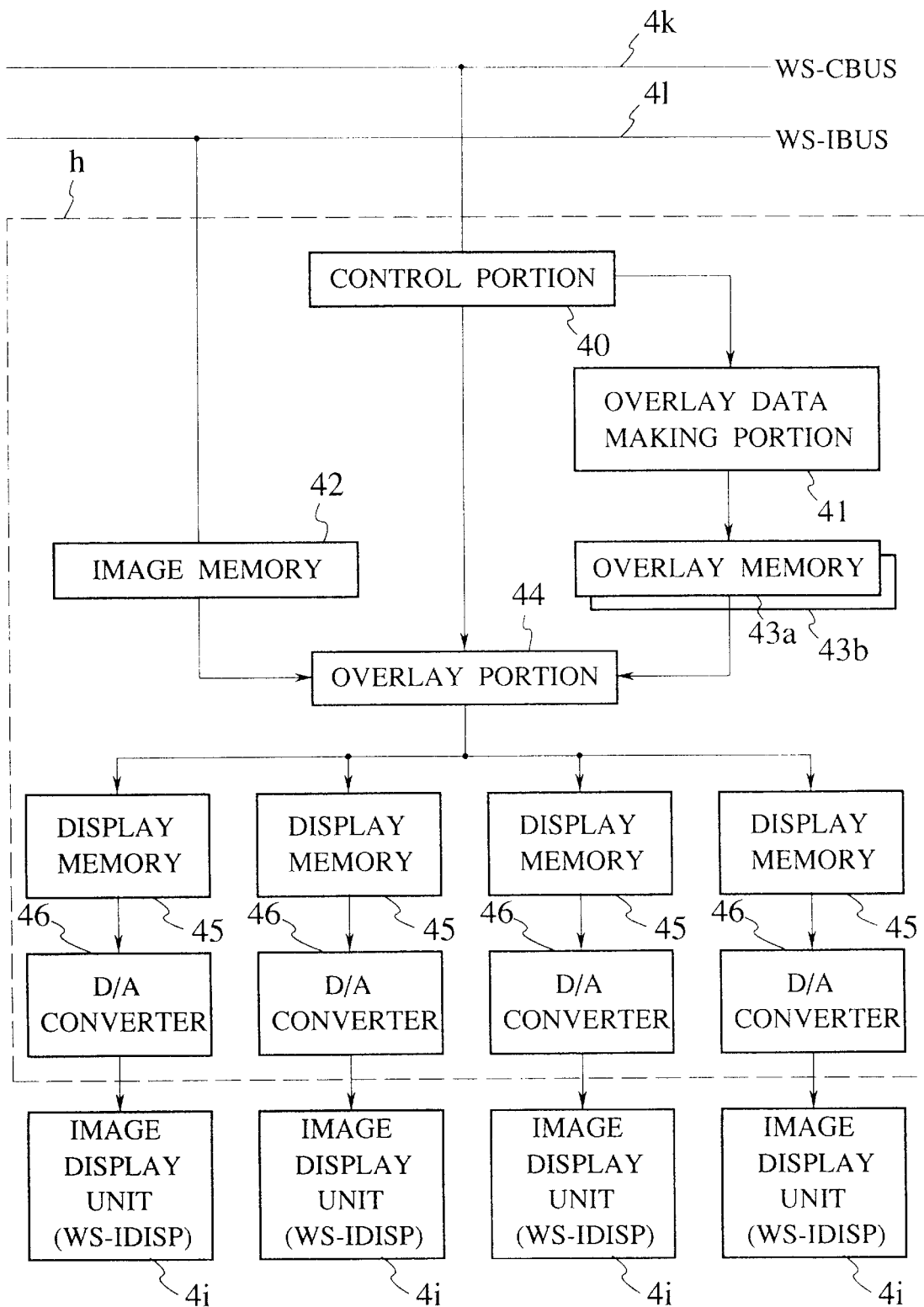
FIG. 3 is a block diagram showing construction of image display manager shown in FIG. 2.

An image display manager 4h is a control concerning a display such as an original image etc. and constructed as shown in FIG. 3.

An image memory 42 receives the synthetic image stored in the image storage 4f through the image bus 4l to be stored therein. The image memory 42 has storage capacity of, for example, 2,048×2,048×10 bits so as to store at least a sheet of synthetic image.

Information of a display mode set by the input unit 4c (a mode displaying only an original image, a mode displaying only abnormality information, a mode displaying synthetic images of the original image and the abnormality image on one screen) and information specifying the image display 4i for use in the display are supplied to a control unit 40 through the control bus 4k.

Furthermore, the overlay display information is supplied from the image storage 4d to the control unit 40. An overlay data creator 41 receives the overlay display information from the control unit 40 and creates overlay data to display the abnormality information (the information showing a type, a position, and a degree) on the reduced image based on this overlay display information. These overlay data are temporarily stored in one overlay memory 43a.

In this connection, the other overlay memory 43b is a memory for storing data of a cursor displayed on a display screen in response to movements of a mouse. An overlay unit 44 creates an overlay display image by superimposing the overlay data on the synthetic image. This overlay display image is displayed on the set image display 4i through display memories 45 and D/A converters 46 corresponding to the image display 4i corresponding to information specifying the image display 4i for use in a display set by the input unit 4c.

Next, operations according to this embodiment having such configuration will be described.

(1) Request of Examination 1-1) The examination request information inputted through the examination order system 7 is transferred to the system manager 1. One example of this examination request information is shown in table 8 as described below.

(To be continued)

TABLE 8

| | |
|---|---|
| Patient ID Number | 870802 |
| Patient Name | E. Suzuki |
| Date of Birth of Patient | August 8, 1952 |
| Sex of Patient | Male |
| Modality | X-ray |
| Region to be Examined | Chest |
| Examination Procedure | Plain Radiography |
| Name of Exam. Requesting Dept | Department of Internal Medicine |
| Name of Exam. Requesting Doctor | T. Yamada |
| Date of Examination Request | May 10, 1992 |
| Desired Date of Examination | May 10, 1992 |
| Desired Time of Examination | 14:00 |
| Purpose of Examination | — |
| Examination ID | — |
| Clinical Information of Patient | — |
| Disclosed Name of Disease | |
| . | |
| . | |
| . | |
| Examination ID | 108801 |

1-2) Next, such examination request information is transferred to an image acqusition apparatus 2a or 2b which is an X-ray machine according to the modality.

(2) An examination is carried out in the image acquisition apparatus to produce images.

2-1) An operator reads contents of the examination request information and a radiography is carried out as indicated there to produce images. These images are assigned image numbers in sequence of their production order.

2-2) When the image acquisition is finished, the additional information as shown in Table 9 is prepared by the image acquisition apparatus 2a.

TABLE 9

| | |
|---|---|
| Examination ID | 108801 |
| Date of Examination | May 10, 1952 |
| Number of Sheet of Image | 2 |
| Image Number | 1 |
| Lateral Length of Pixel | 0.06 cm |
| Longitudinal Length of Pixel | 0.06 cm |
| Lateral Size of Matrix | 2048 |
| Longitudinal Size of Matrix | 2048 |
| Pixel Bit Length of Image | 10 |
| Amount of Data | 5 MB |
| Imaging Direction | P → A |

This additional information is transferred to the database 3 together with the image to be stored therein and will stand by until it is read out to interpret it.

(3) The examination histories of such patient, the past interpretation report, and the examination request information are prepared by the system manager 1 and transferred to the workstations 4A, 4B to be stored in the system memories.

Next, interpreting operations will commence.

(4) A readout demand of the image to be interpreted is sent from the workstation 4A to the database 3. Such image (including the additional information) is sent back to the workstation 4A together with the examination histories of such patient, the past interpretation report, and the examination request information to be stored in the image storage 4f.

(5) The abnormality data table and the finding data table are created.

One of the abnormality data table and the finding data table is created. The abnormality data table is created by the CAD processor 4e. On the other hand, such image is displayed on the image display 4i and observed by an operator to input the results through the input unit 4c. Consequently, the finding data table is created.

One example of the abnormality data table is shown in Table 10. Furthermore, one example of the finding data table is shown in Table 11.

TABLE 10

| Ref No. | Exam. ID Number | Image No. | Type of Abnormality | Central Position of Abnormality on Image | Degree of Abnormality |
|---|---|---|---|---|---|
| 1 | 108807 | 1 | Interstitial lung disease | (350, 1350)* | 9 |
| 2 | 108801 | 1 | Interstitial lung disease | (460, 1500) | 8 |
| 3 | 103541 | 1 | Interstitial lung disease | (300, 1500) | 8 |
| 4 | 103541 | 1 | Interstitail lung disease | (1600, 1300) | 8 |
| 5 | 100902 | 1 | Interstitial lung disease | (350, 1350) | 7 |
| 6 | 100902 | 1 | Interstitial lung disease | (400, 1500) | 7 |
| 7 | 100902 | 1 | Interstital lung disease | (1500, 300) | 1 cm |

*(abscissa, ordinate)

TABLE 11

| | |
|---|---|
| Examination ID Number | 108801 |
| Image Number | 1 |
| Reference Number | 1 |
| Type of Abnormality | Interstitial Lung Disease |
| Central Position of Abnormality on Image (Lateral Coordinate, Longitudinal Coordinate) | (350, 1350) |
| Degree of Abnormality | 9 |
| Reference Number | 2 |
| Type of Abnormality | Interstitial Lung Disease |
| Central Position of Abnormality on Image (Lateral Coordinate, Longitudinal Coordinate) | (400, 1500) |
| Degree of Abnormality | 8 |

These abnormality data table or finding data table will be sent to the image storage 4f to be stored therein.

(6) Creation of Display Image The original image is read out of the database 3 and stored in the image storage 4f. It is transferred to the image data reduction unit 4p and the display image overlay unit 4q. The original image is minified at a predetermined reduction rate, herein at 1/8, by the image data reduction unit 4p. This reduced image is sent to the display image overlay unit 4q and synthesized into the original image and a sheet of synthetic image therein. As this synthesis processing is above-mentioned, the description is omitted.

Of course, this synthetic image can be made instead of the above-mentioned reduced image. Namely, the schema image made by the schema data making storage 4r can be reduced by the image data reduction unit 4p to create a reduced image which is synthesized with the original image to create the synthetic image.

(7) Creation of Overlay Display Information

The abnormality data table (or the finding data table) is supplied from the image storage 4f to the overlay display information maker 4n to make the overlay display information based on this abnormality data table. In a graphic to be displayed as described above, the type thereof is an arrowheaded real line and a size thereof is 32×32 pixels and a display color is white.

Furthermore, as the position of abnormality in the abnormality data table is determined with coordinates defined by a coordinate system of the original image, it is necessary to transform these coordinates into coordinates on the reduced image of a display image. For example, if a pixel matrix size of the original image is 2048×2048 pixels and the position of abnormality in the abnormality data table in this coordinate system is (a,B), the coordinate of such position of abnormality is converted into coordinates (2048-2048/8+a/8, B/8). At the display, the information of abnormality is supperimposed on the reduced image by this coordinate transformation to be displayed. One example of the overlay display information created based on the abnormality data table as shown in Table 10 is shown in Table 12 described below.

(To be continued)

TABLE 12

| | |
|---|---|
| Examination ID | 108801 |
| Image Number | 1 |
| Reference Number | 1 |
| Type of Graphic | Arrowheaded Real Line |
| Size of Graphic | 32 dots |
| Coordinates | (350, 1350) |
| Display Color | White |
| Type of Abnormality | Interstitial Lung Disease |
| Degree of Abnormality | 9 |
| Reference Number | 2 |
| Type of Graphic | Arrowheaded Real Line |
| Size of Graphic | 32 dots |
| Coordinates | (400, 1500) |
| Type of Abnormality | Interstitial Lung Disease |
| Degree of Abnormality | 8 |

Specifically, as for the abnormality of the examination ID 10880, the image number 1, and the reference number 1, the abnormality data table of Table 10 has data such as the position of abnormality on the image (350,1350), the degree of an abnormality "9", and the type of abnormality "pulmonary interstitial disease". According to this information, the position of abnormality (1835,168) which is obtained as a result of the coordination transformation, the degree of abnormality "9", the type of abnormality "interstitial lung disease", the type of graphic "arrowheaded real (solid) line", and the display color "white" are written into the data number 1 in the overlay display information.

Similarly, the position of abnormality (1841, 187), the degree of abnormality "8", the type of abnormality "interstitial lung disease", the type of graphic "arrowheaded real (solid) line", and the display color "white" are written into the data number 2. Incidentally, when the result of coordinate conversion contains a decimal point or less, it is rounded to the nearest whole number to be treated as an integer value. The thus-created overlay display information is stored in the image storage 4f.

(8) Display of Image

Figure 8:
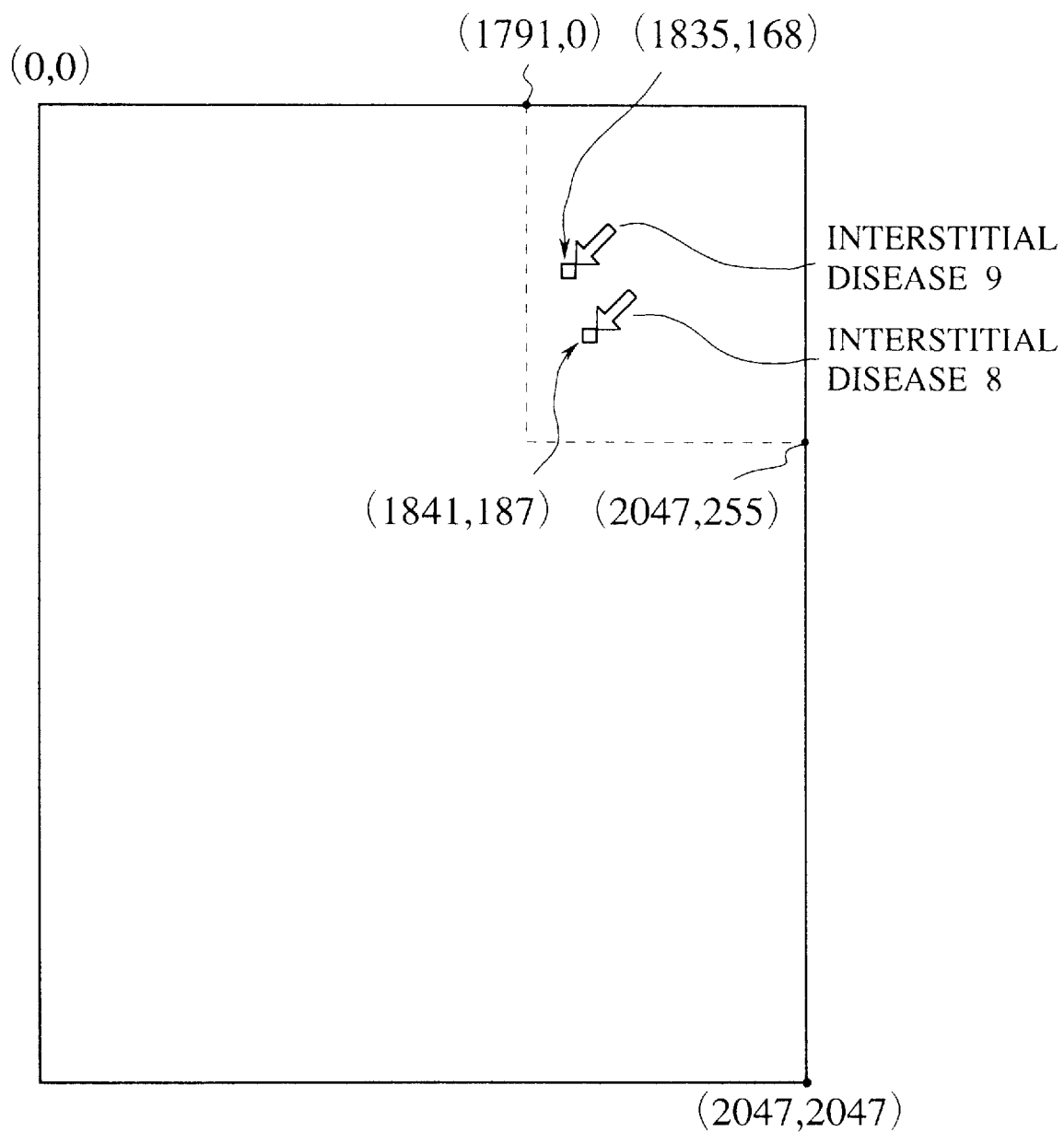
FIG. 8 shows overlay data made by overlay data forming portion shown in FIG. 3.

At displaying the images, under an indication of the control 4a, the synthetic image created by the display image overlay unit 4q is transferred from the image storage 4f to the image memory 42 of the image display manager 4h to be stored therein. Furthermore, under an indication of the control, the overlay display information created by the overlay display information maker 4n is sent from the image storage 4f to the overlay data creator 41 through the control unit 40 in the image display manager 4h. Furthermore, a display mode inputted from the input unit 4c (herein, this is a display mode by superimposing the overlay image on the original image) and information specifying the image display 4i to be displayed are supplied to the control unit 40. The following overlay data are created based on the overlay display information in the overlay data creator 41 and stored in the overlay memory 43a. For example, in the abnormalities of the data number 1, as shown in FIG. 8, bits are erected in an arrowheaded shape in coordinates (1835,168) of the overlay memory 43a, and in the character display of the degree of abnormality "9" and the type of abnormality "interstitial lung disease", bits are erected in a character shape on the overlay memory 43a using a character font in the control 4a. Similarly, in the abnormalities of the data number 2, bits are erected in an arrowheaded shape in coordinates (1841,187) of the overlay memory, and in the character display of the degree of abnormality "8" and the type of abnormality "interstitial lung disease", bits are erected in a character shape on the overlay memory 43a using a character font in the control 4a.

Figure 9:
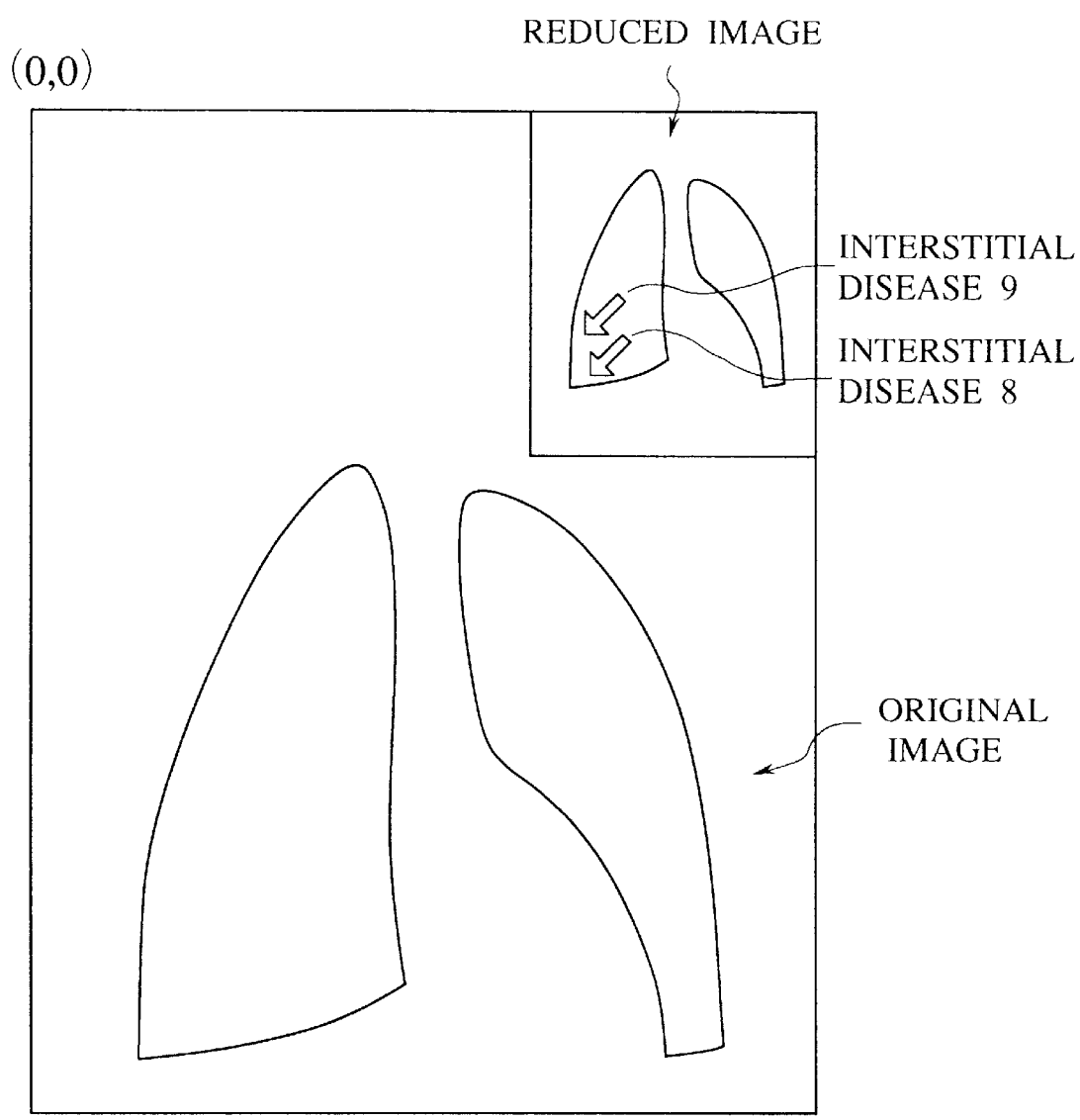
FIG. 9 shows a display example at a final stage.
Figure 10:
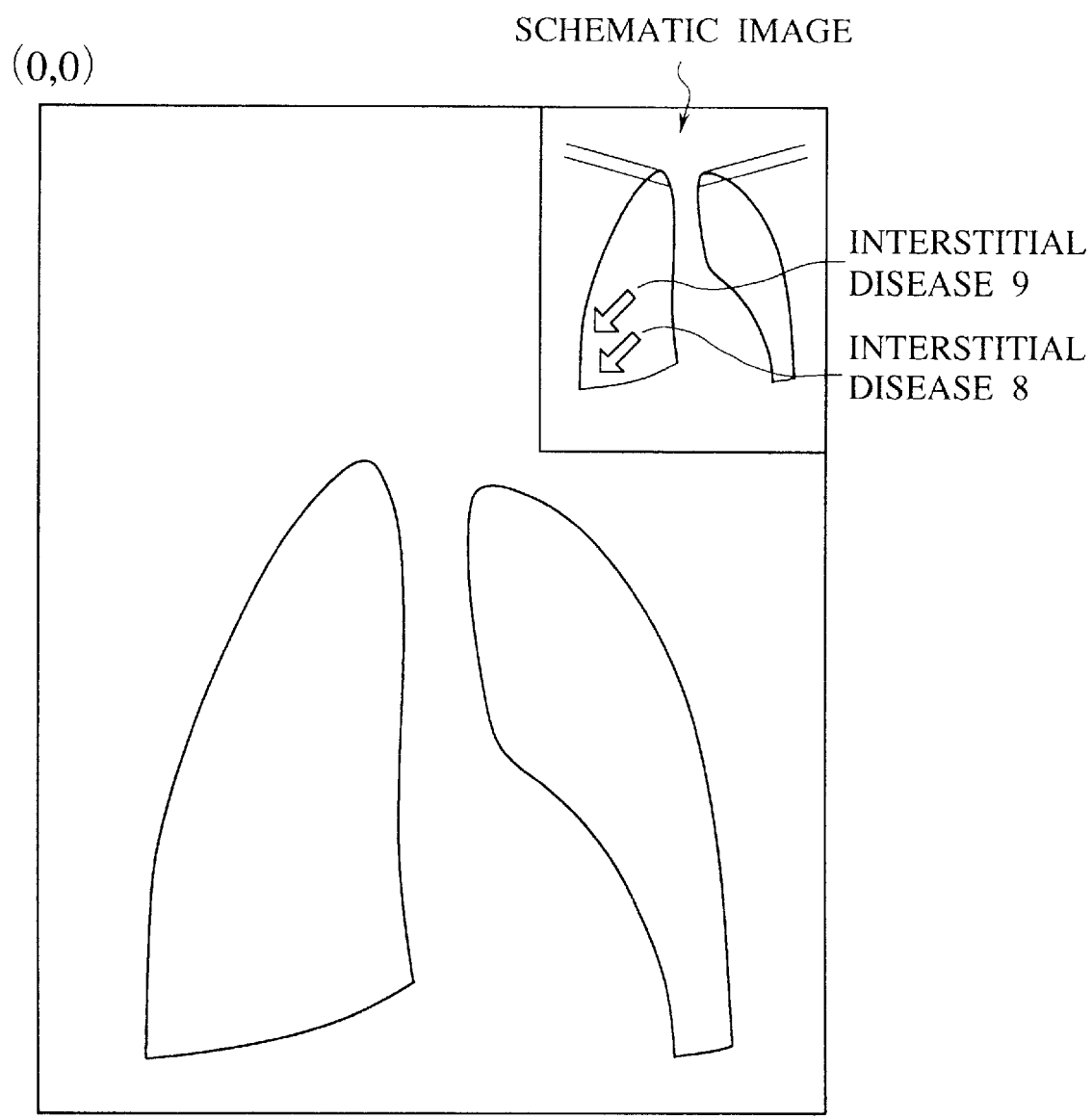
FIG. 10 shows another display example at a final stage.
Figure 11:
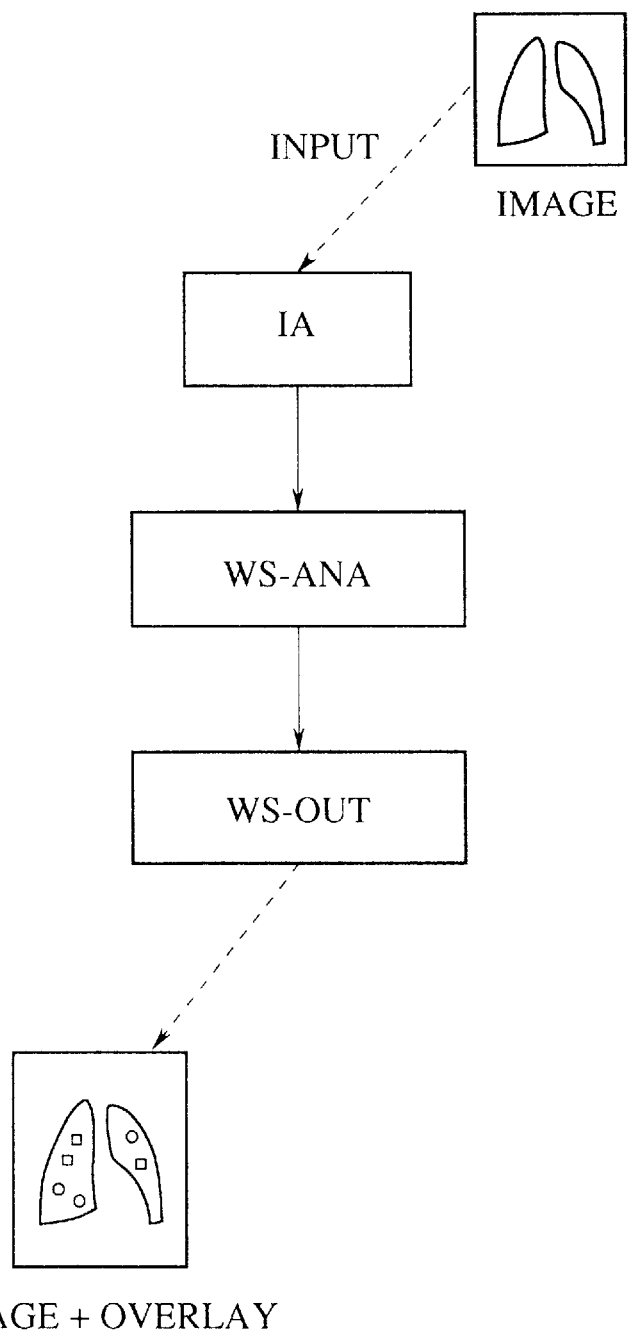
FIG. 11 illustrates that data on abnormality are superposed on original image according to the conventional practice.
Figure 12:
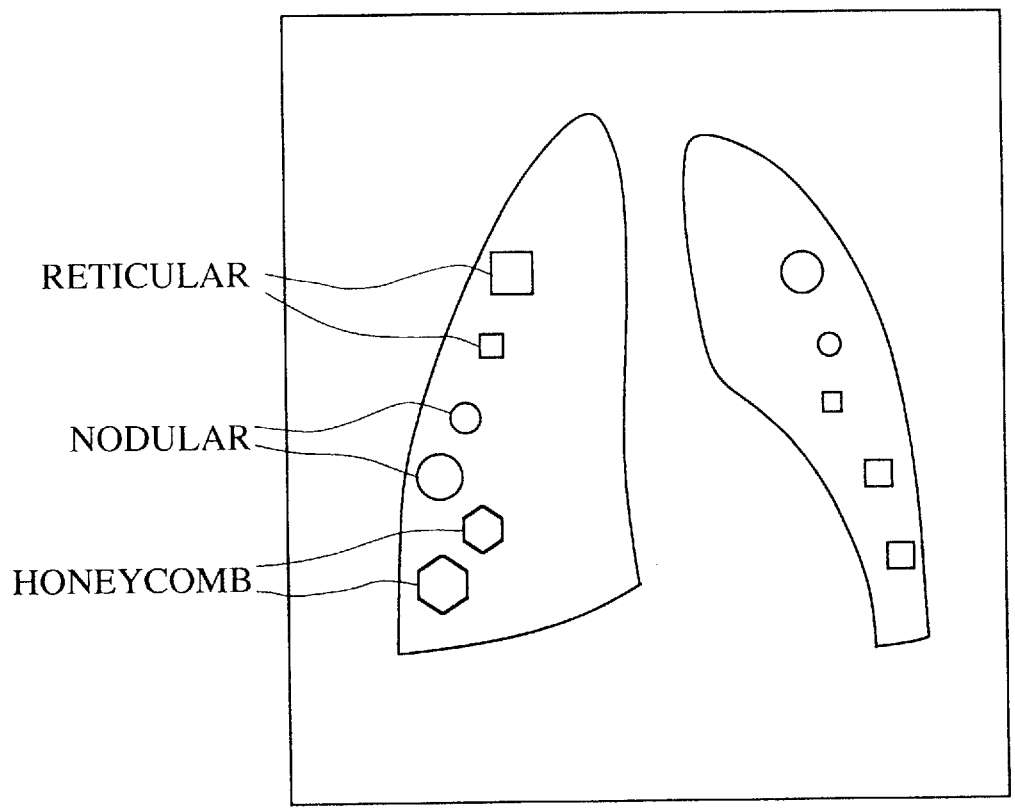
FIG. 12 illustrates an image displayed in the conventional system.

This overlay data are supplied to the overlay unit 44 together with the synthetic image of the image memory 42 and superimposed thereon to be displayed in the image display 4i specified by the input unit 4c. This display example is shown in FIG. 9. Incidentally, when images in which the schema image is synthesized with the original image are displayed instead of the reduced image, its display example is shown in FIG. 10.

(9) Processing after Interpretation.

An interpreting doctor interprets the images which are superimposed on the overlay data, and inputs its interpretation results from the input unit 4c to create the interpretation report. This interpretation report is transferred to the image storage 4f to be stored therein. Furthermore, the interpretation report is transferred from the image storage 4f to the database 3 through the system manager 1 to be stored therein.

As described above, in this embodiment, since the reduced image (or -the reduced image of the schema image) is disposed in a part of the original image and the information of abnormalties is displayed on this reduced image, even if an object of the original image is interfered with the information of abnormalities, the image never disappears and a doctor can interpret the original image on one screen referring to the information of abnormalities. Accordingly, it becomes unnecessary to change between the display of only the original image and the display of the image which superimposes the information of abnormalities on the original image, thereby enhancing operator productivity.

The present invention is not limited to the above-mentioned embodiments, which can be variously changed to execute the other embodiments. For example, in a technique for use in the above-mentioned description, when creating from the original image to the reduced image, the original image is smoothened by the reduction filter processing. The other technique can be utilized. For example, the reduced image can be created by sampling scattered pixels of the original image.

Furthermore, in the above-mentioned description, a sheet of reduced (minified) image is superimposed on the original image, however a plurality of sheets of reduced image can be superimposed thereon each type of abnormality. Furthermore, in the above-mentioned description, a shape or display color of a graphic of the overlay data is one type only, however the shape or display color of a graphic can be changed for each type of abnormality.

Furthermore, in the above-mentioned description, a position of abnormality is shown with an arrow, however the other graphics such as a round, a square, or the like can be used. Furthermore, in the above-mentioned description, the CAD processor is provided with three types of abnormality detecting means, however the other types of abnormality detecting means can be used and also the type of image to which the abnormality detecting means is applied is not limited.

Furthermore, in the schema (schematic) data making storage, each pixel value of the schema (schematic) image is digitized at a threshold value to make the schema (schematic) image, however it may also be made by contour extracting means such as a contour line tracing tomography machine etc.

Furthermore, in the above-mentioned description, the schema image is made from the original image at displaying the image, however the schema image has beforehand been made before displaying the image to be stored in a system disk so that it may be used at displaying the image.

Referring to FIG. 153, it shall be appreciated that the reduced (minified) image (in which the arrow is superimposed) may be displayed in other display unit than that displaying the original image. For example, the original image is displayed in image display unit (WS-IDISP-1) 4*i*, while the reduced image, in which the arrow is superimposed, is displayed in another image display unit (WS-IDISP-1) 4*i*.

In the first embodiment according to the present invention, a medical information processing system comprises: means for inputting an image; means for inputting a position of an abnormal spot containing said image; means for making a reduced image by reducing (minifying) said image; means for creating a synthetic image by synthesizing said image with said reduced image; means for creating a display image by superimposing a graphic showing said abnormal spot on said reduced image of said synthetic image based on said position; and means for displaying said display image.

The graphic showing the abnormal spot is superimposed on the reduced image of the synthetic image which synthesizes the image with the reduced image to display it, whereby even if an object of the image is interfered with the abnormal graphic, the object never disappears, and the original image can be interpreted referring to information of abnormalities on one screen. Accordingly, it is possible to provide the medical information processing system in which it becomes unnecessary to change between the display of only the original image and the display of the image which superimposes the information of abnormalities on the original image unlike the prior art, thereby enhancing operator productivity.

Embodiment No. 2 & Embodiment 3

Hereinafter, other preferred embodiments of the present invention will be explained with reference to the accompanying drawings. In this embodiments, an embodiment of performing a CAD by using a PACS will be described, and first of all, the gist of the present invention will be described, and next a system configuration of the PACS will be described, and finally a procedure in the case of interpreting by using the system of the present invention will be described in detail. The descriptions on the system configuration of the PACS and after will be made with reference to an embodiment of interpreting a chest X-ray image for a lung cancer screening examination.

Figure 13A:
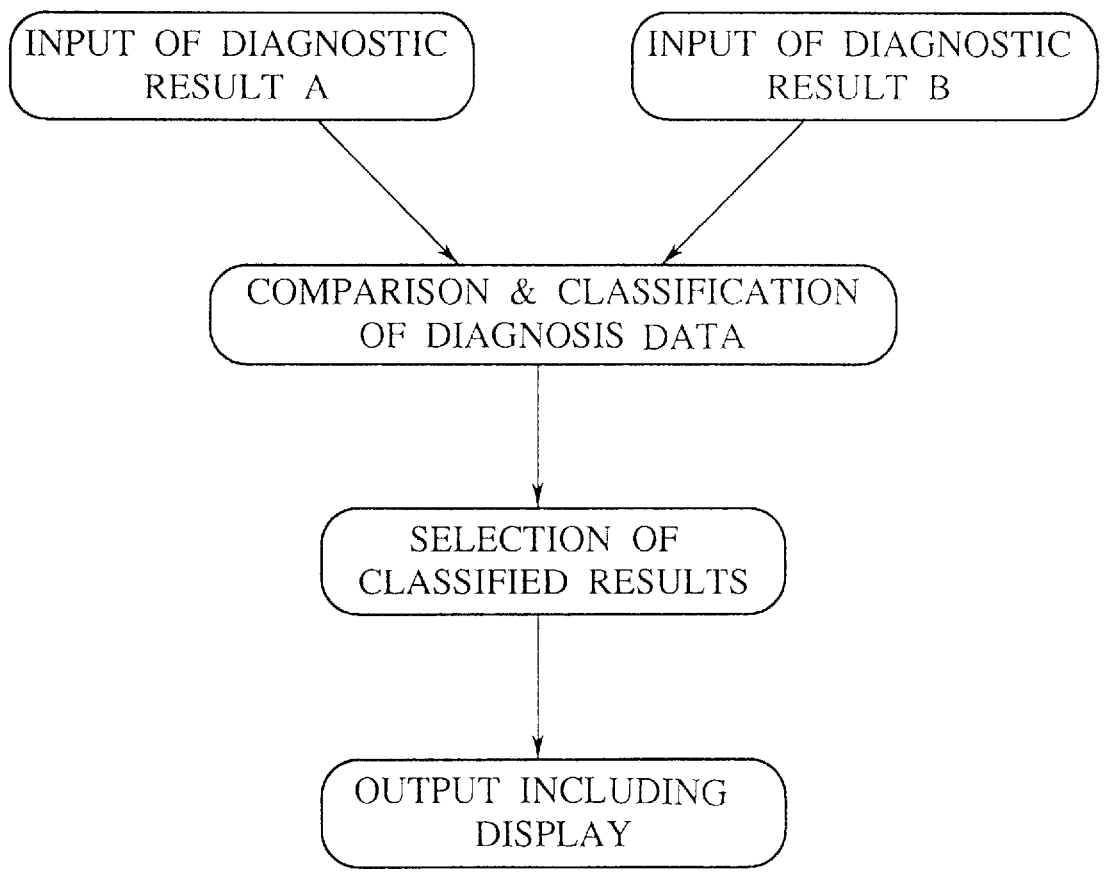
FIGS. 13A and 13B show flowcharts to explain the second embodiment according to the present invention.
Figure 13B:
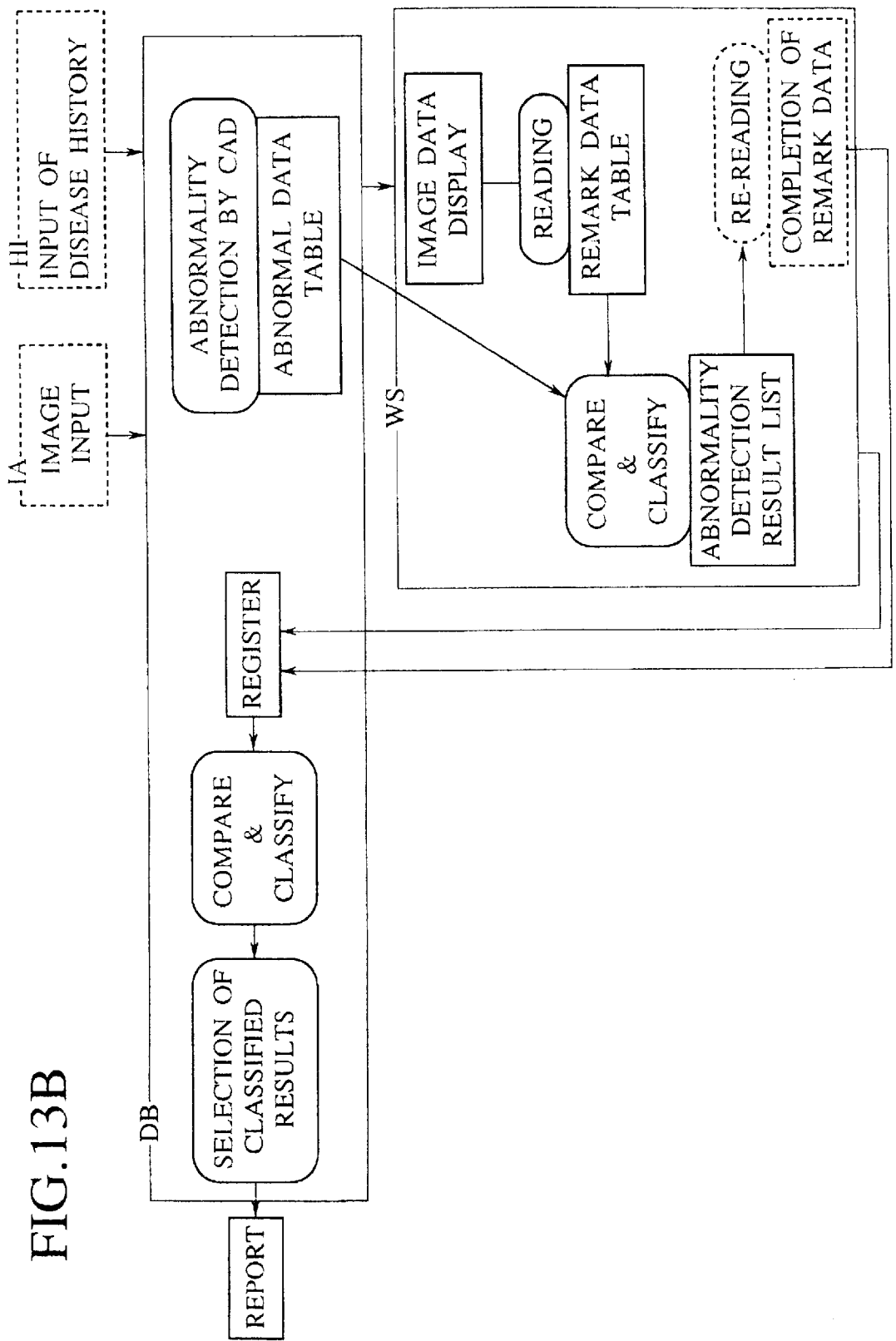
Figure 14:
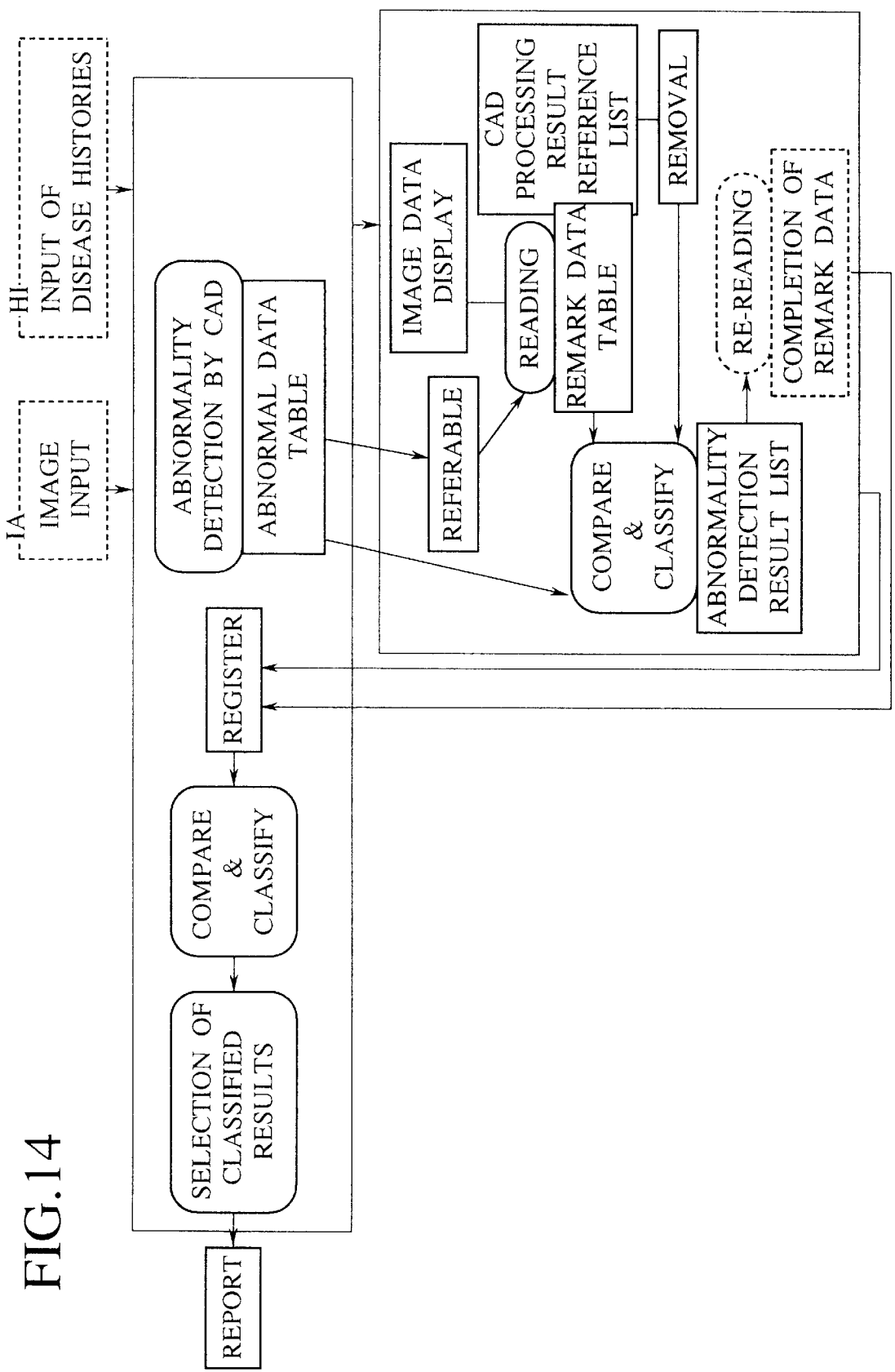
FIG. 14 shows a flowchart to explain the third embodiment.

FIGS. 13A, 13B and 14 are flowcharts for explaining the gist of the present invention. FIGS. 13A and 13B shows the gist of a second embodiment and FIG. 14 shows the gist of a third embodiment. FIG. 13A shows the gist having the broadest sense in the second embodiment. This is the embodiment in which a plurality of diagnostic results having one or more diagnostic data obtained by a medical group examination or mass survey or the like within a medical information processing system exist, and these diagnostic results are to be compared or classified. Assuming that a plurality of diagnostic results are diagnostic results A and diagnostic results B, these results are first compared and classified in each diagnostic information. Next, a great amount of diagnostic information is classified in a listing form etc. and selected and outputted to report. The diagnostic results A and the diagnostic results B may be diagnostic results obtained by the plurality of doctors and may be CAD processing (diagnostic) results and doctors' interpretation (diagnostic reading) results. The latter case will be explained in FIG. 13B and herein the former case will be explained. That is, doctors A and B interpret images in a workstation WS to obtain interpretation results, which are inputted into a database DB, and then a great amount of diagnostic information inputted is compared and classified to be divided into two categories in which a close examination is necessary or unnecessary. When the diagnostic information is classified that a close examination is necessary, identification information of its medical examination data or the medical examination data and diagnostic information and information relating to the medical examination data are outputted. On the other hand, when the diagnostic information is classified that a close examination is unnecessary, the identification information of the medical examination data and the doctor's diagnostic information are outputted.

FIG. 13B is a case of comparing the CAD processing results with the doctor's diagnostic results. Information concerning a hearing examination or disease histories is inputted from a hearing information input unit HI and image data of a certain type of medical examination data are inputted from an image acquisition unit IA. In the database DB into which these are inputted, each image data is CAD-processed to detect an abnormality to obtain the result to create an abnormality data table. On the other hand, the image data, the hearing information, or the like are sent from the database DB to the workstation WS to display the image data therein and a doctor interprets the images. An interpreting doctor creates a finding data table which is interpretation results for each image data to be input therein. When the doctor finishes interpreting the images, he/she compares this finding data table with the abnormality data table which is the CAD processing results and can classify it to create an abnormality detecting result list which is its results, in order to output it for each classification. When the doctor re-interprets the images, he/she outputs (including a display) his/her own favorable classification to complete finding data, and sends the results from the workstation WS to the database DB to be registered therein. The interpretation in the medical group examination is carried out by two or more doctors, and this completed finding data is sent to the database DB in at least two sets. After a plurality of interpretations are inputted into the database DB, this system operates as described in FIG. 13A described above.

FIG. 14 shows the gist of the third invention. Information concerning an oral examination or disese histories is inputted from the hearing information input unit HI, and image data which are a certain type of medical examination data are inputted from the image acquisition unit IA. In the database DB where these image data are input, each image data is CAD-processed to detect an abnormality before a doctor interprets the image data, in order to create the abnormality data table which is its results. On the other hand, based on the image data, the hearing information, or the like which is sent from the database DB to the workstation WS, a doctor interprets the images. In this case, the CAD processing results created previously can be referred to. Then, materials referred at this interpretation are registered in a CAD processing result reference list, and when the finding data table is compared with the abnormality data table to classify it after the doctor's interpretation, the referred materials are removed to compare each other. The tables are compared and classified to create an abnormality detecting result list which is its results. Thereafter, the system operates in the same manner as FIG. 13B.

In this connection, a broken line in the figure shows that the part is not principal in the present invention. Also, the CAD processing has been explained in the embodiment operating by the database DB, however, image data etc. can be sent to the workstation WS to perform the CAD processing therein.

Figures 15, 16:
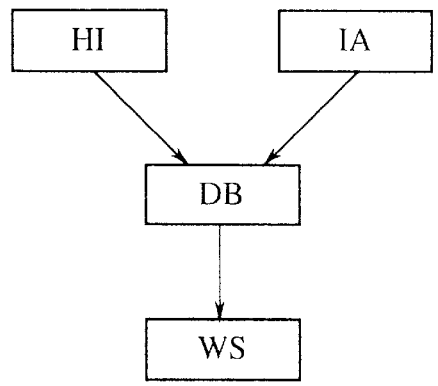
FIG. 15 shows an embodiment having a basic system configuration of the PACS.
FIG. 16 is a table showing items described on the hearing sheet.

Next, FIG. 15 shows an embodiment having a basic system configuration of the PACS. This system is constructed of the following units (subsystem):
1) Hearing information input unit(HI);
2) Image acquisition unit (IA);
3) Database (DB); and
4) Workstation (WS).

The hearing information input unit (HI) is a device for inputting hearing information or disease histories which are obtained by an oral examination to examined persons.

The image acquisition unit (IA) is a medical image acqusition unit for the PACS such as an X-ray machine, an X-ray CT machine, an MRI machine, a film digitizer or the like. Herein, it is defined as an X-ray machine which is placed on a medical examination car.

The database (DB) is used for storing various data to be produced in operations of the medical examination.

The workstation (WS) appropriately processes digital images etc. sent from the database (DB) or the image acquisition unit (IA) to obtain desired results to display or output them. In this embodiment, the workstation is used for interpreting radiographed images.

Communications among these four types of units are carried out by using a data memory medium capable of carrying and rewriting, such as an optical magnetic disk or the like.

Next, a function of each unit (subsystem) and its configura-tional element will be described.

A main function and operation of the hearing information input unit (HI) will be described.

To display a hearing sheet (questioning contents for a person to be examined). Items described on the hearing sheet are shown in FIG. 16.

To input identification information of a person to be examined (person ID number).

To input and display responses of an examined person to the items described in the questioning sheet.

To write inputted responses (hearing information) and the identification information of an examined person into the optical magnetic disk.

The hearing information input unit (HI) can readily be realized by adapting a personal computer to be obtained in the market. As the configuration has no connection with the gist of the present invention, the description is omitted.

As the image acquisition unit (IA), first a main function is described.

To acquire digital image data.

To input the identification information of a person to be examined (person ID number).

To input and display information attached to an examination and an image.

To write the identification information of an examined person, image data, and information attached to an examination and an image into the optical magnetic disk.

Figure 17:
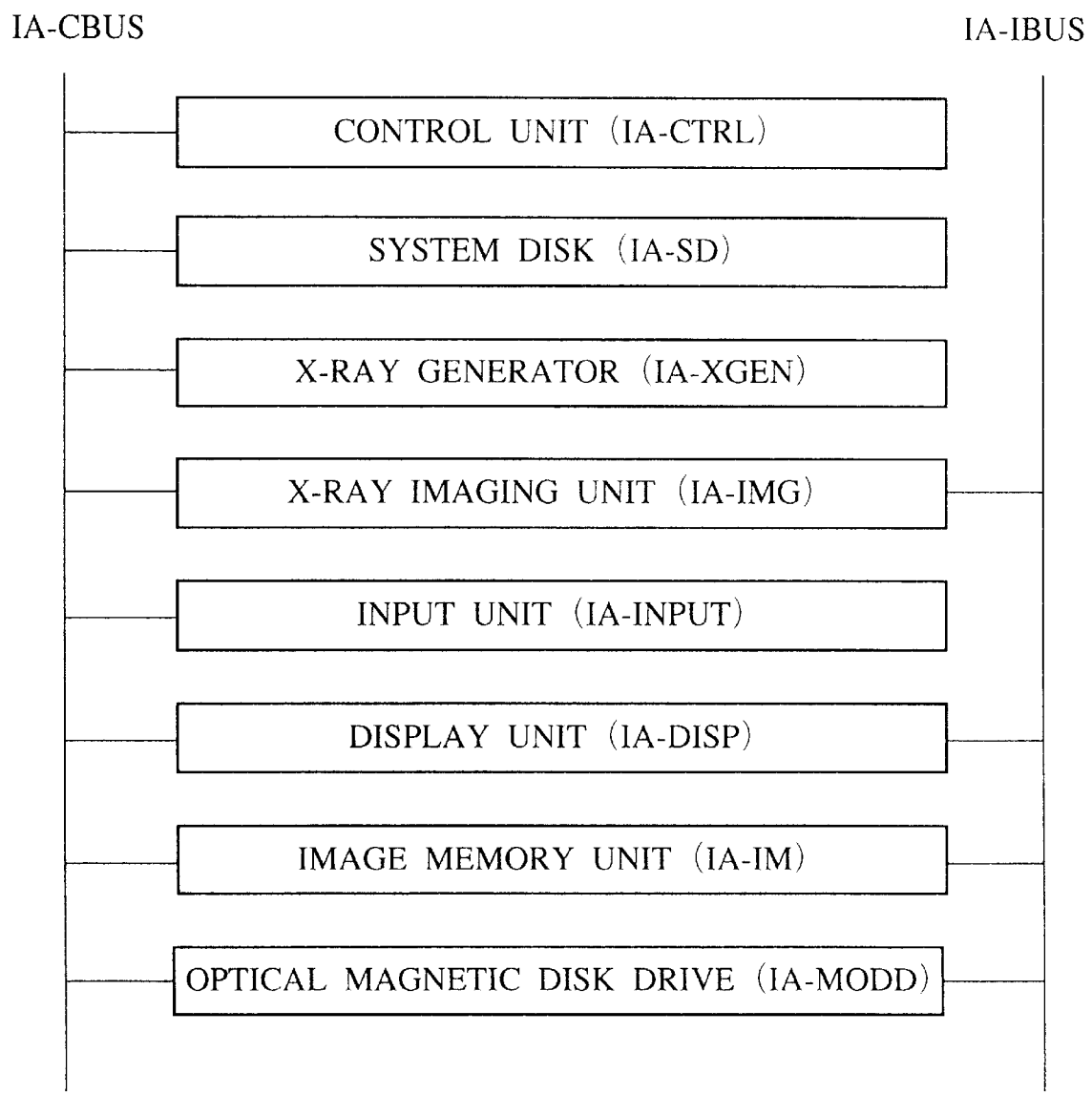
FIG. 17 shows configuration of the image acquisition unit (IA).

As for the image acquisition (IA), a configuration element and its function will be described. The configuration of the image acquisition unit (IA) is shown in FIG. 17.

Control Unit (IA-CTRL)

A control unit contains a central processing unit (CPU) or system memories (namely, semiconductor memory) etc. and controls operations of the entire image acqustion unit.

System Disk (IA-SD)

This is a magnetic disk and stores a program or data, such as:

(a) a program for operating an image acquisition unit;
(b) identification information of a person to be examined; and
(c) information attached to an examination and an image. This program is read out when the image acquisition unit is turned on and written into system memories within the control unit (IA-CTRL). Furthermore, the identification information of an examined person and the information attached to an examination and an image are stored for each examination and a type of the data is shown in FIG. 18 together with a data configuration.

X-ray Generator (IA-XGEN)

This is a device for generating X-rays to irradiate a person to be exposed.

X-ray Imaging Unit (IA-IMG)

This is a device for detecting X-rays transmitted through a person to be exposed, converting them into electric signals, and digitizing the signals to obtain a digital image. This contains an image intensifier, a TV camera, an analog/digital converter and the like.

Input Unit (IA-INPUT)

This is means for inputting information such as commands etc. by an operator and uses a keyboard, a mouse, a touch screen or the like.

Display Unit (IA-DISP)

This is a device for displaying information inputted by an operator and digital image acquired, and uses a CRT display, a liquid crystal panel display or the like.

Image Data Unit (IA-IM)

This is a device for temporarily storing digital image data acquired by the X-ray imaging unit (for example, a semiconductor memory or a magnetic disk)

Optical Magnetic Disk Drive (IA-MODD)

This is a device for reading data out of portable optical magnetic disk or writing data thereinto.

Control Bus (IA-CBUS)

This is a transmission path of various control information within the image acquisition unit.

Image Bus (IA-IBUS)

This is a transmission path of image data within the image acquisition unit.

Also, a clock (not shown in FIG. 18) is integral with the image acquisition unit.

As for the database (DB), first a main function and operations will be explained.

The database (DB) stores identification information of an examined person, hearing information, image data, and information attached to examination information and an image.

The database (DB) stores findings which are doctors' interpretation results.

The database (DB) detects images having doubtful abnormalities from image data.

The database (DB) can write various data into the portable optical magnetic disk or read them out of it.

Figure 19:
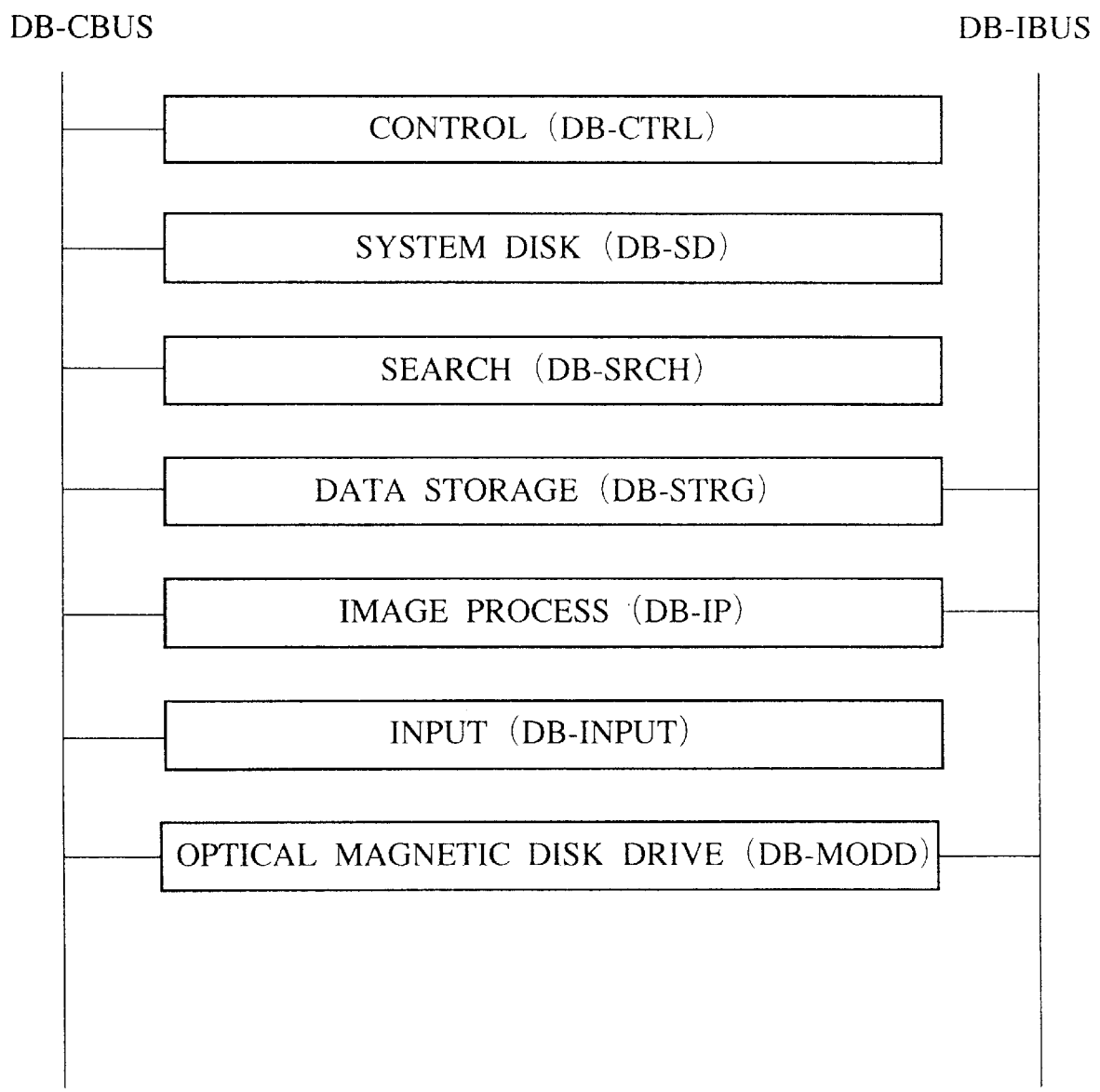
FIG. 19 shows configuration of database (DB).

A configuration element and a function in the database (DB) will be described. The configuration of the database (DB) is shown in FIG. 19.

Control Unit (DB-CTRL)

This includes a central processing unit (CPU), system memories (namely, semiconductor memory) or the like and controls operations of the entire database.

System Disk (DB-SD)

This is a magnetic disk and stores a program for operating the database or the like. This program etc. is read out when an electric power of the database is turned on and written into system memories within the control unit (DB-CTRL).

Search Unit (DB-SRCH)

This searches information conforming to a given keyword according to an instruction from the control unit (DB-CTRL), and is a device having a function of replying searched results to the control unit (DB-CTRL). The search unit includes a directory of information stored in the database and searching means. A magnetic disk is used as storing means of the directory.

Data Storing Unit (BD-STRG)

This is a device for storing identification information of an examined person, hearing information, image data, information attached to examination information and an image, and a doctor's findings for a long-termed period, and an optical disk is used as the data storing unit (BD-STRG).

Image Processing Unit (DB-IP)

This is means for detecting abnormalities from an image, and when image data and data indicating a type of abnormalities (disease) which is an object to be detected are inputted, the image processing unit (DB-IP) detects the type of abnormalities and outputs a position and a degree of abnormalities, and includes a plurality of types of abnormality detecting means. That is:

(a) means for detecting shadows of pulmonary nodules in a front side image in a chest plain X-ray image; and (b) means for detecting shadows of interstitial lung disease in a front side image in a chest X-ray image.

These detecting means are disclosed in the below-mentioned literatures:(1) Japanese Patent Application Laid-Open No. 2-185240(2); Japanese Patent Application Laid-Open No. 2-152443(3); Japanese Patent Application Laid-Open No. 1-125675.

Input Unit (DB-INPUT)

This is means for inputting information such as commands by an operator, and a keyboard, a touch screen, or the like is used for the input unit (DB-INPUT).

Optical Magnetic Disk Drive (DB-MODD)

This is a device which reads data out of the potable optical magnetic disk or writes them into it.

Control Bus (DB-CBUS)

This is a transmission path of various control information within the database.

Image Bus (DB-IBUS)

This is a transmission path of image data within the database.

First, a main function and operations of the workstation (WS) will be described.

To display identification information of an examined person, hearing information, image data, information attached to examination information and an image, and a doctor's findings.

To display various information concerning abnormalities such as a type of abnormalities (disease), a position and degree of abnormalities, or the like.

To input the findings which are doctor's interpreting results.

To write various data into the portable optical magnetic disk or read them out of it.

Figure 20:
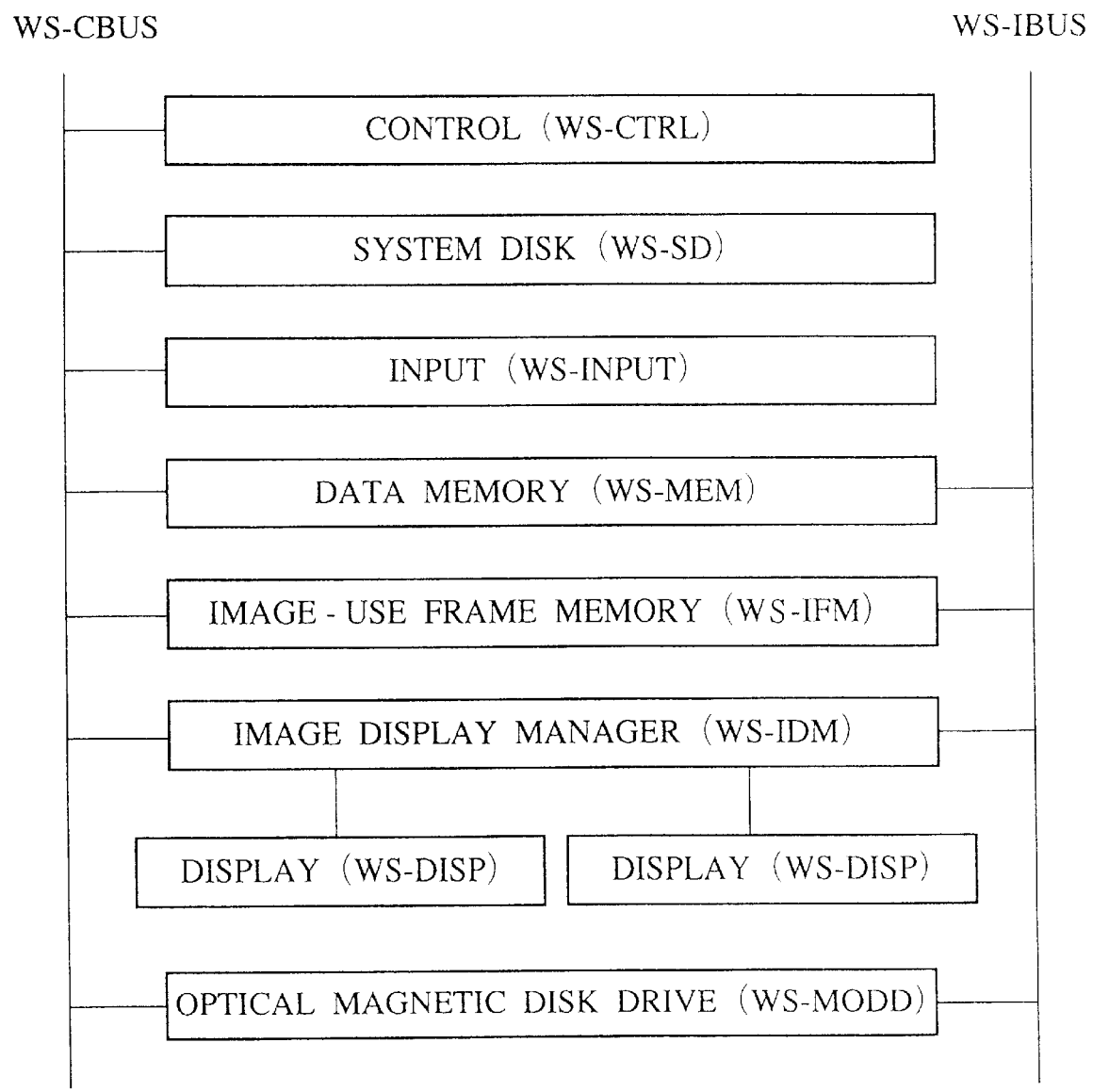
FIG. 20 is a configurational diagram showing the workstation (WS).

Next, a configuration element and a function of the workstation (WS) will be described. FIG. 20 is a configurational diagram of the workstation (WS).

Control Unit (WS-CTRL)

This contains a central processing unit (CPU), system memories (namely, semiconductor memory), and the like and controls operations of the entire workstation.

System Disk (ES-SD)

This is a magnetic disk and stores a program etc. This program is read out when an electric power of the workstation (WS) is switched on, and written into the system memories within the control unit (WS-CTRL).

Input Unit (WS-INPUT)

This is means for inputting information such as commands, interpretation reports (remarks or findings), or the like by an operator, and a keyboard, a mouse, a touch screen, or the like is used for the input unit (WS-INPUT). The touch screen is mounted onto a screen of the display unit (WS-DISP).

Data Memory (WS-MEM)

This is a device for temporarily storing various data such as image data etc. and is a magnetic disk and so on.

Imaging Frame Memory (WS-IFM)

This is a device for temporarily storing a plural sheet of image data and may be a semiconductor memory and son on.

Image Display Manager (WS-IDM)

Figure 21:
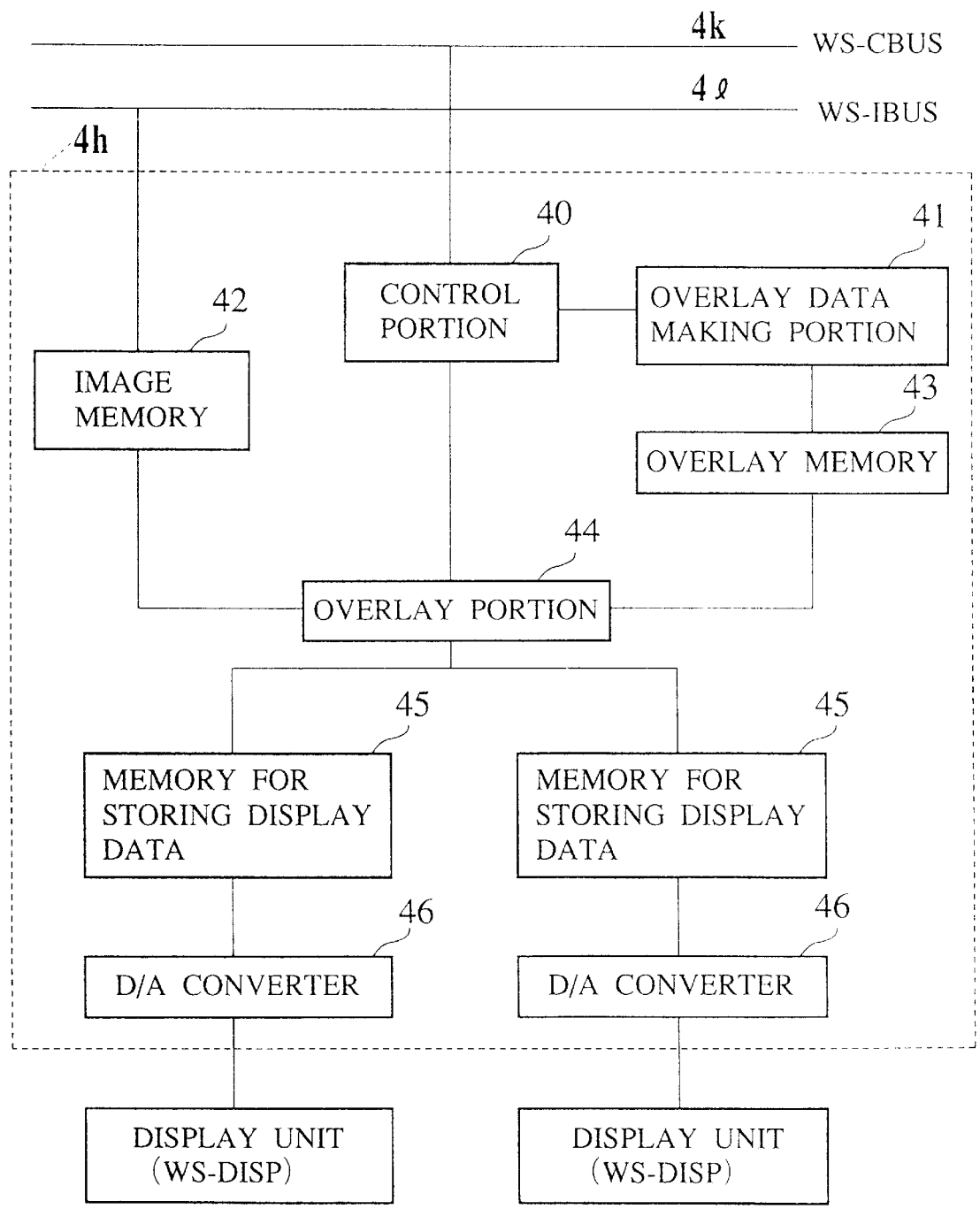
FIG. 21 is a configurational diagram showing the image display manager (WS-IDM).

This operates so as to display an image and an overlay. FIG. 21 is a configurational diagram of the image display manager (WS-IDM) and a part of the image display manager (WS-IDM) is shown within a broken line.

This includes the following portions:

a) Control Portion:

This controls the entire configuration portion of the image display manager (WS-IDM);

b) Overlay Data Making Portion:

This makes overlay data (color) from overlay display information. This contains means for displaying by flickering as to data indicated in the overlay display information;

c) Image Memory for Storing Image Data:

This has memories corresponding to a sheet of image (a matrix size is 2,048×2,048 pixels);

d) Overlay Memory for Storing Overlay Data:

Since the overlay data are displayed in color, the overlay memories corresponding to one screen are constructed of three sheets of overlay memory for red, green, and blue. In the overlay memory for each color, a matrix size is conceptionally 2,048×2,048 pixels, and a bit length of 1 pixel is 1 bit. The relationship between a display color and a bit value of each pixel is shown in FIG. 22. In FIG. 22, for example as shown in Step 2, a pixel value (a bit value of pixel) of a pixel coordinate (X, Y) of the overlay memory for red is 1, and a pixel value of the same coordinate of the overlay memory for both green and blue is 0, and a red color is displayed as to the coordinate. On the other hand, black in a display color means that any colors are not displayed, and when black is doubly displayed on an image, only the image is displayed;

e) Overlay Portion:

An overlay portion superimposes image data on overlay data;

f) Displaying Memory for Storing Display Data

This image display manager (WS-IDM) has two sheets of memory for displaying a sheet of image (a matrix size is 2,048×2,048 pixels). This is equal to the number of the display units (WS-DISP). The memories for displaying correspond to the display units (WS-DISP), respectively; and g) D/A Converter This converts display data of digital data into those of analog data.

This is provided with the same number as the display unit (WS-DISP) so as to correspond to it.

The image display manager (WS-IDM) can receive the following information:

(a) Type of data to be displayed:

One of three types can be displayed: an image only, an overlay only, an image and an overlay;

(b) Designated information of the display unit (WS-DISP) displaying data;

(c) Overlay display information:

A type of a graphic, a size of a graphic, coordinates, a display color, presence or absence of display (containing a flicker), control information, or the like per graphic; and (d) Image Data.

When displaying an image overlapping an overlay, the image display manager (WS-IDM) operates in the following manner:

(1) The control portion of the image display manager (WS-IDM) receives the below-mentioned three information from the control unit (WS-CTRL) of the workstation (WS):

(a) "Images and overlays" as a type of data to be displayed;

(b) A display unit number of the display unit (WS-DISP) display-ing data; and (c) Overlay Display Information.

(2) The image display manager (WS-IDM) receives image data and writes them into the image memories.

(3) The overlay data making portion makes overlay data based on overlay display information by an instruction of the control portion. Then, when control information of present or absence of display is "display", the overlay data making portion makes the overlay data with an indicated graphic, indicated coordinates, and indicated color data.

(4) The image data and overlay data are read out by an instruction of the control portion to input them into the overlay portion to synthesize the data.

(5) The synthesized data are written into dispalying memories with an indicated display unit number.

(6) The synthesized data are converted into analog data by the D/A converter.

The above-mentioned operations (4) to (6) are always repeated during the display.

Only when the control information of present or absence of display (containing a flicker) denotes "display" as to a graphic in cetain coordinates, the overlay data making portion writes the graphic into the overlay memories to display it.

On the other hand, when an image is just displayed, in the above-mentioned operation (1), the overlay data making portion receives:

(a) "only image" as a type of data to be displayed; and (b) a display unit number of the display unit displaying data, however the portion does not receive the overlay display information. Then, in the above-mentioned operation (4), the overlay data making portion does not read out the overlay data, and accordingly does not superimpose the image data on the overlay data.

Display Unit (WS-DISP)

This is a device for displaying characters, graphics, and images, and a CRT display, a liquid crystal panel display, or the like is used for the display unit. A color display is available. In this embodiment, two units are set.

Optical Magnetic Disk Drive (WS-MODD)

This is a device for reading or writing data for a portable optical magnetic disk.

Control Bus (WS-CBUS)

This is a transmission path of various control information within the workstation.

Image Bus (WS-IBUS)

This is a transmission path of image data and overlay data within the workstation.

In this connection, a clock for referring to a date and a time (not shown in the figure) is integral with the workstation (WS).

Utilizing thus-constructed PACS, a flow of a series of system operations is described, for example, when read and interpreted is a chest X-ray image in a lung cancer examination.

The operations will be carried out in the following procedure:

1. Input of hearing information;
2. Acquisition of chest X-ray image;
3. Registration of acquired data;
4. Preparation of interpreting data;
5. Interpretation of image data; and
6. Output of interpreting results.

Hereinafter, the above-mentioned series of system operations will be described in detail.

1. Input of Hearing Examination (1) Display of Hearing Sheet

A hearing sheet is displayed on a display screen of the hearing information input unit (HI).

(2) Input of Hearing Information (i) An oprator inputs examined person identification information from the hearing information input unit (HI). The examined person identification information is assigned to the examined person so as not to overlap each other within such medical examination area, and an examined person ID number described in a register shall here be inputted. The inputted data are displayed in a specific position on a screen.

It is to be noted that following terms such as person ID number, examined person ID number and examined person indentification information are interchangeably used throughout this patent application, all of which have identical meaning to each other.

(ii) An operator inputs a response obtained from the examined person in the hearing information input unit (HI). The inputted data are displayed in a specific position on a screen.

The above-mentioned Subsections (1) and (2) are repeated only by a number of examined persons.

(3) Write Hearing Information into Optical Magnetic Disk

The control unit of the hearing information input unit (HI) reads out hearing information (examined person identification information and responses from the examined persons) stored in the system disk by an instruction of an operator, and writes it into the optical magnetic disk inserted into the optical magnetic disk drive (HI-MODD).

Thus-obtained optical magnetic disk is later carried to a certain position of the database (DB).

2. Acquisition of Chest X-ray Images (1) Input of Examined Person Identification Information An operator inputs examined person identification information from the input unit (IA-INPUT) of the image acquisition unit (IA). The inputted data are displayed in a specific position on a screen of the display unit (IA-DISP).

(2) Acquisition of Digital Image (i) The control unit (IA-CTRL) indicates to expose X-rays and image to the X-ray generator (IA-XGEN) and the X-ray imaging unit (IA-IMG). The X-ray generator (IA-XGEN) generates X-rays and irradiates them onto a person to be exposed (person to be examined). The X-rays transmitted through the person to be exposed are detected by the X-ray imaging unit (IA-IMG) to obtain digital images. The X-ray imaging unit (IA-IMG) transmits image data to the image bus (IA-IBUS). As a result, the image data unit (IA-IM) receives the image data to write them to itself.

(ii) The control unit (IA-CTRL) writes information attached to imaging conditions or images together with examined person identification information into the system disk (IA-SD).

The above-mentioned Subsections (1) and (2) are repeated only by a number of persons to be examined.

(3) Write into Optical Magnetic Disk of Data (i) The control unit (IA-CTRL) reads out information attached to an examination and an image which is stored in the system disk (IA-SD) by an instruction of an operator, and writes it into an optical magnetic disk inserted into the optical magnetic disk drive (IA-MODD).

(ii) The control unit (IA-CTRL) successively reads out image data from the image data unit (IA-IM) and writes them into the optical magnetic disk inseted into the optical magnetic disk drive (IA-MODD).

Thus-obtained optical magnetic disk is later carried to the place where the database exists (DB).

3. Registration of Acquired Data (i) An operator inserts the optical magnetic disk registering hearing information into the optical magnetic disk drive (DB-MODD) of the database (DB), and inputs a hearing information readout command of the optical magnetic disk from the input unit (DB-INPUT). Then, by an instruction of the control unit (DB-CTRL), the optical magnetic disk drive (DB-MODD) reads out the hearing information registered in the optical magnetic disk and writes it into the data storing unit (DB-STRG). The control unit (DB-CTRL) extracts information (hereinafter, referred to as directory information. Refer to FIG. 2;3) registered in a data directory from the hearing information to send it to the search unit (DB-SRCH). The search unit (DB-SRCH) stores the received directory information.

Furthermore, the control unit (DB-CTRL) extracts the previously radiographed image data of examined persons (hereinafter, called previous image data or image data in the past) from the examined person identification information of the hearing information from the data storing unit (DB-STRG) to send them to the search unit (DB-SRCH). The search unit (DB-SRCH) adds the received previous image data to the directory information.

(ii) An operator inserts the optical magnetic disk registering information attached to an examination and an image, and the image data into the optical magnetic disk drive (DB-MODD) of the database (DB), and inputs an image information readout command of the optical magnetic disk from the input unit (DB-INPUT). Then, by an instruction of the control unit (DB-CTRL), the optical magnetic disk drive (DB-MODD) reads out the information attached to an examination and an image, and the image data which are registered in the optical magnetic disk, and writes it into the data storing unit (DB-STRG). The control unit (DB-CTRL) extracts directory information from the information attached to an examination and an image to send it to the search unit (DB-SRCH). The search unit (DB-SRCH) stores the received directory information 4. Preparation of Interpreting Data (1) Abnormality Detection from Image (i) When data registration is completed, the control unit (DB-CTRL) of the database (DB) indicates to search the images (comprisised of images to be interpreted and previous images) registered in the search unit (DB-SRCH) to obtain a response. Successively, the control unit (DB-CTRL) indicates to perform the following abnormality detecting operations for each sheet of images. The detected abnormality is represented by shadows of pulmonary nodules.

Figures 24, 25:
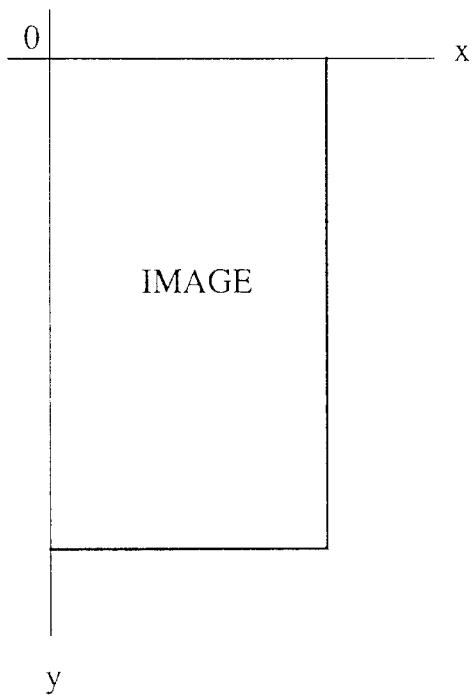
FIG. 24 illustrates a coordinate system of the image.
FIG. 25 is a table showing data on abnormality.

(ii) Image data corresponding to a sheet of image are read out from the data storing unit (DB-STRG) to send them to the image processing unit (DB-IP). The image processing unit (DB-IP) receives the image data and operates pulmonary nodules shadow detecting means having inside to detect specific positions on the images having doubtful abnormalities. The detected positions of abnormalities are recognized by an absolute coordinate system on coordinate axes formed by an image upper end and an image left end as shown in FIG. 24, and written into the abnormality data table as shown in FIG. 25. In the image of the examination ID number 920001, abnormal shadows are detected at two positions of N1 (700, 1200) and N2 (1500, 1000). In abnormality judgments on the entire image, when the abnormality has not entirely been detected, "normal", and when at least one abnormality has been detected, "doubtfully abnormal". In the image of the examination ID number 920001, as the abnormality is detected, the abnormality judgement on the entire image is made as a "doubtful abnormality". The abnormality data table showing detection results are stored in the data storing unit (DB-STRG).

The abnormality data tables in the images of the examination ID numbers 920002 to 920005 are shown in FIGS. 26 to 29.

(2) Preparation of Interpreting Data

When an abnormality detecting processing from images is finished, the control unit (DB-CTRL) of the database (DB) indicates the data storing unit (DB-STRG) to read out data of images to be interpreted, previous image data, hearing information, and information attached to an examination and an image (containing an abnormality data table), and indicates the optical magnetic disk drive (DB-MODD) to write them. The data storing unit (DB-STRG) reads out these data to be sent to the image bus (DB-IBUS). The optical magnetic disk drive (DB-MODD) receives these data to write into the optical magnetic disk.

In a medical group examination, two doctors interpret an image. Accordingly, two sheets of optical magnetic disk are prepared and are carried to workstations (WS), respectively.

5. Interpretation of Image Data (1) Input of Interpreting Data into Workstation (WS)

An operator inserts the optical magnetic disk registering data of images to be interpreted, previous image data, hearing information, and information attached to an examination and an image into the optical magnetic disk drive (DB-MODD) of the workstation (WS) and inputs a data readout command derived from the optical magnetic disk from the input unit (WS-INPUT). Then, by an instruction of the control unit (WS-CTRL), the optical magnetic disk drive (DB-MODD) reads out the data stored in the optical magnetic disk and writes them into the data memory (WS-MEM). The data of images to be interpreted, the previous image data, the hearing information, and the information attached to an examination and an image are memorized corrresponding to each examined person.

(2) Display of Image

The workstation displays the images to be interpreted. Now, as two display units (WS-DISP) are provided, a sheet of image to be interpreted (the examination ID number 920001) is automatically displayed on the left-sided display unit (WS-DISP) and the previous image (the examination ID number 910041) is automatically displayed on the right-sided display unit (WS-DISP). Also, when an image is displayed on the display unit (WS-DISP), its examination ID number (existent in information attached to an image) is displayed.

(3) From the interpretation to inputs of findings as the results, the following procedures are carried out:

(a) An interpreting doctor reads the displayed images.

When the interpreting doctor displays images and interpretation reports other than the displayed one, he/she inputs a command for it from the input unit (WS-INPUT) and operates.

(b) When the interpreting doctor finishes interpreting the image, he/she points out a position of pulmonary nodule shadows on the image to be interpreted by a mouse.

The control unit (WS-CTRL) reads out the coordinates of the abnormality position inputted to store it, and creates a finding data table as shown in FIG. 30. Then, the image display manager (WS-IDM) creates overlay display information describing "arrow, coordinare of abnormality position, white, and display" as to the abnormality in each finding number referring to the finding data table. The created overlay display information is shown in FIG. 31. The image display manager (WS-IDM) reates an overlay according to the overlay display information to display it. As a result, an arrow is displayed in a position that a doctor indicates on the image. The control unit (WS-CTRL) writes the overlay display information created into the data memory (WS-MEM) corresponding to the examination ID number.

(c) When an interpreting doctor recognizes an abnormality other than the pulmonary nodules, he/she inputs an abnormality type selecting command from the input unit (WS-INPUT) to select the corresponding abnormality type among several types of abnormality type displayed. Next, when he/she inputs the position of abnormalities, a method of inputting the position of abnormalities is different according to the type of abnormalities. For example, in interstitial lung disease, he/she inputs an abnormality scope by enclosing it with a closed curved line by using a mouse. In this case, the control unit (WS-CTRL) memorizes an area instead of the position.

A doctor carrys out the same operations and adds information relating to an abnormality to an overlay to be memorized and displays on the image.

(d) When an interpreting doctor inputs all discovered abnormalities, he/she inputs an interpretation completing command.

When the finding data table is inputted as an abnormality, the control unit (WS-CTRL) writes the diagnosed results of the entire image as an "abnormality" into the finding data table, and when the finding data table is not inputted as an abnormality, the control unit (WS-CTRL) writes the diagnosed results of the entire image as a "normality" into the finding data table to memorize into the data memory (WS-MEM).

(4) Comparison and Classification of Diagnostic Information

The control unit (WS-CTRL) reads out a finding data table which is interpreting results and an abnormality data table which is the corresponding CAD processing results from the data memory (WS-MEM).

In the same manner as the overlay display information is created from the finding data table in Section 5, Subsection (3), the image display manager (WS-IDM) creates the overlay display information from the abnormality data table indicating that a display color is "red" and memorizes it into the data memory (WS-MEM) corresponding to the examination ID number. The overlay display information created from the abnormality data table of the CAD processing results concerning the examination ID number 920001 is shown in FIG. 32.

The control unit (WS-CTRL) extracts both the diagnostic results of the entire image from the finding data table and the judged results of the entire image of the CAD processing from the abnormality data table to compare the both results to classify the following four cases:

Case a: The doctor judges as an "abnormality", but the CAD judges as a "normality".

Case b: The doctor judges as an "abnormality", but the CAD judges as a "doubtful abnormality".

Case c: The doctor judges as a "normality", and the CAD also judges as a "normality".

Case d: The doctor judges as a "normality", but the CAD judges as a "doubtful abnormality".

For example, as, concerning the examination ID number 920001, the doctor judges as an "abnormality" and the CAD judges as a "doubtful abnormality", this case is classified into the case b.

According to the above-mentioned classification results, the later operations are different. The available operations are described below.

(a) When classifying into the case a, the following operations are available:

(a-1) An examination ID number is registered in an abnormali-ty detecting result list.

(a-2) No operations.
(b) When classifying into the case b, the following operations are available:
   (b-1) With reference to a finding data table and an abnormality data table, at least a type of an abnormality and its position are compared and classified. An examination ID number of an image having a discrepancy in the type of an abnormality and its position is registered in an abnormality detecting result list.
   (b-2) No operations.
(c) When classifying into case c, no operations.
(d) When classifying into case d, the following operations are available:
   (d-1) An examination ID number is registered in an abnormality detecting result list.
   (d-2) No operations.

Herein, the respective operations (a-1), (b-1), and (d-1) will be explained.

As to the operations (a-1) and (d-1),

The control unit (WS-CTRL) reads out the abnormality detecting result list (if it does not exist, create it) and writes it into an examination ID number to be memorized into the data memory (WS-MEM).

As to the operation (b-1),

The explanation is made according to an example of the examination ID number 920001. When seeing finding numbers 1 and 2 with reference to FIG. 30, the type of an abnormality is pulmonary nodules. In the pulmonary nodules, a scope to be processed by the CAD is the entire image. Also, a method of indicating the position of an abnormality by a doctor is the same as that by the CAD to show it with an arrow on the overlay. Accordingly, it is determined that the position of an abnormality shall be shown with a tip of an arrow to seek its coordinate. From FIGS. 25 and 30, the respective coordinates are A1 (1520, 1040), A2 (1430, 659), N1 (700, 1200), and N2 (1500, 1000).

If distances between the positions of an abnormality (A1, A2) indicated by the doctor and between the positions of an abnormality (N1, N2) detected by the CAD are less than a predetermined value A0 (=100), the identical positions of an abnormality shall be indicated.

Comparison of A1 and N1: $\sqrt{\{(1520-700)^2+(1040-1200)^2\}}=835>100$

Comparison of A1 and N2: $\sqrt{\{(1520-1500)^2+(1040-1000)^2\}}=45<100$

Comparison of A2 and N1: $\sqrt{\{(1430-700)^2+(659-1200)^2\}}=909>100$

Comparison of A2 and N2: $\sqrt{\{(1430-1500)^2+(659-1000)^2\}}=348>100$

Accordingly, A1 and N2 indicate the identical abnormality and the information of controlling presence or absence of a display of N2 in the overlay display information of the CAD processing results is rewritten from a "display" to a "non-display". Only the CAD shall detect N1 and the doctor shall not indicate it, and the information of controlling presence or absence of a display is still a "display". Also, only the doctor shall discover A2 and the CAD shall not detect it.

As described above, when the doctor overlooks abnormalities or diagnoses excessively and the abnormalities pointed out by the doctor and the CAD are inconsistent, the control unit (WS-CTRL) writes the examination ID number of this image into the abnormality detecting result list.

(5) Display of Comparing Results and Creation of Abnormality Detecting Result List The operations corresponding to the number of all sheets of images to be interpreted in Section 5, Subsections (1) to (4) are repeated.

The control unit (WS-CTRL) extracts the diagnostic results and the judging results for the entire image from the finding data table of the doctor and the abnormality data table of the CAD, and a part of results compared and classified is shown in FIG. 33. The interpreted images are 50 sheets of the examination ID numbers 920001 to 920050. The classified results were:

Case a: 5 sheets Case b: 15 sheets

Case c: 26 sheets Case d: 4 sheets

Figure 34:
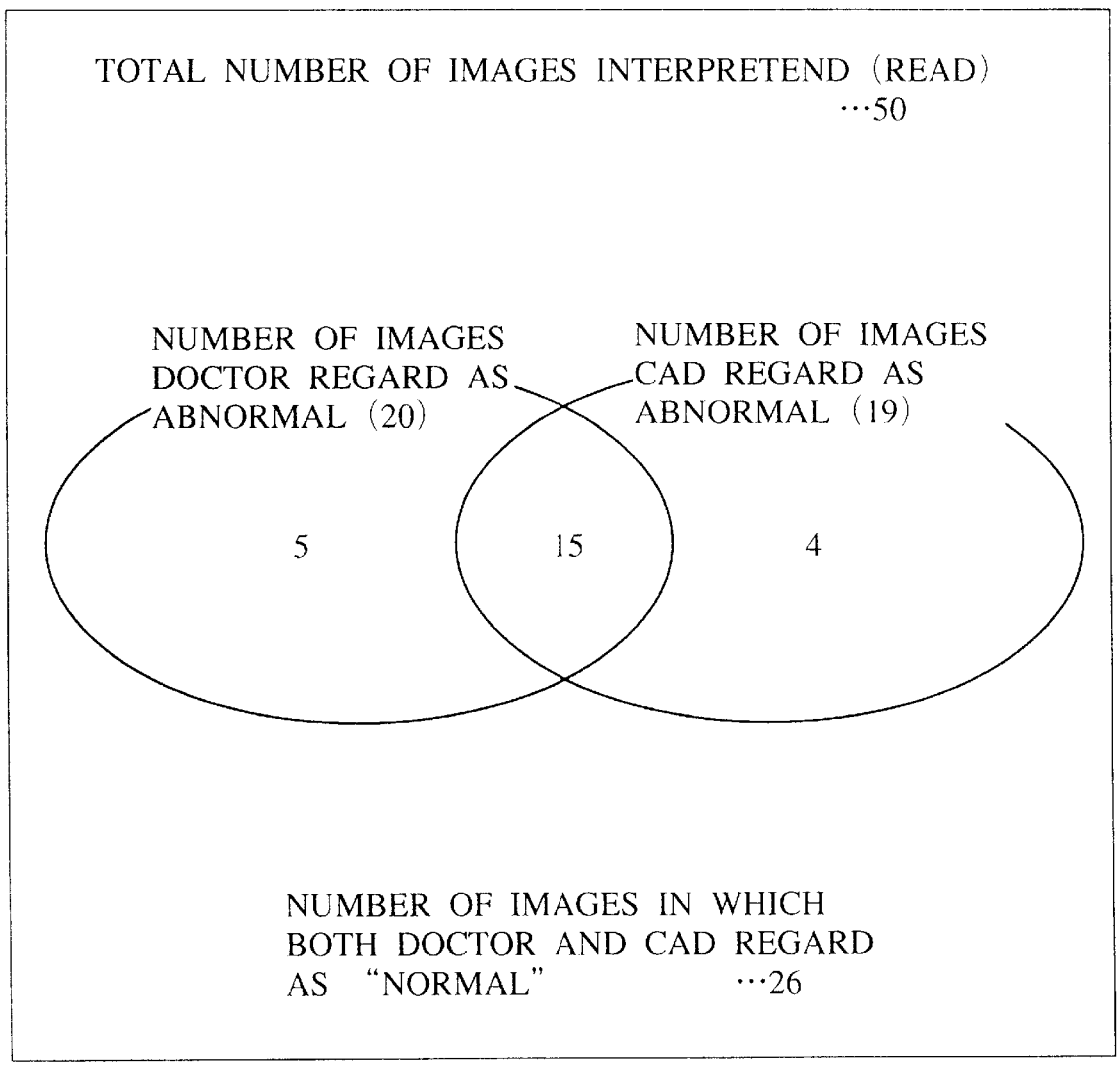
FIG. 34 is a set diagram showing a classified comparison result.
Figure 35:
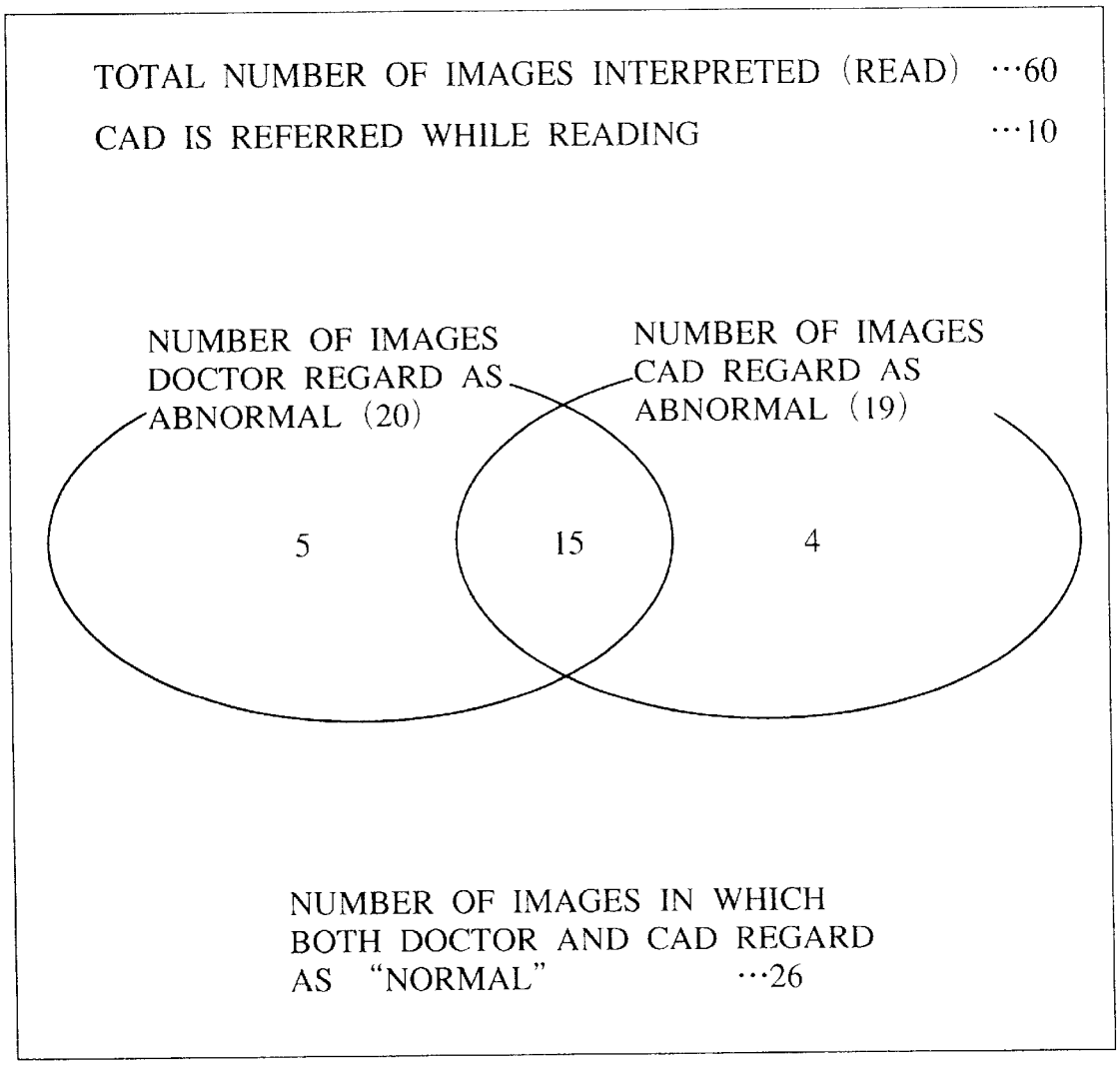
FIG. 35 is another set-expressed diagram showing a classified comparison result.
Figure 36A:
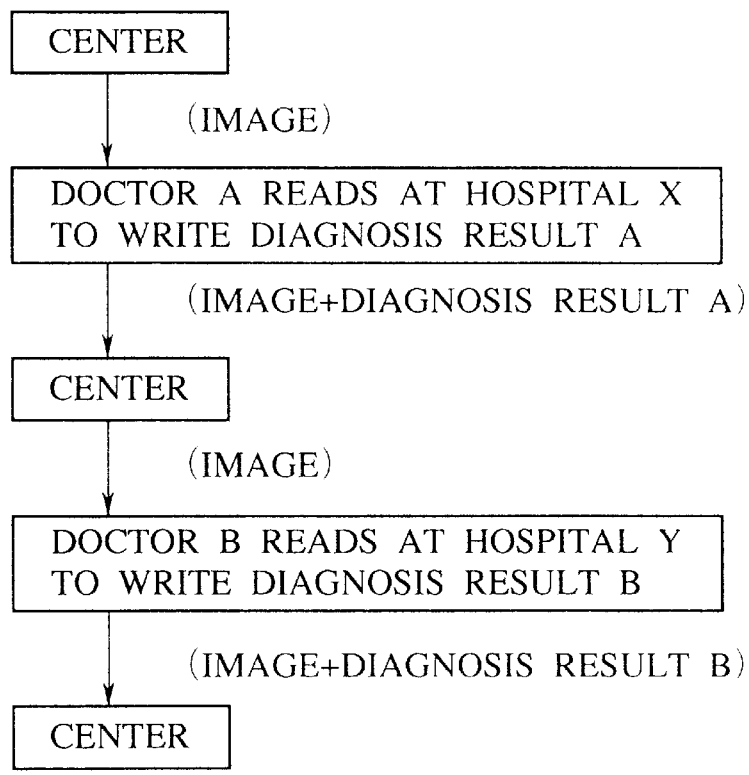
FIG. 36A and FIG. 36B illustrate interpreting ways as doctors read (interpret) images, in a usual manner.
Figure 36B:
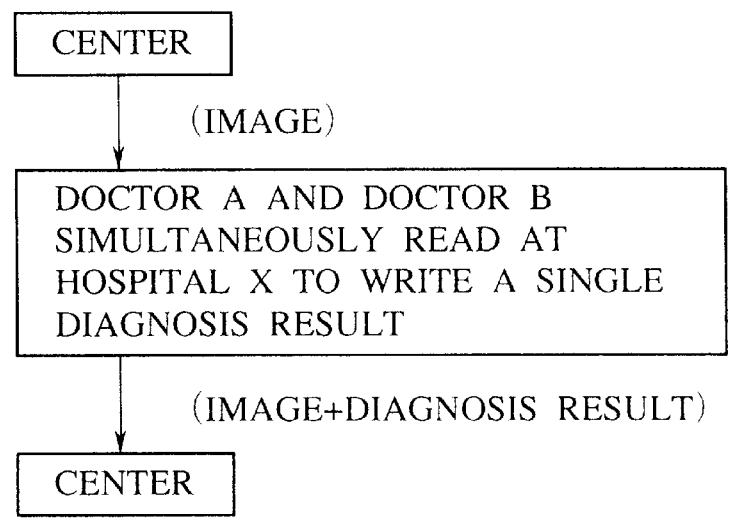

Thereafter, the control unit (WS-CTRL) displays the classified results in Section 5, Subsection (4) in the display unit (WS-DISP) as shown in FIG. 34.

The doctor selects the operations after classified as described in Section 5, Subsection (4). The doctor inputs an operation selection command from the input unit (WS-INPUT) to select an operation conforming to his/her way of thinking. In this embodiment, the doctor shall select (a-2), (b-2), and (d-1). When the doctor inputs the command, the control unit (WS-CTRL) operates (d-1) and creates an abnormality detecting result list.

(6) Re-interpretation and Reference of Abnormality Detecting Result

A doctor inputs a re-interpretation command. Then, the control unit (WS-CTRL) reads out the data of images to be interpreted which register the examination ID number in the abnormality detecting result list and the information relating to the examined persons (hearing information, information attached to an examination and an image (an abnormality data table, a finding data table, overlay display information), previous image data) from the data memory (WS--MEM), and superimposes the image to be interpreted on the overlay meaning his/her finding to display it on the left-sided display unit (WS-DISP) of two display units (WS-DISP), and superimposes the overlay meaning the CAD processing results concerning the image on the image to display it on the right-sided display unit (WS-DISP).

The doctor reads an image and compares his/her finding with the CAD processing results.

When displaying the images and the interpretation reports other than those displayed, the doctor inputs a command for it from the input unit (WS-INPUT) and operates.

When the doctor finishes interpreting the image and discovers shadows of an abnormality, he/she points out its position on the image to be interpreted by a mouse. Also, he/she can correct the position of an abnormality which is previously pointed out by a mouse.

Thereafter, a doctor operates in the same manner as operated in Section 5, Subsection (3), (c) and after, he/she inputs all the discovered abnormalities. The control unit (WS-CTRL) memorizes the corrected finding data table into the data memory (WS-MEM), and the overlay of the next image and the doctor's finding and the overlay of the CAD processing result, which are registered into the abnormality detecting result list, are displayed in the display unit (WS-DISP).

As described above, the procedure as described in Subsection (6) will be carried out for all the images registered in the abnormality detecting result list.

(7) Write of Finding data into Optical Magnetic Disk

The control unit (WS-CTRL) reads out the finding data table concerning all the images to be interpreted from the data memory (WS-MEM) and writes it into the optical magnetic disk inserted into the optical magnetic disk drive (WS-MODD).

These operations in Section 5, Subsections (1) to (7) will be carried out at two locations.

6. Output of Interpretation Results (1) Registration of Finding Data into Database An operator inserts the optical magnetic disk memorizing the finding data additionally into the optical magnetic disk drive (DB-MODD) of the database (DB), and inputs a finding data readout command of the optical magnetic disk from the input unit (DB-INPUT). Then, by an instruction of the control unit (CB-CTRL), the optical magnetic disk drive (DB-MODD) reads out the finding data memorized in the optical magnetic disk and writes them into the data storing unit (DB-STRG). The control unit (DB-STRL) extracts directory information from the finding data to be sent to the search unit (DB-SRCH). The search unit (DB-SRCH) stores the received directory information.

Another sheet of optical magnetic disk is also registered into the database in the same manner. Thus, the two doctors' finding data concerning the identical examination image have been inputted into the database.

(2) Extraction of Persons To Whom Close Examination is Required (i) An operator inputs an extracting command of persons to be made a close examination and an operation selecting command from the input unit (DB-INPUT) of the database (DB). Then, by an instruction of the control unit (DB-CTRL), the search unit (DB-SRCH) searches a finding data table of a chest X-ray examination which has not been made overall judgments of interpretation results (judgements as to whether a close examination is necessary or not), and reads out the examined person identification information and the two doctors' diagnostic result information in the system memory of the control unit (DB-CTRL).

(ii) The control unit (DB-CTRL) extracts the two doctors' diagnostic results of each examined person from the finding data table and the following comparison will be made:

Case $\alpha$: Both of the two diagnosed results are "normal".

Case $\beta$: One of the diagnosed results is "abnormal, but the other "normal".

Case $\gamma$: Both of the two disgnosed results are "abnormal".

A deciding method of overall judgements can be selected. Selection may be made in the following manner:

In the case $\alpha$, the overall judgement is "normal".

In the case $\beta$, the following two selections are available.

($\beta$-1): The overall judgement is made as "abnormal".

($\beta$-2): The overall judgement is made as "normal".

In the case $\gamma$, the following two selections are available.

($\gamma$-1): no operation is carried out and the overall judgement is made as "abnormal".

($\gamma$-2): The diagnostic information in Section 5, Subsection (4) is compared and classified for the position of abnormalities in the two finding data tables, namely compared and classified concerning the position of abnormalities in accordance with the type of abnormalities. In this case, the overall judgement is made as "abnormal".

(iii) In this embodiment, an operator inputs, from input unit (DB-INPUT), a command for selecting the above-mentioned operation ($\beta$-1) and ($\gamma$-1) concurrently with a command of extracting persons to be made a close examination. Then, the overall judgements are transferred to the data storing unit (DB-STRG) and the search unit (DB-SRCH) corresponding to the examined person identification information to be stored therein.

(3) Output of Interpretation Results

The control unit (DB-CTRL) reads out the overall judgements from the data storing unit (DB-STRG). According to results of the overall judgement, the following operations are available:

When the overall judgement results are "normal", the overall judgement results are written into the optical magnetic disk corresponding to the examined person identification information and the name of examined person.

When the overall judgement results are "abnormal", the control unit (DB-CTRL) indicates the search unit (DB-SRCH) to search the image to be interpreted from the data storing unit (DB-STRG) to be read out. The two doctors' finding data table and overall judgements and the images to be interpreted are written into the optical magnetic disk corresponding to the examined person identification information and the name of examined person.

The optical magnetic disk is carried to a person to receive the report.

At this time, a flow of a series of system operations for interpreting the chest X-ray image in the lung cancer examination is completed.

Next, an embodiment according to the third embodiment of the present invention will be explained. As described above in FIGS. 13A, 13B and 14, a flow of a series of system operations in the third embodiment is carried out in the following procedures in the same manner as that in the second embodiment:

1. Input of hearing information
2. Acquisition of chest X-ray image
3. Registration of acquired data
4. Preparation of interpreting data
5. Interpretation of image data
6. Output of interpreting results Then, as the procedures in the items 1 to 3 are same as that of the second embodiment, the description therefor will be omitted. The third embodiment will be described in a similar example as in the second embodiment where the chest X-ray image in the lung cancer examination is interpreted.

4'. Preparation of Interpreting Data (1) Detection of Abnormality from Image (i) When registration of data is completed, the control unit (DB-CTRL) of the database (DB) indicates to search images registered in the search unit (DB-SRCH) (an image to be interpreted and a previous image) and obtains a response. Successively, the following abnormality detecting operation is carried out for each image. The abnormality to be detected is shadows of pulmonary nodules.

(ii) The control unit (DB-CTRL) reads out data corresponding to a sheet of image from the data storing unit (DB-STRG) to be sent to the image processing unit (DB-IP). When the image processing unit (DB-IP) receives the image data, it activates and operates means for detecting shadows of pulmonary nodules which is provided therein to detect a position of a doubtful abnormality on the image. The detected position of the abnormalities is on the coordinate axis of a left end of the image. It is recognized on the absolute coordinate system as shown in FIG. 24 and written into the abnormality data table as shown in FIG. 25. In the image of the examination ID number 920001, the abnormal shadows are detected at two positions of N1 (700, 1200) and N2 (1500, 1000). In the abnormality judgement of the entire image, when an abnormality is not entirely detected, "normal", and when at least one abnormality is detected, "doubtfully abnormal". In the image of the examination ID number 920001, as the abnormality is detected, the abnormality judgement of the entire image is "doubtfully abnormal". The abnormality data table which is detected results is stored in the data storing unit (DB-STRG).

The abnormality data tables in the image of the examination ID numbers 920002 to 920005 are shown in FIGS. 26 to 29.

(2) Preparation of Interpreting Data

When the abnormality detection processing from the images is completed, the control unit (DB-CTRL) of the database (DB) indicates the data storing unit (DB-STRG) to read out data of images to be interpreted, previous image data, hearing information, and information attached to an examination and an image (containing the abnormality data table), and indicates the optical magnetic disk drive (DB-MODD) to write them. The data storing unit (DB-STRG) reads out these data to send to the image bus (DB-IBUS). The optical magnetic disk drive (DB-MODD) receives these data to write into the optical magnetic disk.

In the medical group examination, two doctors interpret images. Accordingly, two optical magnetic disks are prepared and carried to two workstations (WS) each disk.

5'. Interpretation of Image Data (1) Input of Interpreting Data into Workstation An operator inserts the optical magnetic disk memorizing data of images to be interpreted, previous image data, hearing information, and information attached to an examination and an image into the optical magnetic disk drive (WS-MODD) of the workstation (WS), and inputs a data readout command derived from the optical magnetic disk from the input unit (WS-INPUT). Then, by an instruction of the control unit (WS-CTRL), the optical magnetic disk drive (WS-MODD) reads out the data memorized in the optical magnetic disk and writes them into the data memory (WS-MEM). The data of images to be interpreted, the previous image data, the hearing information, and the information attached to an examination and an image are memorized corresponding to each examined person.

The control unit (WS-CTRL) creates the overlay display information from the abnormality data table and the overlay display information is memorized in the data memory (WS-MEM) corresponding to the examination ID numbers. The overlay display information created from the abnormality data table of the examination ID number 920001 is shown in FIG. 32. Similarly, the overlay display information is created for each examination ID number.

(2) Display of Image

The workstation displays images to be interpreted. Now, as two display units (WS-DISP) are provided, a sheet of image to be interpreted (the examination ID number 910001) is automatically displayed in the left-sided display unit (WS-DISP). Furthermore, when an image is displayed in the display unit (WS-DISP), its examination ID number (included in the information attached to an image) is displayed (3) Input of Interpreting Finding From the interpretation to an input of findings which are its results, the following procedure is carried out:

(a) An interpreting doctor reads an image displayed.

When displaying an image or an interpretation report other than the displayed image, the doctor inputs a command for it from the input unit (WS-INPUT) and operates.

When displaying the CAD processing results in the case of referring to the CAD processing results, the doctor inputs a CAD processing result display command from the input unit (WS-INPUT). Then, the control unit (WS-CTRL) indicates the image display manager (WS-IDM) to create an overlay according to the overlay display information and to superimpose it on the image to be interpreted in the left-sided display unit (WS-DISP) to display it, and also to register the examination ID number in the CAD processing result reference list to memorize it in the data memory (WS-MEM). When an operator desires to delete the CAD processing results, he/she inputs a CAD processing result deleting command from the input unit (WS-INPUT). Then, the control unit (WS-CTRL) indicates the image display manager (WS-IDM) to delete the overlay.

(b) When a doctor finishes interpreting an image, he/she points out a position of shadows of pulmonary nodules on the image to be interpreted with a mouse.

The control unit (WS-CTRL) reads a coordinate of the inputted position of an abnormality to memorize to create the finding data table as shown in FIG. 30. Then, the image display manager (WS-IDM) creates overlay display information describing "arrow, coordinate of position of abnormalities, white, display" as to the abnormality of each finding number with reference to the finding data table. The created overlay display information is shown in FIG. 31. The image display manager (WS-IDM) creates the overlay according to the overlay display information to display it. As a result, an arrow is diplayed in a position where the doctor points out on the image. The control unit (WS-CTRL) writes the created overlay display information into the data memory (WS-MEM) corresponding to the examination ID number.

(c) When an interpreting doctor recognizes an abnormality other than pulmonary nodules, he/she inputs an abnormaity type selecting command from the input unit (WS-INPUT) and selects a corresponding type of abnormalities among the displayed several types of abnormalities. Next, the doctor inputs a position of abnormalities and a method of inputting the position of abnormalities is different for each type of abnormalities. For example, in the interstitial lung disease, the doctor inputs it by enclosing a scope of abnormalities with a closed curved line by using a mouse. In this case, the control unit (WS-CTRL) memorizes an area instead of a position.

A doctor carrys out the same operations and adds information relating to an abnormality to an overlay to be memorized and displays on the image.

(d) When an interpreting doctor inputs all discovered abnormalities, he/she inputs an interpretation completing command.

When the finding data table is inputted as an abnormality, the control unit (WS-CTRL) writes the diagnosed results of the entire image as an "abnormality" into the finding data table, and when the finding data table is not inputted as an abnormality, the control unit (WS-CTRL) writes the diagnosed results of the entire image as a "normality" into the finding data table to memorize into the data memory (WS-MEM).

(4) Comparison and Classification of Diagnostic Information

The control unit (WS-CTRL) reads out a finding data table which is interpreted results and an abnormality data table which is the corresponding CAD processing results and the CAD processing result reference list from the data memory (WS-MEM). When the examination ID number is registered in the CAD processing result reference list, the control unit (WS-CTRL) compares diagnostic information. In this case, it classifies into the following case e to complete Subsection (4).

Case e: A doctor has already referred to the CAD processing results as interpreting images.

When the examination ID number is not registered in the CAD processing result reference list, the control unit (WS-CTRL) extracts the diagnosed results of the entire image from the finding data table and the judged results of the entire image of the CAD processing from the abnormality data table, and compares the both results to classify them into the following four cases:

Case a: The doctor judges as an "abnormality", but the CAD judges as a "normality".

Case b: The doctor judges as an "abnormality", but the CAD judges as a "doubtful abnormality".

Case c: The doctor judges as a "normality" and the CAD also judges as a "normality".

Case d: The doctor judges as a "normality", but the CAD judges as a "doubtful abnormality".

For example, as, concerning the examination ID number 920001, the doctor judges as an "abnormality" and the CAD judges as a "doubtful abnormality", this case is classified into the case b.

According to the above-mentioned classification results, the later operations are different. The available operations are described below.

(a) When classifying into the case a, the following operations are available:
   (a-1) An examination ID number is registered in an abnormali-ty detecting result list.
   (a-2) No operations.

(b) When classifying into the case b, the following operations are available:
   (b-1) With reference to a finding data table and an abnormality data table, at least a type of an abnormality and its position are compared and classified. The examination ID number of an image having a discrepancy in the type of an abnormality and its position is registered in an abnormality detecting result list.
   (b-2) No operations.

(c) When classifying into the case c, no operations.

(d) When classifying into the case d, the following operations are available.
   (d-1) An examination ID number is registered in an abnormality detecting result list.
   (d-2) No operations.

Herein, the respective operations (a-1), (b-1), and (d-1) will be explained.

As to the operations (a-1) and (d-1),

The control unit (WS-CTRL) reads out the abnormality detecting result list (if it does not exist, create it) and writes it into the examination ID number to be memorized into the data mamory (WS-MEM).

As to the operations (b-1):

The explanation is made according to an example of the examination ID number 920001. When seeing finding numbers 1 and 2 with reference to FIG. 30, the type of an abnormality is pulmonary nodules. In the pulmonary nodules, a scope to be processed by the CAD is the entire image. Also, a method of indicating the position of an abnormality by a doctor is the same as that by the CAD to show it with an arrow in the overlay. Accordingly, it is determined that the position of an abnormality shall be shown with a tip of an arrow to seek its coordinate. From FIGS. 25 and 30, the respective coordinates are A1 (1520, 1040), A2 (1430, 659), N1 (700, 1200), and N2 (1500, 1000).

If distances between the positions of an abnormality (A1, A2) indicated by the doctor and between the positions of an abnormality (N1, N2) detected by the CAD are less than a predetermined value A0 (=100), the identical positions of an abnormality shall be indicated.

Comparison of A1 and N1: $\sqrt{\{(1520-700)^2+(1040-1200)^2\}}=835>100$

Comparison of A1 and N2: $\sqrt{\{(1520-1500)^2+(1040-1000)^2\}}=45<100$

Comparison of A2 and N1: $\sqrt{\{(1430-700)^2+(659-1200)^2\}}=909>100$

Comparison of A2 and N2: $\sqrt{\{(1430-1500)^2+(659-1000)^2\}}=348>100$

Accordingly, A1 and N2 indicate the identical abnormality and the information of controlling presence or absence of a display of N2 in the overlay display information of the CAD processing results is rewritten from a "display" to a "non-display". Only the CAD shall detect N1 and the doctor shall not indicate it, and the information of controlling presence or absence of a display is still a "display". Also, only the doctor shall discover A2 and the CAD shall not detect it.

As described above, when the doctor overlooks abnormalities or diagnoses excessively and the abnormalities pointed out by the doctor and the CAD are inconsistent, the control unit (WS-CTRL) writes the examination ID number of this image into the abnormality detecting result list.

(5) Display of Comparing Results and Creation of Abnormality Detecting Result List The operations corresponding to the number of all sheets of images to be interpreted in Section 5, Subsections (1) to (4) are repeated.

The control unit (WS-CTRL) extracts the diagnostic results and the judging results for the entire image from the finding data table of the doctor and the abnormality data table of the CAD, and a part of results compared and classified is shown in FIG. 33. The interpreted images are 60 sheets of the examination ID numbers 920001 to 920060. The classified results were:

Case a: 5 sheets Case b: 15 sheets

Case c: 26 sheets Case d: 4 sheets

Case e: 10 sheets

Thereafter, the control unit (WS-CTRL) displays the classified results in Section 5, Subsection (4) on the display unit (WS-DISP) as shown in FIG. 34.

The doctor selects the operations after classified as described in Section 5, subsection (4). The doctor inputs an operation selection command from the input unit (WS-INPUT) to select an operation conforming to his/her way of thinking. In this embodiment, the doctor shall select (a-2), (b-2), and (d-1). When the doctor inputs the command, the control unit (WS-CTRL) operates (d-1) and creates an abnormality detecting result list.

(6) Re-interpretation and Reference of Abnormality Detecting Results

A doctor inputs a re-interpreting command. Then, the control unit (WS-CTRL) reads out the data of images to be interpreted which register the examination ID number in the abnormality detecting result list and the information relating to the examined persons (hearing information, information attached to an examination and an image (an abnormality data table, a finding data table, overlay display information), previous image data) from the data memory (WS-MEM), and superimposes the image to be interpreted on the overlay meaning his/her finding to display it on the left-sided display unit (WS-DISP) of two display units (WS-DISP), and superimposes the overlay meaning the CAD processing results concerning a specific image on the image to display it on the right-sided display unit (WS-DISP).

The doctor reads an image and compares his/her finding with the CAD processing results.

When displaying the images and the interpretation reports other than those displayed, the doctor inputs a command for it from the input unit (WS-INPUT) and operates.

When the doctor completes interpreting the image and discovers shadows of an abnormality, he/she points out its position on the image to be interpreted by a mouse. Also, he/she can correct the position of an abnormality which is previously pointed out by a mouse.

Thereafter, a doctor operates in the same manner as operated in Section 5, Subsection (3), (c) and after, he/she inputs all the discovered abnormalities. The control unit (WS-CTRL) memorizes the corrected finding data table into the data memory (WS-MEM), and the overlay of the next image and the doctor's finding and the overlay of the CAD processing results, which are registered into the abnormality detecting result list, are displayed in the display unit (WS-DISP).

As described above, the procedures as described in Subsection (6) will be carried out for all the images registered in the abnormality detecting result list.

(7) Write of Finding Data into Optical Magnetic Disk

The control unit (WS-CTRL) reads out the finding data table concerning all the images to be interpreted from the data memory (WS.-MEM) and writes it into the optical magnetic disk inserted into the optical magnetic disk drive (WS-MODD).

These operations in Section 5, Subsections (1) to (7) will be carried out at two locations.

6'. Output of Interpretation Results (1) Registration of Finding Data into Database An operator inserts the optical magnetic disk memorizing the finding data additionally into the optical magnetic disk drive (DB-MODD) of the database (DB), and inputs a finding data readout command of the optical magnetic disk from the input unit (DB-INPUT). Then, by an instruction of the control unit (DB-CTRL), the optical magnetic disk drive (DB-MODD) reads out the finding data memorized in the optical magnetic disk and writes them into the data storing unit (DB-STRG). The control unit (DB-STRL) extracts directory information from the finding data to be sent to the screen unit (DB-SRCH). The search unit (DB-SRCH) stores the received directory information.

Another sheet of optical magnetic disk is also registered into the database in the same manner. Thus, the two doctors' finding data concerning the identical examination image have been inputted into the database.

(2) Extraction of Persons to be Made Close Examination (i) An operator inputs an extracting command of persons to be made a close examination and an operation selecting command from the input unit (DB-INPUT) of the detabase (DB). Then, by an instruction of the control unit (DB-CTRL), the search unit (DB-SRCH) searches a finding data table of a chest X-ray examination which has not been made overall judgements of interpretation results (judgements as to whether a close examination is necessary or not), and reads out the examined person identification information and the two doctors' diagnostic result information in the system memory of the control unit (DB-CTRL).

(ii) The control unit (DB-CTRL) extracts the two doctors' diagnostic results of each examined person from the finding data table and the following comparison will be made:

Case α: Both of the two diagnosed results are "normal".

Case β: One of the two diagnosed results is "abnormal", but the other "normal".

Case γ: Both of the two diagnosed results are "abnormal".

A deciding method of overall judgements can be selected.Select in the following.

In the case α, the overall judgement is "normal".

In the case β, the following two selections are available.

(β-1): The overall judgement is made as "abnormal".

(β-2): The overall judgement is made as "normal".

In the case g, the following two selections are available.

(γ-1): No operations are carried out and the overall judgement is made as "abnormal".

(γ-2): The diagnostic information in Section 5, Subsection (4) is compared and classified for the position of abnormalities in the two finding data tables, namely compared and classified concerning the position of abnormalities in accordance with the type of abnormalities. In this case, the overall judgement is made as "abnormal".

(iii) In this embodiment, an operator inputs, from input unit (DB-INPUT) a command for selecting the above-mentioned operations (β-1) and (γ-1) concurrently with a command of extracting persons to be made a close examination. Then, the overall judgements are transferred to the data storing unit (DB-STRG) and the search unit (DB-SRCH) corresponding to the examined person identification information to be stored therein.

(3) Output of Interpretation Results

The control unit (DB-CTRL) reads out the overall judgements from the data storing unit (DB-STRG). According to results of the overall judgement, the following operations are available:

When the overall judgement results are "normal", the overall judgement results are written into the optical magnetic disk corresponding to the examined person identification information and the name of examined person.

When the overall judgement results are "abnormal", the control unit (DB-CTRL) indicates the search unit (DB-SRCH) to search the image to be interpreted from the data storing unit (DB-STRG) to be read out. The two doctors' finding data table and overall judgements and the images to be interpreted are written into the optical magnetic disk corresponding to the examined person identification information and the name of examined person.

The optical magnetic disk is carried to a person to receive the report.

At this time, a flow of a series of system operations for interpreting the chest X-ray image in the lung cancer examination is completed.

In this connection, the findings of the doctor's interpretation results and the CAD processing results are compared and classified and the classified results can be selected after the comparison, and a time of selection may beforehand be indicated before the interpretation or the time of selection may be indicated after interpreting a plurality of images, or the time of selection may be fixed in a recommending form without selecting the time.

When extracting the examined persons (to whom the close examination is required) in the database, the operations after comparing a plurality of doctors' findings may be selected, and the time of selection may be carried out before inputting data into the database or at an inputting time, or at a comparing time, or may be fixed in a recommending form without selecting the time.

In these second and third embodiments, a form of an elliptic set has been used as a method of displaying comparison results, which is however not limited to its form, and any methods of various sets such as a rectangle etc., various graphics such as a rod, a circle etc., and an itemization can be used.

Furthermore, in these embodiments, the time of referring to the CAD processing results was decided before a doctor inputs his/her findings, however the reference time is not limited to this time and the reference time may be decided after the doctor inputs his/her findings.

Furthermore, in these embodiments, the operations on an off-line PACS have been described, however even the operations on an on-line PACS may be carried out without being limited to the off-line PACS.

In these embodiments, the description on the medical images was made. These embodiments can be applied to medical examination data other than images, namely data having a graphic form such as an electrocardiogram, brain waves, or the like, or data arranged numerical values obtained by an automatic chemical analyzer etc.

In these embodiments, the medical examination of a lung cancer was described in an example of the chest X-ray images, however this embodiment can be applied to a medical examination or a detection of an organ of a digestive system such as a stomach or the like other than a chest.

As described above, as, in the present invention, it is unnecessary to indicate the images to be re-interpreted by the doctor every sheet of images and he/she has only to indicate the displayed set, the doctor can reduce his/her work amount. Also, as the doctor can make use of the CAD at interpreting the images, it is possible to prevent the doctor's overlooks in a medical examination or the like. Furthermore, even if the doctor uses the CAD, his/her operation hours do not almost increase.

As it is possible to distinguish the images diagnosed with reference to the CAD processing results from the images diagnosed after the doctor solely interprets them, the images diagnosed with reference to the CAD processing results can be removed when the doctor re-interprets the images, so that the interpreting time can be saved.

In the medical group examination in the center etc., no persons has to work thereon, or at least their work amount can considerably be reduced. Also, the period from the medical examination to the examination result outputs can be shortened.

Embodiment No. 4

Hereinafter, a preferred embodiment (fourth embodiment) according to the third aspect of the present invention will be described with reference to the accompanying drawings. In this embodiment, an example of performing a CAD by using a PACS will again be described. First of all, the gist of the embodiment will be described and next a system configuration of the PACS is described and finally procedures of an interpretation by using the system of the present invention will be described in detail. After the explanation on the system configuration of PACS, taken up is an example where a chest X-ray image is interpreted (read).

Figure 37:
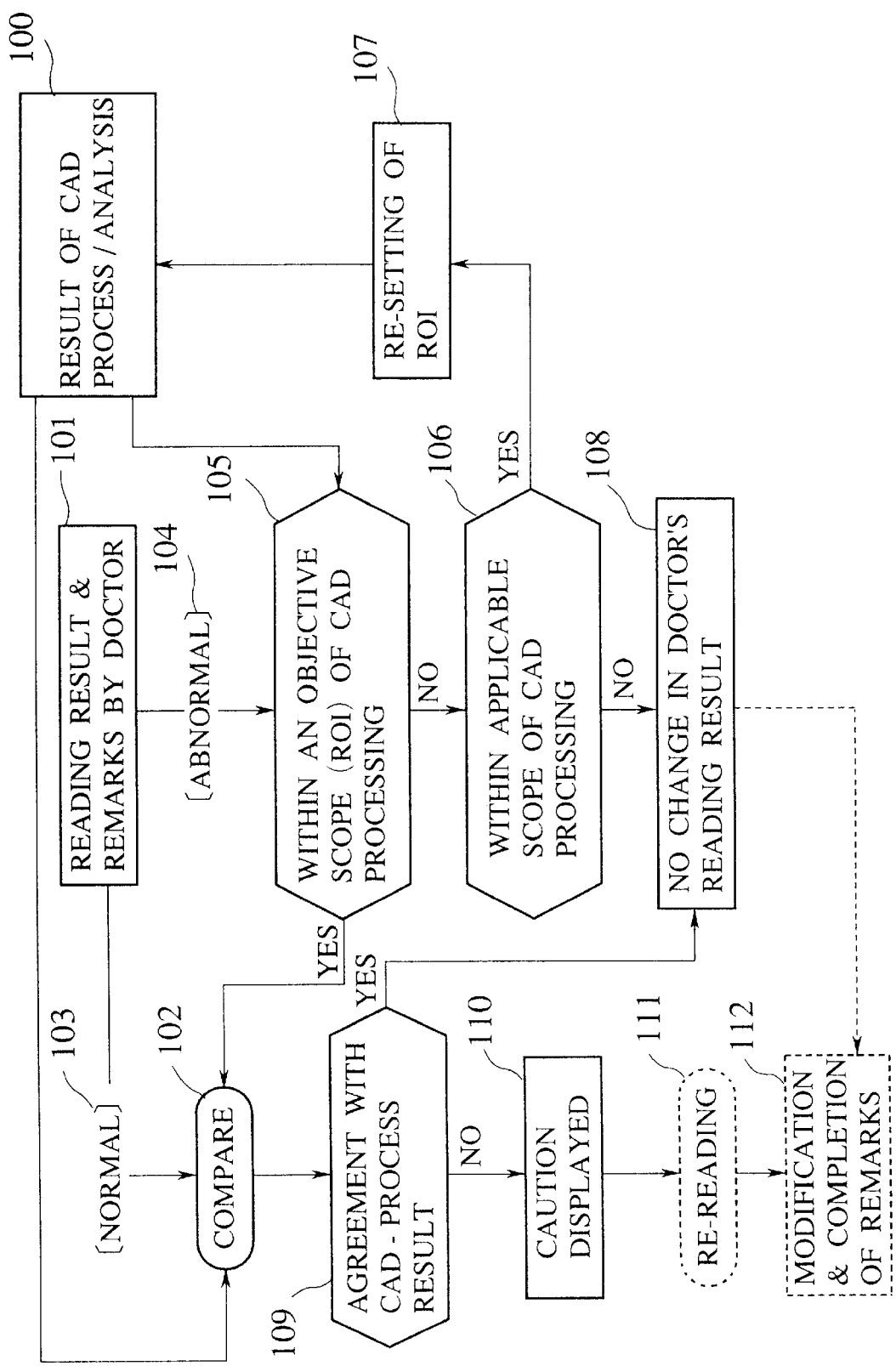
FIG. 37 is a flowchart representing the fourth embodiment.

FIG. 37 is a flowchart for explaining the gist of the present invention. A digital image which is a species of medical examination data is inputted into the PACS from an image acquisition unit and stored in a database and can be supplied to a workstation as occasion demands. When interpreting, the digital image is first sent from the database to the workstation. In FIG. 37, the CAD is applied to the digital image transmitted to the workstation and the digital image is CAD-processed to obtain its analyzing results 100. On the other hand, a doctor etc. interprets digital images and inputs its resultant findings 101. The interpreting finding 101 and the CAD processing result 100 about each disease are compared in detail (102), and in advance of the comparison, the images are classified into two categories: ones judged contents of the interpreting findings 101 as a normality (103); and ones diagnosed as an abnormality (104). The images diagnosed as a normality (103) are deemed as an object of the comparison 102 as it is. The images diagnosed as an abnormality (104) are first judged as to whether or not the images are existent within an objective scope (ROI) of the CAD processing (105). Its decided results can be outputted and displayed. When the images are existent within the objective scope (ROI:region of interest) of the CAD processing as a result of the judgement 105, the comparison 102 is made as it is. However, when the images are existent external to the objective scope (ROI) of the CAD processing as a result of the judgement 105, it is next judged as to whether the images are existent within or external to an applicable scope of the CAD processing (106). If the images are existent within the applicable scope of the CAD processing as a result of the judgement 106, the objective scope (ROI) of the CAD processing is automatically reset (107) and the images are CAD-processed once more to obtain its results 100. Also, if the images are existent external to the applicable scope of the CAD processsing, the CAD does not make anything concerning this abnormality. Accordingly, doctor's interpretation findings as it is are used concerning this abnormality (108). Then, in this case, the effect can be outputted and displayed.

Thus-obtained CAD processing results 100 and the interpretation findings (101) of a doctor etc. are compared in detail (102). By the comparison, the images are classified into two categories as to whether the CAD processing results 109 are consistent or inconsistent with the interpretation findings 101 of a doctor etc. (109). As a result of the classification 109, doctor's interpretation findings as it is are used concerning the consistent images (108). However, concerning the inconsistent images, the effect is displayed (110) to arouse attentions to an interpreting doctor etc. The images displayed (110) are re-interpreted by a doctor etc. (111), and the interpretation findings are corrected if necessary (101) to complete the findings (112) containing the interpretation findings as it is (108). In this connection, it is shown that a part indicated by a broken line in the figure is not a major part in this novel embodiment.

Next, an embodiment of a basic system configuration of the PACS will be shown in FIG. 1. This system comprises various; systems (subsystems) of:
1) system manager (SN) 1
2) image acquisition unit (IA) 2a, 2b
3) database (DB) 3
4) workstation (WS) 4
5) network (NW) 5

A network (NW) 5 is a transmission path between commands and data for communicating among respective units and an optical fiber etc. is used as a transmission medium. The network (NW) 5 shown in FIG. 1 is a ring-type local area network, however the other types such as a star-type one or the like can be used..

Each unit of a system manager (SM) 1, an image acquisition unit (IA) 2, a database (DB) 3, and a workstation (WS) 4 is connected with the network (NW) 5, and these units have a communication protocol and can communicate each other through the network (NW) 5.

The network (NW) 5 in the PACS is connected with an examination order system 7 for making examination request information through a gateway 6 and the examination request information is sent from the examination order system 7 to the system manager (SM) 1 in the PACS through the gateway 6.

The image acquisition unit (IA) 2 is a medical image acquisition unit for the PACS such as an X-ray machine, an X-ray CT machine, an MRI machine, a film digitizer or the like, and a plurality of image acquisition units (the same type of unit or the different type of unit) can be connected with one network (NW) 5.

The database (DB) 3 is a storage of a digital image created in the image acquisition unit (IA) 2 and is provided with a low-speed medium (optical disk etc.) or a high-speed medium (magnetic disk etc.).

The workstation (WS) 4 appropriately processes digital images etc. sent from the database (DB) 3 or the image acquisition unit (IA) 2 to obtain desired results and displays or outputs them.

Next, as to the respective units (subsystems) excluding the network (NW) 5, a function of the subsystems and its configuration element will be described. A film digitizer is picked up as the image acquisition unit (IA) 2.

Main functions and acts of the system manager (SM) 1 will be described.

The system manager (SM) 1 receives examination request information from the examination order system 7 and issues an examination ID number. Types of data included in the examination request information received from the examination order system 7 are shown in FIG. 38.

The system manager (SM) 1 stores the examination request information and the examination ID number.

The system manager (SM) 1 prepares examination histories of a patient and stores them.

The system manager (SM) 1 stores interpretation reports.

The system manager (SM) 1 stores interpreting reference image preparation rule information and indicates the database (DB) 3 to prepare images inside (readout from a low-speed medium to a high-speed medium) based on the information.

The system manager (SM) 1 stores information as to which workstation (WS) 4 interprets and what kind of inspection is interpreted by the image, and the system manager (SM) 1 notifies each workstation (WS) 4 of what kind of inspection is scheduled to be interpreted therein.

A film digitizer serves as the image acquisition unit (IA) 2, and the main functions and acts therefor will be described.

The film digitizer reads film concentration of, for example, an X-ray film and digitizes it to produce a digital image.

The film digitizer demands the system manager (SM) 1 to transfer the examination request information and receives the examination request information sent from the system manager (SM) 1.

The film digitizer inputs information attached to an examination or an image to be displayed.

The film digitizer transfers image data and the information attached to an examination or an image to the database (DB) 3.

Main functions and acts of the database (DB) 3 will be described.

The database (DB) 3 stores the image data and information attached to examination information and an image.

By an instruction from the system manager (SM) 1, the image of the indicated examination is read out from a low-speed medium (optical disk etc.) to a high-speed medium (magnetic disk etc.).

The database (DB) 3 supplies data to the other units as occasion demands.

Main functions and acts of the workstation (WS) 4 will first be described.

The workstation (WS) 4 can display examination request information, examination histories, images, an interpretation report, and the like.

The workstation (WS) 4 can input newly created interpretation reports.

The workstation (WS) 4 processes for a computer-aided diagnosis (CAD). This process is called a CAD processing.

The workstation (WS) 4 stores results of the CAD processing and compares the results with findings of the inputted interpretation reports for each interpretation point.

When the results of the CAD processing are different from the findings of the inputted interpretation reports in the meaning, the workstation (WS) 4 outputs the effect.

When the results of the CAD processing indicate to be abnormal as to a certain interpretation point and the findings of the interpretation report as to the interpretation point have not been inputted, the workstation (WS) 4 outputs the results of the CAD processing.

The workstation (WS) 4 outputs the results of the CAD processing in accordance with doctor's demands.

The workstation (WS) 4 creates a list of the image to be re-interpreted.

Figure 39:
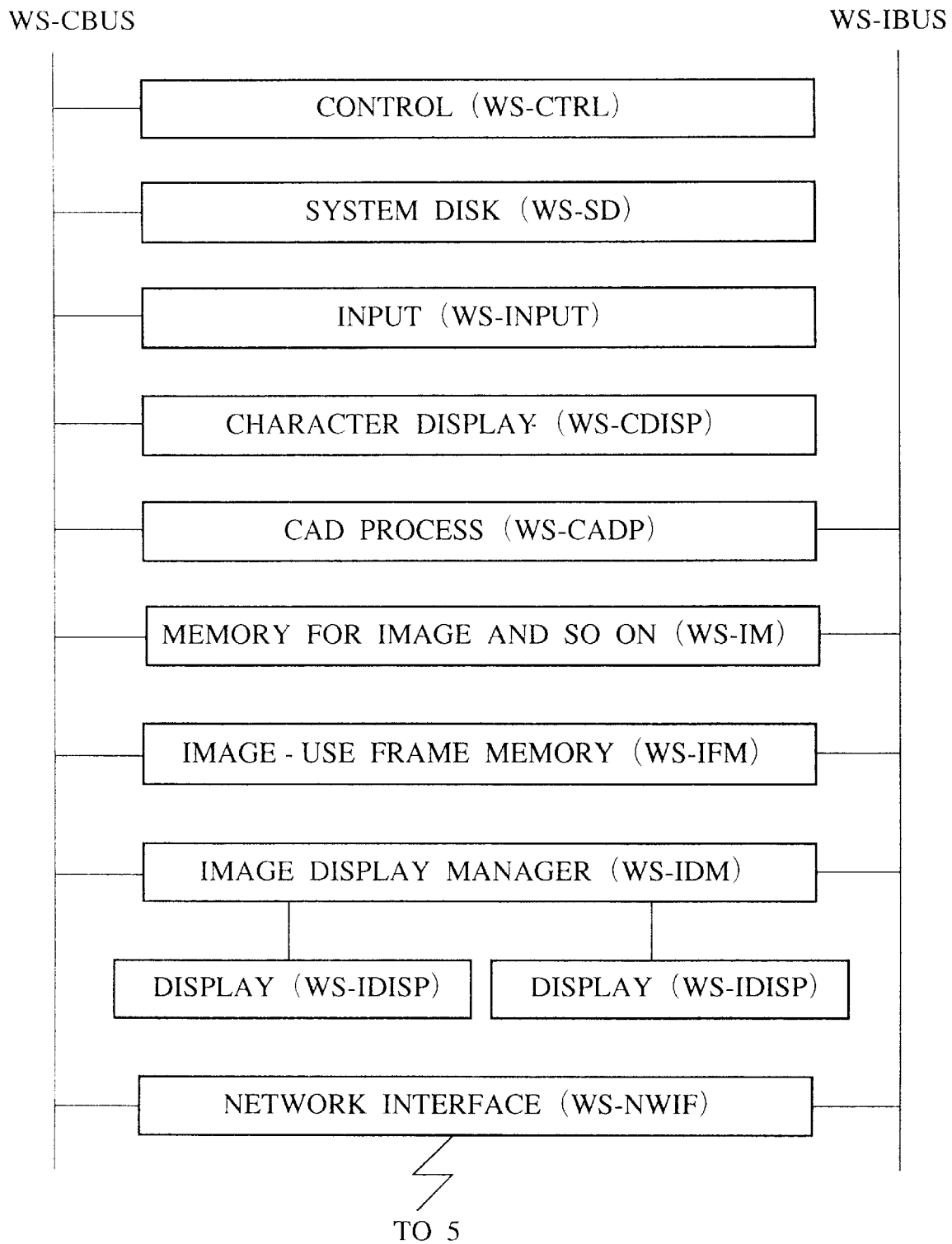
FIG. 39 is a configurational diagram showing the workstation (WS).

Next, a configuration element and a function of the workstation (WS) 4 will be described. FIG. 39 is a configurational diagram of the workstation (WS) 4.

Control Unit (WS-CTRL)

A control unit contains a central processing unit (CPU), a system memory (semiconductor memory), and the like and controls the entire operation of the workstation.

System Disk (WS-SD)

This is a magnetic disk and stores programs or data such as:

(a) a program for programing the workstation;
(b) abnormality detecting means selecting information;
(c) relating information of a temporal change of an abnormality and a display color;
(d) relating information of an imaging direction of an image of a chest plain X-ray radiographing image and a relative display position;
(e) an interpreting doctor's information table; and the like.

These programs or data are read out when an electric power of the workstation (WS) 4 is turned on and written into system memories within the control unit (WS-CTRL).

The abnormality detecting means selecting information of (b) is a table which corresponds a type of image (an examination portion, a modality, a medical examination method, an imaging direction) to a type of an abnormality which can be detected in the image, and more specifically it is the data as shown in FIG. 40. The detectable data showing the type of an abnormality are used as data indicating the abnoramality detecting means for the CAD processing unit (WS-CADP). The abnormality detecting means selecting means can be rewritten.

The relating information of a temporal change of an abnormality and a display color of (c) is information showing which color is displayed when the temporal change of an abnormality is superimposed on the image to be displayed.

The relating information of the imaging direction of the image of the chest plain X-ray radiographing image and the relative display position of (d) is information for deciding automatically a display position of an image, and table data shown in FIG. 41. The meaning of the decription of this table is as follows:

"P→A" indicates that X-rays irradiate from the back side of a patient and in this case, an image is a frontal one.

"L→R" indicates that X-rays irradiate from the left side of a patient and in this case, an image is a right-sided one.

"R→L" indicates that X-rays irradiate from the right side of a patient and in this case, an image is a left-sided one.

C indicates to display in a center.

L indicates to display on the left side of the image (frontal image) of "P→A".

R indicates to display on the right side of the image (frontal image) of "P→A".

In this case, table data shown in FIG. 41 can be rewritten.

The interpreting doctor's information is a table which corresponds an interpreting doctor ID number to a name of an interpreting doctor, and table data as shown in FIG. 42.

In this connection, when each of the above-mentioned writable data is changed, a table relating to the data is displayed in a character display unit (WS-CDISP), and new data are inputted from the input unit (WS-INPUT) and the renewed data are overwritten on the pre-renewed data, whereby the data can be written.

Input Unit (WS-INPUT)

This is means for an operator's inputting information such as commands, interpretation reports, or the like, and a keyboard, a mouse, a touch screen, or the like is used.

Character Display Unit (WS-CDISP)

This is a unit for mainly displaying characters such as examination request information, examination histories, interpretation reports, or the like, and a CRT display, a liquid crystal panel display, or the like is used.

CAD Processing Unit (WS-CADP)

This contains image processing means for seeking a position where an abnormality of an indicated type exists and a degree of an abnormality as to an indicated image, and memorizing means for memorizing results obtained by the CAD processing. The control unit (WS-CTRL) can read out results obtained by the CAD processing.

The CAD processing unit (WS-CADP) contains means for detecting a plurality of types of an abnormality. That is:

(a) means for detecting shadows of an interstitial lung disease in a frontal image of a chest plain X-ray image;

(b) means for detecting shadows of pulmonary nodules in a frontal image of a chest plain X-ray image; and (c) means for detecting shadows of fine calcification of a breast in a breast X-ray image. These detecting means are disclosed in the following literatures:(1) Japanese Patent Application Laid-Open No. 2-185240; (2) Japanese Patent Application Laid-Open No. 2-152443; and (3) Japanese Patent Application Laid-Open No. 1-125675.

When two types of data:(i) data showing a type of an abnormality to be detected; and (ii) image data are inputted into the CAD processing unit (WS-CADP), which analyzes image data by the indicated detecting means, and if detecting the abnormalities, the CAD processing unit (WS-CADP) seeks a position on the image and a degree of an abnormality and memorizes them in the inside memorizing means.

Also, in a normal dissection structure or a region on an image diagnosis, by an indication of the control unit (WS-CTRL), its position or region is partially memorized in the inside memorizing means. A recognition of the normal dissection structure or the region on the image diagnosis is required to decide the region to detect an abnormality, and for example, by using a technique disclosed in Japanese Patent Application Laid-Open No. 1-125675 (Japanese Patent Application No. 63-192171), a center line in the longitudinal direction of vertical intervals, or a lower edge of the collarbone, an upper edge of the diaphragm and a position of ribs of each right and left lung can be recognized. When, as to the ribs recognized, it is inputted what number of ribs a certain rib is, by recognizing successively that upper and lower ribs are the n-th ribs, it can be recognized that the position of the disease is between the n-th rib and the m-th rib and is one having a value of a relative distance from the vertical intervals (a value that a distance from the vertical intervals is divided by a distance between the vertical intervals and a rib end). This can make a comparison with the different images, for example, the image in the past examination of the identical patient.

The CAD processing unit (WS-CADP) seeks the absolute position or region of an abnormality with a coordinate system in which an upper end and a left end of the image are the reference (the origin), and further the relative position or region of an abnormality can be obtained based on the coordinate of the position of ribs by the following procedures:

(i) To seek a position of a center line in the longitudinal direction of vertical intervals (the coordinate in the lateral direction) which is defined as a Y-axis.

(ii) To seek a mean value of a position of an upper edge of the diaphragm of a right and left lung (the coordinate in the longitudinal direction), and a straight line perpendicular to the procedure (i) passing through the position is defined as an X-axis.

(iii) To seek the coordinate by defining an intersecting point of two lines obtained by procedures (i) and (ii) as the origin.

(iv) To recognize the number and position of ribs which are obtained previously to seek the relative position among the ribs.

(v) To add information of the relative position among the ribs to the absolute coordinate of an abnormality.

Position data of the normal dissection structure are shown in FIG. 43. This shows an example of the coordinate of each rib with the coordinate system shown in the procedure (iii).

Image Data Unit (WS-IM)

This is a unit for temporarily storing the following data and a magnetic disk:

(a) Interpreting reference priority order information
(b) Examination request information
(c) Examination histories
(d) Interpretation reports
(e) Information attached to an image
(f) Image data
(g) Overlay display information
(h) Abnormality data table
(i) Temporal change data table of an abnormality Imaging Frame Memory (WS-IFM)

This is a unit for temporarily memorizing a plurality of sheets of image data, and is a semiconductor memory.

Image Display Manager (WS-IDM)

This carries out operations for displaying an image and an overlay. FIG. 21 is a configurational diagram of the image display manager (WS-IDM) and a portion enclosed with a broken line is the image display manager (WS-IDM).

This contains the following units:

a) Control Portion

This controls the entire configuration portion of the image display manager (WS-IDM).

b) Overlay Data Making Portion

This makes overlay data (color) from the overlay display information.

This contains means for displaying only data indicated in the overlay display information.

c) Image Memory

This memorizes image data. This has memories corresponding to a sheet of image (a matrix size is 2,048×2,048 pixels).

d) Overlay Memory

This memorizes overlay data.

As the overlay data are displayed in color, the overlay memory of one screen is constructed of three sheets of overlay memory for red, green, and blue. As to the overlay memory for each color, conceptually a matrix size is 2,048× 2,048 pixels and a bit length of 1 pixel is 1 bit.

The relationship between a display color and a bit value of each pixel is shown in FIG. 22. In FIG. 22, for example, as shown in step 10, assuming that a pixel value (a bit value of a pixel) on the pixel coordinate (X, Y) of the overlay memory for red is 1 and that a pixel value on the same coordinate of the overlay memory for both green and blue is 0, red is displayed on the coordinates. On the other hand, the display color: black means that any colors are not displayed, and when a color is displayed by superimposing it on the image, only the image is displayed.

e) Overlay Portion

This superimposes image data on overlay data.

f) Displaying Memory (Memory for Storing Display Data)

This memorizes display data.

This image display manager (WS-IDM) has two sheets of displaying memory corresponding to a sheet of image (a matrix size is 2,048×2,048 pixels).

This number is same as that of the image display unit (WS-IDISP). The displaying memory corresponds to each image display unit (WS-IDISP).

g) D/A Converter

This converts display data from digital data to analog data.

This corresponds to each image display unit (WS-IDISP) and is provided with the same number as the image display unit (WS-IDISP).

The image display manager (WS-IDM) can receive the following information.

(a) Type of data to be displayed

There are three display types: an image only, an overlay only, the image and overlay combined.

(b) Indicated information of the image display unit (WS-IDISP) displaying data (c) Overlay display information One graphic has a type of a graphic, a size of a graphic, a coordinate, a display color, control information of presence or absence of display (containing a flicker), or the like.

(d) Image Data

When an image overlapping an overlay is displayed, the following operations are carried out:

(1) The control portion 40 of the image display manager (WS-IDM) receives the following three information from the control unit (WS-CTRL) of the workstation (WS) 4.

(a) An "image and overlay" as a type of data to be displayed.

(b) An image display unit number of the image display unit (WS-IDISP) displaying data.

(c) Overlay display information (2) The image display manager (WS-IDM) receives image data and writes them into the image memory 42.

(3) By an instruction of the control portion 40, the overlay data making unit 41 makes overlay data based on overlay display information and makes a specified graphic on a specified coordinate with specified color data.

(4) By an instruction of the control unit 40, the image data and the overlay data are read out and inputted into the overlay 44 to synthesize the data.

(5) The synthesized data are written into the displaying memory 45 of the indicated image display unit number.

(6) The synthesized data are converted into analog data by the D/A converter 46.

The above-mentioned operations (4) to (6) are always repeated during the dispaly.

Only when, as to a certain graphic on a coordinate, control information of presence or absence of a display (containing a flicker) indicates a "display", the overlay data making portion 41 writes the graphic into the overlay memory 43 to display it.

On the other hand, when the image is only displayed, in the operation (1), the control portion 41 receives:

(a) an "image only" as a type of data to be displayed; and (b) an image display unit number of the image display unit displaying data, and does not receive the overlay display information. In the above-mentioned operation (4), the overlay data is not read out, accordingly the image data are not superimposed on the overlay data.

Image Display Unit (WS-IDISP)

This is a unit for mainly displaying an image and can display an image of which a matrix size is 2,048×2,048 pixels. This embodiment has two units.

Network Interface (WS-NWIF)

This is an interface with the network (NW) 5 and is used to communicate with the other subsystems through itself.

Control Bus (WS-CBUS)

This is a transmission path of various control information within the workstation (WS) 4.

Image Bus (WS,-IBUS)

This is a transmission path of the image data and the overlay data within the workstation (WS) 4.

In this connection, a clock for referring to a date and a time (not shown) is integral with the worstation (WS) 4.

Thus-constructed PACS is used and a flow of a series of system operations when interpreting an image by applying the present invention thereto will be described. For example, the interpretation of a chest X-ray image is used in the course of explanation. After the image data are sent from the database (DB) 3 or the image acquisition unit (IA) 2 to the workstation (WS) 4, in the workstation (WS) 4, in the order of:

1. a preparation of an image for interpreting;
2. a production of the CAD processing and the diagnosis information;
3. an interpretation of an image by an interpreting doctor and inputs of an interpretation report;
4. a comparison of the diagnosis information and an arousal of attentions to the interpreting doctor;
5. reference of the CAD processing results by the interpreting doctor and a re-interpretation; and
6. a completion of the interpretation report and its storage, a series of system operations is carried out.

The information sent from the database (DB) 3, the image acquisition unit (IA) 2, or the system manager (SM) 1 to the workstation (WS) 4 is as follows:

(a) Chest X-ray image (frontal image)

(b) Examination ID number and patient ID number (c) Examination request information, examination conditions (radiographing conditions, radiographing method)

(d) Hearing information

This is the image that a patient has previously been examined.

Hereinafter, the above-mentioned series of system operations will be described in detail.

1. Preparation of Image for Interpreting (1-1) Data transmission from the system manager (SM) 1

The system manager (SM) 1 sends data concerning the examination request information (in this case, the examination ID number is 103541 and the patient ID number is 870802), the examination history data of the patient, the interpreting reference priority order information (referring to FIG. 44), and the interpretation report of previous examination of the patient (in this case, three medical examinations) to the workstation WS-1.

(1-2) Storage of data from the system manager (SM) 1 of the workstation WS-1

(1-2-1) When the data are sent from the system manager (SM) 1 to the network interface (WS-NWIF) of the workstation WS-1, the control unit (WS-CTRL) of the workstation WS-1 reads out the received data from the network interface (WS-NWIF) and writes the data into the system memory within the control unit (WS-CTRL).

(1-2-2) The control unit (WS-CTRL) writes the data concerning the examination request information, the examination history data, the interpreting reference priority order information, and the interpretation report of the previous examination of the patient into the image data unit (WS-IM).

(1-3) Image transfer demand to the database (DB) 3

(1-3-1) The control unit (WS-CTRL) of the worstation WS-1 refers to the interpreting reference priority order information and transfers the examination ID number of the examination having the minimum reference priority order number to the network interface (WS-NWIF) and indicates an image transfer demand to the database (DB) 3. The network interface (WS-NWIF) sends the assigned examination ID number and an image demand command to the database (DB) 3.

(1-3-2) The database (DB) 3 receives this demand and reads out the image data and the information attached to an image from the inside memories and sends the data to the workstation WS-1.

(1-3-3) When the image data and the information attached to an image are sent from the database (DB) 3 to the network interface (WS-NWIF) of the workstation WS-1, the control unit (WS--CTRL) of the workstation WS-1 reads out the received data from the network interface (WS-NWIF) and writes them into the image data unit (WS-IM).

(1-4) Image transfer demand of the previous examination to the database (DB) 3

The control unit (WS-CTRL) of the workstation WS-1 demands the database (DB) to transfer the image data and the information attached to an image concerning the other examinations included in the interpreting reference priority order information according to the above-described same procedures, and writes the data into the image data unit (WS-IM). As the image transfer demand to the database (DB) 3 is carried out in order of the minimum reference priority order number, the image data and the information attached to an image concerning the images of the previous examination are available in the order of the examination ID numbers 100902, 102287, and 60563.

2. Production of CAD Processing and Diagnosis Information (2-1) CAD processing

The workstation performs the CAD processing concerning images to which the CAD processing can be applied to all received images. This CAD processing is performed before an interpretation of a doctor etc.

(2-1-1) The control unit (WS-CTRL) of the workstation WS-1 refers to abnormality detecting means selection information (refer to FIG. 40) concerning respective images of the examination to be interpreted (the examination ID number is 103541), and judges as to whether the CAD processing can be applied or not. That is, the control unit (WS-CTRL) investigates as to whether or not a name of an examined portion, a name of a modality, and a combination of an examination method included in the examination information data are existent within the abnormality detecting means selection information. As to the examination of the examination ID number 103541, the image is frontal and the CAD processing can be applied to it. Then, the type of a detectable abnormality is two types of the pulmonary nodules and interstitial lung disease. If the abnormality detecting means is not within the abnormality detecting means selection information, the control unit (WS-CTRL) of the workstation WS-1 moves into the processing of the next image.

Figures 44, 45:
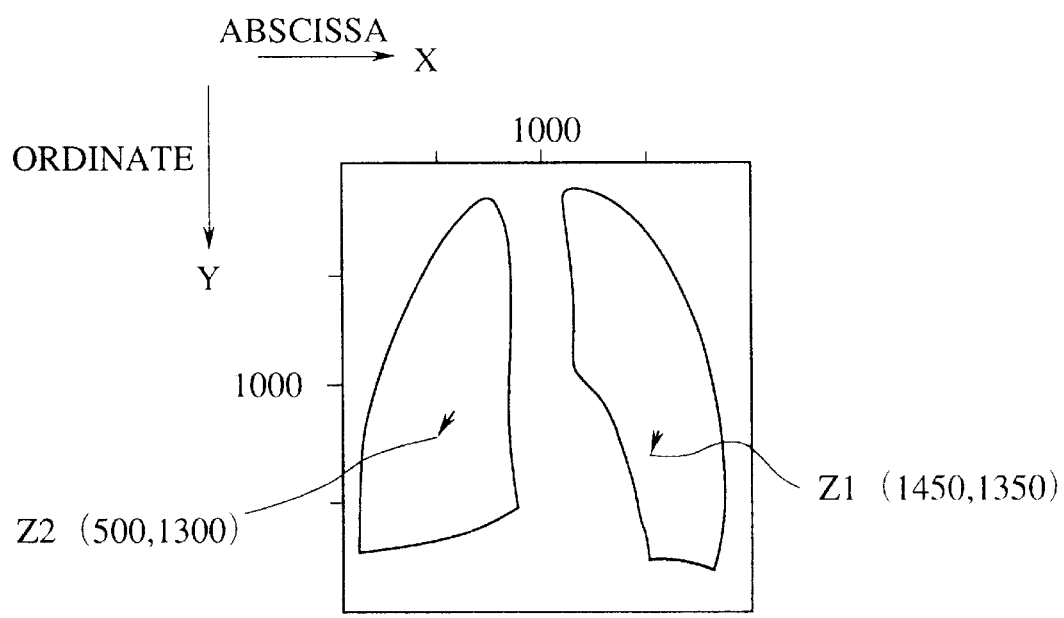
FIG. 44 is a table showing an interpreting reference priority order information.
FIG. 45 is a diagram showing a lung nodule detected by a CAD-processing.

(2-1-2) The control (WS-CTRL) of the workstation WS-1 reads out the image of the examination of the examination ID number 103541 from the image data unit (WS-IM), and inputs the image into the CAD processing unit (WS-CADP) together with data meaning a detection instruction of the "pulmonary nodules". The CAD processing unit (WS-CADP) acts the pulmonary nodule detecting means for the inputted image data and analyzes the image data. The scope to be CAD-processed in this analysis is applied to the entire image. In the abnormalities, as shown in FIG. 45, Z1 and Z2 are detected.

(2-1-3) The control unit (WS-CTRL) of the workstation WS-1 reads out the image of the examination of the examination ID number 103541 from the image data unit (WS-IM), and inputs the image into the CAD processing unit (WS-CADP) together with data meaning a detection instruction of the "interstitial lung disease". Also, the control unit (WS-CTRL) indicates to output a position of a normal dissection structure. If one number of ribs is inputted into this, a relative position among ribs in the detected abnormality position is obtained. This is necessary when the image is compared with the previous image.

Figure 46:
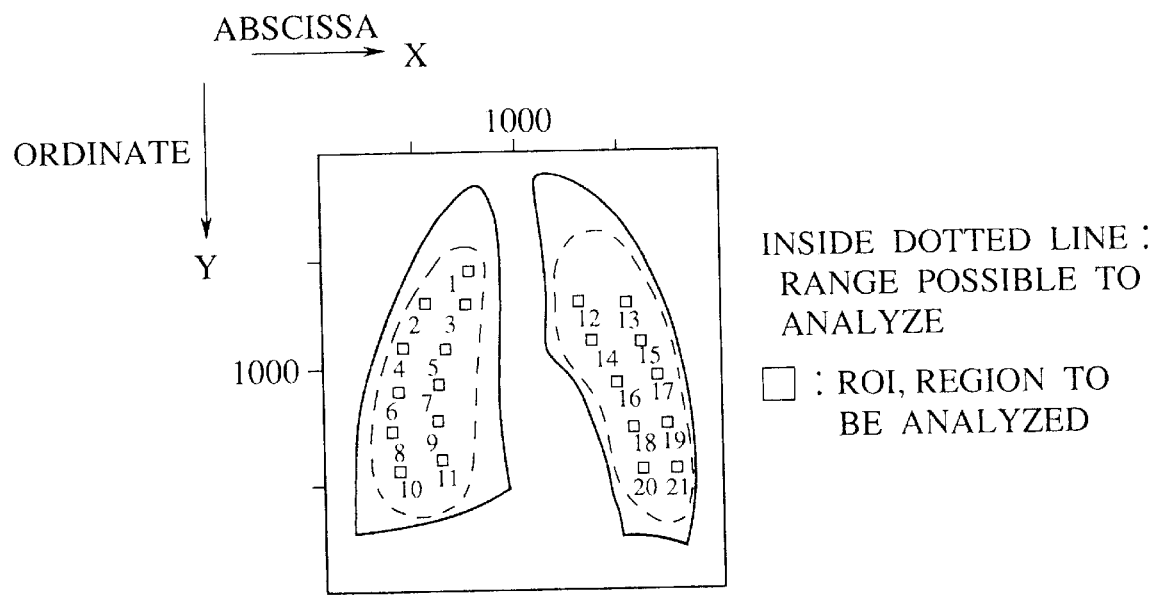
FIG. 46 is a diagram showing the region of interest (ROI) set by CAD in order to detect interstitial lung disease.

The CAD processing unit (WS-CADP) activates the interstitial lung disease detecting means for the inputted image data and analyzes the image data. In this analysis, the following method is taken. Namely, a region of interest (ROI) is set among ribs as an analyzable scope to be CAD-processed within a dotted line region as shown in FIG. 46, namely within an applicable scope of the CAD processing, and an abnormality is detected by analyzing the region of interest (ROI). In this case, the scope to be CAD-processed is limited. The conditions in which the region of interest (ROI) is set are shown in FIG. 46.

Figure 47:
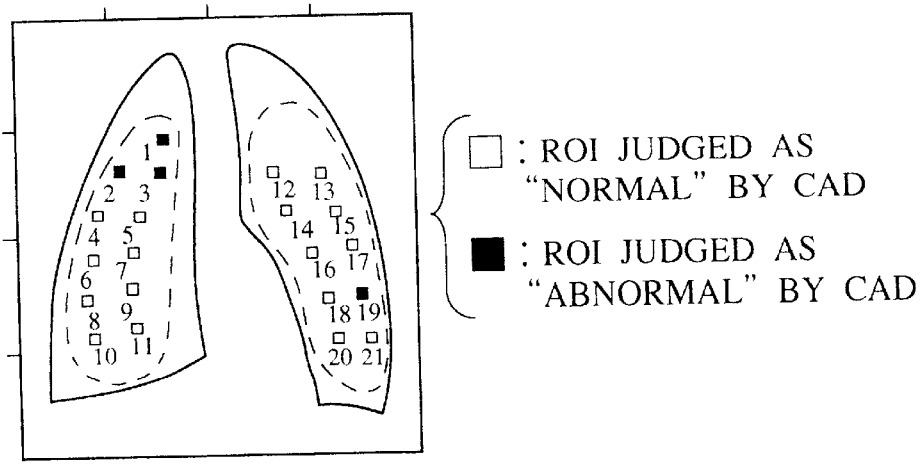
FIG. 47 is a diagram showing the interstitial lung disease detected by the CAD processing.
Figure 48:
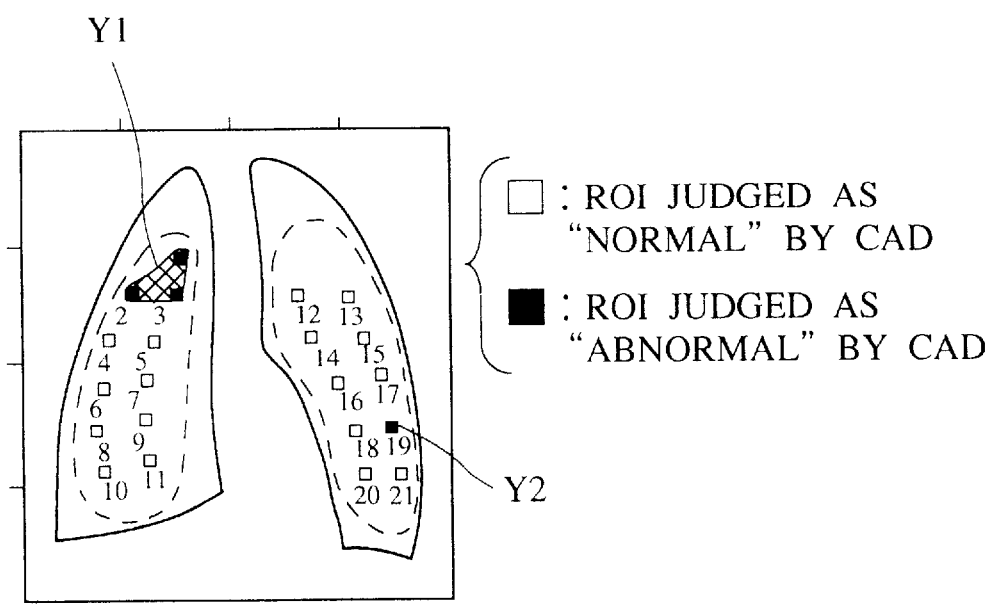
FIG. 48 is a figure showing abnormality regions (Y1 and Y2) determined by the interstitial lung disease result obtained by CAD.

This scope to be CAD-processed is analyzed. As a result of the analysis, a judgement of an "abnormality" or a "normality" is given to each region of interest (ROI). The results of the analysis are shown in FIG. 47. As a result of the analysis, as to ROI1, ROI2, R0I3, and ROI19 which are judged as an "abnormality", if the analysis results of the adjoining ROI are "abnormal", it is deemed that the abnormality distributes uniformly. Accordingly, the ROI1, ROI2, or R0I3 is one of abnormalities distributing widely and the abnormal region is a region Y1 in which an area coupling respective vertexes of the ROI1, ROI2, and ROI3 is the maximum as shown in FIG. 48. On the other hand, as the ROI16, ROI17, ROI18, ROI20 and ROI21 adjacent to the ROI19 are judged as a "normality", the abnormal region Y2 is the ROI19 itself. As a result of the analysis, data of the obtained abnormal region and data of a position of a normal dissection structure are memorized in memories within the CAD processing unit (WS-CADP).

(2-1-4) The control unit (WS-CTRL) of the workstation WS-l investigates, in the same manner as described above, as to whether or not the abnormality detecting means can be applied to the examination image of the other examination ID numbers, and if so, the abnormalities are detected as to the entire abnormality detecting means to be applied by making use of the CAD processing unit (WS-CADP). Also, the control unit (WS-CTRL) seeks a position of the normal dissection structure just once as to each image to be CAD-processed.

At this time, data representing a position of an abnormality which is memorized in memories integrated with the CAD processing unit (WS-CADP) are shown in FIG. 49. The position of an abnormaity has an absolute position coordinate defining an upper left end of an image as the origin and a relative position among ribs using vertical intervals and ribs (refer to FIG. 43), however the absolute position coordinate only is shown in FIG. 49. The data shown in FIG. 49 are called an abnormality data table for clarity. Also, it can be decided which position (among ribs) a certain abnormality exists by using the position data of the normal dissection structure of ribs shown in FIG. 43. This is because the abnormality is detected only in a pulmonary field on the image. The data shown in FIG. 43 is called a position data table for clarity. In this connection, as seen from a viewpoint of FIGS. 43 and 49, a coordinate transformation is required in order to correspond to each other. This is because the coordinate system shown in FIG. 43 is not the above-mentioned absolute position coordinate system.

(2-2) Decision of the normal dissective position (relative position among ribs) where an abnormality exists This decides as to whether or not the detected abnormality is existent between the n-th rib and the m-th rib, and the control unit (WS-CTRL) of the workstation WS-1 refers to position data of the normal dissection structure included in the position data table each data included in the abnormality data table, and judges which position of the normal dissection structure the abnormal position is included in. The data showing the position of each rib are written into the abnormality data table. In this case, the position data shown in FIG. 43 are converted into the above-mentioned absolute position coordinate system.

After the abnormality data table is read out from the inside memory of the CAD processing unit (WS-CADP) to the system memory of the control unit (WS-CTRL), it is processed with the following procedures and the renewed abnormality data table is written into the image data unit (WS-IM).

(a) To extract data of the position data table as to a certain abnormality in which an examination ID number of an image detecting the abnormality coincides with an image number.

(b) A lateral coordinate of an abnormality position is compared with a lateral coordinate of a center line (mediastinum) of right and left lungs, and if a lateral coordinate of the abnormality position is smaller than a lateral coordinate of a center line (mediastinum) of the right and left lungs, a right lung field is determined to be abnormal, and if the former is larger than the latter, a left lung field is determined to be abnormal.

In this embodiment, an object of a frontal image is only an image radiographed by irradiating X-rays from the back of a patient, and this is because, in the case, the left side of the image is a right lung field and the right side thereof is a left lung field. In this connection, the image radiographed by irradiating X-rays from the front side of a patient is also a frontal image and can be treated. In this case, data of "A→P" are used as the imaging direction and the position of the right lung field is reverse to that of the left lung field. This can be judged by referring to data of the imaging direction existing in information attached to an image.

(c) In the lateral coordinate of the position of an abnormality, the longitudinal coordinate of the position of the abnormality is compared with the longitudinal coordinate of the: fourth rib, and if the longitudinal coordinate of the position of the abnormality is smaller than that of the fourth rib, the position of the abnormality is decided to be on the fourth rib and proceed to step (e). If the longitudinal coordinate of the position of the abnormality is greater or equal, proceed to the next step.

(d) In the lateral coordinate of the position of an abnormality, the longitudinal coordinate of the position of the abnormality is compared with that of a rib directly under the rib compared at the last time, and if the longitudinal coordinate of the position of the abnormality is smaller, the position of the abnormality is decided to be between the rib compared at the last time and the rib compared at this time and proceed to step (e).

Until the position of the abnormality is interposed between any ribs, repeat step (d).

(e) The lateral coordinate of the position of an abnormality is divided by the lateral coordinate of a rib end to compute a ratio of the position in a lung field.

(f) The decided relative position data between the right and left lungs and the rib are connected with the position of an abnormality to write the data into the abnormality data table.

The above-mentioned procedures are carried out as to the entire abnormality in the abnormality data table. An example of the abnormality data table after the procedures are completed is shown in FIG. 50. This is the necessary procedures for making a quantitative comparison of the previous image, and by making a quantitative comparison with the previous image, a temporal change of the abnormality is recognized, thereby making a temporal change data table of the abnormality. However, when two diagnostic information concerning the identical image is simply compared, it is sufficient if only the absolute position coordinate (data) is prepared, and the above-mentioned procedures are unnecessary.

(2-3) Production of overlay display information to display an abnormality

In a production of overlay display information showing the detected results of an abnormality on each image, the control unit (WS-CTRL) of the workstation WS-1 refers to the abnormality data table (FIG. 49 or FIG. 50) and produces the overlay display information to show a position of an abnormality (FIG. 51), and the produced overlay data are stored in the image data unit (WS-IM). The position of the abnormality is expressed with a graphic such as an arrow etc. Also, a color of an arrow is red and the following procedures are carried out:

(a) The control unit (WS-CTRL) of the workstation WS-1 reads data of the position of an abnormality on an image as to the abnormality having the reference number 1 in the abnormal data table. As to the data number 1 of the overlay display information, a type of a graphic is written as an "arrow".

An absolute position coordinate is written as a coordinate. Also, a type of a graphic is different according to types of disease.

(b) A display color is decided to be red. "Red" is written as a display color.

(c) As to control information of presence or absence of a display, a "display" is written in this stage.

(d) As to abnormalities of the other reference numbers, the procedures are carried out in the same manner as the procedures (a) to (c). However, as an overlay is superimposed on an image to be displayed, the identical overlay display information data are written only in an abnormality that the examination ID number coincides with the image number.

(e) The control unit (WS-CTRL) of the workstation WS-1 stores the produced overlay display information in the image data unit (WS-IM) corresponding to the examination ID number and the image number.

FIG. 51 is an example of the thus-produced overlay display information.

3. Interpreting Doctor's Interpretation of Images and Inputs of the Interpretation Report Generally, images of a plurality of patients are prepared in the workstation. When an interpreting doctor interprets (reads) images, the doctor is ordinarily indifferent to a priority of interpreting an image of a patient. Therefore, as the doctor interprets from the older date of examination in an examination to be interpreted or in the sequential order of an examination ID number, the workstation automatically decides the order.

(3-1) Data display for an interpretation of an image (3-1-1) Preparation of data Initially, data are prepared in the following procedures:

(a) Readout of examination requeat information

The control unit (WS-CTRL) of the workstation WS-1 reads out an examination ID number, a patient ID number, and an examination request information from the image data unit (WS-IM) and writes them into the system memory within the control unit (WS-CTRL).

(b) Readout of examination histories

The control unit (WS-CTRL) of the workstation WS-1 reads out examination history data having the patient ID number 870802 from the image data unit (WS-IM) and writes them into the system memory within the control unit (WS-CTRL).

(c) Readout of information attached to an image and image data

The control unit (WS-CTRL) of the workstation WS-1 refers to interpreting reference priority order information (refer to FIG. 44) and reads out the information attached to an image on the entire image (refer to FIG. 52, in this case, a sheet of image) as to the examination ID number having the priority order 0 which is interpreted in this case, from the image data unit (WS-IM), and writes it into the system memory within the control unit (WS-CTRL).

Next, the control unit (WS-CTRL) succesively reads out the information attached to an image on the entire image as to the examination ID numbers (100902, 102287, 60563, respectively) having the priority orders 1, 2, 3 and writes them into the system memory within the control unit (WS-CTRL).

(d) Readout of an interpretation report

The control unit (WS-CTRL) of the workstation WS-1 refers to interpreting reference priority order information (refer to FIG. 44) and reads out a format of the interpretation report as to the examination ID number (in this case, 103541) having the priority order 0 which is interpreted in this case, and the interpretation report of the previous examination in the sequential order of the priority order number as to the other examination ID numbers, from the image data unit (WS-IM), and writes them into the system memory within the control unit (WS-CTRL).

(e) Readout of the abnormality data table

The control unit (WS-CTRL) of the workstation WS-1 reads out the previously created abnormality data table (refer to FIG. 49) from the image data unit (WS-IM), and writes it into the system memory within the control unit (WS-CTRL).

(f) Readout of the overlay display information to display detection results of an abnormality on an image The control unit (WS-CTRL) of the workstation WS-1 refers to the abnormality data table memorized in the system memory and reads out the overlay display information to show detection results of an abnormality memorized corresponding to a combination of the examination ID number and the image number, from the image data unit (WS-IM), and writes it into the system memory within the control unit (WS-CTRL).

In this case, the overlay display information corresponding to the examination ID number 103541 and the image number 1 is read out.

(3-1-2) Display of an image

The workstation WS-1 displays an image of an examination to be interpreted. Now, as two image display units (WS-IDISP) are provided, the workstation WS-1 automatically displays a sheet of image of an examination to be interpreted (the examination ID number 103541). The display is made according to the following procedures:

(a) The control unit (WS-CTRL) of the workstation WS-1 first acknowledges an imaging direction from the information attached to an image of a sheet of image having the examination ID number 103541 (refer to FIG. 52). As it is "P→A", the image is frontal.

(b) The control unit (WS-CTRL) decides the imaging direction checking with a relation information table (referring to FIG. 41) of the imaging direction of the image of a chest plain X-ray image and a relative display position.

(c) Thus, the left-sided image display unit of the two image display units (WS-IDISP) arranged laterally displays the image (frontal image) in the image direction "P→A".

(3-1-3) Display of examination request information

The control unit (WS-CTRL) of the workstation WS-1 selects specified data such as an examination object, clinical information, a disease name disclosed previously to a patient, and the like, out of the examination request information read out previously into the system memory, and writes them into the character display unit (WS-CDISP).

An interpreting (reading) doctor reads the displayed image.

When displaying images other than the displayed image or interpretation reports, the doctor inputs commands for them from the input unit (WS-INPUT).

(3-2) Inputs of an interpretation report by an interpreting (reading) doctor

Figures 53, 54:
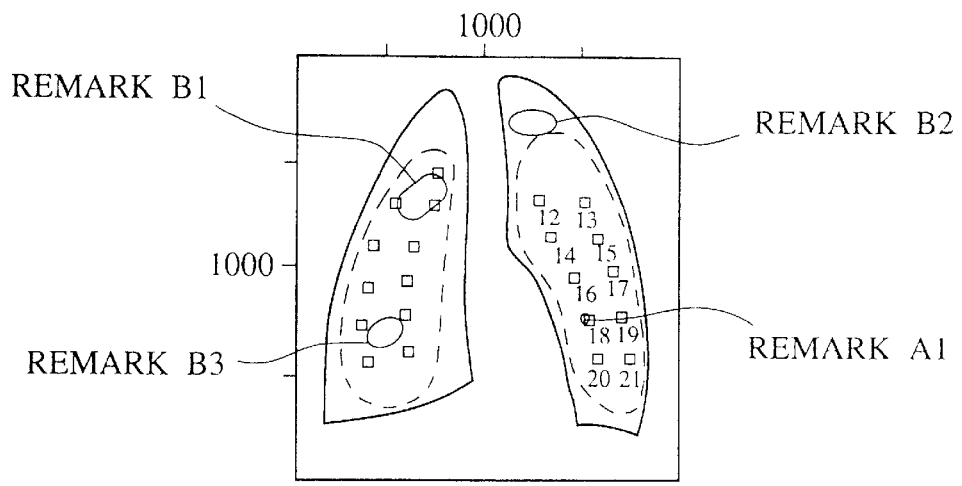
FIG. 53 is a diagram showing remarks 8findings) on the image input by the reading (interpreting) doctor.
FIG. 54 is an example of a format of the interpreting report which is displayed on a screen of the character display unit (WS-CDISP).

After a doctor completes interpreting an image, he/she inputs an interpretation report into the workstation WS-1. The input unit (WS-INPUT) for inputs and the character display unit (WS-CDISP) for displaying are used. The interpretation reports are inputted by selecting a word, a phrase, or a sentense, and indicating a position of an abnormality on an image with a mouse, or enclosing a region of the abnormality on the image with a closed curved line with a mouse. When the interpreting doctor inputs the position of the abnormality or the region of the abnormality with a mouse etc., the control unit (WS-CTRL) of the workstation WS-1 sends this information to the image display manager (WS-IDM) to create an overlay In this overlay, the position of the abnormality is shown by a white arrow and each type of the abnormality is displayed assigning a number. The place or the aspect of the abnormality on the image can be recognized by the overlay. Thus, the obtained image is shown in FIG. 53. In this connection, the word, phrase, or sentense to be selected has previously been registered in the system disk (WS-SD) of the workstation WS-1, and this dictionary is used in common on the entire system.

(3-2-1) Display of an interpretation report creating screen

When an interpreting doctor inputs an interpretation report creating command from the input unit (WS-INPUT)

of the workstation WS-1, the control unit (WS-CTRL) of the workstation WS-1 displays a format of the interpretation report on the character display unit (WS-CDISP). The format of the interpretation report which is displayed on a screen of the character display unit (WS-CDISP) is shown in FIG. 54. In FIG. 54, the region enclosed with a dotted line is one for displaying the word, phase, or sentense to be selected by the interpreting doctor.

(3-2-2) Inputs of an interpretation report

An interpreting doctor inputs the following three items as to each finding according to the format of the interpretation report displayed:

A type of an abnormality

A number in which an abnormality is pointed out in an image

A position and a region in which an abnormality exists

A method of inputting a position or a region of an abnormality is different in a type (disease) of the abnormality. Because pulmonary nodules are detected as circular shadows having a diameter from 5 mm to several cm, or an interstitial lung disease distributes within a wide scope of a lung field. The position of the abnormality like the pulmonary nodules is inputted by pointing out the position of the abnormality on the image with a mouse, and the region of the abnormality like the interstitial lung disease is inputted by enclosing a scope where the abnormalities distribute with a closed curved line by using a mouse etc. The indicated position or region is memorized corresponding to the indicated abnormality. The control unit (WS-CTRL) of the workstation WS-1 displays the inputted data in a specified position on a screen and also memorizes them into the system memory corresponding to the finding number.

When the finding has been finished inputting, a conclusion will be inputted. Then, the interpreting doctor inputs an input completing command of the interpretation report from the input unit (WS-INPUT).

(3-2-3)

Figure 58:
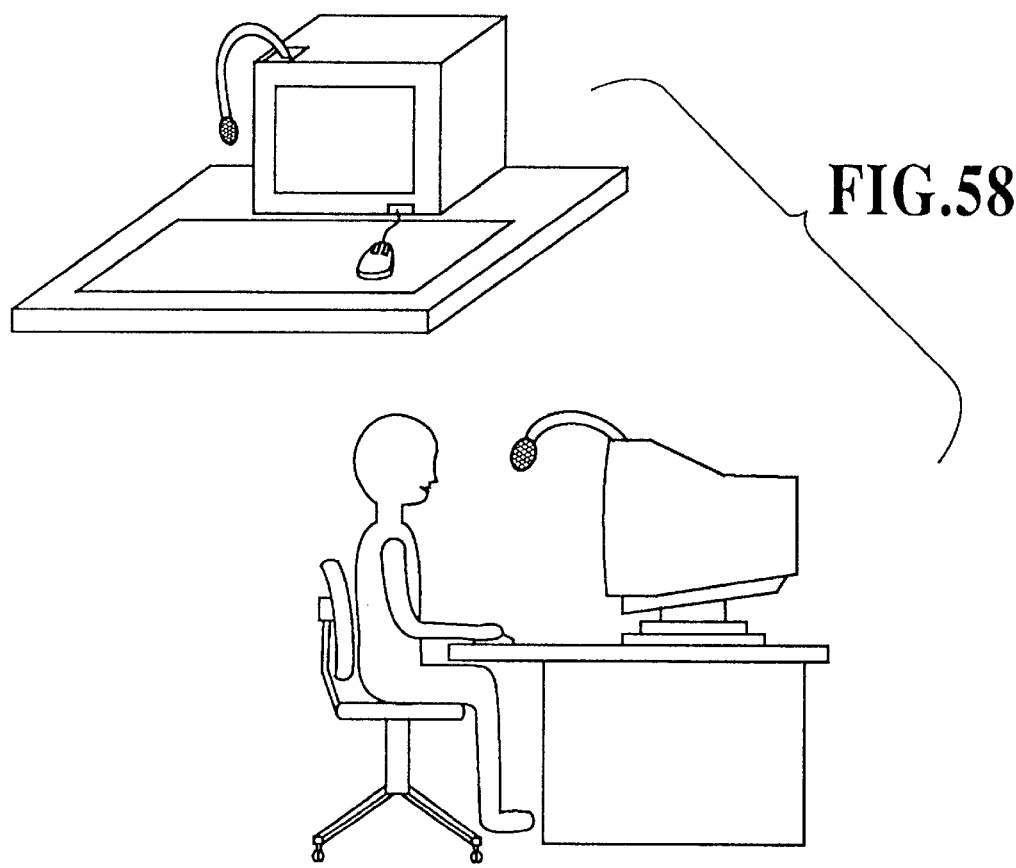
FIG. 58 and FIG. 59 show an example for voice input together with position input, according to the fourth embodiment.
Figure 59:
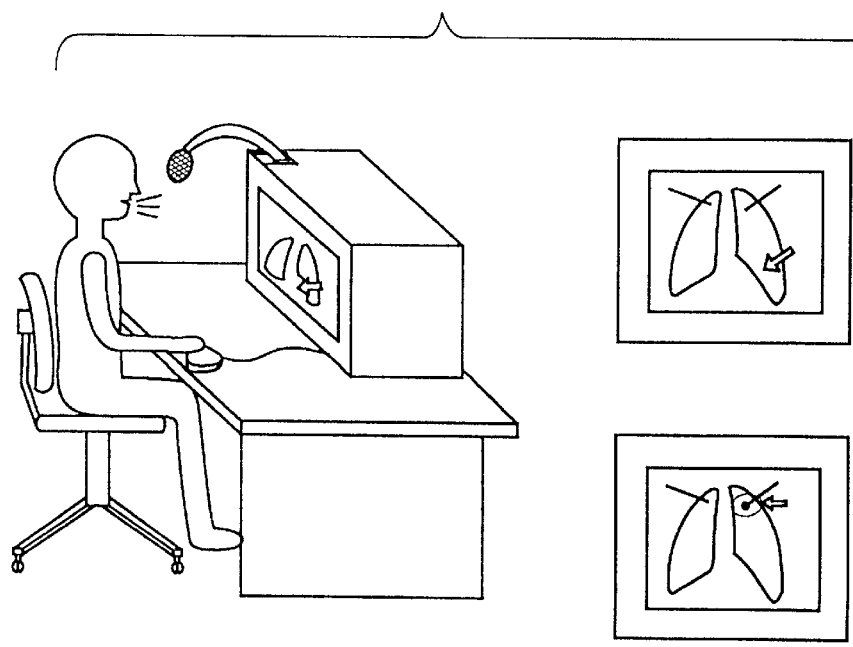

Referring to FIGS. 58 and 59, there will be shown an example for voice input plus position input.

A doctor interprets an image, and indicates a abnormality location with pointing means such as a mouse while speaking his remarks to voice input means such as a microphone.

The voice is recognized by voice recognizing means so that a name of disease is extracted from the doctor's voice. Thereafter, the location specified by the pointing means is corresponded to the name of disease extracted so that a doctor's remarks (findings) are made to be stored.

(3-2-4)

Figure 60:
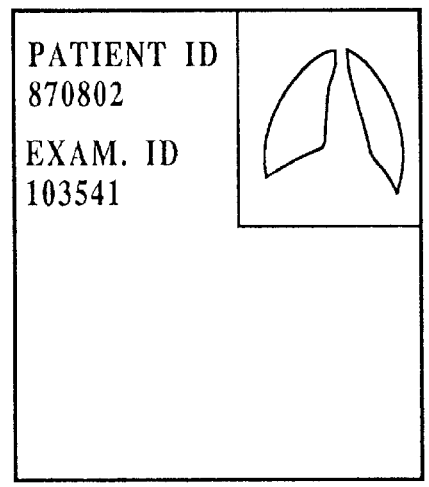
FIG. 60 and FIG. 61 show an example for reading of the characters or the like, according to the fourth embodiment.
Figure 61:
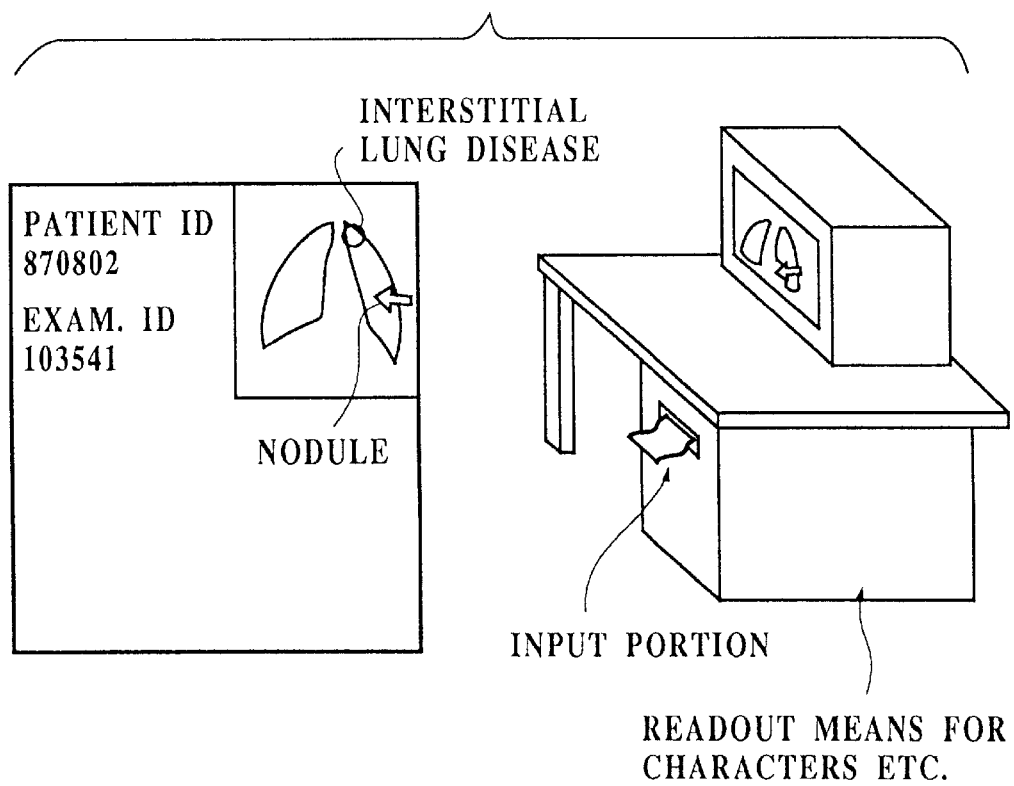

Referring to FIGS. 60 and 61, there is shown an example for reading of the characters or the like.

A doctor writes an abnormality position and remarks (findings) in report paper of a specified form. The report paper is inputted to character reading means and the like so as to read the abnormality location and the name of disease. Thereafter, the abnormality location is corresponded to the name of disease so as to be stored as the doctor's remarks (finding).

It is to be noted that a word, phrase or sentence concerning the type of abnormality or so on may be inputted directly from a keyboard by the doctor.

4. Comparison of Diagnosis Information and Arousal of Attentions to Interpreting Doctor (4-1) Extraction of findings to be compared from the interpretation report Findings to be compared with diagosis information obtained from the CAD processing results (an abnormality data table etc.) will be extracted from the findings of interpretation reports. The control unit (WS-CTRL) of the workstation WS-1 investigates as to whether or not the following combination is existent in the abnormality detecting means selecting information (refer to FIG. 40) as to respective findings of the interpretation reports:

A type of an abnormality (existing in the finding of an interpretation report)

An examination portion of an examination to be interpreted (existing in the examination history)

A modality (existing in the examination history)

An examination method (existing in the examination history)

An imaging direction of an image (which is one concerning an image number in an examination to be interpreted in a finding of an interpretation report and which is existent in information attached to an image)

(4-2) Comparison between the interpretation report and the abnormality data table (4-2-1) The control unit (WS-CTRL) of the workstation WS-1 compares the abnormality corresponding to the finding with each abnormality of the abnormality data table as to the following four sets of data concerning the respective findings of the interpretation reports extracted in Section 4, Subsection (4-1), and extracts each abnormality of the abnormality data table in which the four sets coincident with each other:

An examination ID number of an examination to be interpreted (which is not described in a finding of an interpretation report and which is existent in information attached to an image).

An image number in an examination to be interpreted (which is not described in the finding or remarks of the reading report and which is existent in data attached to the image)

A type of an abnormality

A position and a region in which an abnormality exists

Hereinafter, procedures of a comparison of four sets of data will be described in detail.

(a) A finding having the identical examination ID number and the image number and an abnormality data table will be extracted. In this embodiment, based on the examination ID number 103541 and the image number 1 concerning the image to be interpreted, the abnormality data table which is the results analyzed concerning this image (refer to FIGS. 49 and 50) will be extracted.

(b) The control unit (WS-CTRL) reads as to whether the doctor's interpretation results are "abnormal" or "normal" from the finding (in which anything has not been described), and compares them with the abnormality data table.

(b-1) When the doctor's interpretation results are "normal" and the results of the CAD processing are "normal" (anything has not been decribed in the abnormality data table), the interpreting results are deemed to coincide with those of the CAD process-ing as to this combination.

When the doctor's interpretation results are "abnormal" or the results of the CAD processing are "abnormal", the following processing will be carried out.

(b-2) Concerning the abnormality pointed out by the doctor and the abnormality detected by the CAD processing, a position and a region as to the same type of the abnormality are compared.

Figures 55, 56:
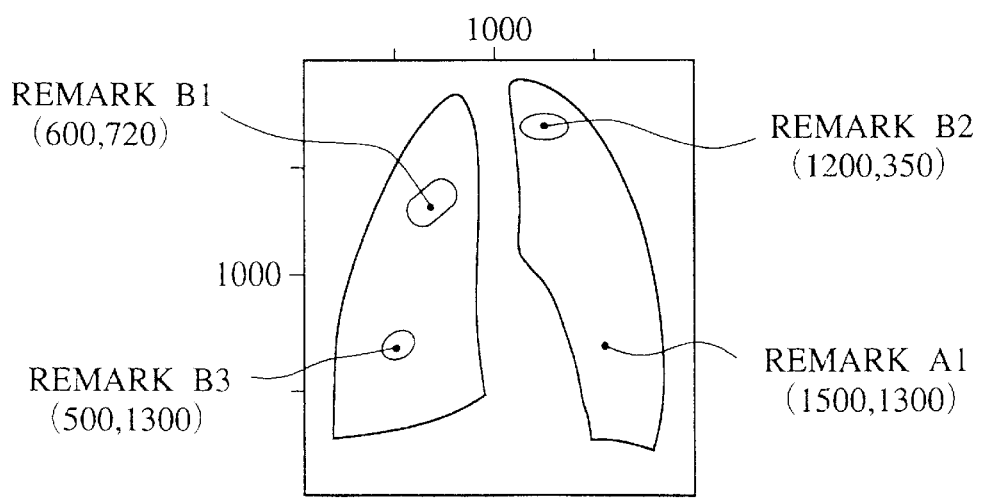
FIG. 55 shows part of doctor's reading (interpreting) report.
FIG. 56 shows a view showing abnormality regions inputted by the reading doctor, expressed in a coordinate system.

In this embodiment, as shown in FIG. 55, when referring to the finding number 1, it is pulmonary nodules, and when referring to finding numbers 2, 3, and 4, they are interstitial lung diseases. On the contrary, when referring to the abnormality data table (refer to FIGS. 49 and 50) which shows the results of the CAD processing, these diseases were detected. Accordingly, the respective findings are compared with the results of the CAD processing as to each disease.

Figure 57:
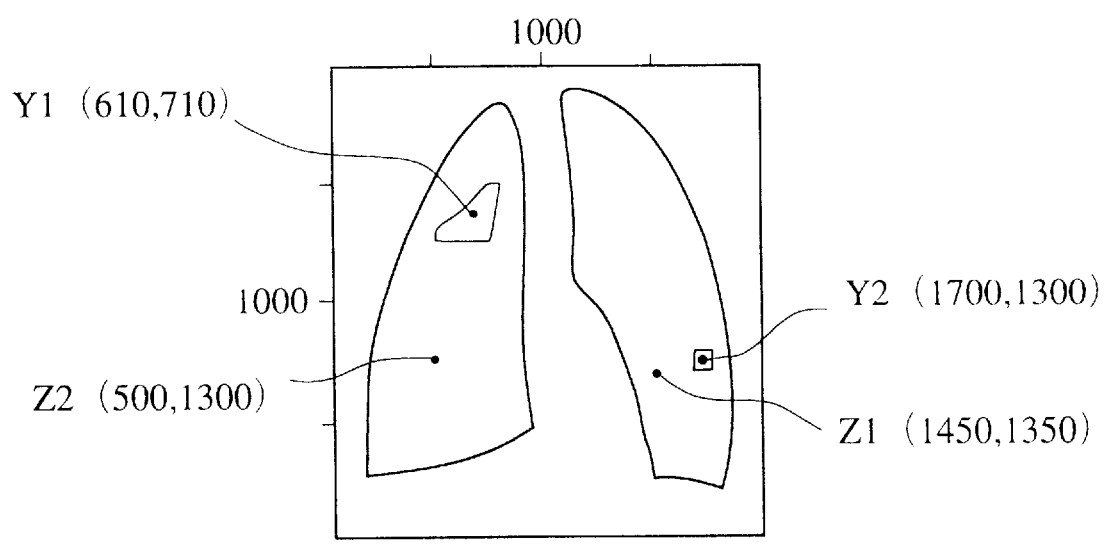
FIG. 57 shows a view showing abnormality regions detected by the CAD, where an image therefor is expressed in the coordinate system.

(i) A comparison is made as to the pulmonary nodules A1 of the finding number 1. As the pulmonary nodules were explained in Section 2, Subsection (2-1-2), a scope to be CAD-processed is the entire image. Also, as a matter of course, a scope to be interpreted by the doctor is the entire image. Herein, the method of indicating a position of an abnormality by the doctor is same as that by the CAD to be displayed by an arrow. Accordingly, if the position of an abnormality is on the coordinate of an arrow tip, as shown in FIGS. 56 and 57, the abnormality A1 of the finding number 1 is (1500, 1300), and abnormalities Z1 and Z2 detected as the results of the CAD processing are respectively Z1 (1450, 1350), Z2 (500, 1300).

If a distance between the abnormality A1 indicated by the doctor and the abnormalities Z1 and Z2 detected by the CAD processing is less than a specific value $A0$ $(=100)$, the position of the identical abnormality shall be pointed out.

Comparison of A1 to Z1: $\sqrt{\{(1500-1450)^2+(1300-1350)^2\}}=71<100$

Comparison of A1 to Z2: $\sqrt{\{(1500-500)^2+(1300\ 1300)^2\}}=1000>100$

Accordingly, the idetical abnormality is pointed out by A1 and Z1 and it is recognized that Z2 is detected by the CAD but is not pointed out by the doctor.

(ii) A comparison among the interstitial lung diseases B1, B2, and B3 of the finding numbers 2, 3, and 4 is made. In the interstitial lung disease, the doctor shows the position of the abnormality with a closed curved line and the CAD processing, results show it with the region enclosed with a straight line (refer to FIGS. 48 and 49). Herein, the scope to be CAD-processed in the interstitial lung disease is not the entire image as shown in Section 2, Subsection (2-1-3) (refer to FIG. 48), but is limited. Also, the scope to be interpreted by the doctor extends to the entire image. Accordingly, it is investigated from the coordinate of each region of interest (ROI) as to whether or not the region of the abnormality to be pointed out by the doctor is existent within the scope to be CAD-processed, or namely whether or not the region of interest (ROI) is existent within the region of the abnormality to be pointed out by the doctor. As a result, in the case where the region of interest (ROI) is existent within the region of the abnormality pointed out by the doctor (case 1), a comparison of a distance among the regions is made as described below. On the other hand, in the case where the region of interest (ROI) is not existent within the region of the abnormality pointed out by the doctor, this case is divided into the following two cases: In the case where the region of interest (ROI) is not existent within the region of the abnormality pointed out by the doctor, and is without the applicable scope of the CAD processing (case 2), and in the case where the region of interest (ROI) is not existent within the region of the abnormality pointed out by the doctor, but is within the applicable scope of the CAD processing (case 3). In the last case 3, the CAD processing unit (WS-CADP) automatically resets the region of interest (ROI) and carries out the CAD processing again to analyze the region of interest (ROI) and repeats from the initial stage of Subsection (b-2), (ii). In this connection, the results of these judgements are memorized in the system memory of the control unit (WS-CTRL) and will be able to be outputted as occasion demands.

When the finding in this embodiment is applied to each case, as three ROIs from the ROI1 to the ROI3 exist within the region B1, this finding is the case 1, and as the ROI does not exist within the region B2 and is without the applicable scope of the CAD processing, this finding is the case 2. In the case of this case 2, the CAD processing unit (WS-CADP) does not carry out anything concerning this region of the abnormality. Furthermore, as the ROI does not exist within the region B3, but is within the applicable scope of the CAD processing, the CAD processing unit (WS-CADP) automatically resets the ROI within the region B3 and carries out the CAD processing again to analyze the ROI. Then, in this embodiment, the CAD processing is carried out again, so that the ROI shall be judged as no abnormalities. Accordingly, as the results of the CAD processing, the detected regions of the abnormality are only Y1 and Y2.

Next, a comparison is made as to each region shown as an abnormality. For the comparison, a distance among respective regions is defined as a distance among respective centers of the gravity of the regions. That is, in the same case as the pulmonary nodules, if the distance among respective centers of the gravity is less than a specific value, say, $B0$ $(=300)$, the identical region of the abnormality shall be pointed out.

The below-mentioned case is that the region is judged as an abnormality as the results of the CAD processing, or that the doctor judges as an abnormality and the region is within the applicable scope of the CAD processing (accordingly, excluding the region B2). Then, the center of the gravity in the respective regions is seeked to compute the coordinate. As shown in FIGS. 23 and 24, each center of the gravity in the regions is shown with a black round and the coordinates of the position are seeked as B1 (600, 720), B3 (500, 1300), Y1 (610, 710), and Y2 (1700, 1300).

Comparison of B1 to Y1: $\sqrt{\{(600-610)^2+(720-710)^2\}}=14<300$

Comparison of B1 to Y2: $\sqrt{\{(600-1700)^2+(720-1300)^2\}}=1243>300$

Accordingly, the B1 and Y1 are judged to show the identical abnormality.

Comparison of B3 to Y1: $\sqrt{\{(500-610)^2+(1300-710)^2\}}=600>300$

Comparison of B3 to Y2: $\sqrt{\{(500-1700)^2+(1300\ 1300)^2\}}=1200>300$

Accordingly, it is judged that the CAD processing results detecting B3 do not exist and the doctor's findings coinciding with the CAD processing results Y2 do not exist.

(b-3) In this stage, in the case where, as to all the findings extracted in Section 4, Subsection (4-1) and all the abnormalities in the abnormality data table, the coincident data exists, it is judged that the interpreting doctor's findings coincide with the results of the CAD processing, and the information of presence or absence of the display of the overlay display information is written from a "display" to a "non-display". Then, the succeeding steps will not be executed. Corresponding to the cases of B1 and Y1 in this embodiment.

Thus, in the case where the interpreting doctor's findings coincide with the results of the CAD processing, the interpreting doctor's findings as it is are acceptable.

(4-3) Arousal of attentions to the interpreting doctor based on the comparative results As the results of the above-mentioned comparison, if the findings having no coincident data or the abnormalities of the abnormality data table exist, it is judged as to them that the interpreting doctor's findings are different from the results of the CAD processing, and attentions to the interpreting doctor are aroused. As the case where the interpreting doctor's findings are different from the results of the CAD processing, the follow-ing two cases are existent:

Case 1: An interpreting doctor judges as a normality (no findings), but the CAD detects as an abnormality.

Case 2: An interpreting doctor judges as an abnormality, but the CAD cannot detect as an abnormality.

The control unit (WS-CTRL) of the workstation WS-1 reads out the findings of the interpretation report having no coincident data and abnormalities of the abnormality data table from the interpretation reports and the abnormality data tables to memorize them in the system memory.

(4-3-1) The control unit (WS-CTRL) of the workstation WS-1 executes the following procedures in the case where the abnormality data belonging to the above-mentioned case 1 exist:

(a) The control unit (WS-CTRL) outputs a "beep" sound, or flickers a screen.

(b) The control unit (WS-CTRL) displays a message that "The CAD detects an abnormality which does not exist in the finding", in a term display region in a portion displaying the interpretation report created by the character display unit (WS-CDISP).

(c) The control unit (WS-CTRL) displays the image detecting an abnormality in the image display unit (WS-IDISP).

(d) The control unit (WS-CTRL) shows the overlay data showing the detecting results of an abnormality as to the image by superimposing the overlay data on the image. (e) The control unit (WS-CTRL) displays only an arrow of the abnormality falling under this case out of arrows displayed as an overlay. That is, when the abnormality falls under this case, the data that the control information of presence or absence of a display in the overlay display information is still a "display" are sent to the image display manager.

(4-3-2) The control unit (WS-CTRL) of the workstation WS-1 arouses attentions to the interpreting doctor even in the case where the abnormality data belonging to the above-mentioned case 2 exist. That is, the control unit (WS-CTRL) displays a finding number and a message for arousing attentions, describing that "Finding 4: The CAD indicates as a normality", in a term display region of a portion displaying the interpretation report created by the character display unit (WS-CDISP).

5. Reference of the CAD Processing Results by the Interpreting Doctor

An interpreting doctor looks at the image displayed herein and the arrow on the overlay and refers to them. In order to superimpose the overlay on the image to be interpreted to be displayed, the interpreting doctor inputs a command, an examination ID number, and an image number from the input unit (WS-INPUT). Then, if necessary, the results of the CAD processing, namely the abnormality data tables, can be displayed in the character display unit (WS-CDISP). For doing so, the interpreting doctor is required to input a command, an examination ID number, and an image number from the input unit (WS-INPUT).

(5-1) In the case where the interpreting doctor superimposes the image on the overlay to be displayed, corresponding operations of the workstation WS-1 will be explained.

(a) The interpreting doctor inputs a command, an examination ID number, and an image number from the input unit (WS-INPUT).

(b) The control unit (WS-CTRL) of the workstation WS-1 judges as to whether or not the indicated image is an applicable image of the CAD processing. The method of this judgement is completely same as described in Section 2, Subsection (2-1-1). If the applicable abnormality detecting means does not exist, proceed to (c). If so, proceed to (d).

(c) As the applicable abnormality detecting means has not existed, the control unit (WS-CTRL) displays that "There are no abnormality detecting means which can be applied to the indicated image", in the character display unit (WS-CDISP). Thus, the interpreting doctor can know that the indicated image was without the applicable image of the CAD processing. After displaying, proceed to (g).

(d) In the case where the applicable abnormality detecting means exists, the control unit (WS-CTRL) investigates as to whether or not the abnormality detected from the image exists in the abnormality data table. If the detected abnormality exists, proceed to (e). If not, proceed to (f).

(e) As the detected abnormality exists, the control unit (WS-CTRL) sends information necessary for superimposing the image on the overlay to be displayed, such as the overlay display information corresponding to the indicated image or the like, to the image display manager (WS-IDM). The control unit (WS-CTRL) dis-plays on the image display unit (WS-IDISP) by superimposing the image on the overlay. The image to be displayed herein was explained in Section 4, Subsection (4-3-1), (d) and (e). After displaying, proceed to (g).

(f) In the case where the abnormality has not be detected, the overlay dispaly information based on the results of the CAD processing corresponding to the image is not existent. In this case, there are two cases. That is, the case where the abnormality is without the applicable scope of the CAD processing at detecting the abnormality (the case 2 of Section 4, Subsection (4-2), (b-2), (ii)); and the case where the abnormality is within the applicable scope of the CAD processing, but has not been detected (the case 3 of Section 4, Subsection (4-2), (b-2), (ii)). In the former case, the control unit (WS-CTRL) displays the indicated image on the image display unit (WS-IDISP) and also displays that "The abnormality is without the applicable scope of the CAD processing and cannot be detected", in the character display unit (WS-CDISP). Furthermore, in the latter case, the control unit (WS-CTRL) displays the indicated image on the image dispaly unit (WS-IDISP) and also displays that "The abnormality cannot be detected from the indicated image", in the character display unit (WS-CDISP). Thus, the interpreting doctor can know as to whether or not the abnormality is within the applicable scope of the CAD processing, or that the CAD processing is applied to the indicated image, so that the abnormality has not been detected. However, at present, this does not mean that the image is a normal one. Because, in the conventional technique, the region capable of detecting the abnormality is limited and the type of the detectable abnormality is limited. Therefore, the interpreting doctor is required to beforehand understand the meaning of these words. After displaying, proceed to (g).

(g) This series of procedures are completed.

(5-2) Even in the case where the interpreting doctor displays the diagnosis information obtained by the CAD processing such as the abnormality data table, the temporal change data table of the abnormality, or the like, operate in the above-mentioned manner. That is:

(a) In the case where any abnormality detecting means cannot be applied to the indicated image;

(b) In the case where the abnormality is without the applicable scope of the CAD processing; and (c) In the case where the CAD processing is applied to the indicated image, so that the abnormality has not been detected.

The effect is displayed on the character display unit (WS-CDISP).

6. Completion of the Interpretation Report and its Storage (6-1) Completion of the interpretation report The interpreting doctor refers to the image that the image displayed in Section 5, Subsection (5-1), (e) is superimposed on the overlay, and interprets again. As a result, the following operations will be carried out:

(a) If the interpreting doctor recognizes to be necessary, he/she corrects the previously inputted interpretation report by inputting from the input unit (WS-INPUT). The control unit (WS-CTRL) of the workstation WS-1 changes the interpretation report memorized in the system memory and displays the changed data in the interpretation report creating region of the character display unit (WS-CDISP).

(b) After completing the correction, the interpreting doctor inputs an interpretation completing command from the input unit (WS-INPUT).

(c) Next, the control unit (WS-CTRL) displays to urge to input the interpreting doctor ID number into the character display unit (WS-CDISP), and the interpreting doctor inputs the interpreting doctor ID number allotted to himself/herself. The control unit (WS-CTRL) investigates as to whether or not the inputted interpreting doctor ID number exists in the interpreting doctor information table (refer to FIG. 42). If so, the control unit (WS-CTRL) selects the name of an interpreting doctor corresponding to the interpreting doctor ID number as a name of an interpreting doctor which is attached to the interpretation report.

(d) The control unit (WS-CTRL) attaches data concerning from the patient ID number to the date of interpretation out of the data included in the interpretation report as shown in FIG. 54 to the finding of the created interpretation report and the conclusion. The examination histories of a patient contain the data other than the name of the interpretation doctor and the date of the interpretation out of these data. The name of the interpreting doctor which has been decided in the above (c) is used. The date of the interpretation can be decided by a clock which is integral with the workstation WS-1.

(6-2) Transfer of the interpretation report and storage (a) The control unit (WS-CTRL) of the workstation WS-1 sends the completed interpretation report to the network interface (WS-NWIF) and indicates to transfer the interpretation report to the system manager (SM) 1. The network interface (WS-NWIF) sends the interpretation report to the system manager (SM) 1.

(b) When the interpretation report is sent from the workstation WS-1 to the network interface of the system manager (SM) 1, the system manager (SM) 1 reads out the interpretation report from the network interface, and writes it into the system memory in its own control unit. Furthermore, the interpretation report is transferred from this system memory to the interpretation report data unit to be memorized.

At this time, a series of operations (Sections 1 to 6) of the CAD processing after the image has been sent to the above-mentioned workstation (WS) 4; and from the production of the diagnosis information to the completion of the interpretation report; and the storage has been finished.

In this connection, in this embodiment, the description as to the medical image was made, however this embodiment may also be applied to the medical examination data other than the image, that is the data of a graphic such as an electrocardiogram, brain waves, or the like, or the data arranging a numerical value obtained by an automatic chemical analyzer etc.

Also, in this embodiment, an example of the chest X-ray image was explained, however this embodiment can be applied to the medical examination data of the image etc. of an organ of a digestive organ system such as a stomach etc. other than a chest.

As described above, in the present invention, the processing results of the CAD processing and the findings of the inputted interpretation report are compared in detail as to the scope to be processed, the position of diseases, or the like, whereby the interpretation report can automatically be checked. Furthermore, the results of the comparison are outputted to be informed the interpretation doctor thereof, whereby the diagnosis of the interpreting doctor can be supported to enhance accuracy in the diagnosis. Furthermore, when the results of the CAD processing are different from the finding of the inputted interpretation report in the results of the comparison, as the results of the comparison are outputted only as to its diagnosis items, efficiency in the interpretation is enhanced.

If the indicated image is within the applicable scope of the CAD processing, the CAD processing can automatically be carried out by the interpreting doctor's indication. Also, even if the interpreting doctor demands to display the results of the CAD processing, when the abnormality was not pointed out, he/she can know separately as to whether or not the abnormality detecting means of the CAD processing which can be applied to the image does not exist, or whether or not the indicated image is without the applicable scope of the CAD processing, or whether or not the abnormality has not been detected even if the CAD processing is carried out. Therefore, this embodiment is effective in that efficiency of the interpretation enhances or the like.

(To be continued)

Embodiment No. 5 and Embodiment No. 6

Hereinafter, the present invention according to fifth and sixth preferred embodiments will be explained with reference to the accompanying drawings FIGS. 62–FIGS. 107. In these embodiments, an embodiment of performing a CAD by using a PACS will be described, and first of all, the gist of the present invention according to fifth and sixth embodiments will be described, and next a system configuration of the PACS will be described, and finally procedures in the case of interpreting by using the system of the present invention according to fifth and sixth embodiments will be described in detail. After the descriptions of the system configuration of the PACS and there will be taken up an example where medically interpreted is a chest X-ray image for a lung cancer examination.

Figure 62A:
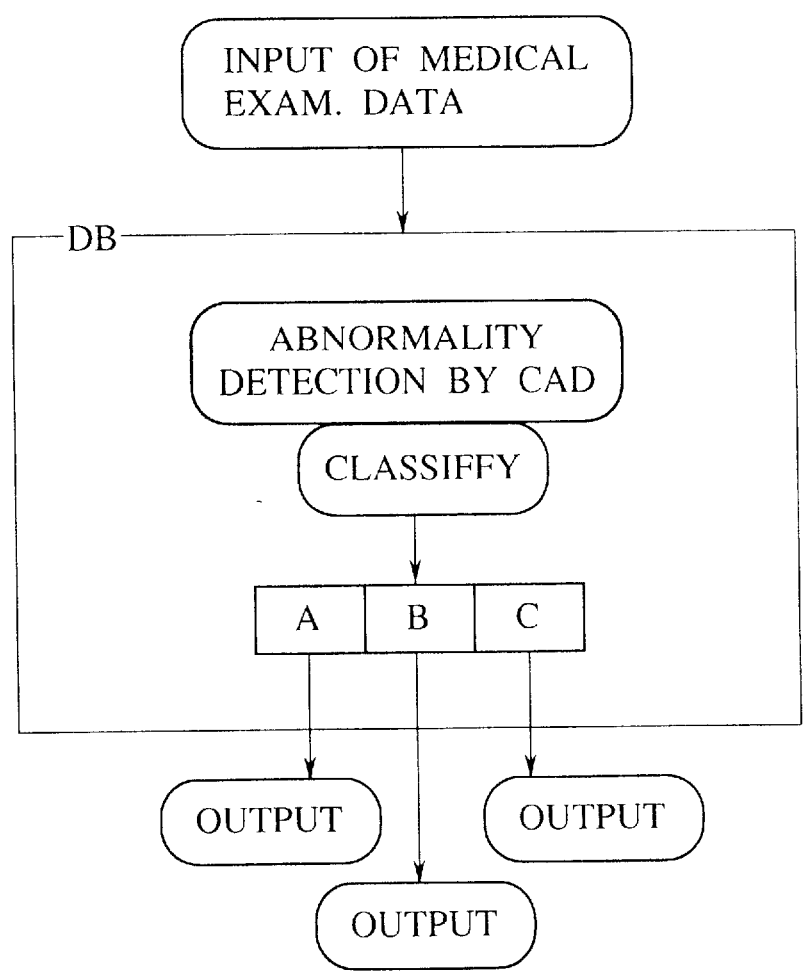
Figure 62B:
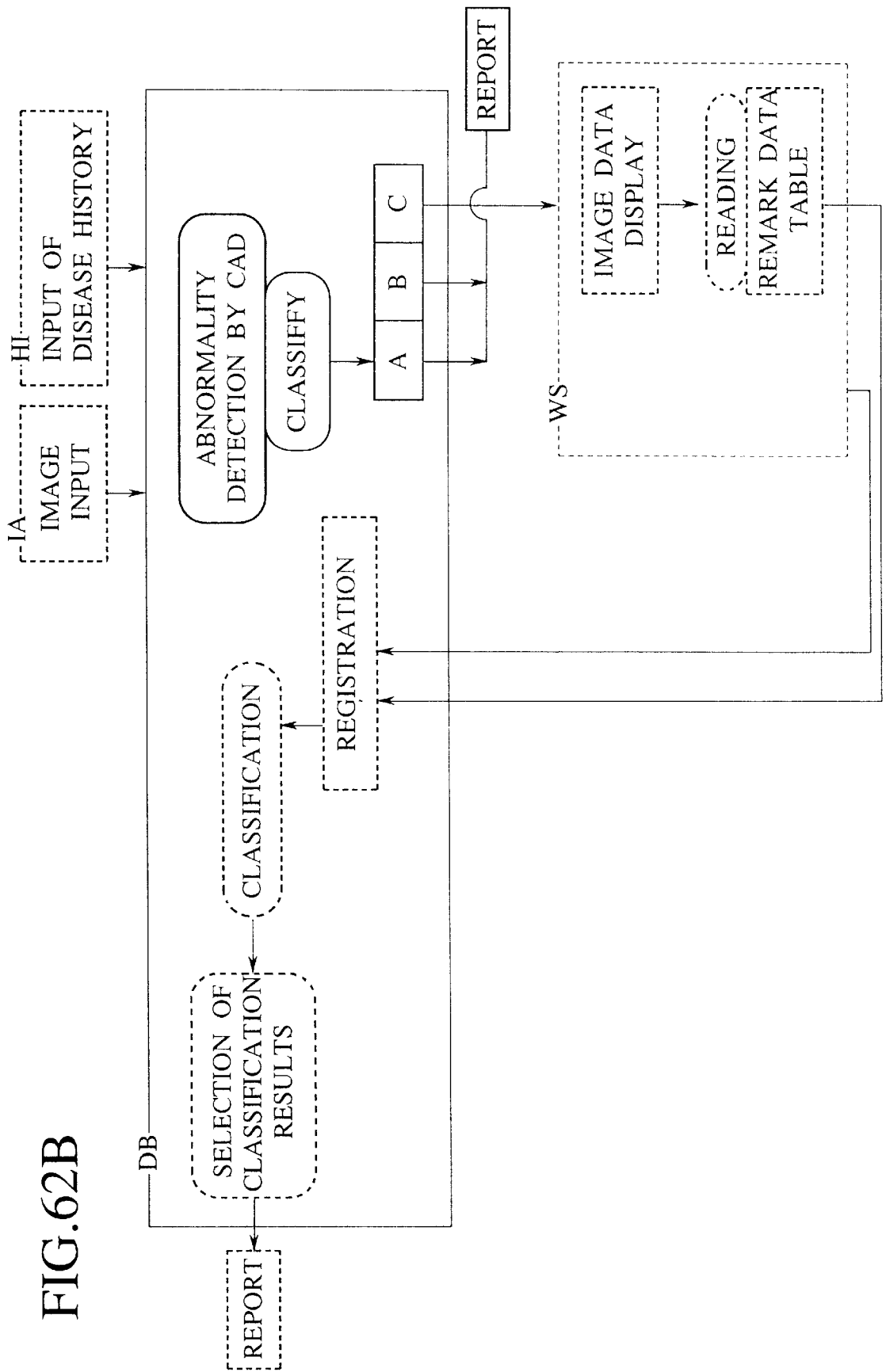
Figure 63A:
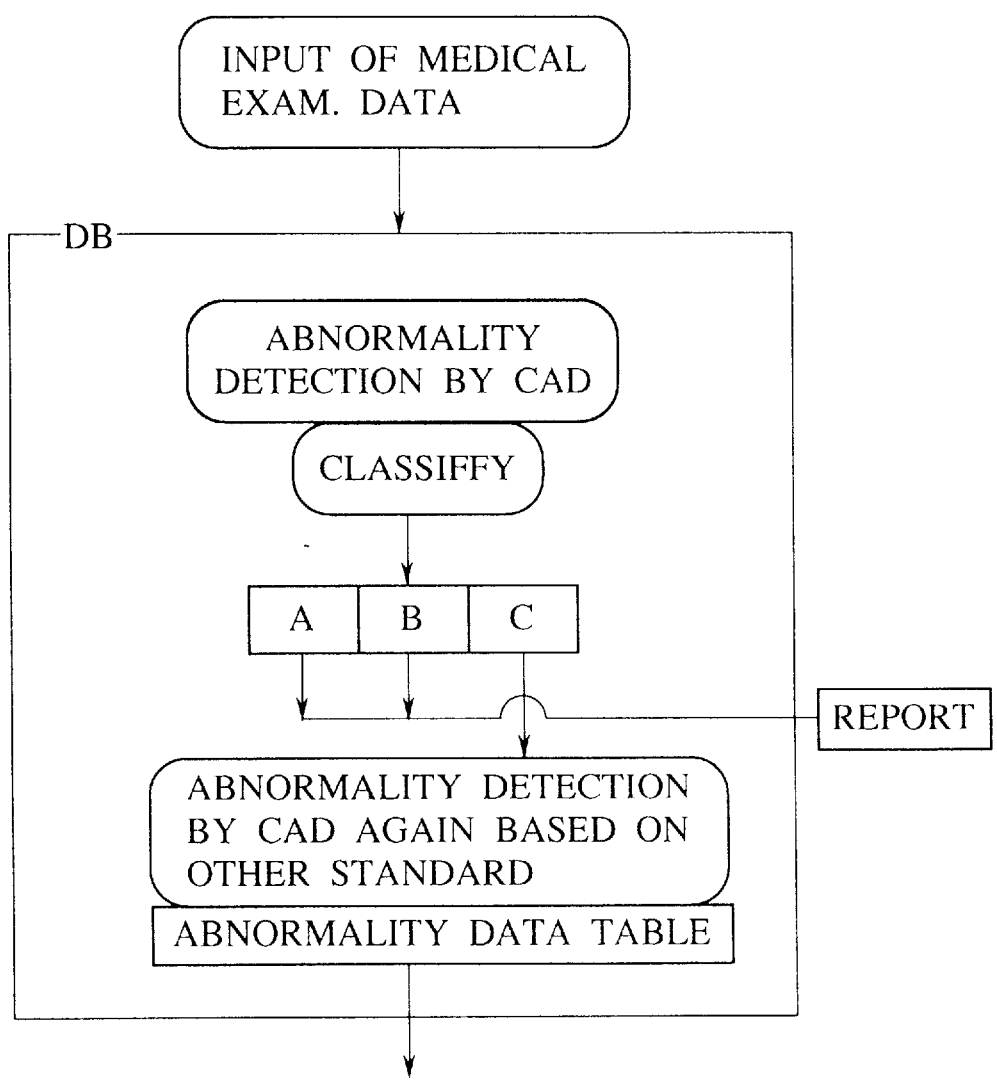
FIGS. 63A and 63B are flowcharts and configurations for explaining the gist of the sixth embodiment in the broadest sense.
Figure 63B:
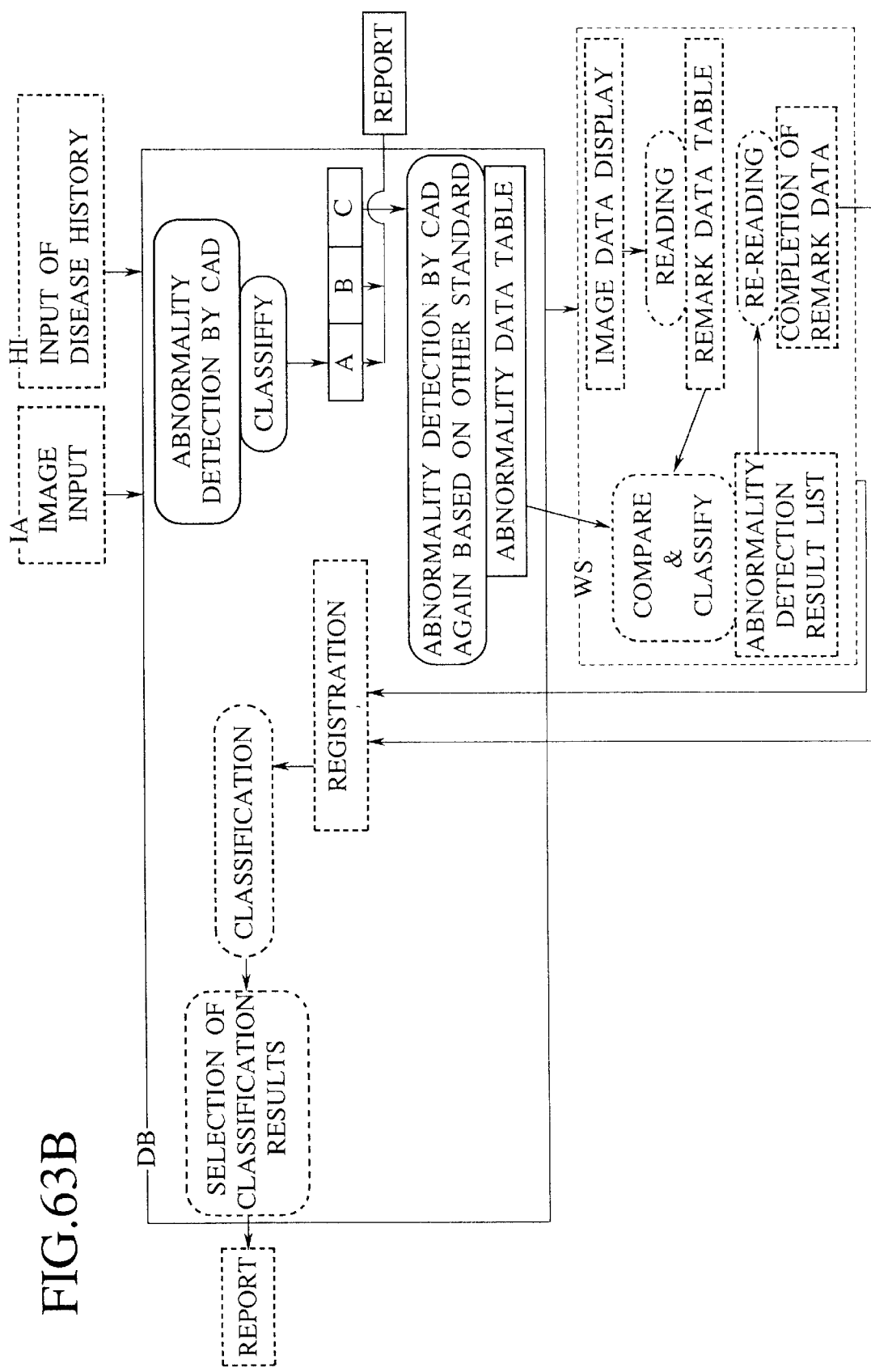

FIGS. 62A & 62B and 63A & 63B are flowcharts for explaining the gist of these embodiments. FIGS. 62A and 62B show the invention according to fifth embodiment and FIGS. 63A and 63B show the gist of the invention according to sixth embodiment.

FIG. 62A shows the gist having the broadest sense in fifth embodiment, and a plurality of medical examination data (image data etc.) obtained by a medical group examination or the like are inputted into a database DB of a medical information processing system. Then, the CAD processing as to each of the inputted medical examination data is carried out to detect an abnormality. This CAD processing can be carried out in any methods, however the method is required to include a processing in which the probability of a normality is high or a processing in which the probability of an abnormality is high. Then, the results of the CAD processing are classified into a plural group to input the medical examination data or identification information of the medical examination data according to the classification results. In this figure, an example of classifying into three groups A, B, and C is shown, however this embodiment is not limited to this. For example, the classification into two groups can be made: this case where only data having the high probability of a normality are beforehand extracted and the remainder is interpreted by a doctor etc.; and that case where only data having the high probability of an abnormality are beforehand extracted and the remainder is interpreted by a doctor etc. As shown in the figure, in the case of classifying into three groups A, B, and C, the classification A is for a normality with the high probability to output the diagnostic results as a "normality", and the classification B is for an abnormality with the high probability to output the diagnostic results as an "abnormality", and the classification C demands a doctor's interpretation to output the medical examination data together with associated information. Thus, by using the CAD, the report can be made in the early stage to the patient (examined person) belonging to the classification B having the high probability of an abnormality, and also as it is possible to reduce the number of sheets of a doctor's interpretation, it contributes to save a doctor's labor.

FIG. 62B shows specifically this embodiment. Information concerning an oral examination or disease histories is inputted from a hearing information input unit HI and image data of a certain type of medical examination data are inputted from an image acquisition unit IA. In the database DB into which these are inputted, each image data is CAD-processed to detect an abnormality to classify the results into the three groups A, B, and C as described in FIG. 62A. Then, as to the classifications A and B, the diagnostic results are outputted, and as to the classification C, image data as a doctor's interpretation, oral examination patient history information relating to the image data, and the like are outputted. As a result, the image data, the oral examination information, etc. belonging to the classification C are sent from the database DB to the workstation WS to display the image data thereon, and a doctor interprets the image data. The interpreting doctor creates and inputs a finding data table which is interpretation results as to each image data. When the doctor finishes interpreting, the results are sent from the workstation WS to the database DB to register therein. The interpretation in the medical group examination is made by two or more doctors and at least two finding data are sent to the database DB. Then, the database DB compares and classifies the registered finding data and selects the classifying results and creates so as to report to each examined person to send the report to a company to which the examined person belongs or a self-government community etc.

FIGS. 63A and 63B show the gist of another embodiment and FIG. 63A shows the gist in a broad sense. Then, as seen by comparing with FIG. 62A, the CAD processing is carried out as -to each of the inputted medical examination data to detect the abnormality, and the results are classified into a plural group to output the medical examination data or the identification information of the medical examination data according to the classification results. These procedures are entirely identical to FIG. 62A so far. In FIG. 63A, as to the data demanding the doctor's interpretation belonging to the classification C, the CAD processing is carried out once more by the other references such as a diagnostic level equal to the doctor etc. to obtain second diagnostic information so that it can be contributory to the doctor's diagnosis. The second results of the CAD processing are outputted by an abnormality detailed data table. Also, the CAD processing is carried out once more according to the other references, and this procedure is applied to not only the case of classifying into three groups, but also the case of classifying into two groups as described above concerning FIG. 62A. That is, in the case where only the data having the high probability of a normality and the high probability of an abnormality are beforehand extracted and the remainder is interpreted by the doctor etc., the CAD processing is carried out once more for the remaining medical examination data.

FIG. 63B shows specifically the gist of still another embodiment. In the same manner as FIG. 63A, the CAD processing is carried out as to the image data to detect an abnormality, and the results are classified into a plural group to output them according to the classification results. These procedures are entirely identical to FIG. 62B so far. In FIG. 63B, as to the data demanding the doctor's interpretation belonging to the classification C, the CAD processing is carried out once more by the other references such as a diagnostic level equal to the doctor etc. to output (containing displaying) the results by an abnormality detailed data table or the like. On the other hand, the image data, the oral examination information, and the like belonging to the classification C are sent from the database DB to the workstation WS to display the image data therein, and the doctor interprets. The interpreting doctor creates a finding data table which is the interpretation results as to each image data to be inputted. When the doctor finishes interpreting a series of data, the finding data table and the abnormality detailed data table of the CAD processing results are compared and classified to create an abnormality detecting result list of the results to output it each classification. Accordingly, the doctor outputs the abnormality detecting result list at re-interpreting the data and refers to associated information and interprets tha data to complete the finding data table, and the results are sent from the workstation WS to the database DB to be registered therein. The interpretation in the medical group examination is carried out by two or more doctors, and at least the two completed finding data tables are sent to the database DB. The later processing is entirely identical to FIG. 62B.

In this connection, the broken line part in the figure indicates not to be a crucial part in the present invention. Also, the CAD processing has been explained in an example which is carried out in the database DB, however the image data etc. can be sent to the workstation WS to be carried out therein.

Next, an example of a basic system configuration of the PACS is shown in FIG. 15. This system comprises respective units (subsystems) as follows:1) Hearing information input unit (HI);2) Image acquisition unit (IA);3) Database (DB);4) Workstation (WS).

The hearing information input unit (HI) is a device for inputting hearing information or disease histories which is obtained by an oral examination of examined persons.

The image acquisition unit (IA) is a medical image acqusition unit for the PACS such as an X-ray machine, an X-ray CT machine, an MRI machine, a film digitizer or the like. Herein, it is defined as an X-ray machine which is placed on a medical examination car.

The database (DB) is used for storing various data to be produced in operations of the medical examination.

The workstation (WS) appropriately processes digital images etc. sent from the database (DB) or the image acquisition unit (IA) to obtain desired results to display or output them. In these embodiments, the workstation is used for interpreting radiographed images.

Communications among these four types of units are carried out by using a data memory medium capable of carrying and rewriting, such as an optical magnetic disk or the like.

Next, functions of each unit (subsystem) and its configurational element will be described.

Main functions and operations of the hearing information input unit (HI) will be described.

To display a hearing sheet (questioning contents for a person to be examined). Items described on the hearing sheet are shown in FIG. 16.

To input identification information of a person to be examined (person ID number)

To input and display responses of an examined person to the items described in the questioning sheet.

To write inputted responses (hearing information) and the identification information of an examined person into the optical magnetic disk.

The hearing information input unit (HI) can readily be realized by adapting a personal computer to be obtained in the market. As the configuration has no connection with the gist of the present invention, the description is omitted.

As the image acquisition unit (IA), first main functions are described.

To acquire digital image data. To input the identification information of a person to be examined (patient ID number).

To input and display information attached to an examination and an image.

To write the identification information of an examined person, image data, and information attached to an examination and an image into the optical magnetic disk.

As for the image acquisition (IA), a configuration element and its functions will be described. The configuration of the image acquisition unit (IA) is shown in FIG. 17.

Control Unit (IA-CTRL)

A control unit contains a central processing unit (CPU) or system memories (namely, semiconductor memory) etc. and controls operations of the entire image acquisition unit.

System Disk (IA-SD)

This is a magnetic disk and stores a program or data, such as: (a) a program for operating an image acquisition unit; (b) identification information of a person to be examined; and (c) information attached to an examination and an image. This program is read out when the image acquisition unit is turned on and written into system memories within the control unit (IA-CTRL). Furthermore, the identification information of an examined person and the information attached to an examination and an image are stored for each examination and a type of the data is shown in FIG. 18 together with a data configuration.

X-ray Generator (IA-XGEN)

This is a device for generating X-rays to irradiate a person to be exposed.

X-ray Imaging Unit (IA-IMG)

This is a device for detecting X-rays transmitted through a person to be exposed, converting them into electric signals, and digitizing the signals to obtain a digital image. This contains an image intensifier, a TV camera, an analog/digital converter and the like.

Input Unit (IA-INPUT)

This is means for inputting information such as commands etc. by an operator and uses a keyboard, a mouse, a touch screen or the like.

Display Unit (IA-DISP)

This is a device for displaying information inputted by an operator and digital image acquired, and uses a CRT display, a liquid crystal panel display or the like.

Image Data Unit (IA-IM)

This is a device for temporarily storing digital image data acquired by the X-ray imaging unit (for example, a semiconductor memory or a magnetic disk).

Optical Disk Drive (IA-MODD)

This is a device for reading data out of a portable optical magnetic disk or writing data thereinto.

Control Bus (IA-CBUS)

This is a transmission path of various control information within the image acquisition unit.

Image Bus (IA-IBUS)

This is a transmission path of image data within the image acquisition unit.

Also, a clock (not shown in FIG. 18) is integral with the image acquisition unit.

As for the database (DB), first main functions and operations will be explained.

The database (DB) stores identification information of an examined person, hearing information, image data, and information attached to examination information and an image.

The database (DB) stores findings which are doctors' interpretation results.

The database (DB) detects images having doubtful abnormalities from image data.

The database (DB) can write various data into the portable optical magnetic disk or read them out of it.

Configuration elements and functions in the database (DB) will be described. The configuration of the database (DB) is shown in FIG. 19.

Control Unit (DB-CTRL)

This includes a central processing unit (CPU), system memories (namely, semiconducting memory) or the like and controls operations of the entire database.

System Disk (DB-SD)

This is a magnetic disk and stores a program for operating the database or the like. This program etc. is read out when an electric power of the database is turned on and written into system memories within the control unit (DB-CTRL).

Search Unit (DB-SRCH)

This searches information conforming to a given keyword according to an instruction from the control unit (DB-CTRL), and is a device having functions of replying searched results to the control unit (DB-CTRL). The search unit includes a directory of information stored in the database and searching means. A magnetic disk is used as storing means of the directory.

Data Storing Unit (DB-STRG)

This is a device for storing identification information of an examined person, hearing information, image data, information attached to examination information and an image, and doctor's findings for a long-termed period, and an optical disk is used as the data storing unit (BD-STRG).

Figure 64:
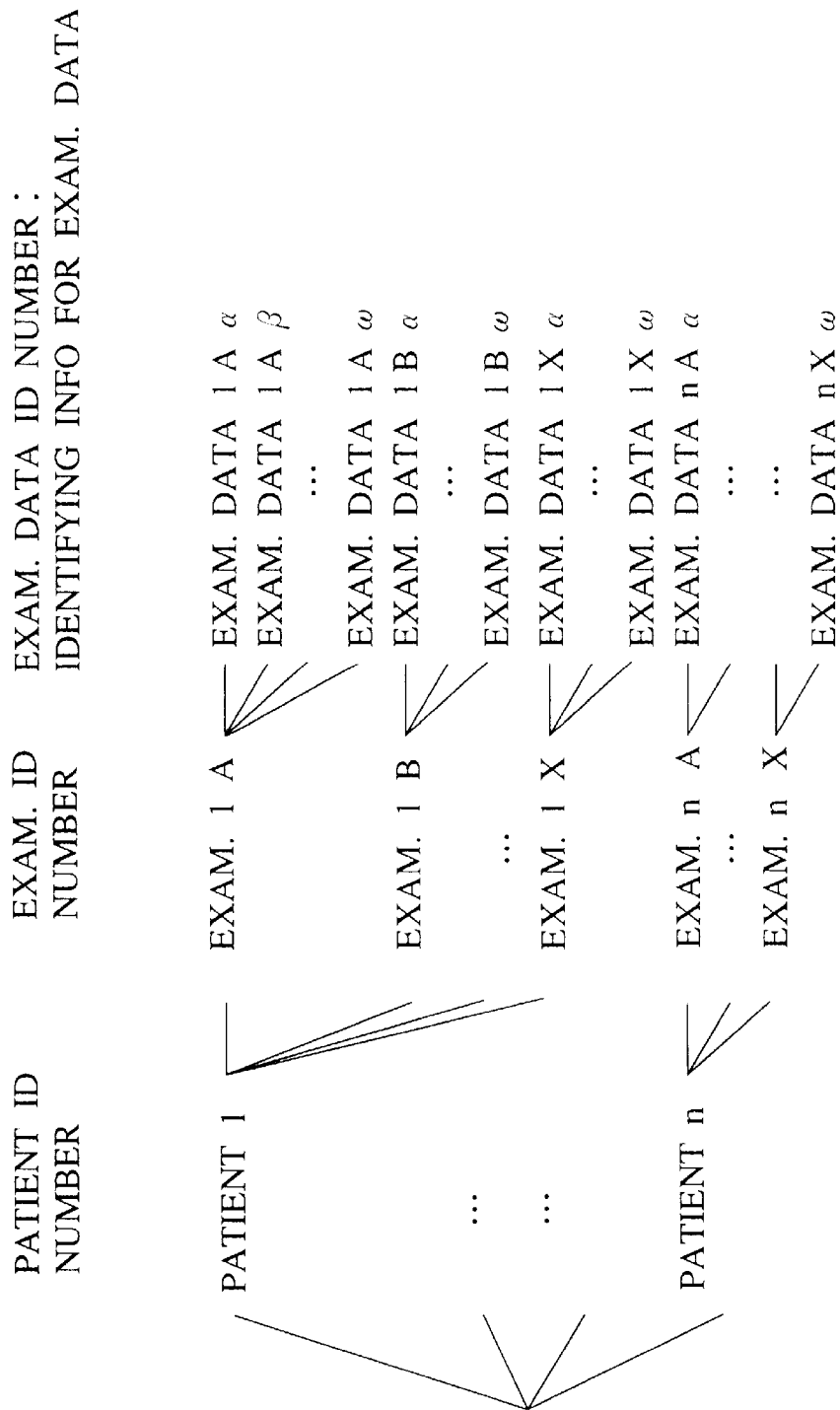

Herein, identification information of medical examination data in association with the identification information of the examined person will be explained. The data of the examined person, the medical inspection, and the examination (image) data are the relationship like a tree-type chart as shown in FIG. 64. This is because there are some possibilities that one examined person is made a plurality of medical examinations and that a plurality of examination (image) data produce each medical examination. Identification information of the medical examination data is one corresponding to the examination (image) data individually and capable of specifying the medical examination (image) data from the identification information. For instance, in the case where the examination data is the image data, the identification information is an image ID number etc. from which an examination ID number, an examined patient ID number, a name of an examined patient, and the like can be searched. In FIG. 64, the identification information is equal to 1Aα to nXω, and for instance, if the image ID number is 2Gδ, 2Gδ means the examined patient ID number 2, the examination ID number 2G, and the G-th examination of the examined patient ID number 2, and δ means the δ-th image of the G-th examination. Alternatively, as shown in FIGS. 65A & 65B and 66A & 66B, a corresponding table of the examined patient ID number, the examination ID number, and the examination (image) data ID number exists in this data storing unit (DB-STRG) to search each other. FIGS. 65A and 85B show the case where the examination (image) data ID number is searched from the examined patient ID number, and as shown in FIG. 65A, the examination ID number is recognized from the examined patient ID number, whereby the examination (image) data ID number can be extracted from this examination ID number as shown in FIG. 65B. Reversely, FIGS. 66A and 66B shows the case where the examined patient ID number is searched from the examination (image) data ID number.

In this embodiment, a medical examination is made once per examined patient in order to avoid complexity and a sheet of example is picked up in the image produced in the examination. Accordingly, the identification information of the medical examination data, the examination identification information, and the examined patient identification information are in the same definition. However, as described above, in the case where one examined patient receives a plurality of medical examinations, or a plurality of examination (image) data produces in one medical examination, the identification information of the medical examination data is required to combine the examined patient ID number, the examination ID number, and the examination (image) data ID number, or search each other.

Image Processing Unit (DB-IP)

This is means for detecting abnormalities from an image, and when image data and data indicating a type of abnormalities (disease) which is an object to be detected are inputted, the image processing unit (DB-IP) detects the type of abnormalities and outputs a position and a degree of abnormalities, and includes a plurality of types of abnormality detecting means. That is:

(a) means for detecting shadows of pulmonary nodules in a front side image in a chest plain X-ray image; and (b) means for detecting shadows of pulmonary interstitial disease in a front side image in a chest X-ray image.These detecting means are disclosed in the below-mentioned literatures:(1) Japanese Patent Application Laid-Open No. 2-185240 (2) Japanese Patent Application Laid-Open No. 2-152443 (3) Japanese Patent Application Laid-Open No. 1-125675.

Input Unit (DB-INPUT)

This is means for inputting information such as commands by an operator, and a keyboard, a touch screen, or the like is used for the input unit (DB-INPUT).

Optical Magnetic Disk Drive (DB-MODD)

This is a device which reads data out of the portable optical magnetic disk or writes them into it.

Control Bus (DB-CBUS)

This is a transmission path of various control information within the database.

Image Bus (DB-IBUS)

This is a transmission path of image data within the database.

First, main functions and operations of the workstation (WS) will be described.

To display identification information of an examined person, hearing information, image data, information attached to examination information and an image, and doctor's findings.

To display various information concerning abnormalities such as a type of abnormalities (disease), a position and degree of abnormalities, or the like.

To input the findings which are doctor's interpreting results.

To write various data into the portable optical magnetic disk or read them out of it.

Next, configuration elements and functions of the workstation (WS) will be described. FIG. 20 is a configurational diagram of the workstation (WS).

Control Unit (WS-CTRL)

This contains a central processing unit (CPU), system memories (namely, semiconductor memory), and the like and controls operations of the entire workstation.

System Disk (ES-SD)

This is a magnetic disk and stores a program etc. This program is read out when an electric power of the workstation (WS) is switched on, and written into the system memories within the control unit (WS-CTRL).

Input Unit (WS-INPUT)

This is means for inputting information such as commands, interpretation reports (findings), or the like by an operator, arid a keyboard, a mouse, a touch screen, or the like is used for the input unit (WS-INPUT). The touch screen is mounted onto a screen of the display unit (WS-DISP).

Data Memory (WS-MEM)

This is a device for temporarily storing various data such as image data etc. and is a magnetic disk.

Imaging Frame Memory (WS-IFM)

This is a device for temporarily storing a plural sheet of image data in a semiconductor memory.

Image Display Manager (WS-IDM)

This operates so as to display an image and an overlay. FIG. 21 is a configurational diagram of the image display manager (WS-IDM) and a part of the image display manager (WS-IDM) is shown within a broken line. This includes the following portions:

a) Control Portion

This controls the entire configuration portion of the image display manager (WS-IDM).

b) Overlay Data Making Portion

This makes overlay data (color) from overlay display information. This contains means for displaying by flickering as to data indicated in the overlay display information.

c) Image Memory for Storing Image Data

This has memories corresponding to a sheet of image (a matrix size is 2,048×2,048 pixels).

d) Overlay Memory for Storing Overlay Data

Since the overlay data are displayed in color, the overlay memories corresponding to one screen are constructed of three sheets of overlay memory for red, green, and blue. In the overlay memory for each color, a matrix size is conceptually 2,048×2,048 pixels, and a bit length of 1 pixel is 1 bit. The relationship between a display color and a bit value of each pixel is shown in FIG. 22. In FIG. 22, for example as shown in Step 2, a pixel value (a bit value of pixel) of a pixel coordinate (X, Y) of the overlay memory for red is 1, and a pixel value of the same coordinate of the overlay memory for both green and blue is 0, and a red color is displayed as to the coordinate. On the other hand, black in a display color means that any colors are not displayed, and when black is doubly displayed on an image, only the image is displayed.

e) Overlay Portion

An overlay portion superimposes image data on overlay data.

f) Displaying Memory for Storing Display Data

This image display manager (WS-IDM) has two sheets of memory for displaying a sheet of image (a matrix size is 2,048×2,048 pixels). This is equal to the number of the display units (WS-DISP). The memories for displaying correspond to the display units (WS-DISP), respectively.

g) D/A Converter

This converts display data of digital data into those of analog data.

This is provided with the same number as the display unit (WS-DISP) so as to correspond to it.

The image display manager (WS-IDM) can receive the following information:

(a) Type of data to be displayed

Three types: an image only, an overlay only, an image and an overlay combined.

(b) Designated information of the display unit (WS-DISP) displaying data (c) Overlay display information A type of a graphic, a size of a graphic, coordinates, a display color, presence or absence of display (containing a flicker), control information, or the like per graphic.

(d) Image Data

When displaying an image overlapping an overlay, the image display manager (WS-IDM) operates in the following manner:

(1) The control portion of the image display manager (WS-IDM) receives the below-mentioned three information from the control unit (WS-CTRL) of the workstation (WS).

(a) "Images and overlays" as a type of data to be displayed.

(b) A display unit number of the display unit (WS-DISP) displaying data.

(c) Overlay Display Information (2) The image display manager (WS-IDM) receives image data and writes them into the image memories.

(3) The overlay data making portion makes overlay data based on overlay display information by an instruction of the control portion. Then, when control information of presence or absence of display is a "display", the overlay data making portion makes the overlay data with an indicated graphic, indicated coordinates, and indicated color data.

(4) The image data and overlay data are read out by an instruction of the control portion to input them into the overlay portion to synthesize the data.

(5) The synthesized data are written into displaying memories with an indicated display unit number.

(6) The synthesized data are converted into analog data by the D/A converter.

The above-mentioned operations (4) to (6) are always repeated during the display.

Only when the control information of presence or absence of display (containing a flicker) denotes a "display" as to a graphic in cetain coordinates, the overlay data making portion writes the graphic into the overlay memories to display it.

On the other hand, when an image is just displayed, in the above-mentioned operation (1), the overlay data making portion receives:

(a) an "only image" as a type of data to be displayed; and (b) a display unit number of the display unit displaying data, however the portion does not receive the overlay display information. Then, in the above-mentioned operation (4), the overlay data making portion does not read out the overlay data, and accordingly does not superimpose the image data on the overlay data.

Display Unit (WS-DISP)

This is a device for displaying characters, graphics, and images, and a CRT display, a liquid crystal panel display, or the like is used for the display unit. A color display is available. In this embodiment, two units are set.

Optical Magnetic Disk Drive (WS-MODD)

This is a device for reading or writing data for a portable optical magnetic disk.

Control Bus (WS-CBUS)

This is a transmission path of various control information within the workstation.

Image Bus (WS-IBUS)

This is a transmission path of image data and overlay data within the workstation.

In this connection, a clock for referring to a date and a time (not shown in the figure) is integral with the workstation (WS).

Thus-constructed PACS is used, and a flow of a series of system operations is described, for example, when a chest X-ray image in a lung cancer examination is interpreted.

The operations will be carried out in the following procedures:

1. Input of hearing information
2. Acquisition of chest X-ray image
3. Registration of acquired data
4. Preparation of interpreting data
5. Interpretation of image data
6. Output of interpreting results Hereinafter, in the the following variations of fifth embodiment (embodiment 5-1, 5-2, 5-3, the above-mentioned series of system operations will be described in detail.

Embodiment No. 5-1

1. Input of Hearing Examination (1) Display of hearing sheet

A hearing sheet is displayed on a display screen of the hearing information input unit (HI).

(2) Input of hearing information (i) An operator inputs examined person identification information from the hearing information input unit (HI). The examined person identification information is assigned to the examined person so as not to overlap each other within such medical examination area, and an examined patient ID number described in a register shall here be inputted. The inputted data are displayed in a specific position on a screen.

(ii) An operator inputs a response obtained from the examined person in the hearing information input unit (HI). The inputted data are displayed in a specific position on a screen.

The above-mentioned Subsections (1) and (2) are repeated only by a number of examined persons.

(3) Write hearing information into optical magnetic disk

The control unit of the hearing information input unit (HI) reads out hearing information (examined person identification information and responses from the examined persons) stored in the system disk by an instruction of an operator, and writes it into the optical magnetic disk inserted into the optical magnetic disk drive (HI-MODD).

The thus-obtained optical magnetic disk is later carried to a certain position of the database (DB).

2. Acquisition of Chest X-ray Images (1) Input of examined person identification information An operator inputs examined person identification information from the input unit (IA-INPUT) of the image acquisition unit (IA). The inputted data are displayed in a specific position on a screen of the display unit (IA-DISP).

(2) Acquisition of digital image (i) The control unit (IA-CTRL) indicates to irradiate X-rays and image to the X-ray generator (IA-XGEN) and the X-ray imaging unit (IA-IMG). The X-ray generator (IA-XGEN) generates X-rays and irradiates them onto a person to be exposed (person to be examined). The X-rays transmitted through the person to be exposed are detected by the X-ray imaging unit (IA-IMG) to obtain digital images. The X-ray imaging unit (IA-IMG) transmits image data to the image bus (IA-IBUS). As a result, the image data unit (IA-IM) receives the image data to write them to itself.

(ii) The control unit (IA-CTRL) writes information attached to imaging conditions or images together with examined person identification information into the system disk (IA-SD).

The above-mentioned Subsections (1) and (2) are repeated by a number of persons to be examined.

(3) Write into optical magnetic disk of data (i) The control unit (IA-CTRL) reads out information attached to an examination and an image which is stored in the system disk (IA-SD) by an instruction of an operator, and writes it into an optical magnetic disk inserted into the optical magnetic disk drive (IA-MODD).

(ii) The control unit (IA-CTRL) successively reads out image data from the image data unit (IA-IM) and writes them into the optical magnetic disk inseted into the optical magnetic disk drive (IA-MODD).

The thus-obtained optical magnetic disk is later carried to a cetain position of the database (DB).

3. Registration of Acquired Data (i) An operator inserts the optical magnetic disk registering hearing information into the optical magnetic disk drive (DB-MODD) of the database (DB), and inputs a hearing information readout command of the optical magnetic disk from the input unit (DB-INPUT). Then, by an instruction of the control unit (DB-CTRL), the optical magnetic disk drive (DB-MODD) reads out the hearing information registered in the optical magnetic disk and writes it into the data storing unit (DB-STRG). The control unit (DB-CTRL) extracts information (hereinafter, referred to as directory information. Refer to FIG. 20) registered in a data directory from the hearing information to send it to the search unit (DB-SRCH). The search unit (DB-SRCH) stores the received directory information.

Furthermore, the control unit (DB-CTRL) extracts the previously radiographed image data (in the past) of examined persons (hereinafter, called previous or past image data) from the examined person identification information of the hearing information from the data storing unit (DB-STRG) to send them to the search unit (DB-SRCH). The search unit (DB-SRCH) adds the received previous image data to the directory information.

Figure 67:
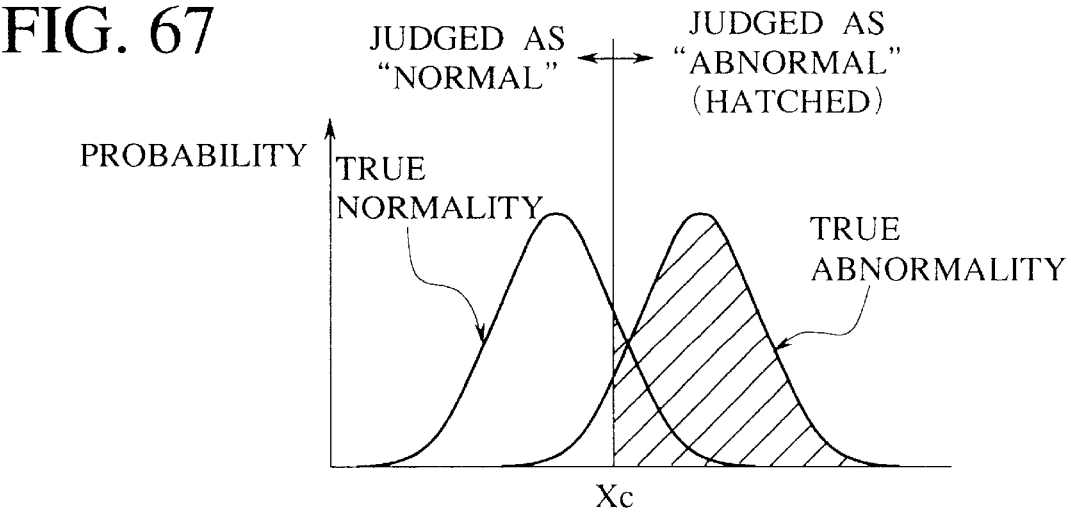
Figure 68:
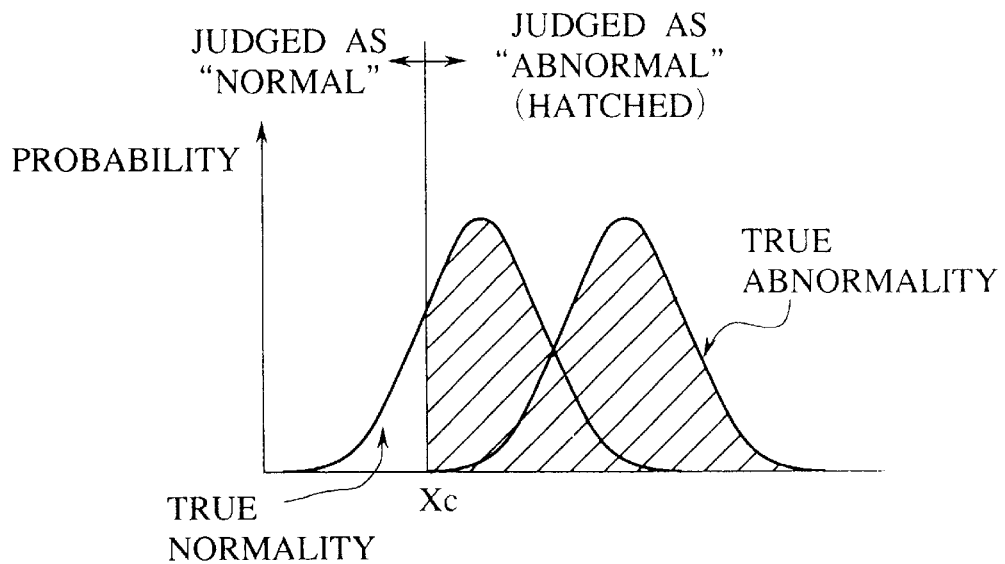
Figure 69:
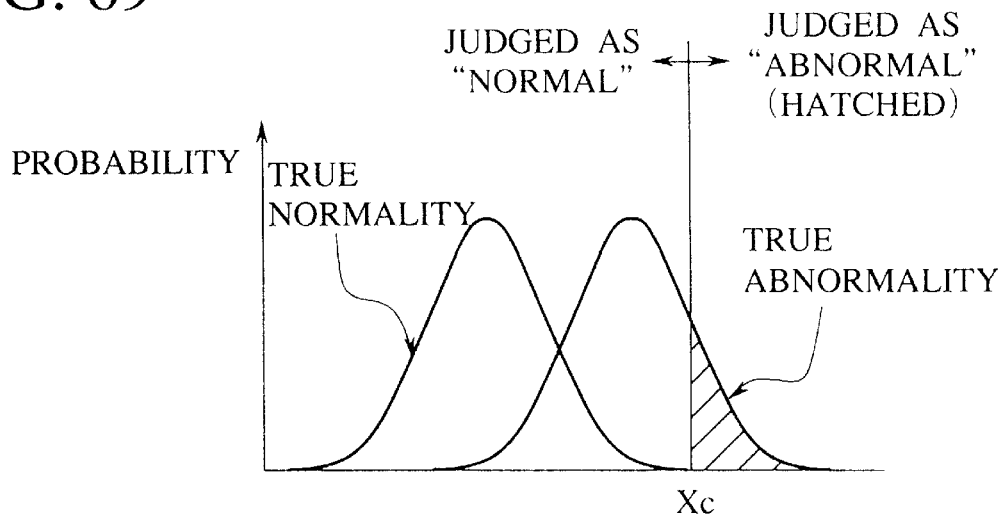

(ii) An operator inserts the optical magnetic disk registering information attached to an examination and an image and the image data into the optical magnetic disk drive (DB-MODD) of the database (DB), and inputs an image information readout command of the optical magnetic disk from the input unit (DB-INPUT). Then, by an instruction of the control unit (DB-CTRL), the optical magnetic disk drive (DB-MODD) reads out the information attached to an examination and an image and the image data which are registered in the optical magnetic disk and writes it into the data storing unit (DB-STRG). The control unit (DB-CTRL) extracts directory information from the information attached to an examination and an image to send it to the search unit (DB-SRCH). The search unit (DB-SRCH) stores the received directory information 4. Preparation of Interpreting Data (1) Detection of an abnormality from an image using a plurality of threshold values (i) When finishing registering the data, the control unit (DB-CTRL) of the database (DB) indicates the search unit (DB-SRCH) to search the registered images (images to be interpreted and previous images) to obtain a response. Successively, the control unit (DB-CTRL) indicates to perform the following abnormality detecting operations for each sheet of images. The abnormality to be detected is shadows of pulmonary nodules or an interstitial lung disease. Herein, a threshold value will be explained. According to statistics, normal persons and abnormal persons distribute as shown in FIG. 67. In FIG. 67, the value of Xc is found and it is judged that a blank portion left-sided from this value is "normal", and that an oblique line portion (hatched area) right-sided from this value is "abnormal", in order to output them. Such judgement reference value Xc of the normality or abnormality is a threshold value. When this threshold value Xc is moved extremely leftwardly as shown in FIG. 68, the scope of the normality becomes narrow, and as the output results, the "normality" is lessened and the "abnormality" is increased. Reversely, as shown in FIG. 69, when the threshold value Xc is moved extremely rightwardly, the scope of the abnormality becomes narrow, and as the output results, the "normality" is increased and the "abnormality" is lessened. In the abnormality detecting means as to the above-mentioned two types of an abnormality, the detection of the abnormality can be realized by changing various parameters and threshold levels. In this embodiment, two threshold values can be respectively applied to each of the abnormality detecting means, and the scope of the normality is set so as to be narrow in the first threshold value and the scope of the abnormality is set so as to be narrow in the second threshold value. The data existent in each scope have the high probability of the normality and abnormality.

(ii) Image data corresponding to a sheet of image are read out from the data storing unit (DB-STRG) and sent to the image processing unit (DB-IP). The image processing unit (DB-IP) receives the image data and operates pulmonary nodules shadow detecting means by using the first threshold value stored inside to detect presence or absence of the abnormalities. The detected results are written into an abnormality data table as first detected results of pulmonary nodules. The image of the examination ID number 920001 is written as the "abnormality". Next, the image processing unit (DB-IP) operates the pulmonary nodules shadow detecting means by using the second threshold value to detect presence or absence of the abnormality. The detected results by the pulmonary nodules shadow detecting means by using the second threshold value are written into the abnormality data table as the second detected results of the pulmonary nodules. The image of the examination ID number 920001 is written as the "abnormality".

(iii) The image processing unit (DB-IP) operates, in the same manner as the pulmonary nodules, the interstitial lung disease detecting means by using the first threshold value stored inside and the interstitial lung disease detecting means by using the second threshold value to detect presence or absence of the abnormality. The detected results are written into the abnormality data table as the first and second detected results. The image of the examination ID number 920001 is written as the "abnormality" at using the interstitial lung disease detecting means by using the first threshold value, and as the "normality" at using the interstitial lung disease detecting means by using the second threshold value.

The abnormality data table concerning the image of the examination ID number 920001 is shown in FIG. 70.

The abnormality data tables in the images of the examination ID numbers 92002 to 920010 are shown in FIGS. 70 to 79. Nodule in the figures denotes pulmonary nodules and ILD denotes an interstitial lung disease.

(2) Classification of data according to the detected abnormalities (i) The control unit (DB-CTRL) compares respective abnormality detected results of the abnormality data table each type of the abnormality. The types of the detected abnormalities are the pulmonary nodules and interstitial lung disease. The results detected by using two threshold values for each type of the abnormality are classified as follows: This is called a first classification.

Case 1: The case where both of the first detected results and the second detected results are "normal".

Case 2: The case where one detected results are "abnormal" and the other detected results are "normal".

Case 3: The case where both of the first detected results and the second detected results are "abnormal".

Next, the above-mentioned classification results are compared each type of the abnormality to classify as follows: This is called a second classification.

Case A: The classified results of the type of all abnormalities have been classified in the case 1.

Case B: There exist even one of the types of the abnormality classified in the case 3.

Case C: This case does not fall under both of the case A and the case B.

The data falling under the cases A, B, and C are listed to register into lists A, B, and C.

(ii) As an embodiment of the classification, the classification of the image of the examination ID number 920001 will be described. The results of the pulmonary nodules in the abnormality data table as shown in FIG. 70 fall under the case 3 in the first classification since both of the first detected results and the second detected results are "abnormal". Also, the results of the interstitial lung disease in the abnormality data table as shown in FIG. 70 fall under the case 2 in the first classification since the first detected results are "abnormal" and the second detected results are "normal".

Accordingly, the data fall under the case B in the second classification.

(iii) The classified results of the images of the examination ID numbers 920001 to 920010 are shown in FIG. 80. Also, the examination ID numbers in which the second classified results fall under the case A, the case B, and the case C are respectively registered in the list A, the list B, and the list C. The created list A, list B, and list C are shown in FIGS. 81, 82, and 83.

(3) Preparation of interpreting data (i) When the abnormality detecting processing from the images is finished, the control unit (DB-CTRL) indicates the data storing unit (DB-STRG) to read out the image data to be interpreted, the previous image data, the hearing information, and the information attached to an examination and an image (containing the abnormality data table) of the examination ID number registered in the list C, and indicates the optical magnetic disk drive (DB-MODD) to write them. The data storing unit (DB-STRG) reads out these data to send to the image bus (DB-IBUS). The optical magnetic drive (DB-MODD) receives these data and writes into the optical magnetic disk C.

(ii) The control unit (DB-CTRL) associates the examined patient identification information, the name of the examined patient, and the abnormality data table corresponding to the examination ID number registered in the list B with each other, and indicates the optical magnetic disk drive (DB-MODD) to write the overall judgement results as an "abnormality". Then, the data storing unit (DB-STRG) reads out these data to send to the image bus (DB-IBUS). The optical magnetic disk drive (DB-MODD) receives these data to write into the optical magnetic disk B.

(iii) The control unit (DB-CTRL) associates the examined patient identification information and the name of the examined patient corresponding to the examination ID number registered in the list A with each other and indicates the optical magnetic disk drive (DB-MODD) to write the overall judgement results as a "normality". Then, the data storing unit (DB-STRG) reads out these data to send to the image bus (DB-IBUS). The optical magnetic disk drive (DB-MODD) receives these data to write into the optical magnetic disk B.

The optical magnetic disk B is carried to the patient to be reported to make such a report recommending the patient who is reported the overall judgement results "abnormality" to make a close examination.

In the medical group examination, the interpretation is carried out by two doctors. Accordingly, two optical magnetic disks C are prepared to carry each sheet to each of two workstations (WS).

5. Interpretation of Image Data (1) Input of interpreting data into workstation (WS)

An operator inserts the optical magnetic disk C registering image data to be interpreted, previous image data, hearing information, and information attached to an examination and an image into the optical magnetic disk drive (DB-MODD) of the workstation (WS) and inputs a data readout command from the optical magnetic disk C from the input unit (WS-INPUT). Then, by an instruction of the control unit (WS-CTRL), the optical magnetic disk drive (DB-MODD) reads out the data stored in the optical magnetic disk C and writes them into the data memory (WS-MEM). The image data to be interpreted, the previous image data, the hearing information, and the information attached to an examination and an image are memorized corrresponding to each examined person.

(2) Display of image

The workstation (WS) displays the images to be interpreted. Now, as two display units (WS-DISP) are provided, a sheet of image to be interpreted (the examination ID number 920007) is automatically displayed on the left-sided display unit (WS-DISP). Also, when an image is displayed on the display unit (WS-DISP), its examination ID number (existent in the information attached to an image) is displayed.

(3) Input of interpretation findings

From the interpretation to input of findings as the results, the following procedures are carried out:

(a) An interpreting doctor reads the displayed images.

When the interpreting doctor displays images and interprtation reports other then the displayed one, he/she inputs a command for it from the input unit (WS-INPUT) and operates.

(b) When the interpreting doctor finishes interpreting the image, he/she points out a position of pulmonary nodule shadows on the image to be interpreted with a mouse.

The control unit (WS-CTRL) reads out the coordinates of the position of the abnormality inputted to store it, and creates a finding data table as shown in FIG. 30. Then, the image display manager (WS-IDM) creates overlay display information describing "arrow, coordinares of the position of an abnormality, white, and display" as to the abnormality in each finding number referring to the finding data table. The created overlay display information is shown in FIG. 31. The image display manager (WS-IDM) creates an overlay according to the overlay display information to display it. As a result, an arrow is displayed in a position that a doctor indicates on the image. The control unit (WS-CTRL) writes the overlay display information created into the data memory (WS-MEM) corresponding to the examination ID number.

(c) When an interpreting doctor recognizes an abnormality other than the pulmonary nodules, he/she inputs an abnormality type selecting command from the input unit (WS-INPUT) to select the corresponding type of an abnormality among several types of abnormality type displayed. Next, when he/she inputs the position of abnormalities, a method of inputting the position of abnormalities is different according to the type of abnormalities. For example, in an interstitial lung disease, he/she inputs a scope of an abnormality by enclosing it with a closed curved line by using a mouse. In this case, the control unit (WS-CTRL) memorizes an area instead of the position.

A doctor carries out the same operations and adds information relating to an abnormality to an overlay to be memorized and displays on the image.

(d) When an interpreting doctor inputs all discovered abnormalities, he/she inputs an interpretation completing command.

When an abnormality is inputted into the finding data table, the control unit (WS-CTRL) writes the diagnosed results of the entire image as an "abnormality" into the finding data table, and when an abnormality is not inputted into the finding data table, the control unit (WS-CTRL) writes the diagnosed results of the entire image as a "normality" into the finding data table to memorize into the data memory (WS-MEM).

(4) Write of the finding data into optical magnetic disk

The control unit (WS-CTRL) reads out the finding data tables concerning all the images to be interpreted from the data memory (WS-MEM) and writes into the optical magnetic disk inserted into the optical magnetic disk drive (WS-MODD).

These operations in Section 5, Subsections (1) to (4) are carried out.

6. Output of Interpretation Results (1) Registration of the finding data into the database An operator inserts the optical magnetic disk registering the finding data table into the optical magnetic drive (DB-MODD) of the database (DB), and inputs a finding data readout command of the optical magnetic disk from the input unit (DB-INPUT). Then, by an instruction of the control unit (DB-CTRL), the optical magnetic disk drive (DB-MODD) reads out the finding data table registered in the optical magnetic disk, and writes into the data storing unit (DB-STRG). The control unit (DB-CTRL) extracts directory information from the finding data table to send to the search unit (DB-SRCH). The search unit (DB-SRCH) stores the received directory information.

The data registered in another optical magnetic disk are also registered in the database in the same manner as the above operations. Thus, the two doctors' finding data as to the identical examination image are inputted into the database.

(2) Extraction of a person required to make a close examination (i) An operator inputs a close examination required person extracting command from the input unit (DB-INPUT) of the database (DB). Then, by an instruction of the control unit (DB-CTRL), the search unit (DB-SRCH) searches the finding data tables of a chest X-ray examination in which the overall judgements of the interpretation results (judgements whether or not the close examination is necessary) are not made, the control unit (DB-CTRL) reads out the examined patient identification information and the diagnosed results information of two doctors in the system memory.

(ii) The control unit (DB-CTRL) extracts the two doctors' diagnosed results of each examined patient from the finding data table and compares each other. If one of the two doctors' diagnosed results is "abnormal", the overall judgements are made as an "abnormality", and when the both are "normal", the overall judgements are made as a "normality".

The overall judgement results are associated with the examined patient identification information to be transferred to the data storing unit (DB-STRG) and the search unit (DB-SRCH) to be stored.

(3) Outputs of the interpretation results

The control unit (DB-CTRL) reads out the overall judgements from the data storing unit (DB-STRG), and after the results of the overall judgements:

In the case where the overall judgement results are "normal", the overall judgement results are associated with the examined patient identification information and the name of the examined patient to write into the optical magnetic disk D.

In the case where the overall judgement results are "abnormal", the control unit (DB-CTRL) indicates the search unit (DB-SRCH) to search images to be interpreted from the data storing unit (DB-STRG) to read out. The two doctors' finding data table, the overall judgements, and the images to be interpreted are associated with the examined patient identification information and the name of the examined patient to write into the optical magnetic disk D.

The optical magnetic disk D is carried to the patient reported.

At this time, a flow of the series of system operations for interpreting a chest X-ray image in the lung cancer examination is completed.

Embodiment No. 5-2

Applications to interpreting supports in the lung cancer group examination will be picked up in the same manner as the embodiment No. 5-1. As Sections 1, 2, and 3 in a flow of a series of system operations for the interpretation are entirely same as the embodiment No. 5-2, the description is omitted. The following will be described:

4. Only a part of the preparation of image data will be described.
5. The interpretaion of image data
6. The output of interpretation results However, in this embodiment, as the embodiment in which the data to be interpreted by the doctor are outputted in a form of the examined patient identification information which is a type of the identification information of the medical image data, the optical magnetic disk registering all the image data in 2. Acquisition of the Chest X-ray Image, (3) Write of the data into the optical magnetic disk is called an optical magnetic disk X. This optical magnetic disk X is used for communicating the image data with the database (DB) etc.

4. Preparation of Interpreting Data (1) Detection of an abnormality from an image using a plurality of algorithms (i) When finishing registering the data, the control unit (DB-CTRL) of the database (DB) indicates the search unit (DB-SRCH) to search the registered images (images to be interpreted and previous images) to obtain a response. Successively, the control unit (DB-CTRL) indicates to perform the following abnormality detecting operations on each sheet of images. The abnormality to be detected is shadows of pulmonary nodules and an interstitial lung disease. Herein, by using the algorithm as described in literatures concerning the CAD described in the column of the prior art, an abnormality is detected. That is, as to an interstitial lung disease, two detecting algorithms of the literatures (1), (4), and (5) shall be used, and as to pulmonary nodules, two algorithms of the literatures (2), (6), (7), and (8) shall be selected and used.

(ii) Image data corresponding to a sheet of image are read out from the data storing unit (DB-STRG) and sent to the image processing unit (DB-IP). The image processing unit (DB-IP) receives the image data and operates pulmonary nodule shadow detecting means by using a first algorithm stored inside to detect presence or absence of the abnormalities. The detected results are written into an abnormality data table as first detected results of the pulmonary nodules. Next, by operating the pulmonary nodule shadow detecting means by a second algorithm to detect presence or absence of the abnormalities. The detection results are, in the same manner, written into the abnormality data table as second detection results of the pulmonary nodules. The images of the examination ID number 930001 are "abnormal" in the first detection results, and also "abnormal" in the second detection results.

(iii) The image processing unit (DB-IP) operates, in the same manner as the pulmonary nodules, the pulmonary interstitial disease detecting means by using 15 the first algorithm stored inside and the pulmonary interstitial disease detecting means by using the second algorithm to write the detected results into the abnormality data table as the first and second detection results of the pulmonary interstitial disease. In the images of the examination ID number 930001, the first detection results were "normal" and the second detection results were "abnormal".

The abnormality data table concerning the image of the examination ID number 930001 is shown in FIG. 84. In this connection, Nodule in the figure denotes pulmonary nodules and ILD denotes a pulmonary interstitial disease.

(2) Classification of data according to the detected abnormalities (i) The control unit (DB-CTRL) compares respective abnormality detected results of the abnormality data table each type of the abnormality. The types of the detected abnormalities are the pulmonary nodules and pulmonary interstitial disease. The results detected by using two algorithms each type of the abnormality are classified as follows: This is called a first classification.

Case 1: The case where both of the first detected results and the second detected results are "normal".

Case 2: The case where one detected result is "abnormal" and the other detected results are "normal".

Case 3: The case where both of the first detected results and the second detected results are "abnormal".

Next, the above-mentioned classified results are compared each type of the abnormality to classify as follows: This is called a second classification.

Case A: The classified results of the type of all abnormalities have been classified in the case 1.

Case B: There exists even one of the types of the abnormality classified in the case 3.

Case C: This case does not fall under both of the case A and the case B.

The data falling under the cases A, B, and C are listed to register into lists A, B, and C.

(ii) As an embodiment of the classification, the classification of the image of the examination ID number 930001 will be described. The results of the pulmonary nodules in the abnormality data table as shown in FIG. 84 fall under the case 3 in the first classification since both of the first detected results and the second detected results are "abnormal". Also, the results of the interstitial lung disease in the abnormality data table as shown in FIG. 84 fall under the case 2 in the first classification since the first detected results are "normal" and the second detected results are "abnormal". Accordingly, the data fall under the case B in the second classification.

(iii) The classified results of the images of the examination ID numbers 930001 to 930010 are shown in FIG. 85. Also, the examination ID numbers in which the second classified results fall under the case A, the case B, and the case C are respectively registered in the list A, the list B, and the list C. The created list A, list B, and list C are shown in FIGS. 86, 87, and 88.

(3) Preparation of interpreting data (i) When the abnormality detecting processing from the images is finished, the control unit (DB-CTRL) associates the list C, and the previous image data, the hearing information, and the information attached to an examination and an image (containing the abnormality data table) of the examined patient identification information corresponding to the examination ID number registered in this list C, and the examined patient identification information and the name of the examined patient corresponding to the examination ID number registered in the list C, and the abnormality data table with each other. The control unit (DB-CTRL) indicates the data storing unit (DB-STRG) to read out and indicates the optical magnetic disk drive (DB- MODD) to write. The data storing unit (DB-STRG) reads out these data and sends to the image bus (DB-IBUS). The optical magnetic drive (DB-MODD) receives these data and writes into the optical magnetic disk C.

(ii) The control unit (DB-CTRL) associates the examined patient identification information, the name of the examined patient, and the abnormality data table corresponding to the examination ID number registered in the list B with each other, and indicates the optical magnetic disk drive (DB-MODD) to write the overall judgement results as an "abnormality". Then, the data storing unit (DB-STRG) reads out these data to send to the image bus (DB-IBUS). The optical magnetic disk drive (DB-MODD) receives these data to write into the optical magnetic disk B.

(iii) The control unit (DB-CTRL) associates the examined patient identification information and the name of the examined patient corresponding to the examination ID number registered in the list A with each other and indicates the optical magnetic disk drive (DB-MODD) to write the overall judgement results as a "normality". Then, the data storing unit (DB-STRG) reads out these data to send to the image bus (DB-IBUS). The optical magnetic disk drive (DB-MODD) receives these data to write into the optical magretic disk B.

The optical magnetic disk B is carried to the patient to be reported to make such a report recommending the patient who is reported the overall judgement results "abnormality" to make a close examination.

In the medical group examination, the interpretation is carried out by two doctors. Accordingly, two sets consisting of two sheets of optical magnetic disk C and X are prepared to carry each set to each of the two workstations (WS).

5. Interpretation of Image Data(1) Input of interpreting data into workstation (WS)

An operator inserts the optical magnetic disk C registering the list C, and the previous image data, the hearing information, and the information attached to an examination and an image in relation to the examination ID number described in this list C, and the examination ID number, the examined patient identification information, and the name of the examined patient corresponding to each other, and the abnormality data table into the optical magnetic disk drive (WS-MODD), and inputs a data readout command from the optical magnetic disk C from the input unit (WS-INPUT). Then, by an instruction of the control unit (WS-CTRL), the optical magnetic disk drive (DB-MODD) reads out the data stored in the optical magnetic disk C and writes them into the data memory (WS-MEM). Furthermore, an operator inserts the optical magnetic disk X registered in all the examination image data into the optical magnetic disk drive (WS-MODD) of the workstation (WS), and inputs a readout command of the image data to be interpreted corresponding to the examination ID number registered in the list C from the input unit (WS-INPUT). Then, by an instruction of the control unit (WS-CTRL), the optical magnetic disk drive (WS-MODD) reads out the image data registered in the list C from the optical magnetic disk X, and writes into the data memory (WS-MEM). Thus, the image data to be interpreted, the previous image data, the hearing information, and the information attached to an examination and an image are memorized corrresponding to each examined person.

(2) Display of Image

The workstation (WS) displays the images to be interpreted. Now, as two display units (WS-DISP) are provided, a sheet of image to be interpreted (the examination ID number 92002) is automatically displayed on the left-sided display unit (WS-DISP). Also, when an image is displayed on the display unit (WS-DISP), its examination ID number (existent in the information attached to an image) is displayed.

(3) Input of interpretation findings

From the interpretation to inputs of findings as the results, the following procedures are carried out:

(a) An interpreting doctor reads the displayed images.

When the interpreting doctor displays images and interpretation reports other then the displayed one, he/she inputs a command for it from the input unit (WS-INPUT) and operates.

(b) When the interpreting doctor finishes interpreting the image, he/she points out a position of pulmonary nodule shadows on the image to be interpreted with a mouse.

The control unit (WS-CTRL) reads out the coordinates of the position of the abnormality inputted to store it, and creates a finding data table. The created finding data table are written into the data memory (WS-MEM) corresponding to the examination ID number.

(c) When an interpreting doctor recognizes an abnormality other than the pulmonary nodules, he/she inputs an abnormality type selecting command from the input unit (WS-INPUT) to select the corresponding type of an abnormality among several types of abnormality type displayed. Next, when he/she inputs the position of abnormalities, a method of inputting the position of abnormalities is different according to the type of abnormalities. For example, in a pulmonary interstitial disease, he/she inputs a scope of an abnormality by enclosing it with a closed curved line by using a mouse. In this case, the control unit (WS-CTRL) memorizes an area instead of the position.

(d) When an interpreting doctor inputs all discovered abnormalities, he/she inputs an interpretation completing command.

When an abnormality is inputted into the finding data table,the control unit (WS-CTRL) writes the diagnosed results of the entire image as an "abnormality" into the finding data table, and when an abnormality is not inputted into the finding data table, the control unit (WS-CTRL) writes the diagnosed results of the entire image as a "normality" into the finding data table to memorize into the data memory (WS-MEM).

(4) Write of the finding data into optical magnetic disk

The control unit (WS-CTRL) reads out the finding data 25 tables concerning all the images to be interpreted from the data memory (WS-MEM) and writes into the optical magnetic disk inserted into the optical magnetic disk drive (WS-MODD).

These operations in Section 5, Subsections (1) to (4) are carried out at two locations.

6. Output of Interpretation Results (1) Registration of the finding data into the database An operator inserts the optical magnetic disk registering the finding data table into the optical magnetic drive (DB-MODD) of the database (DB), and inputs a finding data table readout command of the optical magnetic disk from the input unit (DB-INPUT). Then, by an instruction of the control unit (DB-CTRL), the optical magnetic disk drive (DB-MODD) reads out the finding data table registered in the optical magnetic disk, and writes into the data storing unit (DB-STRG). The control unit (DB-CTRL) extracts directory information from the finding data table to send to the search unit (DB-SRCH). The search unit (DB-SRCH) stores the received directory information.

The data registered in another optical magnetic disk are also registered in the database in the same manner as the above operations. Thus, the two doctors' finding data as to the identical examination image are inputted into the database.

(2) Extraction of a person required to make a close examination (i) An operator inputs a close examination required person extracting command from the input unit (DB-INPUT) of the database (DB). Then, by an instruction of the control unit (DB-CTRL), the search unit (DB-SRCH) searches the finding data tables of a chest X-ray examination in which the overall judgements of the interpretation results (judgements whether or not the close examination is necessary) are not made, the control unit (DB-CTRL) reads out the examined patient identification information and the diagnosed results information of two doctors in the system memory.

(ii) The control unit (DB-CTRL) extracts the two doctors' diagnosed results of each examined patient from the finding data table and compares each other. If one of the two doctors' diag-nosed results is "abnormal", the overall judgements are made as an "abnormality", and when the both are "normal", the overall judgements are made as a "normality".

The overall judgement results are associated with the examined patient identification information to be transferred to the data storing unit (DB-STRG) and the search unit (DB-SRCH) to be stored.

(3) Output of the interpretation results

The control unit (DB-CTRL) reads out the overall judgements from the data storing unit (DB-STRG), and after the results of the overall judgements:

In the case where the overall judgement results are "normal", the overall judgement results are associated with the examined patient identification information and the name of the examined patient to write into the optical magnetic disk D.

In the case where the overall judgement results are "abnormal", the control unit (DB-CTRL) indicates the search unit (DB-SRCH) to search images to be interpreted from the data storing unit (DB-STRG) to read out. The two doctors' finding data table, the overall judgements, and the images to be interpreted are associated with the examined patient identification information and the name of the examined patient to write into the optical magnetic disk D.

The optical magnetic disks D and X are carried to the patient reported.

At this time, a flow of the series of system operations for interpreting a chest X-ray image in the lung cancer examination is completed.

Embodiment No. 5-3

Applications to interpreting supports in the lung cancer group examination will be taken up in the same manner as the embodiment no. 5-1. As Sections 1, 2, 3, 5, and 6 in a flow of a series of system operations for the interpretation are entirely same as the embodiment 1, only a part of 4. Preparation of Interpreting Data will be explained.

4. Preparation of Interpreting Data (1) Computation of a characteristic value of an image (i) When finishing registering the data, the control unit (DB-CTRL) of the database (DB) indicates the search unit (DB-SRCH) to search the registered images (images to be interpreted and previous images) to obtain a response. Successively, the control unit (DB-CTRL) indicates to perform the following abnormality value operations each sheet of images. The computed abnormality value is shadows of pulmonary nodules and an interstitial lung disease. Herein, a method of computing a characteristic value will be explained.

In the case of the pulmonary nodules, after a filter is put on the image to undergo several tests, the remainder is deemed to be the abnormal shadows. Then, as to all the image in the database (DB), the number of candidate of the abnormal shadows which have passed each test is seeked and a set which makes it a population is seeked. In the objective image, the number of candidate of the abnormal shadows which have passed each test is seeked and each deviation value is seeked. A mean value of the deviation value is deemed to be an abnormal value concerning the pulmonary nodules.

In the case of the interstitial lung disease, with reference to the literatures, about twenty regions of interest (ROI) is set on the image, and its inside is made a texture analysis to obtain a single index, and the judgement of an abnormality or a normality is made by the value. Then, as to all images in the database (DB), a set in which the single index of the upper five ROIs of each image is a population is seeked. The upper five values of the single index of each ROI of the objective image are seeked. The deviation value of the five single indexes in the previously acquired set is seeked, and the mean value of five deviation values is an abnormal value concerning the pulmonary interstitial disease.

As compared with the abnormal value acquired each type of each disease, the maximum value is deemed to be a characteristic value of the image.

(ii) The data storing unit (DB-STRG) reads out a sheet of image data and sends to the image processing unit (DB-IP). The image processing unit (DB-IP) receives image data and operates the pulmonary nodule detecting means stored inside, and stores the number of candidate of abnormal shadows in each stage. Next, the image processing unit (DB-IP) acquires a deviation value in a population as to respective values, and further acquires a mean value of the acquired deviation value which is an abnormal value concerning the pulmonary nodules. The acquired abnormal value is written into the abnormality data table. Each computed value as shown in FIG. 89 is referred to before the abnormality data table concerning the image of the examination ID number 940001 is seeked.

(iii) The image processing unit (DB-IP) operates the pulmonary interstitial disease detecting means stored inside in the same manner as the pulmonary nodules, and computes the single index of each ROI. Next, the upper five values are acquired. Also, a deviation value in a population as to respective values is aquired. Further, the mean value of the acquired deviation value is acquired to be an abnormal value concerning the interstitial lung disease. The aquired abnormal value is written into the abnormality data table. Each computed value as shown in FIG. 90 is referred to before the abnormality data table concerning the image of the examination ID number 940001 is acquired.

(iv) In the acquired abnormal value, the pulmonary nodules are 73.75, and the interstitial lung disease is 70.84. Accordingly, the maximum value is 73.75, which is written into the abnormality data table as a characteristic value of the image of the examination ID number 940001. The abnormality data table of the image of the examination ID number 940001 is shown in FIG. 91.

(2) Classification of data corresponding to the computed characteristic value (i) The control unit (DB-CTRL) compares two set points X, Y (X<Y) which are beforehand decided as to the characteristic value of the image of the abnormality data table, and the classification will be made as follows:

Case A: The characteristic value of the image is less than a set point X.

Case B: The characteristic value of the image is a set point Y or more.

Case C: The characteristic value of the image is a set point X or more and less than a set point Y.

The image data falling under the cases A, B, and C are respectively listed and registered in the lists A, B, and C.

(ii) As an embodiment of the clasification, the classification of the image of the examination ID number 940001 will be described. The characteristic value of the image of the abnormality data table as shown in FIG. 91 is 73.75. The set points X, Y are respectively set as follows:

Set point X=32.00, Set point Y=68.00

Accordingly, this falls under the case B in the classification.

(iii)The classified results of the images of the examination ID numbers 940001 to 940010 are shown in FIG. 92. Also, the examination ID numbers in which the classified results fall under the case A, the case B, and the case C are respectively registered in the list A, the list B, and the list C. The created list A, list B, and list C are shown in FIGS. 93, 94, and 95.

(3) Preparation of interpreting data (i) When finishing the abnormality detecting processing from the images, the control unit (DB-CTRL) indicates the data storing unit (DB-STRG) to read out the image data to be interpreted, the previous image data, the hearing information, and the information attached to an examination and an image (containing the abnormality data table) of the examination ID number registered in the list C, and indicates the optical magnetic disk drive (DB-MODD) to write. The data storing unit (DB-STRG) reads out these data to send to the image bus (DB-IBUS). The optical magnetic disk drive (DB-MODD) receives these data to write into the optical magnetic disk C.

(ii) The control unit (DB-CTRL) associates the examined patient identification information, the name of the examined patient, and the abnormality data table corresponding to the examination ID number registered in the list B with each other, and indicates the optical magnetic disk drive (DB-MODD) to write the overall judgement results as an "abnormality". Then, the data storing unit (DB-STRG) reads out these data to send to the image bus (DB-IBUS). The optical magnetic disk drive (DB-MODD) receives these data to write into the optical magnetic disk B.

(iii)The control unit (DB-CTRL) associates the examined patient identification information and the name of the examined patient corresponding to the examination ID number registered in the list A with each other and indicates the optical magnetic disk drive (DB-MODD) to write the overall judgement results as a "normality". Then, the data storing unit (DB-STRG) reads out these data to send to the image bus (DB-IBUS). The optical magnetic disk drive (DB-MODD) receives these data to write into the optical magnetic disk B.

The optical magnetic disk B is carried to the patient to be reported to make such a report recommending the patient who is reported the overall judgement results "abnormality" to make a close examination.

In the medical group examination, the interpretation is carried out by two doctors. Accordingly, two sheets of optical magnetic disk C are prepared to carry each sheet to each of two workstations (WS).

The succeeding operations are same as the embodiment No. 5-1.

Next, in the embodiments no. 6-1 and no. 6-2 concerning the first and second variation for the sixth embodiment according to the present invention, a series of system operations; will be described in detail.

Embodiment No. 6-1

Even in this embodiment, as a series of system operations 1, 2, and 3 are entirely identical to the embodiment 1, the description is omitted. The following will be described:

4. Preparation of interpreting data
5. Interpretation of imaging data
6. Output of interpretation results Then, the embodiment in which the interpretaion of a chest X-ray image in the identical lung cancer examination to the embodiment no. 5-1 is carried out will be described below.

4. Preparation of Interpreting Data (1) Detection of an abnormality from an image using a plurality of threshold values (i) When finishing registering the data, the control unit (DB-CTRL) of the database (DB) indicates the search unit (DB-SRCH) to search the registered images (images to be interpreted and previous images) to obtain a response. Successively, the control unit (DB-CTRL) indicates to perform the following abnormality detecting operations each sheet of images. The abnormality to be detected is shadows of pulmonary nodules and an interstitial lung disease. Herein, the method of setting a threshold value is same as the embodiment no. 5-1. That is, as to various types of an abnormality, two threshold values can respectively be applied, and the first threshold value is set so as to be narrow in the scope of a normality and the second threshold value is set so as to be narrow in the scope of an abnormality. The respective scopes cover the high probability of a normality and an abnormality.

(ii) Image data corresponding to a sheet of image are read out from the data storing unit (DB-STRG) and sent to the image processing unit (DB-IP). The image processing unit (DB-IP) receives the image data and operates pulmonary nodules shadow detecting means by using a first threshold value stored inside to detect presence or absence of the abnormalities. The detected results are written into an abnormality data table as first detected results of the pulmonary nodules. The image of the examination ID number 920001 is judged to be "abnormal". Next, by operating the pulmonary nodule shadow detecting means by using a second threshold value to detect presence or absence of the abnormalities. The detected results by the pulmonary nodules shadow detecting means by using the second threshold value are written into the abnormality data table as the second detection results of the pulmonary nodules. The image of the examination ID number 920001 is judged to be "abnormal".

(iii)The image processing unit (DB-IP) operates, in the same manner as the pulmonary nodules, the interstitial lung disease detecting means stored inside by using the first threshold value and the pulmonary interstitial disease detecting means by using the second threshold value to detect presence or absence of the abnormality. The detected results are written into the abnormality data table as the first and second detection results. The image of the examination ID number 920001 is "abnormal" in the pulmonary interstitial disease detecting means by using the first threshold value, and "normal" in the pulmonary interstitial disease detecting means by using the second threshold value.

The abnormality data table concerning the image of the examination ID number 920001 is shown in FIG. 96. In this connection, Nodule in the figure denotes pulmonary nodules and ILD denotes an interstitial lung disease.

(2) Classification of data according to the detected abnormalities (i) The control unit (DB-CTRL) compares respective abnormality detected results of the abnormality data table each type of the abnormality. The types of the detected abnormalities are the pulmonary nodules and pulmonary interstitial disease. The results detected by using two threshold values each type of the abnormality are classified as follows: This is called a first classification.

Case 1: The case where both of the first detected results and the second detected results are "normal".

Case 2: The case where one detected results is "abnormal" and the other detected results are "normal".

Case 3: The case where both of the first detected results and the second detected results are "abnormal".

Next, the above-mentioned classified results are compared each type of the abnormality to classify as follows: This is called a second classification.

Case A: The classified results of the type of all abnormalities have been classified in the case 1.

Case B: There exists even one of the types of the abnormality classified in the case 3.

Case C: This case does not fall under both of the case A and the case B.

The data falling under the cases A, B, and C are listed to register into lists A, B, and C.

(ii) As an embodiment of the classification, the classification of the image of the examination ID number 920001 will be described. The results of the pulmonary nodules in the abnormality data table as shown in FIG. 96 fall under the case 3 in the first classification since both of the first detected results and the second detected results are "abnormal". Also, the results of the pulmonary interstitisl disease in the abnormality data table as shown in FIG. 96 fall under the case 2 in the first classification since the first detected results are "normal" and the second detected results are "abnormal". Accordingly, the data fall under the case B in the second classification.

(iii)The classified results of the images of the examination ID numbers 920001 to 920030 are shown in FIG. 97. Also, the examination ID numbers in which the second classified results fall under the case A, the case B, and the case C are respectively registered in the list A, the list B, and the list C. The created list A, list B, and list C are shown in FIGS. 98, 99 and 100.

Out of the image data registered in the lists created, the image data registered in the list A and list B are respectively judged to be "normal" and "abnormal" to be reported. The image data registered in the remaining list C are required a doctor's interpretation.

(3) Re-detection of an abnormality from the interpreting image (i) When finishing registering the lists, the control unit (DB-CTRL) indicates (instructs) the search unit (DB-SRCH) to search the image registered in the list C (an image to be interpreted and a previous image) to obtain a response. Successively, the following abnormality detecting operations are carried out again for each sheet of image. The detected abnormalities are the pulmonary nodule shadows and interstitioal disease. A third threshold value to be used this time is not as narrow in the scope of a normality as in the first threshold value, and the third threshold value is not as narrow in the scope of an abnormality as in the second threshold value. The third threshold value is such that it has a true positive fraction to a degree that the doctor can check the overlookedness, and at the same time a false positive fraction becomes a minimum. In other words, the third threshold value to be used this time is suitable for a diagnosis of the substantially same level as the level of the doctor's diagnosis.

(ii) A sheet of image data is read out from the data storing unit (DB-STRG) to send to the image processing unit (DB-IP). The image processing unit (DB-IP) receives the image data and operates the pulmonary nodule shadow detecting means using the third threshold value stored inside to detect presence or absence of an abnormality and its position in the case of the abnormality. The detected results are written into the abnormality detailed data table as the abnormality detailed detection results of the pulmonary nodules.

(iii)The image processing unit (DB-IP) operates, in the same manner as the pulmonary nodules, the pulmonary interstitial disease detecting means using the third threshold value stored inside and detects presence or absence of the abnormality and its position in the case of the abnormality. The detected results are written into the abnormality detailed data table as the abnormality detailed detection results of the interstitial lung disease.

(iv) In the case where the abnormality is detected in any abnormality detecting operations, the CAD processed results are written into the abnormality detailed data table as an "abnormality", and in the case where the abnormality is not detected even in any abnormality detecting operations, the CAD processed results are written into the abnormality detailed data table as a "normality".

The abnormality detailed data table concerning the image of the examination ID number 92002 is shown in FIG. 101.

As described above, Paragraphs (ii) to (iv) of Subsection (3) are repeated for all the images registered in the list C. At a doctor's interpretation, the abnormality detailed data table or the like of the CAD processed results is referred to and used for a disgnosis.

(4) Preparation of interpreting data (i) When the abnormality detecting processing from the images is finishing, the control unit (DB-CTRL) indicates the data storing unit (DB-STRG) to read out the image data to be interpreted, the previous image data, the hearing information, the abnormality detailed data table, and the information attached to an examination and an image of the examination ID number registered in the list C, and indicates the optical magnetic disk drive (DB-MODD) to write them. The data storing unit (DB-STRG) reads out these data and sends to the image bus (DB-IBUS). The optical magnetic drive (DB-MODD) receives these data and writes into the optical magnetic disk C.

(ii) The control unit (DB-CTRL) associates the examined patient identification information, the name of the examined patient, and the abnormality data table corresponding to the examination ID number registered in the list B with each other, and indicates the optical magnetic disk drive (DB-MODD) to write the overall judgement results as an "abnormality". Then, the data storing unit (DB-STRG) reads out these data to send to the image bus (DB-IBUS). The optical magnetic disk drive (DB-MODD) receives these data to write into the optical magnetic disk B.

(iii) The control unit (DB-CTRL) associates the examined patient identification information and the name of the examined patient corresponding to the examination ID number registered in the list A with each other and indicates the optical magnetic disk drive (DB-MODD) to write the overall judgement results as a "normality". Then, the data storing unit (DB-STRG) reads out these data to send to the image bus (DB-IBUS). The optical magnetic disk drive (DB-MODD) receives these data to write into the optical magnetic disk B.

The optical magnetic disk B is carried to the patient to be reported to make such a report recommending the patient who is reported the overall judgement results "abnormality" to make a close examination.

In the medical group examination, the interpretation is carried out by two doctors.

Accordingly, these two sheets of optical magnetic disk C are prepared and are carried to workstations (WS). 5. Interpretation of Image Data (1) Input of Interpreting Data into Workstation (WS)

An operator inserts the optical magnetic disk C registering the image data to be interpreted, the previous image data, the hearing information, and the information attached to an examination and an image into the optical magnetic disk drive (WS-MODD) of the workstation (WS), and inputs a data readout command from the optical magnetic disk C from the input unit (WS-INPUT). Then, by an instruction of the control unit (WS-CTRL), the optical magnetic disk drive (DB-MODD) reads out the data stored in the optical magnetic disk C and writes them into the data memory (WS-MEM). The image data to be interpreted, the previous image data, the hearing information, the abnormality detailed data table, and the information attached to an examination and an image are stored corresponding to each examined patient.

(2) Display of Image

The workstation (WS) displays the images to be interpreted. Now, as two display units (WS-DISP) are provided, a sheet of image to be interpreted (the examination ID number 92002) is automatically displayed on the left-sided display unit (WS-DISP). Also, when an image is displayed on the display unit (WS-DISP), its examination ID number (existent in the information attached to an image) is displayed.

(3) Input of interpretation findings

From the interpretation to inputs of findings as the results, the following procedures are carried out:

(a) An interpreting doctor reads the displayed images.

When the interpreting doctor displays images and interpretation reports other then the displayed one, he/she inputs a command for it from the input unit (WS-INPUT) and operates.

(b) When the interpreting doctor finishes interpreting the image, he/she points out a position of pulmonary nodule shadows on the image to be interpreted with a mouse.

The control unit (WS-CTRL) reads out the coordinates of the position of the abnormality inputted to store it, and creates a finding data table as shown in FIG. 102. Then, the image display manager (WS-IDM) refers to the finding data table and creates the overlay display information describing "arrow, coordinates of the position of an abnormality, white, display" in the abnormality of each finding number. The created overlay display information is shown in FIG. 103. The image display manager (WS-IDM) creates the overlay according to the overlay display information and displays. As a result, an arrow is displayed in a position that a doctor points out on the image. The control unit (WS-CTRL) associates the created overlay display information with the examination ID number and writes it into the data memory (WS-MEM).

(c) When an interpreting doctor recognizes an abnormality other than the pulmonary nodules, he/she inputs an abnormality type selecting command from the input unit (WS-INPUT) to select the corresponding type of an abnormality among several types of abnormality type displayed. Next, when he/she inputs the position of abnormalities, a method of inputting the position of abnormalities is different according to the type of abnormalities. For example, in a pulmonary interstitial disease, he/she inputs a scope of an abnormality by enclosing it with a closed curved line by using a mouse. In this case, the control unit (WS-CTRL) memorizes an area instead of the position.

By performing the same operations, the information concerning the abnormality is added to the overlay and stored to display on the image.

(d) When an interpreting doctor inputs all discovered abnormalities, he/she inputs an interpretation completing command.

When an abnormality is inputted into the finding data table, the control unit (WS-CTRL) writes the diagnosed results of the entire image as an "abnormality" into the finding data table, and when an abnormality is not inputted into the finding data table, the control unit (WS-CTRL) writes the diagnosed results of the entire image as a "normality" into the finding data table to memorize into the data memory (WS-MEM).

(4) Comparison and classification of diagnostic information and registration into an abnormality detection result list (i) The control unit (WS-CTRL) reads out a finding data table which is interpretation results and an abnormality detailed data table from the data memory (WS-MEM).

In the same manner as the overlay display information is created from the finding data table in Section 5, Subsection (3), the image display manager (WS-IDM) creates the overlay display information from the abnormality detailed data table indicating that a display color is "red" and memorizes it into the data memory (WS-MEM) corresponding to the examination ID number. The overlay display information created from the abnormality detailed data table of the CAD processing results concerning the examination ID number 920002 is shown in FIG. 104.

The control unit (WS-CTRL) extracts both the diagnostic results of the entire image from the finding data table and the judged results of the entire image of the CAD processing from the abnormality detailed data table to compare the both results to classify them into the following four cases:

Case a: The doctor judges as an "abnormality", but the CAD judges as a "normality".

Case b: The doctor judges as an "abnormality", and the CAD also judges as an "abnormality".

Case c: The doctor judges as a "normality", and the CAD also judges as a "normality".

Case d: The doctor judges as a "normality", but the CAD judges as an "abnormality".

For example, as, concerning the examination ID number 920002, the doctor judges as an "abnormality" and the CAD judges as an "abnormality", this case is classified into the case b.

(ii) According to the above-mentioned classification results, the later operations are different. The operations are described below.
(a) When classifying into the case a, no operations.
(b) When classifying into the case b, no operations.
(c) When classifying into the case c, no operations.
(d) When classifying into the case d, register in the abnormality detection result list.

Herein, "register in the abnormality detection result list" means that the control unit (WS-CTRL) reads out the abnormality detection result list (or creates in the case where it does not exist) and writes the examination ID number into the data memory (WS-MEM) to store. An example of the abnormality detection result list is shown in FIG. 105.

(5) Display of comparison results

The operations corresponding to the number of all sheets of images to be interpreted in Section 5, Subsections (1) to (4) are repeated.

The control unit (WS-CTRL) extracts the disgnostic results and the judgement results for the entire image from the finding data table of the doctor and the abnormality detailed data table of the CAD, and the results compared and classified is shown in FIG. 106. The interpreted images are 19 sheets registered in the list C.

Figure 107:
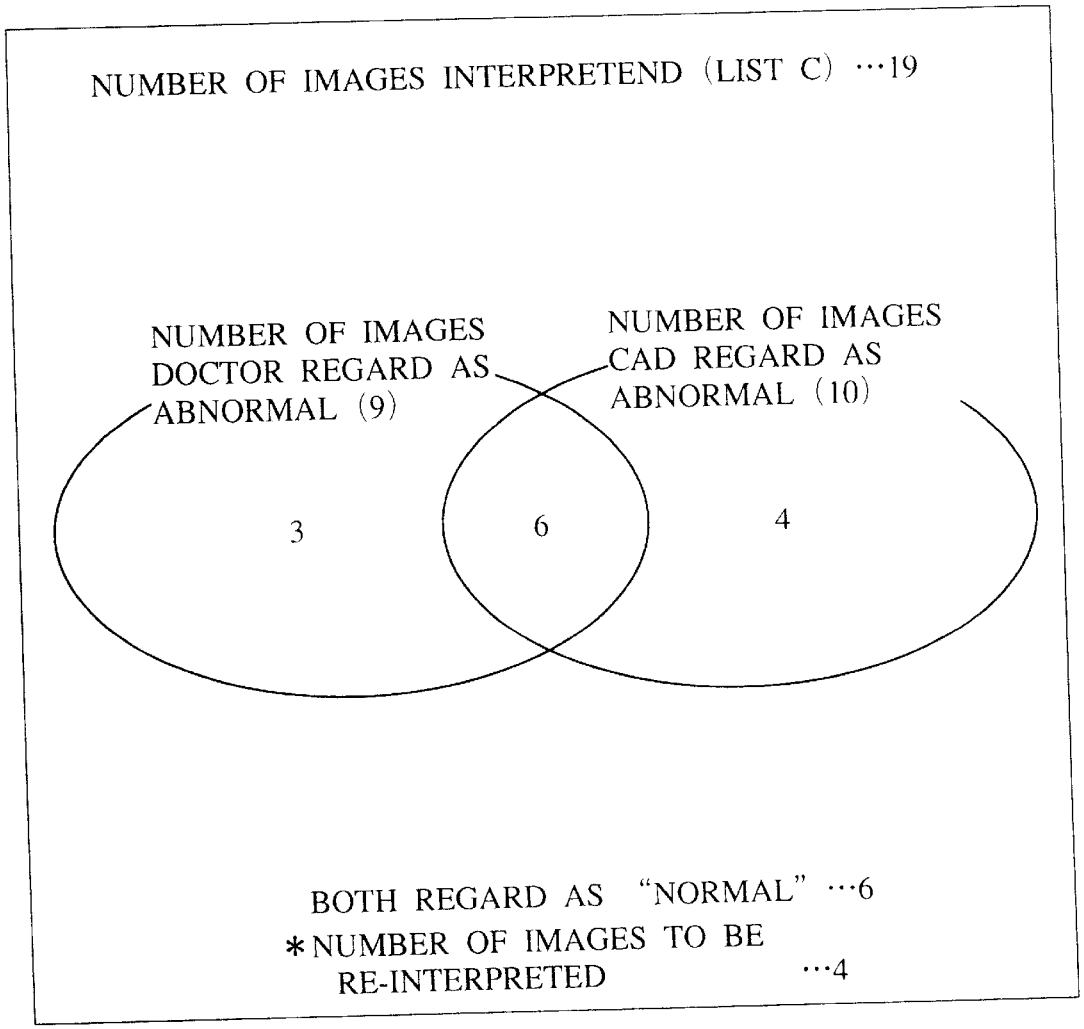

The classified results were:
Case a: 3 sheets Case b: 6 sheets
Case c: 6 sheets Case d: 4 sheets Thereafter, the control unit (WS-CTRL) displays the classified results in Section 5, Subsection (4) in the display unit (WS-DISP) as shown in FIG. 107.

(6) Re-interpretation and reference of abnormality detection results

A doctor inputs a reinterpreting command. Then, the control unit (WS-CTRL) reads out the image data to be interpreted which register the examination ID number in the abnormality detection result list and the information relating to the examined patient (the hearing information, the information attached to an examination and an image (an abnormality detailed data table, a finding data table, an overlay display information), the previous image data) from the data memory (WS-MEM), and superimposes the image to be interpreted on the overlay meaning his/her finding to display it on the left-sided display unit (WS-DISP) of two display units (WS-DISP), and superimposes the image to be interpreted on the overlay meaning the CAD processing results concerning a specific image to display it on the right-sided display unit (WS-DISP).

The doctor reads an image and compares his/her finding with the CAD processing results.

When displaying the images and the interpretation reports other than those displayed, the doctor inputs a command for it from the input unit (WS-INPUT) and operates.

When the doctor finishes interpreting the image and discovers shadows of an abnormality, he/she points out its position on the image to be interpreted with a mouse. Also, he/she can correct the position of an abnormality which is previously pointed out with a mouse.

Thereafter, a doctor operates in the same manner as operated in Section 5, Subsection (3), Paragraph (c) and after, he/she inputs all the discovered abnormalities. The control unit (WS-CTRL) memorizes the corrected finding data table into the data memory (WS-MEM), and the overlay of the next image and the doctor's finding and the overlay of the CAD processing results, which are registered into the abnormality detection result list, are displayed in the display unit (WS-DISP).

As described above, the procedures as described in Subsection (6) will be carried out for all the images registered in the abnormality detection result list.

(7) Write of finding data into the optical magnetic disk

The control unit (WS-CTRL) reads out the finding data table concerning all the images to be interpreted from the data memory (WS-MEM) and writes it into the optical magnetic disk inserted into the optical magnetic disk drive (WS-MODD).

These operations in Section 5, Subsections (1) to (7) will be carried out at two locations.

6. Output of Interpretation Results (1) Registration of finding data into the database An operator inserts the optical magnetic disk memorizing the finding data table additionally into the optical magnetic disk drive (DB-MODD) of the database (DB), and inputs a finding data readout command of the optical magnetic disk from the input unit (DB-INPUT). Then, by an instruction of the control unit (DB-CTRL), the optical magnetic disk drive (DB-MODD) reads out the finding data memorized in the optical magnetic disk and writes into the data storing unit (DB-STRG). The control unit (DB-STRL) extracts directory information from the finding data table to send to the search unit (DB-SRCH). The search unit (DB-SRCH) stores the received directory information.

Another sheet of optical magnetic disk is also registered into the database (DB) in the same manner. Thus, the two doctors' finding data concerning the identical examination image have been inputted into the database (DB).

(2) Extraction of persons to make a close examination (i) An operator inputs a close examination examined patient extracting command from the input unit (DB-INPUT) of the database (DB). Then, by an instruction of the control unit (DB-CTRL), the search unit (DB-SRCH) searches a finding data table of a chest X-ray examination which has not been made overall judgements of interpretation results (judgements as to whether a close examination is necessary or nor), and reads out the examined patient identification information and the two doctors' diagnostic result information in the system memory of the control unit (DB-CTRL).

(ii) The control unit (DB-CTRL) extracts the two doctors' diagnostic results of each examined patient from the finding data table to compare. If even one of the diagnostic results of two doctors is "abnormal", the overall judgement is made as an "abnormality", and if only the both are "normal", the overall judgement is made as a "normality".

The overall judgement results are associated with the examined patient identification information, and are transferred to the data storing unit (DB-STRG) and the search unit (DB-SRCH) to store therein.

(3) Output of the interpretation results

The control unit (DB-CTRL) reads out the overall judgements from the data storing unit (DB-STRG). According to results of the overall judgements, the following operations are available:

In the case where the overall judgement results are "normal", the overall judgement results are written into the optical magnetic disk D corresponding to the examined patient identification information and the name of the examined patient.

In the case where the overall judgement results are "abnormal", the control unit (DB-CTRL) indicates the search unit (DB-SRCH) to search the image to be interpreted from the data storing unit (DB-STRG) to read out. The two doctors' finding data table and overall judgements and the images to be interpreted are written into the optical magnetic disk D corresponding to the examined patient identification information and the name of the examined patient.

The optical magnetic disk D is carried to a person to receive the report.

At this time, a flow of a series of system operations for interpreting the chest X-ray image in the lung cancer examination is completed.

Embodiment No. 6-2

Even in this embodiment, as Sections 1, 2, 3, 5, and 6 of the series of system operations are entirely identical to the embodiment no. 6-1, the description is omitted, and only a part of 4. Preparation of Interpreting Data will be described. Then, an example of interpreting a chest X-ray image in the identical lung cancer examination to the embodiment no. 6-1 will be hereinafter described.

4. Preparation of Interpreting Data (1) Detection of abnormality from image by using a different algorithm (i) When data are finished registering, the control unit (DB-CTRL) of the database (DB) indicates to search images registered in the search unit (DB-SRCH) (an image to be interpreted and a previous image) and obtains a response. Successively, the following abnormality detecting operations are carried out each image. The abnormality to be detected is the pulmonary nodule shadow and interstitial lung disease. Herein, the algorithms as described in the literatures concerning the CAD as described in the column of the prior art are used to detect the abnormality. That is, the two detecting algorithms of the literatures (1), (4), and (5) are used as to the pulmonary interstitial disease, and the two algorithms of the literatures (2), (6), (7), and (8) are selectively used as to the pulmonary nodules.

(ii) The control unit (DB-CTRL) reads out the image data corresponding to a sheet of image from the data storing unit (DB-STRG) to send to the image processing unit (DB-IP). When the image processing unit (DB-IP) receives the image data, it operates the pulmonary nodule shadow detecting means by the first algorithm stored inside to detect presence or absence of the abnormality. The detected results are written into the abnormality data table as the first detection results of the pulmonary nodules. Next, the pulmonary nodule shadow detecting means is operated by the second algorithm to detect presence or absence of the abnormality. The detection results are similarly written into the abnormality data table as the second detection results of the pulmonary nodules. In the image of the examination ID number 920001, the first detection results were "abnormal", and the second detection results were "abnormal".

(iii) The image processing unit (DB-IP), in the same manner as the pulmonary nodules, operates the pulmonary interstitial disease detecting means by the first algorithm stored inside, and the interstitial lung disease detecting means by the second algorithm, and writes the detected results into the abnormality data table as the first and second detection results of the pulmonary interstitial disease. In the images of the examination ID number 920001, the first detection results were "normal", and the second detection results were "abnormal".

The abnormality data table concerning the image of the examination ID number 920001 is shown in FIG. 96. In this connection, Nodule in the figure denotes pulmonary nodules and ILD denotes an interstitial lung disease.

(2) Classification of data according to the detected abnormalities (i) The control unit (DB-CTRL) compares respective abnormality detected results of the abnormality data table each type of the abnormality. The types of the detected abnormalities are the pulmonary nodules and interstitial lung disease. The results detected by using two algorithms each type of the abnormality are classified as follows: This is called a first classification.

Case 1: The case where both of the first detected results and the second detected results are "normal".

Case 2: The case where one detected result is "abnormal" and the other detected results are "normal".

Case 3: The case where both of the first detected results and the second detected results are "abnormal".

Next, the above-mentioned classified results are compared each type of the abnormality to classify as follows: This is called a second classification.

Case A: The classified results of the type of all abnormalities have been classified in the case 1.

Case B: There exists even one of the types of the abnormality classified in the case 3.

Case C: This case does not fall under both of the case A and the case B.

The data falling under the cases A, B, and C are listed to register into lists A, B, and C.

(ii) As an embodiment of the classification, the classification of the image of the examination ID number 920001 will be described. The results of the pulmonary nodules in the abnormality data table as shown in FIG. 96 fall under the case 3 in the first classification since both of the first detected results and the second detected results are "abnormal". Also, the results of the pulmonary interstitial disease in the abnormality data table as shown in FIG. 96 fall under the case 2 in the first classification since the first detected results are "abnormal" and the second detected results are "normal". Accordingly, the data fall under the case B in the second classification.

(iii) The classified results of the images of the examination ID numbers 920001 to 920030 are shown in FIG. 97. Also, the examination ID numbers in which the second classified results fall under the case A, the case B, and the case C are respectively registered in the list A, the list B, and the list C. The created list A, list B, and list C are shown in FIGS. 98, 99, and 100.

(3) Re-detection of an abnormality from the interpreting image (i) When finishing registering the lists, the control unit (DB-CTRL) indicates the search unit (Db-SRCH) to search the image registered in the list C (an image to be interpreted and a previous image) to obtain a response. Successively, the following abnormality detecting operations are carried out again for each sheet of image. The detected abnormalities are the pulmonary nodule shadows and interstitioal disease. A third algorithm to be used this time is is not as narrow in the scope of a normality as in the first algorithm, and the third algorithm is not as narrow in the scope of an abnormality as in the second algorithm. The third algorithm is such that it has a true positive fraction to a degree that the doctor can check the overlookedness, and at the same time a false positive fraction becomes a minimum. In other words, the third algorithm to be used this time is suitable for a diagnosis of the substantially same level as the level of the doctor's diagnosis.

(ii) A sheet of image data is read out from the data storing unit (DB-STRG) to send to the image processing unit (DB-IP). The image processing unit (DB-IP) receives the image data and operates the pulmonary nodule shadow detecting means using the third algorithm stored inside to detect presence or absence of an abnormality and its position in the case of the abnormality. The detected results are written into the abnormality detailed data table as the abnormality detailed detection results of the pulmonary nodules.

(iii) The image processing unit (DB-IP) operates, in the same manner as the pulmonary nodules, the interstitial lung disease detecting means using the third algorithm stored inside and detects presence or absence of the abnormality and its position in the case of the abnormality. The detected results are written into the abnormality detailed data table as the abnormality detailed detection results of the interstitial lung disease.

(iv) In the case where the abnormality is detected in any abnormality detecting operations, the CAD processed results.

(v) The control unit (DB-CTRL) associates the examined patient identification information, the name of the examined patient, and the abnormality data table corresponding to the examination ID number registered in the list B with each other, and indicates the optical magnetic disk drive (DB-MODD) to write the overall judgement results as an "abnormality". Then, the data storing unit (DB--STRG) reads out these data to send to the image bus (DB-IBUS). The optical magnetic disk drive (DB-MODD) receives these data to write into the optical magnetic disk B.

(vi) The control unit (DB-CTRL) associates the examined patient identification information and the name of the examined patient corresponding to the examination ID number registered in the list A with each other and indicates the optical magnetic disk drive (DB-MODD) to write the overall judgement results as a "normality". Then, the data storing unit (DB-STRG) reads out these data to send to the image bus (DB-IBUS). The optical magnetic disk drive (DB-MODD) receives these data to write into the optical magnetic disk B.

The optical magnetic disk B is carried to the patient to be reported to make such a report recommending the patient who is reported the overall judgement results "abnormality" to make a close examination.

In the medical group examination, the interpretation is carried out by two doctors. Accordingly, these two sheets of optical magnetic disk C are prepared to carry each of the two workstations (WS).

The succeeding operations will be same as the embodiment no. 6-1.

In this connection, in each of the embodiments, the medical examination data and the identification information of the medical examination data were stored corresponding to each other, however the medical examination data may not have any identification information, or the image data to output as a doctor's interpretation may be limited to only the medical examination data.

In each of the embodiments, the image data registered in the list A was written into the optical magnetic disk B, however the image data registered in the list A is not written into the optical magnetic disk B, but into the optical magnetic disk D together with the results of the list C interpreted by the doctor.

In each of the embodiments, the examined images were classified into three types of list, however the images are classified into two types and the list A may be incorporated into the list B without being limited to the above description, and the images may be classified by the other classifying method and classified into the other number of classification.

In the display method of the comparison results in each of the embodiments, a form of an elliptic set was used, however various sets such as a rectangle or the like, various graphics such as a rod, a circle, or the like, and itemization can be used without being limited to the above description.

A method of acquiring a characteristic value of the image in the embodiment no. 5-3 is not limited to the method described in the embodiments. For example, various values are regularized and the regularized value is weighted to add to obtain the sum, which is set as the characteristic value or the like. If the characteristic value expresses the characteristic of the images, it can be used.

Also, in the embodiment of the second invention, the reference time of the CAD processing results was decided before the doctor inputs the findings, however the reference time thereof can be decided after the doctor has inputted without being limited to the above description.

In the embodiments, the business of the medical group examination was explained, however the other interpretation businesses such as a medical examination in medical institutes or the like can be explained without being limited to the above description.

In the embodiments, the operations on the digital system were described, however the realizable system is not limited to the above description. For example, the doctors' interpretation can be made on a film viewer, and the image radiographed by a roll film can be digitized.

Furthermore, in the embodiments, the operations on the off-line PACS were described, however the operations can be carried out even on the on-line PACS without being limited to the above description.

In the embodiments, the medical images were described, however this embodiment can be applied to medical examination data other than the image, that is data having a graphic form such as an electrocardiogram, brain waves, or the like, or data arranging a numerical value obtained by an automatic chemical analyzer etc.

In the embodiments, the medical examination of the lung cancer was described in the example of a chest X-ray image, however this embodiment can also be applied to a medical examination or inspection of an organ of a digestive organ system other than a chest, for example a stomach or the like.

As described above, according to the above embodiments of the present invention, as a doctor can reduce the number of sheet of image to be interpreted, an interpretation time per sheet of image can be prolonged, and it becomes possible to interpret with high precision based on much more information.

Furthermore, for the examined patient having the extremely high probability of an abnormality, it is possible to recommend to make a close examination not through the doctor's interpretation. The period from the time of the medical examination to the output of the examination results can be made fairly short, and the discovery in the earlier stage which is an original object of the medical group examination can be made.

It is possible to save uselessness in interpreting the image of the examined patient having the extremely high probability of a normality.

Furthermore, according to another embodiment, when a doctor interprets the images, as the CAD having performance (diagnostic level) which is suitable and useful for the doctor's interpretation is used, it becomes possible to diagnose by interpreting with high precision.

Embodiment No. 7

Figure 108:
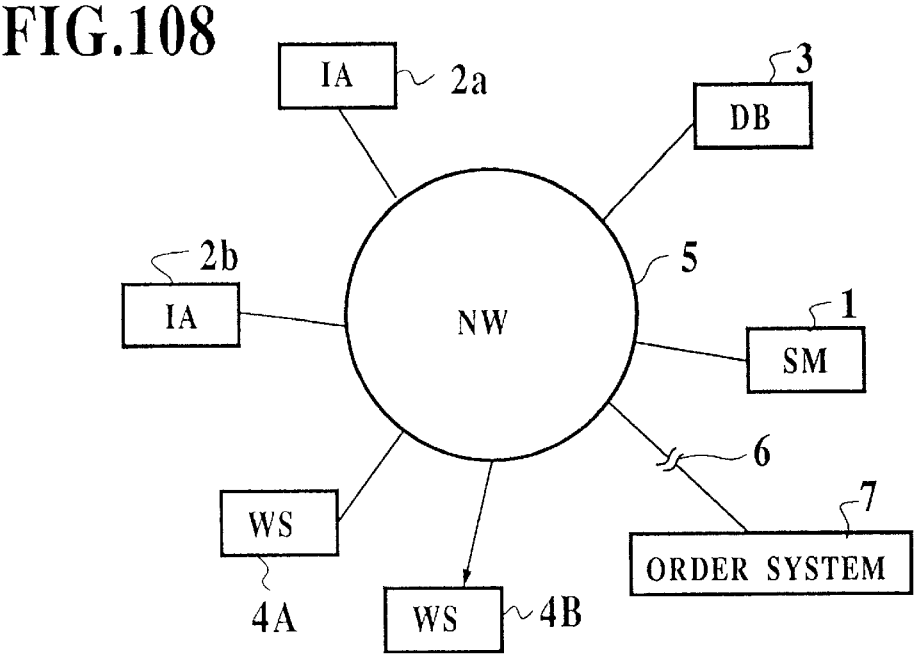
FIG. 108 shows a schematic configuration of a medical archiving communication system (PACS) to describe the seventh embodiment.

Hereinafter, the seventh embodiment including three modifications (variations) according to the present invention will be described. FIG. 108 shows a schematic configuration of a medical picture archiving communication system (PACS).

Embodiment No. 7-1

A network (NW) 5 is a transmission path for an image communication among respective units and an optical fiber is used as a transmission medium in order to make an attempt to communicate at high speed. Herein, a ring-type local area network is adopted, of course the other types such as a star-type one or the like may be used.

This network 5 is connected with a system manager (SM) 1, a plurality of types of image acquisition unit (IA) 2a, 2b, a database (DB) 3, and workstations (WS) 4A, 4B, and the respective units can be mutually linked by means of a communication protocol.

Furthermore, this network 5 is connected with an examination order system 7 through a gateway 6. This examination order system 7 is equipped with inputting means of a keyboard etc. Examination request information for requesting an aquisition of images is inputted from the examination order system 7. An example of this examination request information is shown in FIG. 120.

The image acquisition units 2a, 2b are image acquisition units such as an X-ray machine, an ultrasonic diagnostic machine, an X-ray computed tomography machine, a magnetic resonance imaging machine, or the like. These image acquisition units 2a, 2b assign an image number to a generated image in the order of its generation, and also attach annexed information thereto as peculiar information concerning the image, and send to the database 3 according to an instruction of the system manager 1. An example of this annexed information is shown in FIG. 121.

Figure 109:
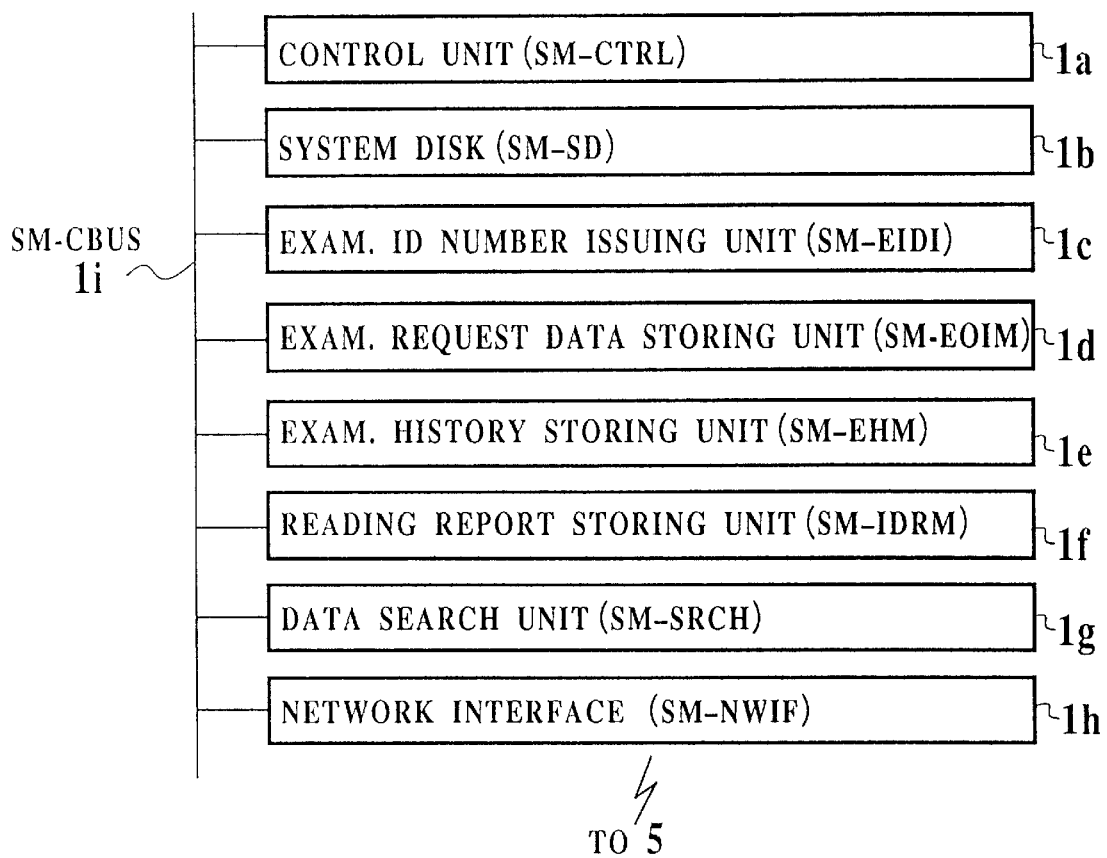
FIG. 109 shows system manager 1 shown in FIG. 108.

The system manager 1 is constituted as shown in FIG. 109.

A control bus (SM-CBUS) 1i is a transmission path between various control information within the system manager 1 and data. The control bus (SM-CBUS) 1i is connected with the network 5 through a network interface (SM-NWIF) 1h. The control bus 1i is also connected with a control unit (SM-CTRL) 1a, a system disk (SM-SD) 1b, an examination ID number issuing unit (SM-EIDI) 1c, an examination request information storing unit (SM-EQIM) 1d, an examination history storing unit(SM-EHM) 1e, an interpretation report storing unit (SM-IDRM) 1f, and an information search unit (SM-SRCH) 1g.

The control unit 1a contains a CPU and system memories, and the system manager 1 controls the entire operation. The system disk 1b, for example a magnetic disk, archives a program for operating in relation to each part of the system manager 1, and supplies this program to the control unit 1a when an electric power is turned on. The examination ID number issuing unit 1c issues the examination ID number in the order of the examination request information received from the examination order system 7. The examination request information storing unit 1d stores the examination request information and the examination ID number. The examination history storing unit 1e stores all examination histories produced so far by the workstations 4A, 4B. The interpretation report storing unit 1f stores all interpretation reports produced so far by the workstations 4A, 4B. An example of this interpretation report is shown in FIG. 122.

The information search unit 1g searches various information stored in the examination request information storing unit 1d, the examination history storing unit 1e, or the interpretation report storing unit 1f in response to search demands from the workstations 4A, 4B.

Figure 110:
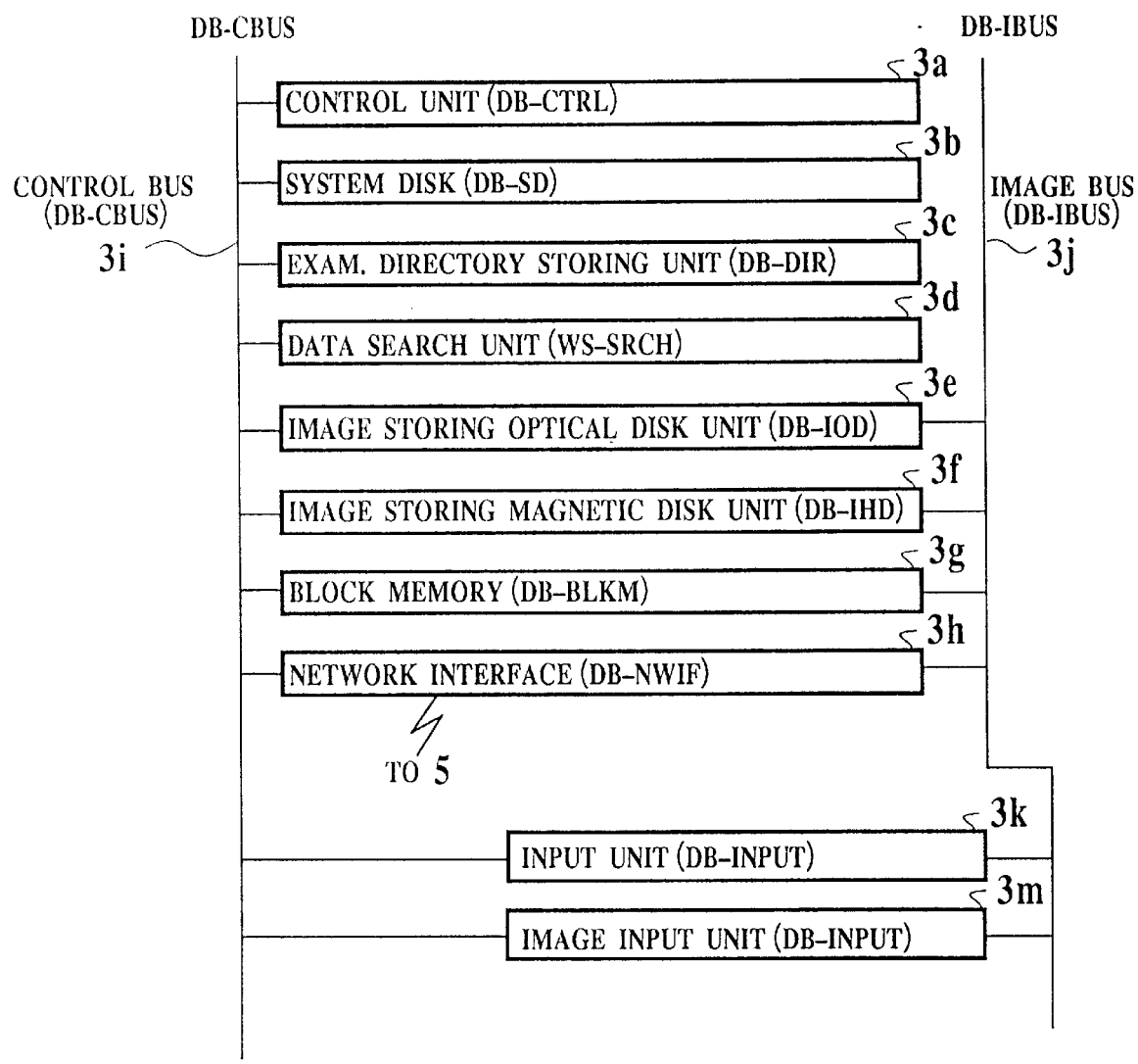
FIG. 110 illustrates construction of database 3 shown in FIG. 108.

The database 3 is constituted as shown in FIG. 110.

A control bus (DB-CBUS) 3i is a transmission path of various control information within the database 3 and an image bus (DB-IBUS) 3j is a transmission path of data. The control bus (DB-CBUS) 3i and image bus (DB-IBUS) 3j are connected with the network 5 through the network interface (DB-NWIF) 3h. The control bus 3i and image bus 3j are also connected with a control unit (DB-CTRL) 3a, a system disk (DB-SD) 3b, an examination directory storing unit (DB-DIR) 3c, an information search unit (DB-SRCH) 3d, an image storing optical disk unit (DB-IOD) 3e, an image storing magnetic disk unit (DB-IHD) 3f, a block memory (DB-BLKM) 3g, an input unit (DB-INPUT) 3k, and an image input unit (DB-IINPUT) 3m.

The control unit 3a contains the CPU and the system memories and controls the entire operation of the database 3. The system disk 3b, for example a magnetic disk, archives a program for operating in relation to each part of the system manager 1 and supplies this program to the control unit 3a when an electric power is turned on. The examination directory storing unit 3c stores an examination directory as administration information of images stored in the image storing optical disk unit 3e. One example of this examination directory is shown in FIG. 23.

The information search unit 3d searches an examination directory in response to search information from the workstation 4A, 4B. The image storing optical disk unit 3e stores an image (containing attached information) acquired by the image acquisition units 2a, 2b, a representative typical disease example image of various disease examples, and overlay data by using an optical disk having a large amount of capacity as a storing medium. The image storing magnetic disk unit 3f temporarily stores information which is inputted into or outputted from the image storing optical disk unit 3e by using a magnetic disk as a storing medium. A block memory 3g temporarily memorizes an image or annexed information by using a semiconductor memory as a storing medium. The input unit 3k, for example a keyboard, a touch screen, is inputting means for inputting various commands or the annexed information. The image input unit 3m, for example a digitizer for reading a film, reads mainly a typical disease example image.

Figure 111:
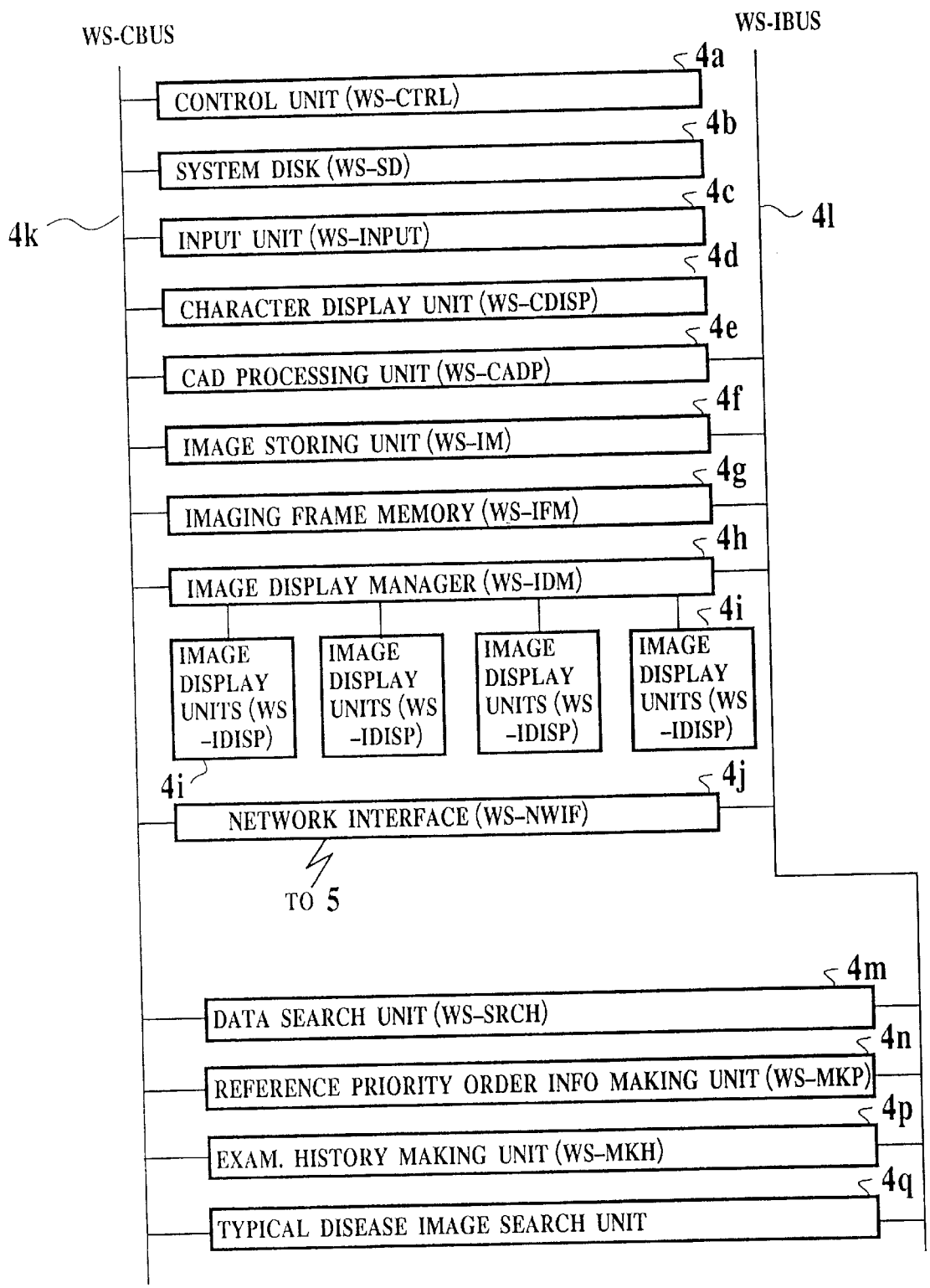
FIG. 111 illustrates construction of workstation 4 shown in FIG. 108.

The workstation 4A is constituted as shown in FIG. 111. In this connection, as the workstation 4B has the same configuration as the workstation 4A, the description is omitted.

A control bus (WS-CBUS) 4k is a transmission path of various control information within the workstation 4A and an image bus (WS-IBUS) 4l is a transmission path of data. The control bus (WS-CBUS) 4k and image bus (WS-IBUS) 4l are connected with the network 5 through a network interface (WS-NWIF) 4j. The control bus 4k and image bus 4l are also connected with a control unit (WS-CTRL) 4a, a system disk (WS-SD) 4b, an input unit (WS-INPUT) 4c, a character display unit (WS-CDISP) 4d, a CAD processing unit (WS-CADP) 4e, an image storing unit (WS-IM) 4f, an imaging frame memory (WS-IFM) 4g, an image display manager (WS-IDM) 4h, an information search unit (WS-SRCH) 4m, a reference priority order information making unit (WS-MKP) 4n, and an examination history making unit (WS-MKH) 4p. Furthermore, herein the plurality of image display managers are connected with four image display units (WS-IDISP) 4i.

The control unit 4a contains the CPU, system memories, or the like, and controls the entire operation of the workstation. The system disk 4b archives a program relating to associated operations of each part of the workstation 4A, abnormality detecting means selecting information, and various reference order rules by using a magnetic disk as a storing medium. The reference order rules are the rules for deciding a priority order to refer to previous images or typical disease example images. This program is sent to the control unit 4a when an electric power is turned on. FIG. 40 as described below shows the abnormality detecting means selecting information, and FIGS. 123 to 128 show one example of various reference order rules.

The input unit 3c, for example a keyboard, a touch screen, is inputting means for inputting various commands or interpretation reports. The character display unit 4d, for example a CTR (Cathode Ray Tube) display or a liquid crystal panel display, displays mainly character information such as examination request information, examination histories, an interpretation report, or the like.

The CAD processing unit 4e is equipped with a Computer-Aided Diagnosis (CAD) function to detect various abnormalities of an uninterpreted image to create an abnormality data table. An example of this abnormality data table is shown in FIG. 129.

This CAD processing unit 4e contains a plurality of types of abnormality detecting means. The abnormality detecting means has (a) means for detecting shadows of an interstitial lung disease in a frontal image of a chest plain X-ray image; (b) means for detecting shadows of pulmonary nodules in a frontal image of a chest plain X-ray image; and (c) means for detecting shadows of a fine calcification of a breast in a breast X-ray image. Furthermore, this CAD processing unit 4e contains dissecting division recognizing means. This dissecting division recognizing means recognizes to which dissecting division an abnormality detected by the abnormality detecting means belongs in internal organs to be examined. The dissecting division is, for example in lungs, each region which is trisected vertically in each of two right and left lungs, and the regions are respectively called an "upper left lung field", a "middle left lung field", a "lower left lung field", an "upper right lung field", a "middle right lung field", and a "lower right lung field".

This specifying means has various ones, and a technique adopted herein has been disclosed in Japanese Patent Application Laid-Open No. 1-125675. In this connection, the dissecting division of the lungs should precisely be sectioned based on the position relationship with a tip of a rib, however as it is difficult to recognize the tip of rib by a computer, in the above-mentioned technique, generally by using a fact that a lower edge of the collarbone exists in a center position of the upper lung field and that an upper edge of the diaphragm coincides with a lower edge of the lung field, based on the position relationship of the lower edge of the collarbone with the upper edge of the diaphragm as it is easy to comparatively recognize them from an image, it is possible to recognize a scope of each division on the image. If the center position of the abnormality is checked up with the coordinates on the image which specify each region, it is possible to specify the dissecting division relating to the position of the abnormality.

This CAD processing unit 4c outputs judgement results of the abnormality detecting means or a region containing an abnormality into an abnormality data table in a lump.

The image storing unit 4f temporarily stores examination request information to be treated during operations of the workstation, examination histories, an interpretation report, an uninterpreted image, a typical disease example image, annexed information, overlay display information, an abnormality data table, and reference priority order information by using a magnetic disk as a storing medium. The reference priority order information is a previous image decided by the reference priority order information making unit 4n based on the image reference preparation rules or priority order information to be referred to in the typical disease example image. The imaging frame memory 4g temporarily memorizes an image by using a semiconductor memory as a storing medium.

The image display manager 4h is constituted as shown in FIG. 21.

The image bus 4l is connected with an overlay portion 44 through an image memory 42. The control bus 4k is also connected with the overlay portion 44 through a control portion 40, an overlay data making portion 41, and an overlay memory 43, in order. Furthermore, the overlay portion 44 is connected with the image display 4i through a displaying memory 45 and a D/A converter 46, in order.

An uninterpreted image, a previous image, and a typical disease example image are inputted from the image bus 4l to be sent to the overlay portion 44 through the image memory 2. Furthermore, overlay display information concerning such uninterpreted image is inputted from the control bus 4k to send to the overlay data making portion 41 through the control portion 40 to produce overlay data (images showing an abnormality). This overlay data are sent to the overlay portion 44 through an overlay memory 43a. The overlay portion 44 synthesizes the uninterpreted image with the overlay data to produce a synthesized image, which is displayed on the image display unit 4i through any of the displaying memory 45 and D/A converter 46. Furthermore, the previous images or typical disease example image are respectively sent to the other displaying memory 45 through the overlay portion 44 and displayed on the image display unit 4i through the D/A converter 46.

Referring back to FIG. 111, the information search unit 4m searches various information stored in the image storing unit 4f based on the search information inputted from the input unit 4b. The examination history making unit 4p adds examination information concerning the uninterpreted image which is sent to the workstation 4A to the previous examination histories which do not contain the examination information of such uninterpreted image to renew these examination histories. In this connection, the examination information is selected from the examination request information and annexed information to obtain the necessary information. An example of the examination histories is shown in FIG. 130.

The reference priority order information making unit 4n decides a priority order of the previous image and typical disease example image to be referred to when interpreting such uninterpreted image based on various image reference rules, and makes refernce priority order information according to the decided contents. The reference rules contain the image reference rules in the case where an abnormality was detected in the CAD processing results in the previous examinations of the same patient as such uninterpreted image, and the image reference rules in the case where an abnormality was not detected in the CAD processing results in the previous examinations of the same patient as such uninterpreted image, and the image reference rules concerning the typical disease example image.

Next, operations of this embodiment having such configuration will be described.

At installing, a plurality of types of typical disease example image have beforehand been inputted from the image input unit 3m of the database 3 and stored in the image storing optical disk 3e through the image storing magnetic disk 3f. Furthermore, various annexed information of the plurality of types of typical disease example image is inputted from the input unit 3k of the database 3, and stored in the image storing optical disk 3e through the image storing magnetic disk 3f. An embodiment of this annexed information is shown in FIG. 131.

Next, a flow from a generation of an image from an examination request to its archive in the image storing optical disk 3e will be explained.

First, the examination request information is inputted through the examination order system 7 to make an examination request. An embodiment of this examination request information is shown in FIG. 132.

The examination request information consists of individual information concerning a patient, and examination information indicating an examination portion, an examination procedure, or the like which is necessary for the radiography, and clinical information of a patient, and a disclosed disease name. In this connection, as the clinical information of a patient is inputted only when a judgement diagnosis has already been established at requesting such examination, there are some cases where any information does not exist when occasion demands.

This examination request information is sent to the system manager 1 through the network 5, and transferred from the system manager 1 to the appropriate image acquisition unit 2a. The radiography is performed by a radiographer according to an instruction of the examination request information and an image is produced in the image acquisition unit 2a. The annexed information is attached to this image to send to the database 3 through the network 5 to be stored in the image storing optical disk 3e through the image storing magnetic disk 3f. An embodiment of this annexed information is shown in FIG. 133.

Furthermore, by an instruction of the system manager 1, this image and the annexed information are sent together with the examination request information to the workstation 4A through the network 5 and stored in the image storing unit 4f. The examination history making unit 4q adds the examination histories of such patient which are stored in the image storing unit 4f to information extracted from the annexed information of such examination and the examination request information to renew these examination histories. An embodiment of these renewed examination histories is shown in FIG. 134.

These renewed examination histories are returned to the image storing unit 4f and stored therein.

Furthermore,, such uninterpreted image is sent from the image storing unit 4f to the CAD processing unit 4e to execute the CAD processing. The CAD processing unit 4e is provided, as described above, with three types of means comprising (a) means for detecting shadows of an interstitial lung disease in a frontal image of a chest plain X-ray image; and (b) means for detecting shadows of pulmonary nodules in a frontal image of a chest plain X-ray image; and (c) means for detecting shadows of fine calcification of a breast in a breast X-ray image. The CAD processing unit 4e specifies a detectable type of an abnormality concerning this image by using abnormality detecting means selecting information and the abnormality detecting means according to these results. Herein, as an examination portion is a chest and a procedure of an examination is a plain radiodraphy and an imaging direction is P→A, the abnormality detecting means capable of detecting an interstitial lung disease and the abnormality detecting means capable of detecting pulmonary nodules are selected. By the selected abnormality detecting means, an abnormality detection processing executes concerning an original image and it is possible to judge presence or absence of an abnormality, a type of an abnormality (to be detected at a time when the abnormality detecting means is selected), a position of an abnormality, a degree of an abnormality, and a region containing an abnormality of a dissecting division. These judgement results are sent to the image storing unit 4f and added to the abnormality data table. Thus, the abnormality data table is renewed and an embodiment of the renewed abnormality data table is shown in FIG. 135.

The information added newly in this abnormality data table is information of reference numbers 1 and 2.

After the processing described in FIG. 135, an interpreting doctor inputs an instruction of an interpretation start from the input unit 4c of the workstation 4. According to this, the oldest uninterpreted image is decided as an initial image to be interpreted. This initial image to be interpreted will be explained as the uninterpreted image of the examination ID number: 108801 as described above.

Such uninterpreted image is sent to the image display manager 4h from the image storing unit 4f and displayed on any image display unit 4i.

At this time, by the reference priority order information making unit 4n, the reference priority order information is made. The processing for making this reference priority order information will be explained below.

First of all, the abnormality data table and such uninterpreted image and the examination histories concerning the identical patient are sent from the image storing unit 4f to the reference priority order information making unit 4n. Then, all the examination ID numbers of these examination histories are extracted. It is judged as to whether or not at least one examination ID number exists in the abnormality data table. In the case where the examination ID number exists in the abnormality data table, this means that the abnormality has been discovered by the CAD processing in the examination of such examination ID number.

As the results of this judgement, when at least one examination ID number exists in the abnormality data table, the following processings 1 to 4 and processing 6 are sequentially executed, and when any examination ID number does not exist, the processings 5 and 6 are sequentially exercised.

Processing 1

In the processing 1, a priority order is decided by using the image reference rules as shown in FIG. 123. For this reason, these image reference rules are sent from the image storing unit 4f to the reference priority order information making unit 4n. Also, the abnormality data table and examination histories are sent from the image storing unit 4f to the reference priority order information making unit 4n.

Then, by using the abnormality data table and examination histories, the examination portion, the modality, the type of an abnormality, the position of an abnormality of such uninterpreted image are extracted. Similarly, the examination portion, the modality, the type of an abnormality, and the position of an abnormality as to each previous examination are extracted, and the identification with the examination portion of such uninterpreted image etc. is judged. As the results of this judgement, the previous examination identical to such uninterpreted image in the examination portion etc. is selected.

As to each of the selected previous examination, it is judged by using the examination histories as to whether or not the clinical information exists. When characteristic items such as a dose of medicines, an appearance in a change of the condition of a disease, or the like generate in the stage of each examination, a responsible doctor inputs the clinical information into the examination information as his/her comments, and most of the examinations having this clinical information is generally very material in the interpretation.

As the results of this judgement, all the examinations having the clinical information are an object to decide a priority order of this processing 1. As to all the examinations, the priority order is decided based on contents of the clinical information and a date of the examination. First of all, as shown in the image reference rules (a) as shown in the table, an examination acquiring the first priority order is one having the clinical information of contents that "a change in the condition of a disease appears". Then, as shown in the image reference rules (b) as shown in the table, the examination having the clinical information which does not have these contents acquires a higher priority order which is next to the first priority order from an examination having the later date of the examination. The thus-obtained priority order information is written into the reference priority order information.

Here, a description will be made with reference to an embodiment, and as at least any examination having the clinical information does not exist in the examination histories of FIG. 134, in such processing 1, any examination acquiring the priority order does not exist.

Processing 2

In the processing 2, a priority order is decided by using the image reference rules as shown in FIG. 124. For this reason, these image reference rules are sent from the image storing unit 4f to the reference priority order information making unit 4n. Also, the abnormality data table and examination histories are sent from the image storing unit 4f to the reference priority order information making unit 4n. In the processing 2, presence or absence of the clinical information is not a factor of deciding the priority order unlike the processing 1. In the processing 2, all previous examinations having the identical examination portion, modality, type of an abnormality, position of an abnormality to such uninterpreted images are an object of the priority order. All examinations satisfying this identification acquire a priority order based on the relationship with the sequential date of the examination. In short, as shown in the image reference rules (a) and (b) as shown in FIG. 124, the oldest, namely most previous examination acquires a first priority order in such processing 2. The older the other examinations are, the higher priority order they acquire next to the first priority order. The thus-obtained priority order in the processing 2 is allocated lower than the priority order of the processing 1 and written into the reference priority order information.

More specifically, the examination having the examination ID number: 100902 in the examination histories of FIG. 134 is adapted for the image reference rules (a) as shown in FIG. 124, and the examination having the examination ID number: 103541 is adapted for the image reference rules (b) as shown in FIG. 124. Accordingly, as any examination is not adapted for the image reference rules in the processing 1, each of the above-mentioned examinations adapted for the image reference rules (a), (b) of FIG. 124 in such processing 2 is written into the first and second priority orders of the reference priority order information, as shown in FIG. 136.

Processing 3

In the processing 3, a priority order is decided by using the image reference rules as shown in FIG. 125. For this reason, these image reference rules are sent from the image storing unit 4f to the reference priority order information making unit 4n. Furthermore, the abnormality data table and the examination histories are sent from the image storing unit 4f to the reference priority order information making unit 4n. In the processing 3, the previous examination having the identical examination portion to the uninterpreted image is an object of a priority order. The priority order in the objective examinations is decided based on the date of an examination and the type of a modality as shown in the image reference rules (a) to (c) as shown in the table. Here, the latest examination in the examinations by an X-ray tomography machine acquires a first priority order in the processing 3. Subsequently to this examination, the latest examination in the examination by an X-ray computed tomography machine (CT) and the latest examination in the examination by a magnetic resonance imaging machine (MR) acquire higher priority orders sequentially. The thus-obtained priority order in the processing 3 is allocated lower than the priority order of the processing 2, and written into the reference priority order information.

More specifically, as any examination which is adapted for the image reference rules as shown in FIG. 125 does not exist in the examination histories of such patient, any examination which is written into the reference priority order information does not exist in the processing 3.

Processing 4

In the processing 4, a priority order is decided by using the image reference rules as shown in FIG. 126. For this reason, these image reference rules are sent from the image storing unit 4f to the reference priority order information making unit 4n. Furthermore, the abnormality data table and the examination histories are sent from the image storing unit 4f to the reference priority order information making unit 4n. In the processing 4, the previous examination having the identical examination portion to the uninterpreted image is an object of a priority order. The priority order in the objective examinations is decided based on the relationship with the type of an abnormality of an uninterpreted image and the sequential date of an examination as shown in the image reference rules (a) to (f) as shown in FIG. 126. Furthermore, the different modality has beforehand been decided each type of an abnormality of the uninterpreted image. Accordingly, in the processing 4, the type of an abnormality of the uninterpreted image is specified from the abnormality data table, and the latest examination of the examinations using the modality corresponding to the type of this abnormality is selected. The thus-obtained priority order in the processing 4 is allotted lower than the priority order in the processing 3 and written into the reference priority order information.

More specifically, as any examination which is adapted for the image reference rules as shown in FIG. 126 does not exist in the examination histories of such patient, any examination which is written into the reference priority order information does not exist in the processing 3.

Processing 5

As described above, in the processing 5, the abnormality data table does not have any examination ID number of the examination histories of such patient. In other words, when any abnormalities have not been discovered by the CAD processing even in any previous examination of such patient, a priority order is immediately decided without executing the abovementioned processings 1 to 4. Namely, in the processing 5, the priority order is decided by using the image reference rules as shown in FIG. 127. For this reason, these image reference rules are sent from the image storing unit 4f to the reference priority order information making unit 4n. Furthermore, the previous examination request information of such patient and the examination histories of such patient are sent from the image storing unit 4f to the reference priority order information making unit 4n. In the processing 5, all examinations of such patient are an object of the priority order. As for the priority order in these objective examinations, as shown in the image reference rules (a) to (h) as shown in FIG. 127, the previous examination for the identical examination portion to the uninterpreted image is prior to the previous examination for the different examination portion from the uninterpreted image. Furthermore, the previous examination by the identical modality to the uninterpreted image is prior to the previous examination by the different modality. Furthermore, the examination having the later date of an examination is prior to that having the older date of an examination. According to these rules, the prior order in the processing 5 is decided. The prior order in the processing 5 which is obtained according to these three types of rule is written into the reference priority order information as a first priority order in the same manner as the processing 1.

More specifically, as the examination ID number having at least one examination history of such patient exists in the abnormality data table, the priority order is not decided.

Processing 6

The processing 6 is a processing for setting a priority order concerning a typical disease example image and is regularly executed following the processing 4 or 5. In the processing 6, a priority order is decided by using the image reference rules as shown in FIG. 128. For this reason, the abnormality data table and the examination request information of such uninterpreted image are sent from the image storing unit 4f to the reference priority order information making unit 4n. In the processing 6, it is first judged as to whether or not the examination ID number of such uninterpreted image exists, that is whether or not an abnormality is discovered in such uninterpreted image by the CAD processing. Herein, when an abnormality is not discovered in such uninterpreted image by the CAD processing, at the time this processing 6 is completed.

Figure 112:
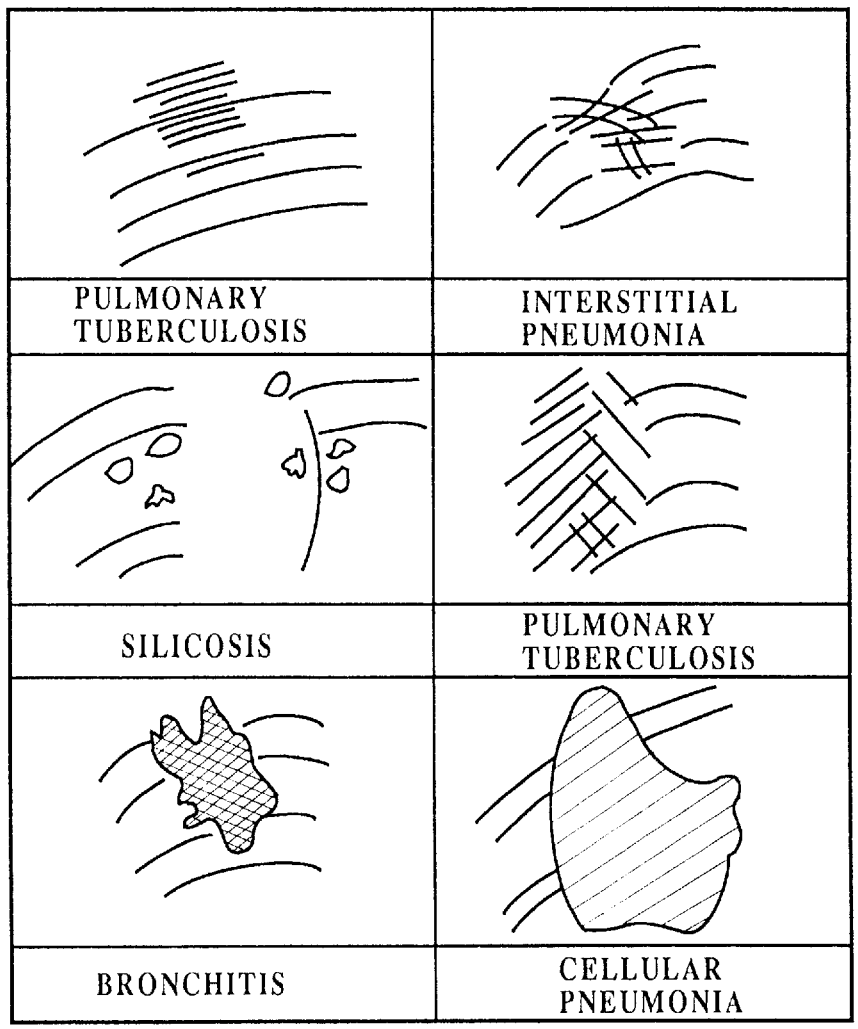
FIG. 112 shows typical disease images.

On the other hand, when the examination ID number of such uninterpreted image exists in the abnormality data table, a priority order is decided according to the typical disease example image reference rules as shown in the table as to a plurality of types of typical disease example image. This deciding processing is carried out as follows: First of all, in a typical disease example image search unit; 4q, when the CAD processing results of the uninterpreted image is a cancer and its size is 1 cm or more according to the typical disease example image reference rules (a), a first priority order is set in the processing 6 for the typical disease example image which has the identical examination portion and modality to the uninterpreted image and which is further made a benign judgement. An embodiment of the plurality of typical disease example image to which this first priority order is set is shown in FIG. 112. Subsequently to this first priority order, according to the typical disease example image reference rules (b), (c), the typical disease example image having the identical type of an abnormality to the uninterpreted image is an object to which a priority order is given. An embodiment of the annexed information of the typical disease example image having the identical type of an abnormality (interstitial lung disease) to this uninterpreted image is shown in FIGS. 137A, 137B.

Here, there are two types of the disease example 5 and the disease example 10. A second priority order in the processing 6 is set to the typical disease example image (disease example 5) having the identical position of an abnormality to the uninterpreted image herein, and a third priority order in the processing 6 is set to the typical disease example image (disease example 10) having the different position of an abnormality from the uninterpreted image. The thus-obtained priority order in the processing 6 is sent to the reference priority order information making unit 4n and allocated lower than the priority order in the processing 4 or the processing 5, and is written into the reference priority order information. In this connection, when the typical disease example image in the processing 6 is written into the reference priority order information, a tag of a "disease example" showing the typical disease example image is added thereto. An embodiment of the thus-created reference priority order information is shown in FIG. 138.

This reference priority order information is sent to the information search unit 4m. A calling demand of a reference image of the examination ID included in this reference priority order information is sent from the information search unit 4m to the database 3. In response to this calling demand, a plurality of sheets of reference image of such examination ID is sent from the database 3 to the image storing unit 4n and stored. In this connection, the image storing unit 4n has a small amount of storing capacity, so that, as described above, only six sheets of image cannot be stored. The uninterpreted images consist of a set of two sheets and the images included in each of the examination ID numbers having the prior orders 1, 2 consist of two sheets, respectively. Therefore, the total four sheets of reference image included in each of the examination ID numbers having the priority orders 1, 2 are sent initially to the image storing unit 4n, and stored therein. The remaining images of the examination ID are transferred from the image storing optical disk unit 3e of the database 3 to the image storing magnetic disk unit 3f so that the remaining images may promptly cope with a calling demand from the workstation 4.

When an instruction of the effect of displaying the previous image is inputted from the input unit 4c, according to the reference priority order information, the previous image to which a disease example tag is not attached is sent from the image storing unit 4n to the image display manager 4h from the higher priority order sequentially, and is displayed on the image display unit 4i other than the image display unit 4i displaying the uninterpreted image. At this image, corresponding to the number of the image display unit 4i, a plurality of sheets of reference image may be sent to the image display manager 4h and displayed on the separate image display unit 4i. When an instruction of the effect of displaying the previous image is inputted once more from the input unit 4c, corresponding to the reference priority order information, the previous image having a lower priority order than the image displayed presently is sent from the image storing unit 4n to the image display manager 4h to display on the image display unit 4i. Thus, by repeatedly inputting an instruction of the effect of displaying the previous image, a plurality of sheets of previous image are exchanged and displayed according to the priority order of the reference priority order information.

Additionally, when an instruction of the effect of displaying the typical disease example image from the input unit 4c, corresponding to the reference priority order information, the typical disease example image to which a disease example tag is attached is sent from the image storing unit 4n to the image display manager 4h from the higher priority order sequentially, and displayed on the image display unit 4i other than the image display unit 4i displaying the uninterpreted image. An instruction of the effect of displaying the typical disease example image is inputted once more to exchange and display the typical disease example image having the lower priority order.

A doctor interprets with reference to this reference image and creates an interpretation report. This interpretation report is archived in the image storing unit 4f to complete such interpretation.

As described above, according to this embodiment, as the priority order of the reference image is decided based on the CAD processing results, an interpreting doctor is not required to select the reference image from the list and can also refer to a reference image even if he/she cannot judge a type of an abnormality of the uninterpreted image. Also, as the reference image is transferred in the sequential order of the priority order from the database to the workstation to be stored therein, the reference image indicated by the interpreting doctor is not stored in the workstation unlike the prior art, therefore a frequency of calling directly from the workstation to the database reduces and accordingly interpreting work can be progressed with efficiency.

In this embodiment, there are provided four image display units in the above description, and this embodiment is not limited to this and the number of image display unit can be more or less than four units. Also, generally, as for an arrangement of a plurality of concurrent display images, a side picture is disposed in the lateral side of a frontal picture, however it can be displayed with the other arrangement. Furthermore, the finding information is treated as an interpretation report in the above description, however the other information containing findings other than the interpretation report can also be treated. The decision of the priority order according to the reference rules was explained in the above description, however if these rules reflect the CAD processing results, the priority order can be decided according to the other reference rules. Furthermore, the typical disease example image can selectively be displayed according to the indication of the interpreting doctor without setting the priority order, too.

Embodiment No. 7-2

Next, a second embodiment will be described.

Figure 113:
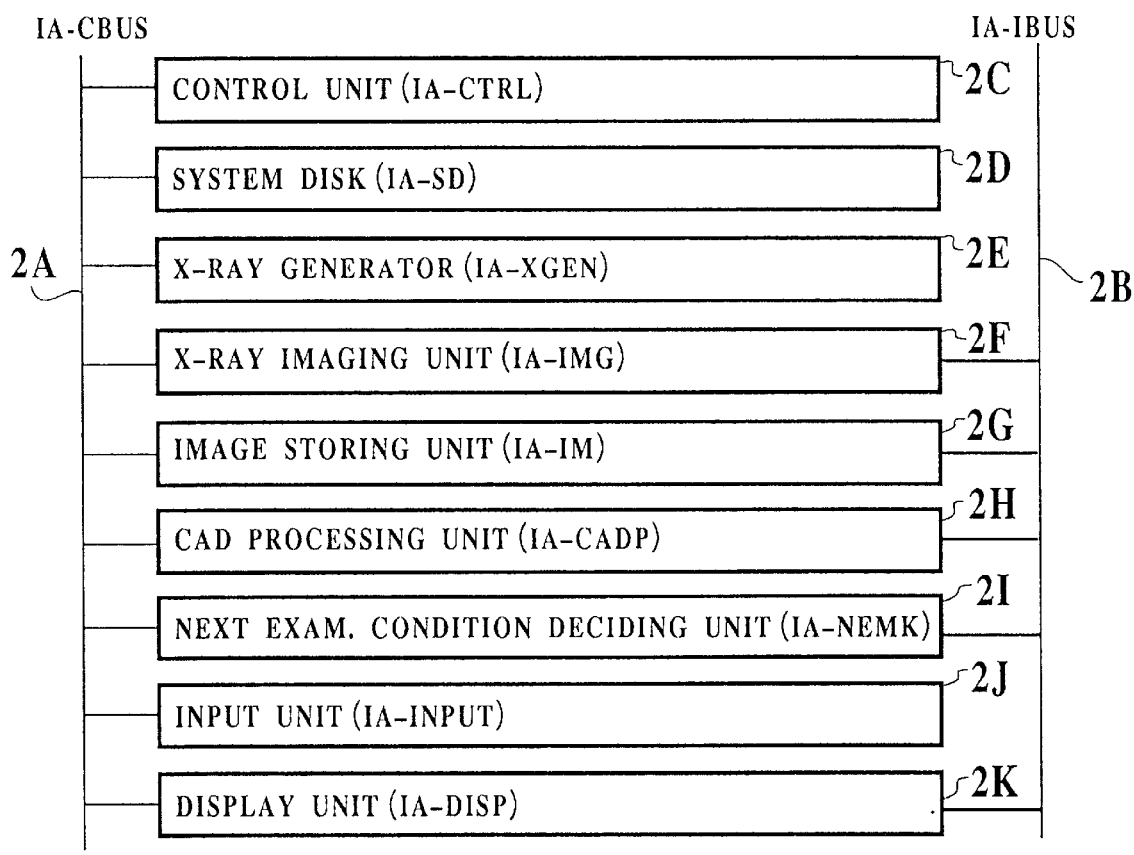
FIG. 113 is an embodied configuration of the image aquisition units 2A, 2B shown in FIG. 108.

This embodiment relates to an image acquisition unit of FIG. 108 in the first embodiment. An embodied configuration of this image acquisition unit is shown in FIG. 113. The description of the other parts which are identical to FIGS. 109, 110, 111 and 21 is omitted.

In FIG. 113, reference numeral 2A is a control bus which is a transmission path of various control signals, and reference numeral 2B is an image bus which is a transmission path of an image data. The control bus 2A and the image bus 2B are connected with a control unit 2C, a system disk 2D, an X-ray generator 2E, an X-ray machine 2F, an image storing unit 2G, a CAD processing unit 2H, a next examination condition deciding unit 2I, an input unit 2J, and a display unit 2K.

The control unit 2C contains a system memory such as a CPU, a semiconductor memory, or the like, and controls operations of the entire image acquisition unit. The system disk 2D stores a basic program required to control operations of the entire image acquisition unit, and supplies the basic program to the control unit 2C when an electric power is turned on. The X-ray generator 2E contains a high voltage electric power and applies a high electric voltage to the X-ray machine 2F according to an instruction of the control unit 2C. The X-ray machine 2F contains an X-ray tube, an image intensifier, a TV camera, an analog/digital converter and the like, and is a unit for radiographing an X-ray image of a person to be examined and for outputting it as digital signals. The image storing unit 2G stores temporarily digital image data outputted from the X-ray machine 2F by using, for example, a semiconductor memory or a magnetic disk as a storing medium. The CAD processing unit 2H is identical to the CAD processing unit as shown in FIG. 111 of the above first embodiment, and executes the CAD processing as to the digital image outputted from the X-ray machine 2F, and outputs the abnormality data table. The next examination condition deciding unit 2I decides necessity of an additional examination by using the abnormality data table of the CAD processing unit 2H, and also sets examination conditions (imaging conditions) of the additional examination when the additional examination is required. The input unit 2J is a keyboard, a mouse, or a touch screen, and is used for inputting commands of a radiographer or various information. The display unit 2K is a CTR display or a liquid crystal panel, and displays an image or various character information.

Next, operations of the image acquisition unit having such configuration will be explained.

The examination request information is sent to the X-ray machine 2F, A radiology technologist starts, for example, a chest plain X-ray imaging according to the examination request information. The following advance preparations are made before this examination start. First, the imaging conditions such as a tube current, a tube voltage, an exposing time interval, or the like are set from the input unit 2J. These imaging conditions are judged by a radiographer based on a physical characteristic of a person to be examined such as his/her age, sex, thickness, or the like. The imaging conditions are set at, for example, the tube current 200 mA, the tube voltage 80 kV, the exposing time interval 0.1 sec. Also, according to an examination portion or an examination direction of the examination request information, the imaging conditions are set so that the person to be examined for the X-ray tube or the intensifier of the X-ray machine 2F may be exposed to X-rays from his/her back side while he/she keeps the posture.

When the above-mentioned advance preparations are completed, X-rays are exposed actually and an imaging is carried out. The thus-obtained image data are outputted as digital image data through the analog/digital converter.

These image data are immediately sent to the CAD processing unit 2H, and CAD-processed therein. As the results of this CAD processing, the abnormality data table is outputted from the CAD processing unit 2H. This abnormality data table contains each information such as presence or absence of an abnormality, a type of an abnormality, a position of an abnormality (region having an abnormality), and a progress degree of an abnormality as described also in the first embodiment.

Figure 114:
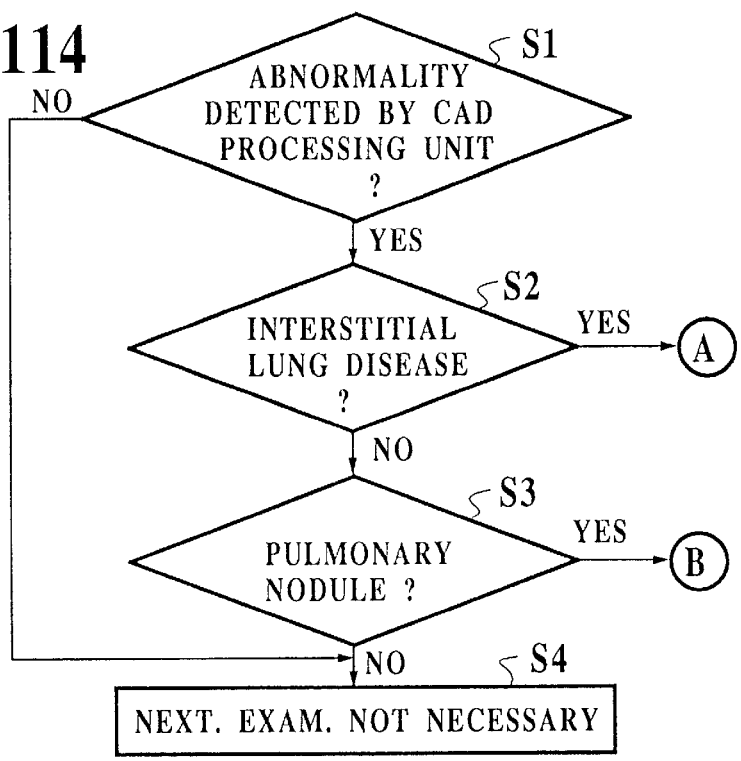
FIG. 114 is a flowchart showing the procedures of judgments of necessity of the additional examination.

This abnormality data table is sent to the next examination condition deciding unit 2I. The next examination condition decision unit 2I judges necessity of an additional examination, and also decides examination conditions of the additional examination (imaging conditions) when the additional examination is required. The procedures will be described. FIG. 114 is a flowchart showing the procedures of judgments of necessity of the additional examination by the next examination condition deciding unit 2I and decisions of the examination conditions of the additional examination (imaging conditions) when the additional examination is required, and FIG. 115 is a detailed flowchart of block A of FIG. 114, and FIG. 116 is a detailed flowchart of block B of FIG. 114.

As shown in FIG. 114, the next examination condition deciding unit 2I judges as to whether or nor an abnormality is detected by the CAD processing unit 2H (S1). This judgement is made on the basis of whether or not such examination ID exists in the abnormality data table. If such examination ID exists in the abnormality data table, an abnormality is indicated to detect by the CAD processing unit 2H, and if such examination ID does not exist in the abnormality data table, an abnormality is indicated not to detect by the CAD processing unit 2H. When No in S1, namely an abnormality is not detected in such acquired image, proceed to S4, and it is judged that the next examination (additional examination) is unnecessary. According to this judgement, a message "No next examination" is displayed in the display unit 2K. When Yes in S1, namely an abnormality is detected in such acquired image, proceed to a judgement step of S2. In S2, it is judged as to whether or not a type of such abnormality is a specified type, herein an interstitial lung disease. Here, if it is the interstitial lung disease, proceed to a contactor A, and if it is not the interstitial lung disease, proceed to a judgement step of S3. In S3, it is judged as to whether or not a type of such abnormality is the other specified type, herein pulmonary nodules. Here, if it is the pulmonary nodules, proceed to a contactor B, and if it is not the pulmonary nodules, proceed to S4, and it is judged that the next examination (additional examination) is unnecessary. According to this judgement, a message "No next examination" is displayed in the display unit 2K.

Figure 115:
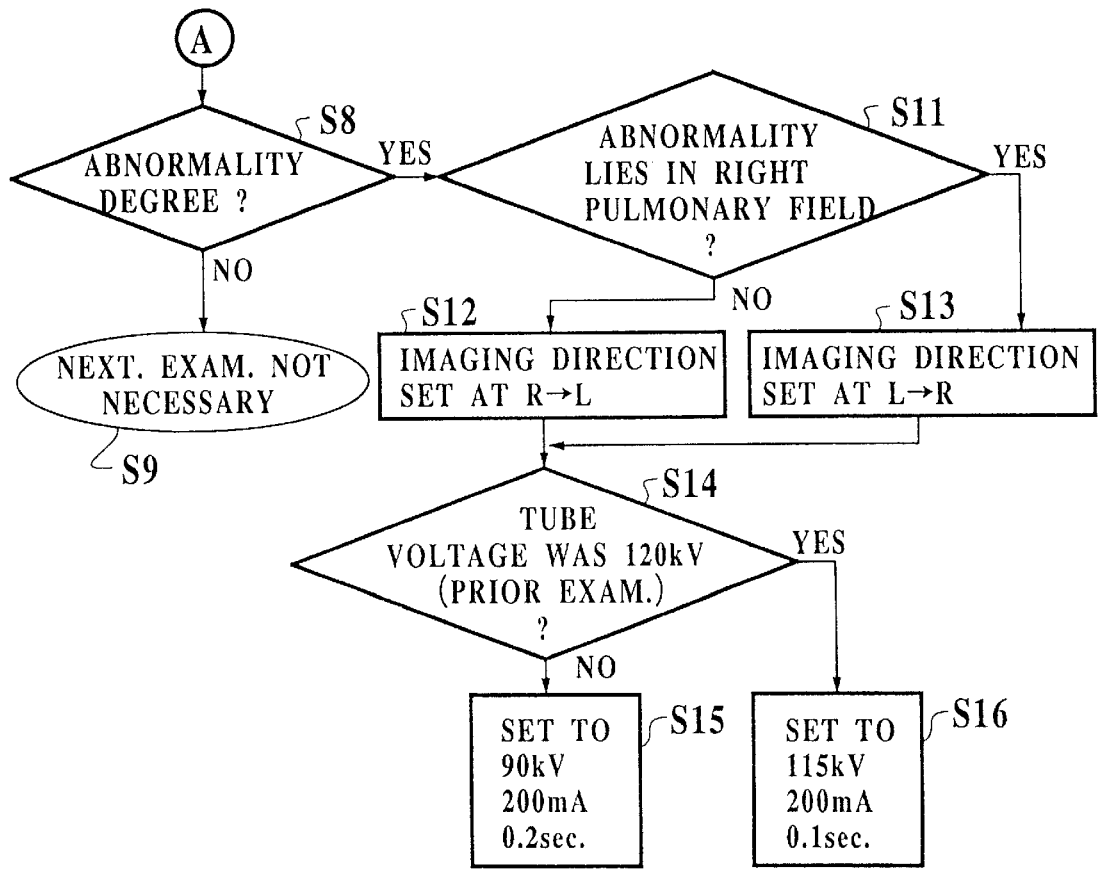
FIG. 115 is a detailed flowchart of block A shown in FIG. 114.
Figure 116:
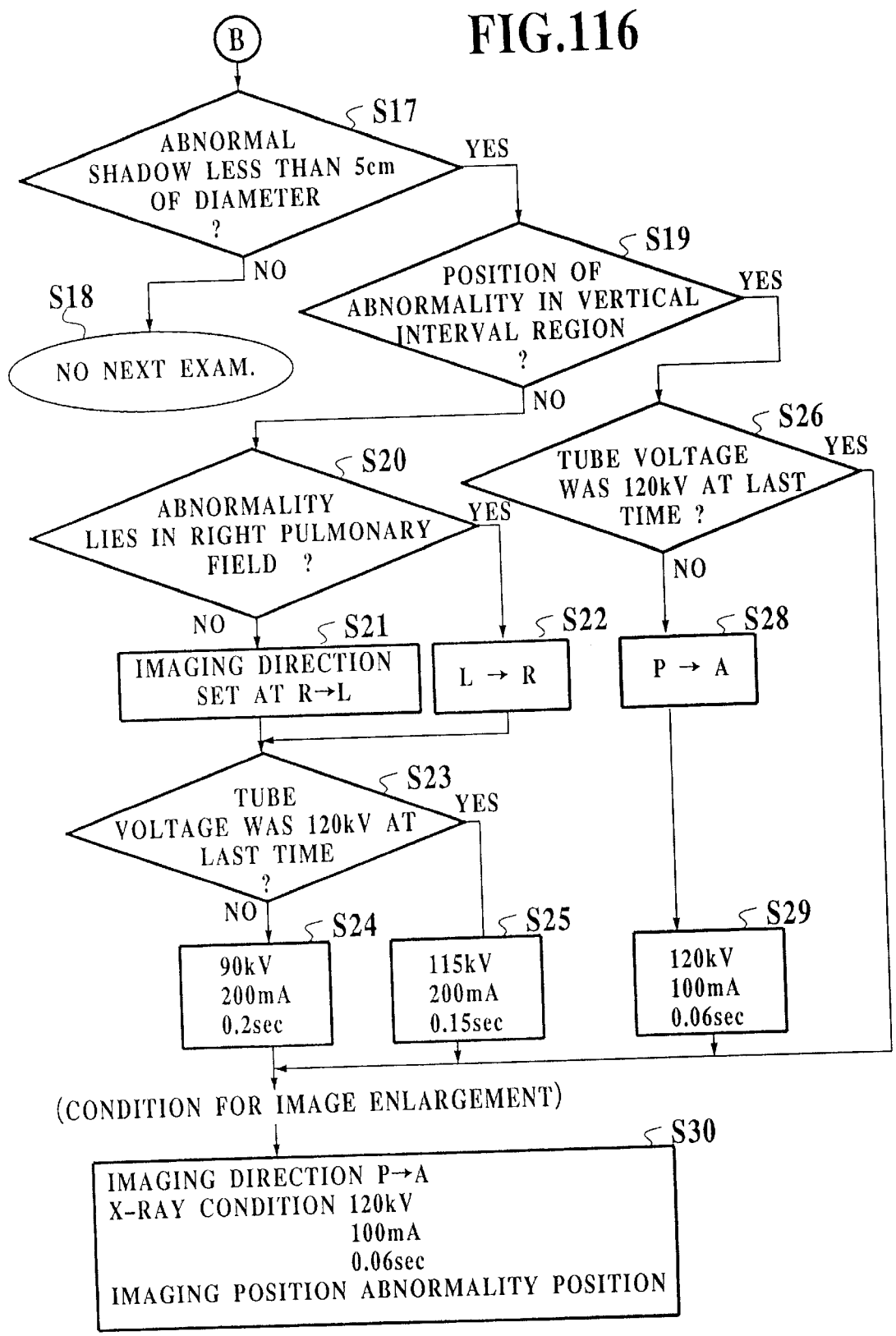
FIG. 116 is a detailed flowchart of block B shown in FIG. 114.
Figure 117:
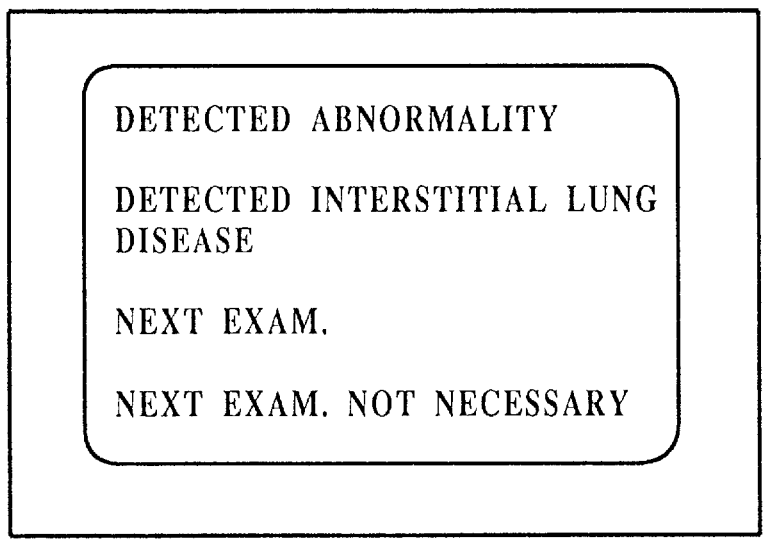
FIG. 117 is a display image plane indicating a case where the next examination is not necessary.
Figure 118:
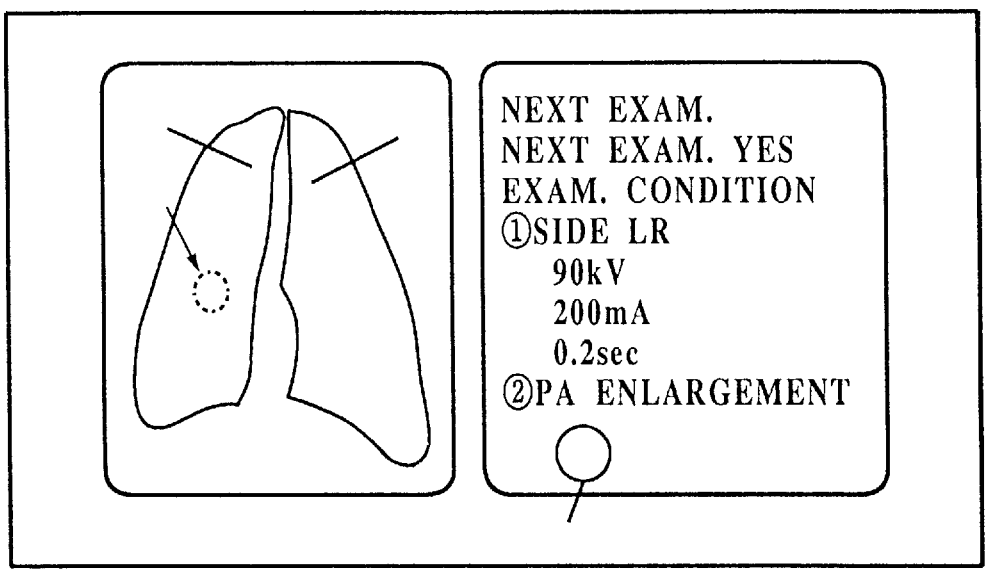

FIG. 115 is a flowchart showing processing procedures following the contactor A of FIG. 114. Here, first a judgement step of S8 is executed. In the judgement step of S8, it is judged as to whether or not a degree of such abnormality (herein an interstitial lung disease) is included within a predetermined scope. Here, when the degree of such abnormality is included within a predetermined scope, proceed to S9, and it is judged that the next examination (additional examination) is unnecessary. According to this judgement, as shown in FIG. 117, the type of an abnormality "Interstitial Lung Disease" detected in the display unit 2K and the message "No next examination" are displayed. On the other hand, when a degree of such abnormality is included in a predetermined scope in S9, it is judged that the additional examination is necessary, and proceed to a selection routine of examination conditions of the additional examination. This predetermined scope is here set at scopes 5 to 7. The scope of the detectable degree of an abnormality in the CAD processing is 1 to 10 (1: the lightest degree, 10: the weightiest degree). It is judged that the degree of such abnormality is included in this predetermined scope and that the next examination (additional examination) is unnecessary, and a basis of the judgement is as follows: In short, these are some possibilities that an element of an erroneous detection is included in the CAD processing when detecting the degree of an abnormality of 4 or less, and as, even if the additional examination is carried out, there are high possibilities that the erroneous detection generates again, it is judged that the additional examination is unnecessary. Furthermore, as an interpreting doctor can confirm that the abnormality having the degree of an abnormality of 8 or more exists definitely in the interpreting work, it is judged that the additional examination is unnecessary. Accordingly, it is flexible that the degree of an abnormality is included in this predetermined scope as an indefinite element such as an erroneous detection or the like may be interposed in the course of the judgement of presence or absence of the abnormality, and furthermore the interpreting doctor cannot always confirm definitely the existence of the abnormality in the interpreting work, and if the examination conditions are altered to reexamine, higher interests can be obtained. When Yes in S8, namely the degree of such abnormality is included in the predetermined scope, proceed to the judgement step of S11. In S11, it is judged as to whether or not a position of an abnormality is a specified position. This specified position is herein a right lung field. When Yes in S11, namely the position of the abnormality is not in a right lung field, but in a left lung field, S12 is executed and the imaging direction in the examination conditions of the additional examination is set at R→L which is suitable for the imaging of the left lung field. Furthermore, when No in S11, namely the position of the abnormality is in the right lung field, S13 is executed and the imaging direction in the examination conditions of the additional examination is set at L→R which is suitable for the imaging of the right lung field. When the imaging direction in the examination conditions of the additional examination in S12 or S13, proceed to a judgement step of S14. In S14, it is judged as to whether or not a tube voltage of such examination is a predetermined value, herein 120 kV. There are some possibilities that a contrast of an image is reduced due to a high tube voltage, as this result, an erroneousness in the degree of the abnormality by the CAD processing generates, and it is avoided by the additional examination based on this judgement. Accordingly, when No in S14, the examination conditions of the additional examination are set at a slightly lower value than a tube voltage of such examination, for example, a tube voltage of 90 kV. Corresponding to this tube voltage, the tube current is set at, for example, 200 mA, and an exposing time is set at, for example, 0.2 sec. On the other hand, when Yes in S14, similarly the examination conditions of the additional examination are set at a slightly lower value than the tube voltage of such examination, for example, the tube voltage of 115 kV. Corresponding to this tube voltage, the tube current is set at, for example, 200 mA, and the exposing time is set at, for example, 0.15 sec. The selection routine of the examination conditions of the additional examination is repeatedly executed as to all interstitial lung diseases. The thus-obtained examination conditions of the additional examination is displayed on the display unit 4K together with the message "Next examination" as shown in FIG. 118, and the additional examination under these examination conditions is called forth.

When No in S2, S3 is executed. In S3, it is judged as to whether or not the type of an abnormality is a specified type, herein pulmonary nodules. When Yes in S3, namely the type of an abnormality is the pulmonary nodules, the other selection routine of the examination conditions is executed.

This routine is shown in FIG. 116. First of all, in S17, it is judged as to whether or not a size of abnormal shadows is less than a predetermined diameter, herein a diameter 5 cm. When No in S17, namely a size of the abnormal shadows exceeds a predetermined diameter, the existence of the abnormality is considered to be substantially confirmed, and proceed to S18 and then it is judged that the additional examination is unnecessary. According to this judgement, the detected type of the abnormality "pulmonary nodules" and the message "No next examination" are displayed on the display unit 4K. On the other hand, when Yes in S17, namely a size of abnormal shadows is less than a predetermined diameter, it is judged that presence or absence of an abnormality is flexible containing the possibility in an erroneous detection and that the additional examination is necessary, and the examination conditions of the additional examination in S19 and after are set.

In S19, it is judged as to whether or not a position of an abnormality exists in a specified region, herein in a vertical interval region. Here, if No, proceed to S20, and also if Yes, proceed to S26. In S20, it is judged as to whether or not a position of an abnormality is in a specified position, herein in a right lung field.

When No in S20, namely a position of an abnormality is not in a right lung field, but in a left lung field, S21 is carried out, and the imaging direction in the examination conditions of the additional examination is set at R→L which is suitable for the imaging of the left lung field. Furthermore, when Yes in S20, namely the position of an abnormality is in the right lung field, S22 is carried out, and the imaging direction of the examination conditions of the additional examination is set at L→R which is suitable for the imaging in the right lung field. When the imaging direction of the examination conditions of the additional examination is decided in S21 or S22, proceed to a judgement step of S23. In S23, it is judged as to whether or not a tube voltage of such examination is a predetermined value, herein 120 kV. There are some possibilities that a contrast of an image is reduced due to a high tube voltage, as this result, an erroneousness in the degree of the abnormality by the CAD processing generates, and it is avoided by the additional examination based on this judgement. Accordingly, when No in S23, the examination conditions of the additional examination are set at a slightly lower value than a tube voltage of such examination, for example, a tube voltage of 90 kV. Corresponding to this tube voltage, the tube current is set at, for example, 200 mA, and an exposing time is set at, for example, 0.2 sec. On the other hand, when Yes in S23, similarly the examination conditions of the additional examination are set at a slightly lower value than the tube voltage of such examination, for example, the tube voltage of 115 kV. Corresponding to this tube voltage, the tube current is set at, for example, 200 mA, and the exposing time is set at, for example, 0.15 sec.

On the other hand, when Yes in S19, namely the position of an abnormality exists in a specified region, herein in a vertical interval region, S26 is carried out. It is judged in S26 as to whether or not the tube voltage of such examination is 120 kV. Herein, when No, namely the tube voltage of such examination is not 120 kV, the imaging direction of the additional examination is set at P→4 A in S28, and successively the tube voltage of the additional examination is set at 120 kV and the tube current is set at 100 mA and the exposing time is set at 0.06 sec in S29.

When Yes in S26 (the tube voltage of such examination is 120 kV), after the examination conditions of the additional examination are set in S24, S25, or S29, proceed to S30. S30 is a step for setting examination conditions of an enlarging imaging. The examination conditions of the additional examination by the enlarging imaging to be set; herein are: the imaging direction: P→A; the tube voltage: 120 kV; the tube current: 100 mA; the exposing time: 0.06 sec; the imaging position; and the position of an abnormality.

The examination conditions of the additional examination set in S24, S25, or S29 and the examination conditions of the enlarging image are displayed together with the message "Next examination" on the display unit 4K, and the additional examination containing the enlarging imaging under these examination conditions is called forth.

Thus, with this embodiment, such image is CAD-processed immediately after the image is acquired, and it is judged as to whether or not the additional examination is necessary based on these processing results, and also in the case where the additional examination is necessary, the examination conditions of the additional examination can be set to display to a radlographer. Accordingly, as the radiographer carries out the additional examination according to this display and the interpreting doctor can always interpret the excellent image, it can be avoided to delay due to a re-request of the examination and efficiency in work from the examination start to the interpreting completion can be realized.

In this connection, in the above-mentioned description, the examination conditions of the additional examination is just displayed, however an X-ray generator or an X-ray machine may be set according to these examination conditions. In this case, in regulating an imaging position or an imaging angle, a person to be examined is fixed while an inspection pedestal on which a person to be examined is placed is moved to an appropriate location like a digestive organ diagnostic apparatus, or a person to be examined is stationary while a radiography is moved to an appropriate location like a circulatory organ diagnostic apparatus, or a method can also be used in which the both are combined. Furthermore, in the above-mentioned description, the image acquisition unit is incorporated with the CAD processing unit or the next examination condition deciding means, however these may also be incorporated into an external unit, for example, a workstation or a database and the images acquired by the image acquisition unit are sent to the external unit, which may receive the decided next examination conditions to display. Furthermore, this embodiment may not be an on-line PACS but an off-line PACS, or may not be a form of the PACS. Furthermore, this embodiment is equipped with a film digitizer, and films imaged by an X-ray analog machine are inputted from this film digitizer, and these images may be objects of judgements of presence or absence of necessity in the next examination or settings of the examination conditions. Furthermore, in the above-mentioned description, the chest plain X-ray image was explained as an objective image of judgements of presence or absence of necessity in the next examination or settings of the examination conditions, however this embodiment is not limited to this image, and may be applied to the other types of image, for example a breast X-ray image, a stomach X-ray image, a cross-sectional image by an X-ray computed tomography machine, an MR image by a magnetic resonance imaging machine, or the like. Furthermore, in the above-mentioned description, the medical image was described as an object of judgements of presence or absence of necessity in the next examination, however this embodiment is not limited to this image, and may be applied to the other examination data, for example graphic data such as an electrocardiogram, brain waves, or the like, numerical value data by an automatic chemical analyzer or the like.

Embodiment No. 7-3

Next, a third embodiment will be explained.

In the same manner as the second embodiment, this embodiment indicates to a radiographer presence or absence of the next examination and the examination conditions immediately after completing the examination, in order to mitigate precision in the acquired images and troubles in a reexamination. An image detection unit according to this embodiment has the same configuration as FIG. 113 in the second embodiment. However, unlike the second embodiment, this embodiment uses a next examination condition setting table which has beforehand been made in order to decide the necessity in the next examination and the next examination conditions for it. Therefore, this next examination condition setting table has beforehand been made and is archived in the image storing unit 2G of FIG. 113. This next examination condition setting table is such a table that various combinations of a type of an abnormality which is detected in the CAD peocessing unit 2H, a size of an abnormality, a position of an abnormality, and an examining direction are associated with and corresponded to the necessity in the next examination, the examining direction of the next examination, and the examination conditions of the next examination (an imaging mode such as an enlarging imaging etc., a tube voltage, a tube current, an imaging time). FIG. 139 shows an example in the case where a type of an abnormality is an interstitial lung disease, and FIG. 140 shows an example in the case where it is pulmonary nodules.

Operations for deciding the necessity in the next examination and the examination conditions for it by using this next examination condition setting table will hereinafter be described with reference to a flowchart of FIG. 119.

In the step (S1), in order to obtain the examination request information and also perform a chest plain X-ray imaging for a person to be examined, a radiographer sets imaging conditions such as a tube voltage, a tube current, or the like of the X-ray generator 2E from a physical characteristic of the person to be examined (an age, a sex, a thickness of body etc.). For example, in the case of the chest plain X-ray imaging of a male adult, the tube voltage 80 kV and the tube current 200 mA are set. Also, for example an X-ray tube is arranged in the back side of the person to be examined and the X-ray machine 2F is arranged in the position opposing to the X-ray tube, namely on the belly side of the person to be examined, and the examining direction is set at P→A orienting from the back side to the belly side.

In the step (S2), the X-rays are exposed under these conditions to acquire images. These acquired images are sent to the image storing unit 2G through the image bus 2A and temporarily stored. Then, in the step (S3), these images are sent to the CAD processing unit 2H under control of the control unit 2C and CAD-processed therein.

These CAD processing results are supplied to the next examination deciding means 2I. Also, at this time, the next examination condition deciding table is associated with the type of an abnormality based on these CAD processing results and supplied from the image storing unit 2G to the next examination condition deciding means 2I by an instruction of the control unit 2C. In the step (S4), the next examination condition deciding means 2I checks a degree of an abnormality in the CAD processing results (or a size of shadows), a disease portion (or a position of an abnormality), an examining direction, and a tube voltage with such next examination condition deciding table to judge the necessity in the next examination. Herein, if the next examination is not necessary, such processing is completed. On the other hand, if the next examination is judged to be necessary, the step (S5) is carried out.

In the step (S5), the next examination condition deciding table is also used. The examining direction of the next examination and the examination conditions of the next examination (an imaging mode such as an enlarging imaging etc., a tube voltage, a tube current, an imaging time) corresponding to various conditions of the above-mentioned CAD processing results are read out from the next examination condition deciding table. For example, if the type of an abnormality is "pulmonary nodules", FIG. 140 is used. Then, in the CAD processing results, if, for example, a size of an abnormality is "1 cm" and the position of an abnormality exists in a vertical interval region and in a right lung field, the next examination is necessary in any cases. The results are obtained that two next examinations are necessary. That is, the one next examination is an examining direction: P→A, an examination mode: an enlarged imaging, a tube voltage: 120 kV, a tube current: 100 mA, and an imaging time: 0.06 sec. and the other next examination is an examining direction: the side L→R, a tube voltage: 90 kV, a tube current: 200 mA, and an imaging time: 0.2 sec. When completing the step (S5), return to the step (S2) and the same processing is repeated until any images are not left.

The thus-obtained checking results are displayed on the display unit 2K. The radiographer sets the examination conditions according to these display contains and executes promptly the next examination, namely for a period when the person to be examined is not required to come again.

Similarly, the necessity in the next examination is judged for the acquired images in this reexamination, and the examination conditions of the next examination after the next one are decided as occasion demands. This reexamination is repeated until the judging results are finally obtained that the next examination is unnecessary.

Thus, in this embodiment, the same effects as the second embodiment are obtained.

In this connection, the present invention is not limited to the above-described embodiment, of course it can be changed in various modes and executed within the scope which does not deviate from the gist.

This embodiment according to the present invention detects the type of an abnormality as to each image of images for an examining doctor and a plurality of sheets of medical image archived in the archiving means, and according to these detected results, that is such images are selectively displayed as images to refer to the medical images having the same type of an abnormality as the images for the examining doctor. Therefore, the reference image preparation supporting unit can be provided in which it is possible to prepare the images to refer to without interposing an operator, and which the images can be prepared for the interpretation of the images for the examining doctor.

Furthermore, this embodiment according to the present invention detects an abnormality by the abnormality detecting means as to the acquired images, and as the detected results, the abnormality detecting means outputs data that the additional examination is necessary when the type of an abnormality is a specified one and the degree of an abnormality exists within a predetermined scope, and urges to execute instantly the additional examination. Therefore, the image acquisition unit can be provided in which the additional examination can be executed immediately after the images are acquired without awaiting the interpretation work of such images, and which accordingly examination efficiency is enhanced significantly.

Embodiment No. 7-4

Figure 141:
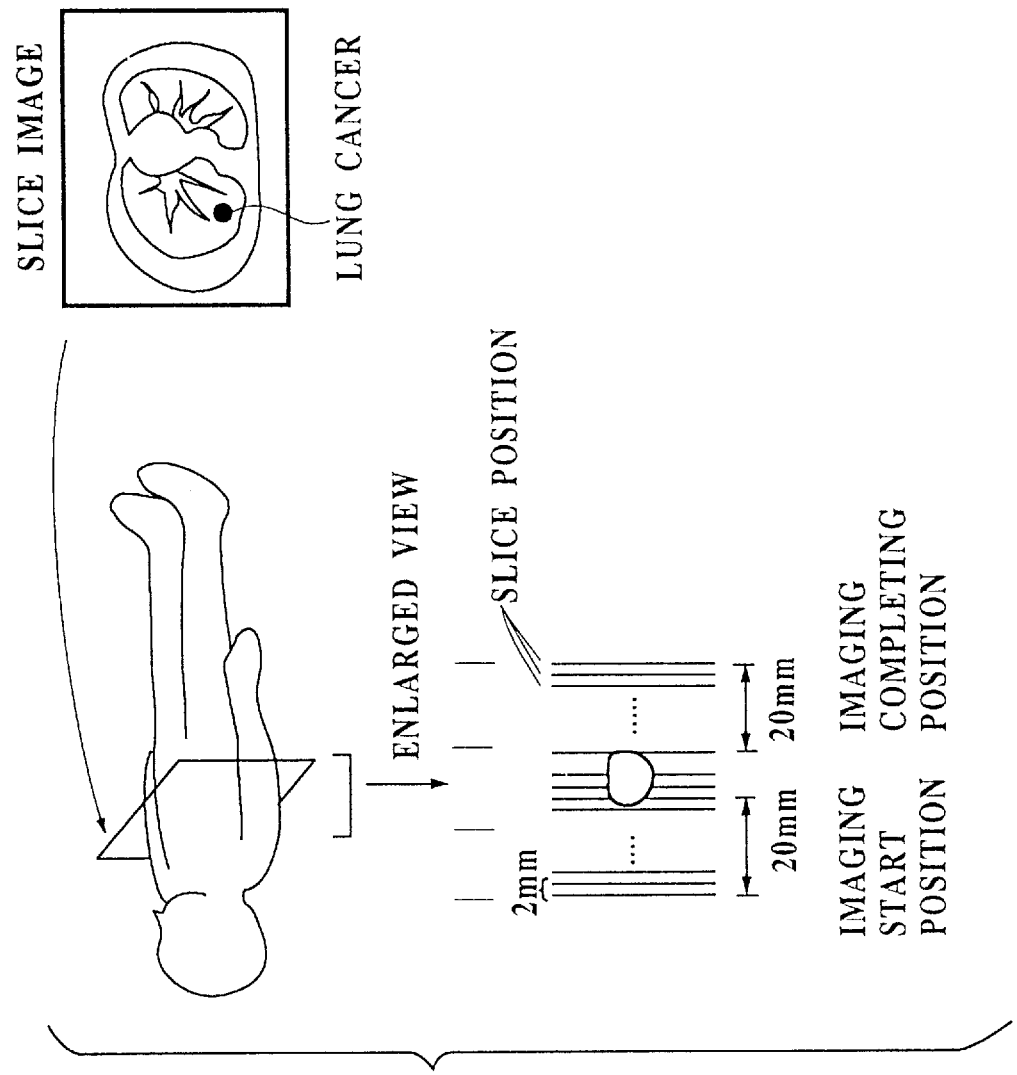
FIG. 141 illustrates embodiment no. 7-4.

Referring to FIG. 141, fourth variation of the seventh embodiment will be described.

Suppose that a group examination is performed to detect the lung cancer by CT.

Step 1): The images are obtained in accordance with predetermined conditions such as:

Imaging condition
  tube voltage at 120 kV
  tube current at 50 mA
  slice thickness of 10 mm
  bed moving rate at 20 mm/rotation
Imaging range
  from 20 mm above the collarbone to a leg side for 300 mm
Image constructing condition
  image pitch at 10 mm
  image reconstructing technique utilizing opposition interpolating technique;

Step 2): Immediately after the images are obtained, the lung cancer is detected by the computer utilizing a predetermined process algorithm.

Step 3): If no cancer is found, stop here. If abnormality is detected from the image, the image shall be collected so that the position of the detected lung cancer is obtained under a precision examination condition (thin slicing etc.). When such image is collected under the precision examination condition, a bed portion is automatically moved to the image collecting position. Thereafter, the operator inputs an instruction to acquire the precision image so as to image the position in question. The image is obtained preferably with conditions such as:

Imaging condition
  tube voltage at 120 kV
  tube current at 50 mA
  slice thickness of 2 mm (so as to obtain finer concentrated area)
  bed moving rate at 2 mm/rotation
Imaging range
  from 20 mm above an upper end of the detected lung cancer to 20 mm below a lower end of the detected lung cancer (see FIG. 141)
Image constructing condition
  image pitch at 2 mm
  image reconstructing technique utilizing opposition interpolating technique; and Step 4): Thus-obtained images in Step 3) are corresponded to those obtained at Step 1) so as to be stored.

It is appreciated that the operator may attend to move the bed portion while he/she only outputs the imaging conditions at the time of collecting additional precision images.

In this embodiment, the patient need not come again to go through re-examination (additional precision examination), so that a burden for the patient is significantly reduced. Moreover, a cancer whose spreading rate is rather fast can be treated promptly. Moreover, as for an examination-conducting side who runs the group examination, arrangement for the examination can be made easy; for example, the arrangement for a examination car, examination doctors and interpreting doctors is simplified. Thereby, cost necessary for the examination can be significantly reduced.

Embodiment No. 8

Hereinafter, the eighth embodiment according to the present invention will be described. FIG. 108 shows a schematic configuration of a medical picture archiving communication system (PACS).

A network (NW) 5 is a transmission path for an image communication among respective units and an optical fiber is used as a transmission medium in order to make an attempt to communicate at high speed. Herein, a ring-type local area network is adopted, of course the other types such as a startyle one or the like may be used.

This network 5 is connected with a system manager (SM) 1, image acquisition units (IA) 2a, 2b, a database (DB) 3, and workstations (WS) 4A, 4B, and the respective units can be mutually linked by means of a communication protocol.

Furthermore, this network 5 is connected with an examination order, system 7 through a gateway 6. This examination order system 7 is equipped with inputting means of a keyboard etc. Examination request information for requesting an acquisition of images is inputted from the examination order system 7. One example of this examination request information is shown in FIG. 120.

As shown in FIG. 120, the examination request information consists of respective items of a patient ID number, a patient name, a date of birth, a sex, a name of examination requesting department, a name of examination requesting doctor, a modality of an examination (an X-ray machine, an X-ray computed tomography machine, a magnetic resonance imaging machine etc.), an examination portion, a purpose of an examination, clinical information or the like.

The examination request information is sent from the examination order system 7 to the system manager 1.

The system manager 1 transfers this examination request information to the appropriate acquisition unit 2a or 2b.

The image acquisition units 2a, 2b are image acquisition units such as an X-ray machine, an ultrasonic diagnostic apparatus, an X-ray computed tomography apparatus, a magnetic resonance imaging apparatus, or the like. These image acquisition units 2a, 2b assign an image number to a generated image in the order of its generation, and also attach annexed information thereto as peculiar information concerning the image, and send to the database 3 according to an instruction of the system manager 1. An example of this annexed information is shown in FIG. 121.

As shown in Table 121, the annexed information contains an examination ID, a date of an examination, an image number, an image size, a data amount, and information concerning such image in the imaging direction.

The system manager 1 creates examination histories from the examination request information or the annexed information and stores therein. One example of the examination is shown in FIG. 130 described below.

These examination histories are sent from the system manager 1 to the workstation 4B when interpreting images to refer to the interpretation.

The interpretation report making support unit is incorporated with the workstations 4A, 4B.

Figure 148:
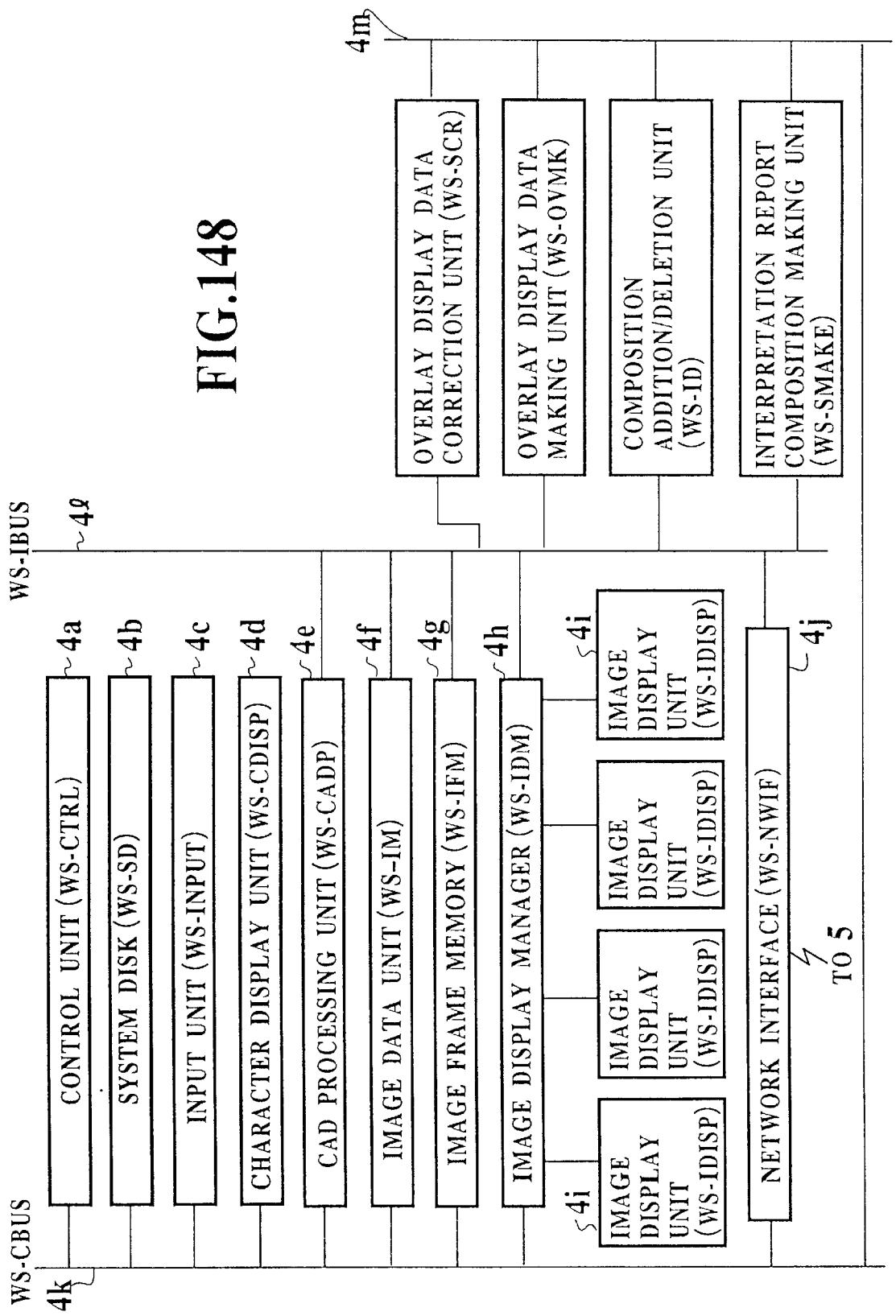

FIG. 148 is a block diagram showing a configuration of the workstation 4A. In this connection, as the workstation 4B has the same configuration as the configuration of the workstation 4A as shown in FIG. 148, herein the description of the workstation 4B is omitted. In the figure, reference numerals 4k and 4m are control buses (WS-CBUS). Also, the reference numeral 4l is an image bus (WS-IBUS). The image bus 4l is connected with the network 5 through a network interface 4j. Hereinafter, functions of each unit which is connected with the control buses 4k, 4m, and the image bus 4l will respectively be described.

<Control Unit (WS-CTRL)>

The control unit 4a contains a central processing unit (CPU), a system memory (for example, a semiconductor memory), or the like and controls operations of the entire workstation.

<system disk (WS-SD)>

The system disk 4b is, for example, a magnetic disk and archives various programs which are necessary to control operations of the entire workstation. These programs are read out into the control unit 4a when an electric power is turned on and are stored in a system memory within the control unit 4a.

<Character Display Unit (WS-CDISP)>

The character display unit 4d is a unit for displaying mainly character information such as an interpretation report etc., and for example, a CRT (Cathode Ray Tube) display, a liquid crystal panel display, or the like is used for this unit.

<Imaging Frame Memory (WS-IFM)>

An imaging frame memory 4g is, for example, a semiconductor memory and temporarily archives an original image to be interpreted which is transferred from the database 3.

<Image Storing Unit (WS-IM)>

An image storing unit 4f is, for example, a magnetic disk and temporarily stores examination request information to be treated during interpreting operations, an interpretation report, image annexed information, original image data, overlay display information, an abnormality data table, or the like. Also, The image storing unit 4f archives abnormality detecting means selection information. One example of this abnormality detecting means selection information is shown in FIG. 124.

This abnormality detecting means selection information is information for selecting the abnormality detecting means capable of being applied each type of an original image, and is sent to a CAD processing unit 4e when computer-aided diagnostic functions are activated.

The image storing unit 4f further stores a typical sentence table. An example of this typical sentence table is shown in FIG. 142.

In FIG. 142, a circle shows presence of each information of a type, a position, a degree, and a condition of an abnormality.

This typical sentence table contains a plurality of types of typical composition for constituting the type, position, or degree of an abnormality detected in the below-described CAD processing unit 4e as a predetermined sentence. The typical sentence shows a typical composition structure when preparing compositions. Herein, 12 types of this typical sentence exist. Each typical sentence is different in a combination of each information of the type, position, degree, and condition of an abnormality. This typical sentence table is sent to an interpretation report composition making unit 4r described below when an interpretation report is produced. Then, a basic sentence type for constituting a composition concerning the type, position, and degree of an abnormality detected by the CAD processing unit 4e is selected and is used for making a composition for the type, position and degree of an abnormality according to this basic sentence type.

<CAD processing unit (WS-CADP)>

A CAD processing unit 4e is a unit in charge of a Computer-Aided Diagnosis (CAD) and archives a plurality of types of abnormality detecting means. For example, the abnormality detecting means has (a) means for detecting shadows of an interstitial lung disease in a frontal image of a chest plain X-ray image; (b) means for detecting shadows of pulmonary nodules in a frontal image of a chest plain X-ray image; and (c) means for detecting shadows of a fine calcification of a breast in a breast X-ray image. These abnormality detecting means are selectively used based on the abnormality detecting means selection information.

The abnormality detecting means judges presence or absence of an abnormality, a center position of an abnormality on an image (XY coordinates), a degree of an abnormality, and a spacial magnitude of an abnormality.

Furthermore, the CAD processing unit 4e comprises means for specifying a dissecting division in accordance with coordinates on an image matrix judged by the abnormality detecting means. Herein, the dissecting regional division is, for example in lungs, trisected vertically in each of two right and left lungs, and each of the divisions is respectively called an "upper left lung field", a "middle left lung field", a "lower left lung field", an "upper right lung field", a "middle right lung field", and a "lower right lung field".

This specifying mean has various ones, and a technique adopted herein has been disclosed in Japanese Patent Application Laid-Open No. 1-125675. In this connection, the dissecting division of the lungs should precisely be sectioned based on the position relationship with a tip of a rib, however as it is difficult to recognize the tip of rib by a computer, in the above-mentioned technique, generally by using a fact that a lower edge of the collarbone exists in a center position of the upper lung field and that an upper edge of the diaphragm coincides with a lower edge of the lung field, based on the position relationship of the lower edge of the collarbone with the upper edge of the diaphragm as it is easy to comparatively recognize them from an image, it is possible to recognize a scope of each division on the image. If the center position of the abnormality is checked up with the coordinates on the image which specify each region, it is possible to specify the dissecting division relating to the position of the abnormality. This specified dissecting division is hereinafter called a "region containing an abnormality".

The CAD processing unit 4e finally creates an abnormality data table showing one example in FIG. 129 by using judgement results of the abnormality detecting means or the region containing an abnormality.

The abnormality data table consists of respective items of a reference number, an examination ID number, a type of an abnormality, a center position of an abnormality on an image, a degree of an abnormality, and a region containing an abnormality. This abnormality data table is transferred to the image storing unit 4f to stand by until the time of displaying the abnormality information.

<Input Unit (WS-INPUT)>

An input unit 4c is inputting means for inputting various commands such as an image search etc. or character information etc. by an interpreting doctor, or for correcting overlay display information, and are, for example, a keyboard, a mouse, a light pen, a touch screen, or voice inputting means.

This voice inputting means picks up a voice generated by an interpreting doctor by a microphone and recognizes his/her sound signals, and makes a code conversion the signals and outputs them as a coding scheme, thereby fetching various commands or input information in the same manner as inputting means through a keyboard.

<Overlay Display Information Making Unit (WS-OVMK)>

An overlay display information making unit 4n inputs the abnormality data table stored in the image storing unit 4f and makes an element of an image expressing the type, position, and degree of an abnormality based on this abnormality data table (hereinafter, referred to as an "overlay display information").

One example of this overlay display information is shown in FIG. 143 described below.

As shown in FIG. 143, in this overlay display information, graphic information of a marker for showing the position of an abnormality on the image is added to the abnormality data table. In this connection, a "position" in the overlay display information means a "region containing an abnormality" specified in the CAD processing unit 4e. Graphic information of a marker is the previously set information and consists of each information of a type of a graphic, a size of a graphic, and a display color.

This overlay display information is sent to the image storing unit 4f and stored therein.

<Image Display Manager (WS-IDM)>

The image display manager 4h makes a display image by superimposing the overlay display information on the original image. This configuration is shown in FIG. 3.

The original image sent through the image bus 4l is sent to an overlay portion 44 through an image memory 42.

A control portion 40 is connected with the control bus 4k and the overlay display information concerning such original image is inputted from the image storing unit 4f. This overlay display information is sent to an overlay data making portion 41, which is converted into overlay data (images composed of abnormality information) having the same image matrix as the original image.

These overlay data are sent to the overlay portion 44 through an overlay memory 43a. In this connection, an overlay memory 43b is a memory for a cursor display for displaying a cursor on an image corresponding to a mouse. The data in this memory are sent to the overlay portion 44.

The overlay portion 44 makes a display image by synthesizing the original image data, the overlay data, and the cursor display data. This display image is sent to the display unit 4i through a displaying memory 45 and a D/A converter 46.

<Image Display Unit (WS-IDISP)>

An image display unit 4i is, for example, a color CRT display and a plurality of units, herein four units, are prepared.

Referring back to FIG. 148, the description is hereinafter continued.

<Overlay Display Information Correction Unit (WS-SCR)>

An overlay display information correction unit 4p is for correcting overlay display information.

Figure 149:
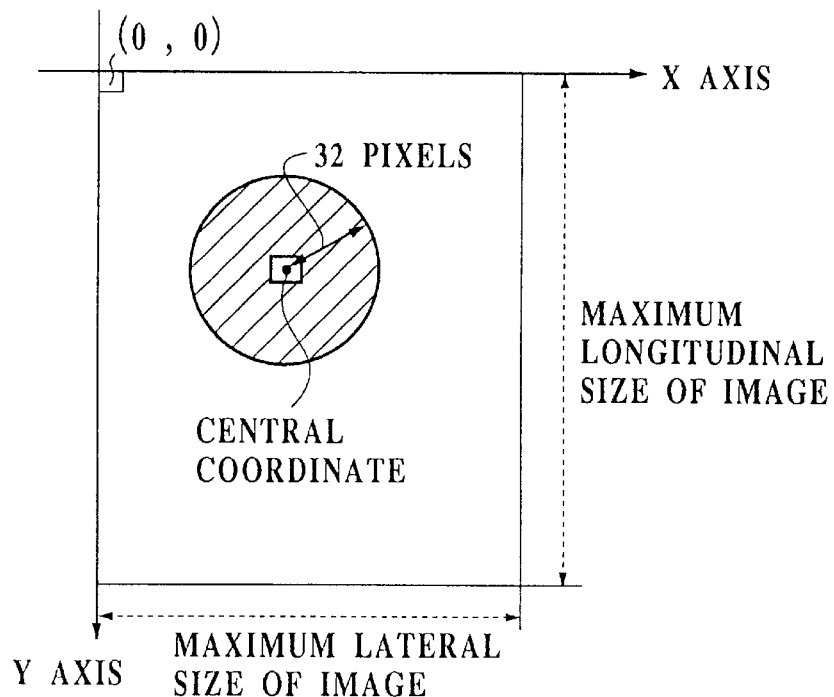

This correction is carried out by operating the input unit 4c while an interpreting doctor observes a display image of the display unit 4i. For example, when an interpreting doctor discovers an abnoramality which cannot be extracted by the CAD processing unit 4e, a cursor is put on the position on a screen by traveling a mouse to add the position information of an abnormality thereto. This position information is converted into a "region containing an abnormality" by the CAD processing unit 4e. Also, a type or degree of an abnormality is inputted by operating a keyboard of the input unit 4c. Each information of the region containing an abnormality and the type and degree of an abnormality is added to the overlay display information by the overlay dispaly information correction unit 4p. Also, when a doctor desires to delete an abnormality extracted by the CAD processing unit 4e, a cursor is put on a marker to be deleted on the screen by traveling a mouse to indicate a deletion. In this connection, at this time, as shown in FIG. 149, by setting a comparatively wide scope as shown by an oblique line (for example, a circular scope having the radius 32 pixels) as a moving pitch of a cursor, it is possible to dissolve troubles in putting a cursor on a marker by one pixel unit. The corrected overlay display information is sent immediately to the image display manager 4h. Based on this corrected overlay display information, the overlay data are newly made, this newly made overlay data are synthesized with the original image to display on the display unit 4i.

<Interpretation Report Composition Making Unit (WS-SMAKE)>

An interpretation report composition making unit 4r makes a finding composition of an interpretation report based on the overlay display information to complete the interpretation report. The interpretation report is shown in FIG. 122.

An interpretation report is constituted of information concerning a patient, information concerning an examination, a finding of an interpreting doctor, and a conclusion.

As information concerning a patient and information concerning an examination exist in the examination request information, the annexed information, and the abnormality data table, such information is created by duplicating the information solely. An interpreting doctor's finding was created by conventionally operating a keyboard and manually inputting it by him/her. The interpretation report composition making unit 4r automatically makes this finding.

In short, the interpretation report composition making unit 4r fetches each information of the type of an abnormality, the degree of an abnormality, and the position of an abnormality from the overlay display information and specifies a corresponding typical sentence from the typical sentence table according to presence or absence of each information. and arranges each information in a predetermined position of the typical sentence, thereby making a composition of a finding. The interpretation report composition making unit 4r incorporates this finding with the information concerning a patient and the information concerning an examination to complete the interpretation report. This interpretation report is sent to the image diaplay manager 4h to display on the display unit 4i.

<Composition Addition/Deletion Unit (WS-ID)>

A composition addition/deletion unit 4q contains character inputting means of a keyboard etc. and is made so that an interpreting doctor may read an interpretation report displayed on the display unit 4i and add newly words or sentences to the contents of finding as occasion demands or delete unnecessary parts.

Next, operations of this embodiment constituted above will be explained.

(1) Request of an examination (1-1) Examination request information inputted through the examination order system 7 is sent to the system manager 1. An embodiment of this examination request information is shown in FIG. 132 described below.

This example consists of a patient ID number: 870802, a name of a patient:for example, E. Suzuki, a sex: information concerning a patient of a male etc., a modality: X-ray, an examination portion: chest, and a procedure of an examination: information concerning an examination such as a plain radiography etc.

1-2) This examination request information is transferred to an appropriate: unit, herein the image acquisition unit 2a or 2b of the X-ray machine by the system manager 1.

(2) Acquisition and archival of an image 2-1) A radiographer carries out an image acccording to the examination request information to produce an image.

2-2) This image information is assigned an image number in the sequential order of the generation, and the annexed information is also attached thereto. An embodiment of the annexed information is shown in FIG. 133.

The image information is sent to the database 3 together with an image number or an annexed information, and archived therein.

(3) Readout of examination histories or the like

Before an interpretation, examination histories of such patient, a previous interpretation report, and examination request information which are to be referred to at the interpretation are read out from the database 3, and sent to the workstation 4A and archived in the system memory. An embodiment of these examination histories is shown in FIG. 134.

(4) Readout of an image to be interpreted

An interpreting doctor inputs a readout demand of a desired image to be interpreted through the input unit 4c of the workstation 4A. This demand is sent from the database 3 through the system manager 1. Such image information is read out from the database 3 and sent to the image storing unit 4f and temporarily stored therein.

(5) Computer-aided diagnosis processing

The image stored in the image storing unit 4f is sent to the CAD processing unit 4e according to an instruction of the control unit 4a.

As described above, the CAD processing unit 4e comprises three types of abnormality detecting means of
(a) means for detecting shadows of an interstitial lung disease in a frontal image of a chest plain X-ray image;
(b) means for detecting shadows of pulmonary nodules in a frontal image of a chest plain X-ray image; and (c) means for detecting shadows of a microcalcification of a breast in a breast X-ray image.

By using the abnormality detecting means selection information of FIG. 124, the CAD processing unit 4e specifies the detectable type of an abnormality concerning this image and selects the abnormality detecting means according to these results. Herein, as an examination portion is a chest and a procedure of an examination is a plain radiography and an imaging direction is P→A, the CAD processing unit 4e selects the abnormality detecting means capable of detecting an interstitial lung disease and the abnormality detecting means capable of detecting lung nodules.

By the selected abnormality detecting means, the abnormality detecting processing is executed as to an original image to judge presence or absence of an abnormality, a type of an abnormality (to be decided at the time when the abnormality detecting means is selected), a position of an abnormality, and a degree of an abnormality. Also, if the position of an abnormality is in a region containing an abnormality of the dissecting division, for example an examination portion is in the lungs, it is recognized to which region of the "upper left lung field", the "middle left lung field", the "lower left lung field", the "upper right lung field", the "middle right lung field", and the "lower right lung field" the position of an abnormality belongs. The abnormality data table is made by using presence or absence of an abnormality, the type of an abnormality, the position of an abnormality, the degree of an abnormality, the region containing an abnormality, the image number, and the examination ID number.

An embodiment of the abnormality data table made by the CAD processing unit 4e is shown in FIG. 135.

The abnormality data table made by this CAD processing unit 4e is sent to the image storing unit 4f and stored therein.

(6) Creation of overlay display information

The abnormality data table is sent from the image storing unit 4f to the overlay display information making unit 4n. The overlay display information is made based on this abnormality data table. An embodiment of this overlay display information is shown in FIG. 144.

As shown in FIG. 144, in the overlay display information, each information of a type of a graphic of a marker, a size of a graphic, and a display color of a graphic which have beforehand been set is added to the abnormality data table.

Figure 150:
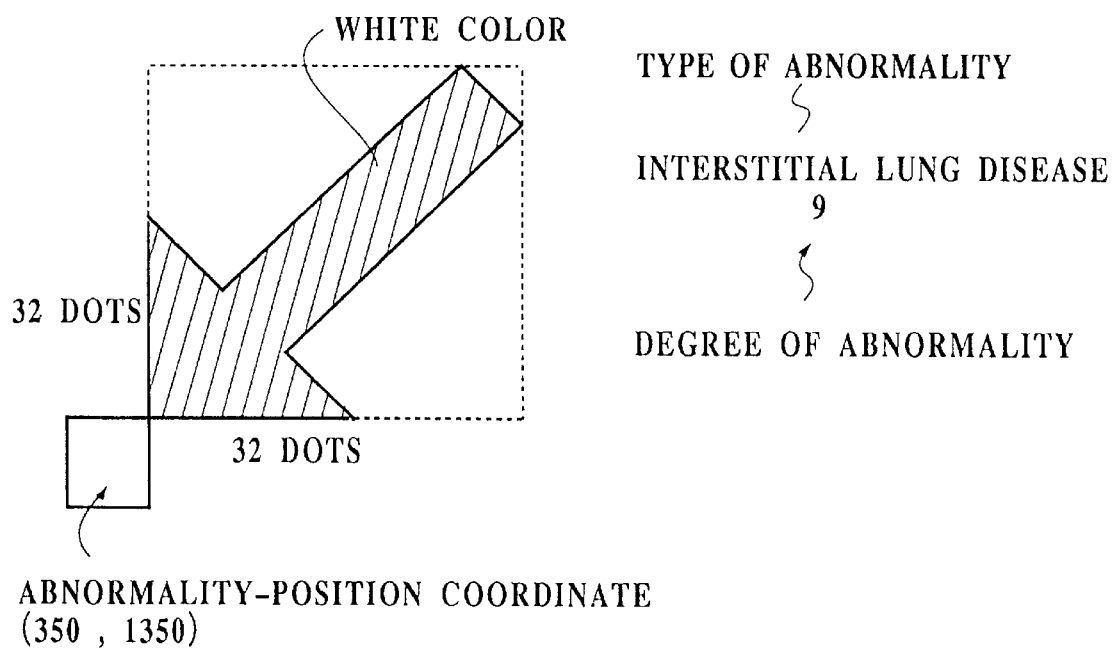

A graphic of this marker is, for example, an arrow in a real line and in 32×32 dots, as shown in FIG. 150, and then a display color is decided to be white. At displaying, a tip of an arrow is allocated in the coordinate position of the overlay display information, and the type and degree of an abnormality come close to the marker to display by characters.

This overlay display information is sent to the image storing unit 4f and stored therein.

(7) Creation and display of a display image

The original image and the overlay display information are sent from the image storing unit 4f to the display manager 4h by an instruction of the control unit 4a. The original image is sent to the overlay portion 44 through the image memory 42. Also, the overlay display information is sent to an overlay data making portion 41 through the control unit 4a, and markers concerning all abnormalities are arranged on an image matrix of the original image to make the overlay data as the image information concerning an abnormality.

As to, for example, the reference number 1 of FIG. 144, as shown in FIG. 150, a tip of a marker is arranged in the coordinate (350, 1350) on the image matrix of the original image. Character information of the degree of an abnormality "9" and the type of an abnormality "interstitial lung disease" is arranged in a position close to this marker by using a character font.

Figure 151:
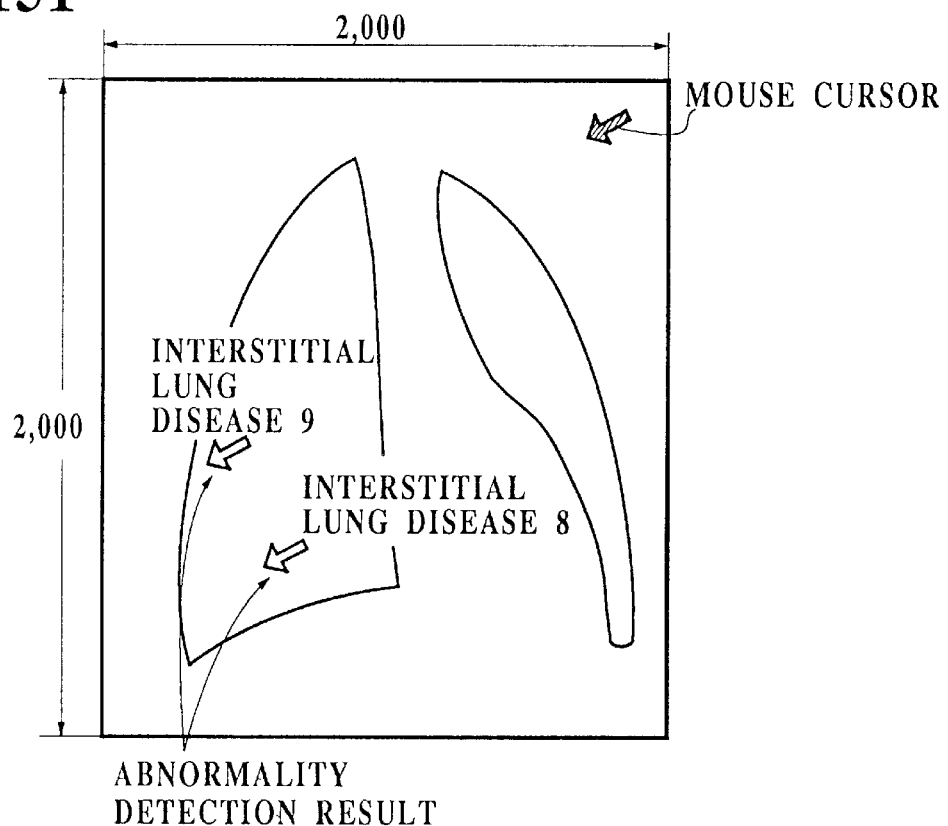

These overlay data are sent to the overlay portion 44 through the overlay memory 43a, and are synthesized with the original image to create a display image. This display image is sent to the display unit 4i through the displaying memory 45 and the D/A converter 46 and displayed therein. One example of this display screen is shown in FIG. 151.

(8) Creation of an interpretation report

The overlay display information and the typical sentence table of FIG. 144 is sent from the image storing unit 4f to the interpretation report composition making unit 4r by an instruction of the control unit 4a. The interpretation report composition making unit 4r separately judges as to whether or not each information of the type of an abnormality and the position of an abnormality and the degree of an abnormality in the overlay display information exist.

As the results of judgement, a combination of these present information is checked with the typical sentence table of FIG. 142 to select the typical sentence corresponding to such combination. For example, in the case of the reference number 1 in FIG. 144, as each information of the type of an abnormality and the position of an abnormality and the degree of an abnormality exists, the typical sentence of the number 6 of the typical sentense table is selected.

The composition structure of this typical sentence is that a "type" of an abnormality is recognized in a "position" at a "degree". The information of the type of an abnormality and the position of an abnormality and the degree of an abnormality which are picked up from the overlay display information is set to this composition structure, in order to make the composition that "a pulmonary interstitial disease is recognized in a lower right lung field at a degree 9". This created composition is inseted into finding items of an interpretation report to complete the interpretation report together with information concerning the patient or information concerning the examination. As the information concerning the patient and the information concerning the examination exist in the examination request information, the annexed information, and the abnormality data table, the interpretation report is made by duplicating the information solely. The interpretation report made based on the overlay display information of FIG. 144 is shown in FIG. 145.

This interpretation report is sent to the character display unit 4d and displayed therein.

(9) Indirect correction of an interpretation report

In order to indirectly correct an interpretation report, the overlay display information is corrected by the overlay display information correction unit 4p.

The correction of the overlay display information is carried out as follows: That is, an interpreting doctor operates the input unit 4c while he/she observes a display image of the display unit 4i. For example, when the interpreting doctor discovers the abnormality which could not be extracted by the CAD processing unit 4e, he/she puts a cursor on a screen on the poition by traveling a mouse to add the position information of an abnormality thereto. This position information is converted into a "region containing an abnormality" by the CAD processing unit 4e. Also, the type or degree of an abnormality is inputted by operating a keyboard of the input unit 4c. Each of the information of the region containing the abnormality and the type and degree of the abnormality is added to the overlay display information by the overlay display information correction unit 4p. Also, when the doctor desires to delete the abnormality extracted by the CAD processing unit 4e, he/she puts a cursor on a marker to be deleted on a screen by traveling a mouse and indicates to delete it. At this time, as shown in FIG. 149, a comparative wide scope as shown by an oblique line (for example, a circular scope having the radius 32 pixels) is set as a moving pitch of a cursor, whereby it is possible to dissolve troubles in putting a cursor on a marker by one pixel unit. This corrected overlay display information is immediately sent to the image display manager 4h. Based on this corrected overlay display information, the overlay data are newly created and this newly created overlay data are synthesized with an original image to display on the display unit 4i.

Herein, procedures of the correction will be concretely explained with reference to the case where the data of the reference number 2 of FIG. 144 are corrected.

The data of the reference number 2 are the type of an abnormality "pulmonary interstitial disease", the degree of an abnormality "8", and the position of an abnormality "middle right lung field". This is corrected to the type of an abnormality "pulmonary nodule shadows", the degree of an abnormality "6", and the position of an abnormality "lower right lung field".

The mouse of the input unit 4c is traveled by the interpreting doctor and the cursor on a screen is moved to the position of a tip of the marker displayed thereon (the coordinate (400, 1500)) according to the data of the reference number 2. A deletion instruction is inputted from the mouse in this position. This instruction is sent to the overlay display information correction unit 4p and the data concerning the reference number 2 of the overlay display information is deleted according to this deletion instruction.

Then, the cursor is moved to the position in which an abnormality is confirmed, for example the position of the coordinate (300, 1500) on a screen. The instruction of information addition is inputted from the mouse in this position. In response to the input of this information addition instruction, the prompts "input the type of an abnormality " and "input the degree of an abnormality" are displayed on the character display unit 4d. According to these prompts, "pulmonary nodule shadows" and "6" judged by the interpreting doctor are inputted from a keyboard of the input unit 4c. At this time, when the type or the degree of an abnormality is not proved positively, the doctor does not need to input these information. At this time, the doctor immediately inputs an input completing instruction. Herein, as the presently inputted position is coordinate information, this is required to be replaced with a dissecting division. For this reason, the coordinate information is sent to the CAD processing unit 4e. Therein, it is judged which dissecting division the position of such coordinate falls under. As these results, the position of such coordinate corresponds to the "lower right lung field". Each of the thus-inputted information of the coordinate (300, 1500), the type of an abnormality "pulmonary nodule shadows", the degree thereof "6", and the position of an abnormality "lower right lung field" is added to the overlay display information as the information of the latest unused reference number 2 by the overlay display information correction unit 4p.

This corrected overlay display information is immediately sent to the image display manager 4h. Based on this corrected overlay display information, the overlay is newly created and these overlay data are newly synthesized with the original image to display on the display unit 4i.

Furthermore, this corrected overlay display information is sent to the interpretation report composition making unit 4r, and the finding 2 is altered therein to the contents "the pulmonary nodule shadows are recognized in the lower right lung field" at the degree of the abnormality 6" according to this overlay display information to make the new altered interpretation report to display on the character display unit 4d. The finding 2 is altered into the composition "the lung nodule shadows are recognized in the middle right lung field at the degree thereof 6". This new interpretation report is shown in FIG. 146.

(10) Direct correction of an interpretation report

As for the direct correction of an interpretation report, an interpreting doctor reads the interpretation report displayed on the character display unit 4d and corrects directly the contents from a composition addition/deletion unit 4q. For example, the composition corresponding to the reference number 1 of FIG. 144 "an interstitial lung disease is recognized in a lower right lung field at a degree of an abnormality 9" is corrected to the more embodied contents "a pulmonary interstitial disease is recognized in a lower right lung field in a degree of an abnormality 9 expanding to a wide scope". In short, the paragraph "expanding to a wide scope" is added thereto. This new interpretation report is shown in FIG. 147.

In this case, in the same manner as an insertion mode by a word processor functions, a cursor is moved to a position to be added to input a paragraph to be added by a key. In the case of deletion, operations are carried out in the same manner as deletion operations by the word processor functions.

Thus, the complete interpretation report is completed. This complete interpretation report is sent to the image storing unit 4f. Then, this interpretation report is transferred from the image storing unit 4f to the system manager 1, and archived therein and stands by for a readout demand from an examination requesting doctor. After passing through the preceding steps, the interpretation work has been completed.

As described above, according to this embodiment, the interpretation report is automatically made based on the CAD processing results and the contents can be corrected from time to time as occasion demands, whereby the work amount can remarkably be reduced as compared with the case where the interpreting doctor manually inputs the interpretation reports, in particular, findings in the conventional practice.

The present invention is not limited to the above-described embodiments and can be changed into various modes to realize. For example, in the above-mentioned description, the display image is an image that the overlay data are synthesized with the original image, however it may be a contour image instead of the original image. Also, in the above-mentioned description, one type of an arrow in a real line was used in the type of a graphic, however, for example, the other types such as an arrow in a dotted line or the like can selectively be added thereto as shown in FIG. 152. In this case, for example, a marker corresponding to the settled findings can be expressed with an arrow in a real line, and a marker corresponding to the unsettled findings can be expressed with an arrow in a dotted line, so that the settled conditions can be distinguished by the type of a graphic to display. Further, in the above-mentioned description, one type of the types of a graphic and the display colors was used, however the graphic or display color may be altered each type of an abnormality to display by using the plurality of types of a graphic such as a round, a square, or the like or the plurality of display colors such as red, blue, or the like.

The interpretation report making support unit according to the present invention comprises: means for inputting the image; means for detecting the type and position of an abnormality included in the image; means for storing the typical sentences to constitute the type and position of an abnormality as the predetermined compositions; and means for making the compositions containing the type and position of an abnormality which are detected by the detecting means, based on the typical sentences. As the compositions containing the type and position of an abnormality which are detected by the detecting means are made based on the typical sentences, it is possible to provide the interpretation report making support unit in which the troubles in manually inputting these compositions in the conventional practice can be saved and the work in making the interpretation report can be made optimally efficient.

Besides those already mentioned above, many modifications and variations of the above embodiments may be made without departing from the novel and advantageous features of the present invention. Accordingly, all such modifiactions and variations are intended to be included within the scope of the appended claims.

What is claimed is:

1. A medical information processing system for supporting a diagnosis, the system comprising:

a first diagnosis processing portion obtaining first diagnostic results relative to a computer-aided diagnosis of medical images of a portion of a patient's body;

a second diagnosis processing portion obtaining second diagnostic results from at least one doctor relative to a diagnosis performed by the at least one doctor relative to the portion of the patient's body;

a selection and display device displaying selected ones of the medical images of the portion of the patient's body related to obtained first diagnostic results;

a display detecting portion detecting that particular ones of the medical images relating to particular ones of the obtained first diagnostic results have been displayed and storing a first list indicating which particular ones of the first diagnostic results have had related medical images selected and displayed;

a comparison and classification portion for comparing the first diagnostic results and the second results and, when the first and second diagnostic results do not agree, for creating a second list including a listing of examination identification numbers corresponding to any of the first diagnostic results not on said first list; and a control portion controlling the selection and display device so as to display the medical images associated with the first diagnostic results appearing on the second list for the at least one doctor's further interpretation.

2. A medical information processing system according to claim 1, wherein the first diagnosis processing portion obtains the first diagnostic results relative to the computer-aided diagnosis of medical images of a small nodular shadow.

3. A medical information processing system according to claim 1, wherein the first diagnosis processing portion obtains the first diagnostic results relative to the computer-aided diagnosis of medical images of interstitial malady shadow of a lung.

4. A medical information processing system according to claim 1, wherein the first list and the second list are lists of examination ID numbers of images.

* * * * *

UNITED STATES PATENT AND TRADEMARK OFFICE
CERTIFICATE OF CORRECTION

PATENT NO. : 5,807,256
DATED : September 15, 1998
INVENTOR(S) : Katsuyuki TAGUCHI, et al.

It is certified that error appears in the above-identified patent and that said Letters Patent is hereby corrected as shown below:

On the title page, in Item [75], the second inventor's name is incorrect. It should read:

-- Shinichi YAMADA --

Signed and Sealed this

Thirteenth Day of July, 1999

Attest:

Q. TODD DICKINSON

Attesting Officer

Acting Commissioner of Patents and Trademarks